US010307455B2

(12) United States Patent
Kumar et al.

(10) Patent No.: US 10,307,455 B2
(45) Date of Patent: Jun. 4, 2019

(54) ACTIVIN TYPE 2 RECEPTOR ANTIBODIES

(71) Applicants: Acceleron Pharma Inc., Cambridge, MA (US); Adimab, LLC, Lebanon, NH (US)

(72) Inventors: Ravindra Kumar, Cambridge, MA (US); Jonathan Belk, Lebanon, NH (US); Asya Grinberg, Cambridge, MA (US); Dianne Sako, Cambridge, MA (US); Roselyne Castonguay, Cambridge, MA (US)

(73) Assignees: Acceleron Pharma Inc., Cambridge, MA (US); Adimab, LLC, Lebanon, NH (US)

( * ) Notice: Subject to any disclaimer, the term of this patent is extended or adjusted under 35 U.S.C. 154(b) by 0 days.

(21) Appl. No.: 15/456,392

(22) Filed: Mar. 10, 2017

(65) Prior Publication Data

US 2017/0281711 A1 Oct. 5, 2017

Related U.S. Application Data

(60) Provisional application No. 62/306,354, filed on Mar. 10, 2016.

(51) Int. Cl.

| | |
|---|---|
| ***C07K 14/00*** | (2006.01) |
| ***C07K 14/47*** | (2006.01) |
| ***A61K 38/00*** | (2006.01) |
| ***A61K 38/02*** | (2006.01) |
| ***A61K 38/16*** | (2006.01) |
| ***A61K 39/395*** | (2006.01) |
| *C07K 5/00* | (2006.01) |

(52) U.S. Cl.

CPC .............. *A61K 38/02* (2013.01); *A61K 38/16* (2013.01); *C07K 14/001* (2013.01); *C07K 14/47* (2013.01); *A61K 38/00* (2013.01); *C07K 5/00* (2013.01)

(58) Field of Classification Search

None

See application file for complete search history.

(56) References Cited

U.S. PATENT DOCUMENTS

| | | | |
|---|---|---|---|
| 6,656,475 | B1 | 12/2003 | Lee et al. |
| 6,682,736 | B1 | 1/2004 | Hanson et al. |
| 6,696,260 | B1 | 2/2004 | Lee et al. |
| 6,891,082 | B2 | 5/2005 | Lee et al. |
| 6,914,128 | B1 | 7/2005 | Salfeld et al. |
| 7,037,498 | B2 | 5/2006 | Cohen et al. |
| 7,052,873 | B2 | 5/2006 | Tsuchiya |
| 7,807,155 | B2 | 10/2010 | Di Padova et al. |
| 7,842,663 | B2 | 11/2010 | Knopf et al. |
| 8,110,355 | B2 | 2/2012 | Atwood et al. |
| 8,551,482 | B2 | 10/2013 | Berger et al. |
| 8,765,385 | B2 | 7/2014 | Kumar et al. |
| 9,365,651 | B2 | 6/2016 | Feige et al. |
| 9,493,556 | B2 | 11/2016 | Seehra et al. |
| 9,624,301 | B2 | 4/2017 | Kumar et al. |
| 2005/0014733 | A1 | 1/2005 | Whittemore et al. |
| 2005/0257278 | A1 | 11/2005 | Lee et al. |
| 2006/0008846 | A1 | 1/2006 | Vale et al. |
| 2006/0034831 | A1 | 2/2006 | Tobin |
| 2006/0068468 | A1 | 3/2006 | Knopf et al. |
| 2006/0251632 | A1 | 11/2006 | Tremblay et al. |
| 2009/0074768 | A1 | 3/2009 | Knopf et al. |
| 2010/0120627 | A1 | 5/2010 | Belouchi et al. |
| 2010/0272734 | A1 | 10/2010 | Berger et al. |
| 2011/0280873 | A1 | 11/2011 | Presta et al. |
| 2012/0121576 | A1 | 5/2012 | Seehra et al. |
| 2012/0237521 | A1 | 9/2012 | Berger et al. |
| 2012/0316071 | A1 | 12/2012 | Smider et al. |
| 2013/0108650 | A1 | 5/2013 | Kumar et al. |
| 2013/0189269 | A1 | 7/2013 | Kumar et al. |
| 2013/0209481 | A1 | 8/2013 | Zhou et al. |
| 2013/0344091 | A1 | 12/2013 | Berger et al. |
| 2014/0199317 | A1 | 7/2014 | Seehra et al. |
| 2014/0275490 | A1 | 9/2014 | Ohori et al. |
| 2014/0294827 | A1 | 10/2014 | Gastwirt et al. |
| 2015/0030606 | A1 | 1/2015 | Kumar et al. |
| 2015/0152194 | A1 | 6/2015 | Han et al. |
| 2016/0000020 | A1 | 1/2016 | Sugimoto |
| 2017/0015751 | A1 | 1/2017 | Seehra et al. |

(Continued)

FOREIGN PATENT DOCUMENTS

| | | | |
|---|---|---|---|
| CA | 2575563 | A1 | 2/2006 |
| CA | 2677160 | A1 | 8/2008 |

(Continued)

OTHER PUBLICATIONS

International Search Report and Written Opinion for International Application No. PCT/US17/21958 dated Sep. 29, 2017.

"International Nonproprietary Names for Pharmaceutical Substances (INN) Denominations Communes Internationales des Substances Pharmaceutiques (DCI)," WHO Drug Information, 26(4):401-471 (2012).

Beiboer et al., "Guided selection of a pan carcinoma specific antibody reveals similar binding characteristics yet structural divergence between the original murine antibody and its human equivalent," J Mol Biol, 296(3):833-849 (2000).

Bogdanovich et al., "Functional Improvement of Dystrophic Muscle by Myostatin Blockade," Nature 420:418-421 (2002).

Bogdanovich et al., "Myostatin Blockade Improves Function but not Histopathology in a Murine Model of Limb-Girdle Muscular Dystrophy 2C," Muscle & Nerve, 37(3):308-316 (2008).

(Continued)

*Primary Examiner* — Elly-Gerald Stoica

(74) *Attorney, Agent, or Firm* — Foley Hoag LLP

(57) ABSTRACT

This disclosure provides ActRII-binding proteins such as anti-ActRIIA and anti-ActRIIB antibodies, and compositions and methods for making the ActRII-binding proteins. In certain aspects the ActRII-binding proteins inhibit, or antagonize ActRII activity. In addition, the disclosure provides compositions and methods for diagnosing and treating diseases and conditions associated muscle wasting; a fibrotic condition; an inflammatory, cardiovascular, pulmonary, musculoskeletal, neurologic, ocular, skeletal, autoimmune, or metabolic disease or condition; wound healing; and cancer, and other ActRII-mediated diseases and conditions.

14 Claims, 12 Drawing Sheets

Figure 1A:
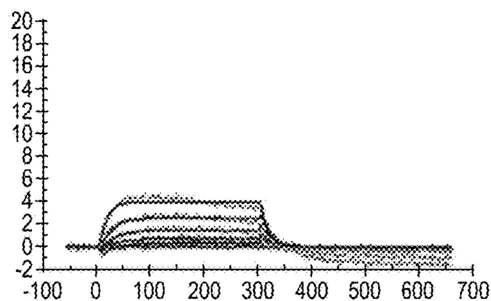
Figure 1B:
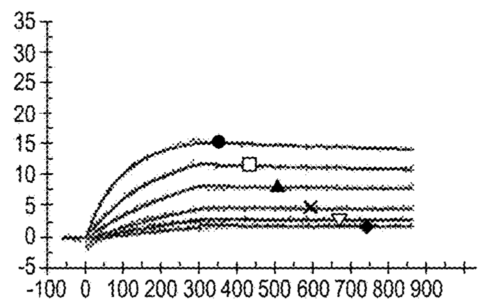
Figure 1C:
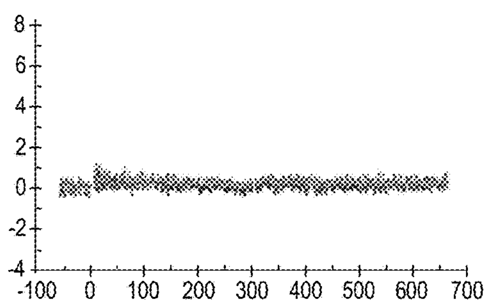

Specification includes a Sequence Listing.

(56) References Cited

U.S. PATENT DOCUMENTS

2017/0107288 A1 4/2017 Han et al.
2018/0051088 A1 2/2018 Kumar et al.

FOREIGN PATENT DOCUMENTS

CN 1326687 A 12/2001
WO WO-1997/043910 A1 11/1997
WO WO-9743910 A1 11/1997
WO WO-1999/006559 A1 2/1999
WO WO-2002/010214 A2 2/2002
WO WO-2006/012627 A2 2/2006
WO WO-2006/073493 A2 7/2006
WO WO-2007/027957 A2 3/2007
WO WO-2007/067616 A2 6/2007
WO WO-07109668 A2 9/2007
WO WO-08097541 A2 8/2008
WO WO-2008/109167 A2 9/2008
WO WO-2010/062383 A2 6/2010
WO WO-2010/125003 A1 11/2010
WO WO-2010125008 A1 11/2010
WO WO-2013/006437 A1 1/2013
WO WO-2013/063536 A1 5/2013
WO WO-2013/106175 A1 7/2013
WO WO-2013/188448 A2 12/2013
WO WO-2015/022658 A2 2/2015
WO WO-2015/162590 A1 10/2015
WO WO-2016/092439 A1 6/2016

OTHER PUBLICATIONS

Bradley et al., "Myostatin as a Theraputic Target for Musculoskeletal Disease," Cellular molecular Life Science 65:219-2124 (2008).
Brown et al., "Tolerance of Single, but not Multiple, Amino Acid Replacements in Antibody VH CDR 2: A Means of Minimizing B Cell Wastage from Somatic Hypermutation?," The Journal of Immunology, 156(9): 3285-3291 (1996).
Casset et al., "A peptide mimetic of an anti-CD4 monoclonal antibody by rational design," Biochem Biophys Res Comm, 307:198-205 (2003).
Chen et al., "Selection and analysis of an optimized anti-VEGF antibody: crystal structure of an affinity-matured fab in complex with antigen," J Mol Biol, 293:865-881 (1999).
Clackson et al., "Making antibody fragments using phage display libraries," Nature, 352:624-628 (1991).
Davies et al., "Affinity Improvement of Single Antibody VH Domains: Residues in All Three Hypervariable Regions Affect Antigen Binding," Immunotechnology, 2:169-179 (1996).
DePascalis et al., "Grafting of "Abreviated" Complementarity-Determining Regions Containing Specificity-Determining Residues Essential for Ligand Contact to Engineer a Less Immuogenic Humanized Monoclonal Antibody," Journal of Immunology, 169(6):3076-2084 (2002).
Extended European Search Report for European Patent Application No. EP 13804428.4, dated Jul. 1, 2016, 8 pages.
Fakhfakh et al., "Blocking the Myostatin Signal With a Dominant Negative Receptor Improves the Success of Human Myoblast Transplantation in Dystrophic Mice," The American Society of Gene & Cell Therapy, 19(1):204-210 (2011).
Fournier et al., "; Blockade of the Activin Receptor IIB Activates Functional Brown Adipogenesis and Thermogenesis by Inducing Mitochondrial Oxidative Metabolism," Mol Cell Biol, 32(14):2871-2879 (2012).
Funaba et al., "Expression and localization of activin receptors during endochondral bone development," Eur J Endocrinol, 144:63-71 (2001).
Funaba et al., "Immunolocalization of Type I or Type II Activin Receptors in the Rat Brain," J Neuroendocrinol, 9(2):105-111 (1997).
Giusti et al., "Somatic Diversification of S107 from an Antiphosphocholine to an Anti-DNA Autoantibody is Due to a Single Base Change in its Heavy Chain Variable Region," Proceedings of the National Academy of Sciences of the United States of America, 84:2926-2930 (1987).
Gray et al., "Cripto forms a complex with activin and type II activin receptors and can block activin signaling," PNAS, 100(9):5193-5198 (2003).
Helms, "Enablement Issues in the Examination of Antibodies," Jun. 13, 2007.
Holm et al., "Functional mapping and single chain construction of the anti-cytokeratin 8 monoclonal antibody TSI," Mol Immunol, 44(6):1075-1084 (2007).
Holt et al., "Domain Antibodies: Proteins for Therapy," Trends in Biotechnology 21(11):484-490 (2003).
Holzbaur et al., "Myostatin Inhibition Slows Muscle Atrophy in Rodent Models of Amyotrophic Lateral Sclerosis," Neurology of Disease 23(3):697-707 (2006).
International Search Report and Written Opinion for International Application No. PCT/US2011/059818 dated Mar. 5, 2012.
Jung et al., "Activin Signaling in Microsatellite Stable Colon Cancers Is Disrupted by a Combination of Genetic and Epigenetic Mechanics," Gastrology 132:633-644 (2007).
Klimka et al., "Human anti-CD30 recombinant antibodies by guided phage antibody selection using cell panning," British J Cancer, 83:252-260 (2000).
Kumar et al., "Regulation of FSHβ and GnRH receptor gene expression in activin receptor II knockout male mice." Mol Cell Endocrinol, 212(1-2):19-27 (2003).
Kussie et al., "A Single Engineered Amino Acid Substitution Changes Antibody Fine Speceficity," Journal of Immunology, 152(1):146-152 (1994).
Lee et al., "Superconductivity in the PbO-type structure α-FeSe," PNAS, 105(38):14262-14264 (2008).
Lui et al., "Fine Mapping of the Antigen-Antibody Interaction of scFv215, a Recombinant Antibody Inhibiting RNA Polymerase II from *Dropsophila melanogaster,*" Journal of Molecular Recognition, 12(103-111 (1999).
Lynch et al., "Theraputic Approaches for Muscle Wasting Disorders," Pharmacology & Theraputics 113:461-487 (2007).
MacCallum et al., "Antibody-antigen Interactions: Contact Analysis and Binding Site Topography," J Mol Bio, 262:732-745 (1996).
Mariuzza et al., Annu Revn Biophys Chem, 16:319-159 (1987).
Mathews et al., The Jounral of Biological Chemistry, 268(25):19013-19018 (1993).
Matsuzaki et al., "Regulation of Endocytosis of Activin Type II Receptors by a Novel PDZ Protein through Ral/Ral-binding Protein 1-dependent Pathway," J Biol Chem, 277:19008-19018 (2002).
Maynard et al., "Antibody Engineering," Annual Review of Biomedical Engineering 2:339-376 (2000).
Paul, W. E. (1993). Fundamental immunology (pp. 292-295). Raven Press.
PCT International Search Report and Written Opinion for PCT/US2013/045245, dated Feb. 18, 2014, 17 Pages.
Pini et al., "Human Antibodies With Subnanomolar Affinity Against a Marker of Angiogenesis Eluted from a Two-Dimensional Gel," Journal of Biological Chemistry, 273(34):21769-21776 (1998).
Portolano et al., "Lack of promiscuity in autoantigen-specific H and L chain combinations as revealed by human H and L chain "roulette"," J Immunol, 150(3):880-887 (1993).
R&D Systems Catalog No. AF339 [online], Oct. 13, 2008 [retrieved on Jun. 15, 2012]. Retrieved from the Internet<URL:http://www.rndsystems.com/pdf/af339.pdf>.
Rudikoff et al., "Single Amino Acid Substitution Altering Antigen-Binding specificity," Proc Natl Acas Sci USA, 79(6):1979-1983 (1982).
Rudikoff et al., "Somatic Diversification of Immunoglobulins," Proceedings of the National Academy of Sciences of the United States of America, 79:1979-1983 (1982).
Schildbach et al., "Contribution of a Single Heavy Chain Residue to Specificity of an Anti-Digoxin Monoclonal Antibody," Protein Science, 3(5):737-749 (1994).
Taketa et al., "Differential expression of myostatin and its receptor in the porcine anterior pituitary gland," Animal Science Journal, 79(3):382-390 (2008).

(56) References Cited

OTHER PUBLICATIONS

Vajdos et al., "Comprehensive Functional Maps of the Antigen-binding Site of an Anti-ErbB2 Antibody Obtained with Shotgun Scanning Mutagenesis," J Mol Bio, 320(2):415-428 (2002).
Walsh et al., "Myostatin: A Modulator of Skeletal-Muscle Stem Cells," Biochemical Society Transactions, 33(6):1513-1517 (2005).
Whittenmore et al., "Inhibition of Myostatin in Adult Mice Increases Skeletal Muscle Mass and Strength," Biochemical and Biophyscial Research Communications, 300:965-971 (2003).
Wiater et al., "Inhibin Is an Antagonist of Bone Morphogenetic Protein Signaling," J Bio Chem, 278:7934-7941 (2003).
Xiang et al., "Study of B72.3 Combining Sites by Molecular Modeling and Site-Directed Mutagenesis," Protein Engineering, 13(5):339-344 (2000).
Yang et al., "Extracellular Signal-Regulated Kinase 1/2 Mitogen-Activated Protein Kinase Pathway Is Involved in Myostatin-Regulated Differentiation Repression," Cancer Res, 66(3):1320-1326 (2006).
Zhou et al., "Reversal of Cancer Cachexia and Muscle Wasting by ActRIIB Antagonism Leads to Prolonged Survival" Cell, 142(4):531-543 (2010).
Zhu et al., "Activin Acutely Sensitizes Dorsal Root Ganglion Neurons and Induces Hyperalgesia via PKC-Mediated Potentiation of Transient Receptor Potential Vanilloid I," J Neurosci, 27(50):13770-13780 (2007).

ACTIVIN TYPE 2 RECEPTOR ANTIBODIES

CROSS REFERENCE TO RELATED APPLICATION

This application claims the benefit of U.S. Provisional Appl. No. 62/306,354, filed Mar. 10, 2016, which is incorporated herein by reference

REFERENCE TO SEQUENCE LISTING SUBMITTED ELECTRONICALLY

The content of the electronically submitted sequence listing in ASCII text file 3174_0030001_SeqListing.txt (Size: 177 kilobytes; and Date of Creation: Mar. 10, 2017) filed with the application is herein incorporated by reference in its entirety.

BACKGROUND

The transforming growth factor-beta (TGF-beta) family contains a variety of growth factors that are known to exert biological effects on a large variety of cell types in both vertebrates and invertebrates. Members of the TGF-beta family perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family includes proteins that are variously described as Growth and Differentiation Factors (GDFs), Bone Morphogenetic Proteins (BMPs), activins and inhibins.

TGF-beta family members transduce signals through a mechanism that includes a multistep process in which the TGF-beta family member binds a type II serine/threonine kinase receptor expressed on the cell surface, the type II receptor forms a heteromeric complex with a cognate type I receptor and activates the type I receptor through phosphorylation, the activated type-I receptor phosphorylates and activates Smad proteins that transduce the signal from the cytoplasm to the nucleus, and nuclear Smad oligomers bind to DNA and associate with transcription factors to regulate the expression of target genes.

Two related type II TGF-beta receptor family members, ActRIIB and ActRIIA, have been identified as type II receptors for activin A and activin B and other TGF-beta family members including BMP7, BMP9, BMP10, GDF1, GDF3, GDF8 (myostatin), GDF11, and Nodal (Yamashita et al., *J. Cell Biol.* 130:217-226 (1995); Lee et al., *PNAS* 98:9306-9311 (2001); Yeo et al., *Mol. Cell* 7:949-957 (2001); and Oh et al., *Genes Dev.* 16:2749-54 (2002)). ALK4 and ALK7 are the primary type I TGF-beta receptor family member receptors for activin A and activin B, respectively.

Alterations in the expression and activity of members of the TGF-beta ligand and receptor families have been proposed to be associated with a variety of disorder and conditions including muscle, bone, neurological and metabolic disorders and conditions, and cancer. It is an object of this disclosure to provide ActRII antagonists and uses for the same in the diagnosis and treatment, prevention and/or amelioration of a disease or condition associated with ActRII and/or ActRII ligands.

BRIEF SUMMARY

The disclosure provides activin receptor type II (ActRII)-binding proteins and methods of using the ActRII-binding proteins. In particular aspects, the ActRII-binding proteins are capable of inhibiting or blocking the binding of ActRII to one or more cognate ActRII ligands and/or one or more cognate ActRI receptors. In some aspects, the ActRII-binding proteins are capable of inhibiting or blocking the binding to ActRII to an ActRII ligand (e.g., activin A, activin B, GDF1, GDF3, GDF8 (myostatin), GDF11, BMP6, BMP7, BMP9, or BMP10). The disclosure also provides methods of using ActRII-binding proteins for the diagnosis, or treatment, prevention and/or amelioration of a disease or condition associated with ActRII expression and/or elevated ActRII-mediated signaling. Such diseases or conditions include, but are not limited to, muscle disorders such as degenerative muscle disease, muscular dystrophy, muscle atrophy, or muscle wasting disorders; a fibrotic condition; an inflammatory, autoimmune, cardiovascular, pulmonary, musculoskeletal, skeletal, ocular, neurologic, or metabolic disease or condition; obesity; wound healing; and cancer.

In some aspects, the ActRII-binding protein specifically binds ActRIIB. In further aspects, the provided ActRII-binding protein specifically binds ActRIIB and has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of ALK4 and/or ALK7 in cells expressing ActRIIB and ALK4 and/or ALK7 in the presence of an ActRIIB ligand (e.g., activin A and/or GDF8 (myostatin)); (c) decreases the phosphorylation of Smads (e.g., Smad2 and/or Smad3) in cells expressing ActRIIB in the presence of an ActRIIB ligand (e.g., activin A and/or GDF8); and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics. In further aspects, the ActRIIB-binding protein competes for binding to ActRIIB with an antibody having an ActRIIB-binding VH and VL pair disclosed herein. In further aspects, the ActRIIB-binding protein is an anti-ActRIIB antibody or an ActRIIB-binding antibody fragment.

In some aspects, the ActRII-binding protein specifically binds ActRIIB and ActRIIA. In further aspects, the provided ActRII-binding protein specifically binds ActRIIB and ActRIIA and has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of ALK4 and/or ALK7 in cells expressing ActRIIB and/or ActRIIA, and ALK4 and/or ALK7, in the presence of an ActRIIB and/or ActRIIA ligand (e.g., activin A and/or GDF8 (myostatin)); (c) decreases the phosphorylation of Smads (e.g., Smad2 and/or Smad3) in cells expressing ActRIIB and/or ActRIIA in the presence of an ActRIIB and/or ActRIIA ligand (e.g., activin A and/or GDF8); and (d) binds to ActRIIB with a $K_D$ of ≤1 nM and ≥1 pM (e.g., as determined by BIACORE® analysis). In some aspects, the ActRIIB- and ActRIIA-binding protein has 2, 3, or 4 of the above characteristics. In some aspects, the ActRIIB- and ActRIIA-binding protein has at least 2 or at least 3 of the above characteristics. In further aspects, the ActRIIB-binding protein competes for binding to ActRIIB and ActRIIA with an antibody having an ActRIIB- and ActRIIA binding VH and VL pair disclosed herein. In further aspects, the ActRIIB- and ActRIIA-binding protein is an anti-ActRIIB and ActRIIB antibody or an ActRIIB- and ActRIIB binding antibody fragment.

In some aspects, the ActRII-binding protein specifically binds ActRIIA. In further aspects, the provided ActRII-binding protein specifically binds ActRIIA and has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIA; (b) decreases the phosphorylation of ALK4 and/or ALK7 in cells expressing ActRIIA and ALK4 and/or ALK7 in the presence of an ActRIIA ligand (e.g., activin A and/or GDF8 (myostatin)); (c) decreases the phosphorylation of Smads (e.g., Smad2 and/or Smad3) in cells expressing ActRIIA in the presence of an ActRIIA ligand (e.g., activin A and/or GDF8); and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics. In further aspects, the ActRIIA-binding protein competes for binding to ActRIIA with an antibody having an ActRIIA-binding VH and VL pair disclosed herein. In further aspects, the ActRIIA-binding protein is an anti-ActRIIA antibody or an ActRIIA-binding antibody fragment.

In some aspects, the ActRII-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3, wherein the CDRs are present in a heavy chain variable region (VH) and a light chain variable region (VL) pair disclosed in Table 1. In some aspects, the ActRII-binding protein comprises a set of CDRs present in a VH and a VL pair selected from the group consisting of: (a) a VH sequence of SEQ ID NO:2, 16, 22, 28, 34, or 40, and a VL sequence of SEQ ID NO:9, and wherein the protein binds ActRIIB, (b) a VH sequence of SEQ ID NO:63 or 77, and a VL having the amino acid sequence of SEQ ID NO:70, and wherein the protein binds ActRIIB; (c) a VH sequence of SEQ ID NO:45 or 57, and a VL sequence of SEQ ID NO:50, and wherein the protein binds ActRIIB; (d) a VH sequence of SEQ ID NO:84, 98, 105, 112, or 119, and a VL sequence of SEQ ID NO:91, and wherein the protein binds and ActRIIB and activin receptor type IIA (ActRIIA), and (e) a VH sequence of SEQ ID NO:125, and a VL sequence of SEQ ID NO:132, and wherein the protein binds ActRIIA.

In some aspects, the ActRII-binding protein comprises a set of CDRs present in a VH having the amino acid sequence of SEQ ID NO:144 and a VL having the amino acid sequence of SEQ ID NO:151, and wherein the protein binds ActRIIB.

In some aspects, the ActRII-binding protein comprises a set of CDRs present in a VH having the amino acid sequence of SEQ ID NO:165 and a VL having the amino acid sequence of SEQ ID NO:172, and wherein the protein binds ActRIIA and ActRIIB.

In additional aspects, the ActRII-binding protein specifically binds ActRII and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 has the amino acid sequence of SEQ ID NO:3, 17, 23, 29, 35 or 41; (ii) VH-CDR2 has the amino acid sequence of SEQ ID NO:4, 18, 24, 30, or 36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:64 or 78; (ii) VH-CDR2 has the amino acid sequence of SEQ ID NO:65 or 79; (iii) VH-CDR3 has the amino acid sequence of SEQ ID NO:66 or 80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (c)(i) VH-CDR1 has the amino acid sequence of SEQ ID NO:3 or 58; (ii) VH-CDR2 has the amino acid sequence of SEQ ID NO:4 or 59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (d)(i) VH-CDR1 has the amino acid sequence of SEQ ID NO:85, 99, 106, or 113; (ii) VH-CDR2 has the amino acid sequence of SEQ ID NO:86, 100, 107, 114, or 120; (iii) VH-CDR3 has the amino acid sequence of SEQ ID NO:87, 101, 108, 115, or 121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (e)(i) VH-CDR1 has the amino acid sequence of SEQ ID NO:126; (ii) VH-CDR2 has the amino acid sequence of SEQ ID NO:127; (iii) VH-CDR3 has the amino acid sequence of SEQ ID NO:128; (iv) VL-CDR1 has the amino acid sequence of SEQ ID NO:133; (v) VL-CDR2 has the amino acid sequence of SEQ ID NO:134; and (vi) VL-CDR3 has the amino acid sequence of SEQ ID NO:135; and wherein the protein binds ActRIIA.

In additional aspects, the ActRII-binding protein specifically binds ActRIIB and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which (i) VH-CDR1 has the amino acid sequence of SEQ ID NO:145; (ii) VH-CDR2 has the amino acid sequence of SEQ ID NO:146; (iii) VH-CDR3 has the amino acid sequence of SEQ ID NO:147; (iv) VL-CDR1 has the amino acid sequence of SEQ ID NO:152; (v) VL-CDR2 has the amino acid sequence of SEQ ID NO:153; and (vi) VL-CDR3 has the amino acid sequence of SEQ ID NO:154.

In additional aspects, the ActRII-binding protein specifically binds Act IIRA and ActRIIB and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which (i) VH-CDR1 has the amino acid sequence of SEQ ID NO:166; (ii) VH-CDR2 has the amino acid sequence of SEQ ID NO:167; (iii) VH-CDR3 has the amino acid sequence of SEQ ID NO:168; (iv) VL-CDR1 has the amino acid sequence of SEQ ID NO:173; (v) VL-CDR2 has the amino acid sequence of SEQ ID NO:174; and (vi) VL-CDR3 has the amino acid sequence of SEQ ID NO:175.

In some aspects, the ActRII-binding protein specifically binds ActRII and comprises a set of CDRs in which: (a)(i) VH-CDR1 has the amino acid sequence of SEQ ID NO:3, 17, 23, 29, 35 or 41; (ii) VH-CDR2 has the amino acid sequence of SEQ ID NO:4, 18, 24, 30, or 36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:64 or 78; (ii) VH-CDR2 has the amino acid sequence of SEQ ID NO:65 or 79; (iii) VH-CDR3 has the amino acid sequence of SEQ ID NO:66 or 80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (c)(i) VH-CDR1 has the amino acid sequence of SEQ ID NO:3 or 58; (ii) VH-CDR2 has the amino acid sequence of SEQ ID NO:4 or 59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (d)(i) VH-CDR1 has the amino acid sequence of SEQ ID NO:85, 99, 106, or 113; (ii) VH-CDR2 has the amino acid sequence of SEQ ID NO:86, 100, 107, 114, or 120; (iii) VH-CDR3 has the amino acid sequence of SEQ ID NO:87, 101, 108, 115, or 121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (e)(i) VH-CDR1 has the amino acid sequence of SEQ ID NO:126; (ii) VH-CDR2 has the amino acid sequence of SEQ ID NO:127; (iii) VH-CDR3 has the amino acid sequence of SEQ ID NO:128; (iv) VL-CDR1 has the amino acid sequence of SEQ ID NO:133; (v) VL-CDR2 has the amino acid sequence of SEQ ID NO:134; and (vi) VL-CDR3 has the amino acid sequence of SEQ ID NO:135; and wherein the protein binds ActRIIA.

In some aspects, the ActRII-binding protein specifically binds ActRIIB and comprises a set of CDRs in which (i) VH-CDR1 has the amino acid sequence of SEQ ID NO:145; (ii) VH-CDR2 has the amino acid sequence of SEQ ID NO:146; (iii) VH-CDR3 has the amino acid sequence of SEQ ID NO:147; (iv) VL-CDR1 has the amino acid sequence of SEQ ID NO:152; (v) VL-CDR2 has the amino acid sequence of SEQ ID NO:153; and (vi) VL-CDR3 has the amino acid sequence of SEQ ID NO:154.

In some aspects, the ActRII-binding protein specifically binds ActIIRA and ActRIIB and comprises a set of CDRs in which (i) VH-CDR1 has the amino acid sequence of SEQ ID NO:166; (ii) VH-CDR2 has the amino acid sequence of SEQ ID NO:167; (iii) VH-CDR3 has the amino acid sequence of SEQ ID NO:168; (iv) VL-CDR1 has the amino acid sequence of SEQ ID NO:173; (v) VL-CDR2 has the amino acid sequence of SEQ ID NO:174; and (vi) VL-CDR3 has the amino acid sequence of SEQ ID NO:175.

In some aspects, the ActRII-binding protein specifically binds ActRII and comprises a set of CDRs that has a total of one, two, three, four, five, six, seven, eight, nine, ten, fewer than ten, or zero, amino acid substitutions, deletions, and/or insertions from a reference set of CDRs in which: (a)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:17; (ii) VH-CDR2 has the amino acid sequence of SEQ ID NO:18; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (c)(i) VH-CDR1 has the amino acid sequence of SEQ ID NO:23; (ii) VH-CDR2 has the amino acid sequence of SEQ ID NO:24; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (d)(i) VH-CDR1 has the amino acid sequence of SEQ ID NO:29; (ii) VH-CDR2 has the amino acid sequence of SEQ ID NO:30; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (e)(i) VH-CDR1 has the amino acid sequence of SEQ ID NO:35; (ii) VH-CDR2 has the amino acid sequence of SEQ ID NO:36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (f)(i) VH-CDR1 has the amino acid sequence of SEQ ID NO:41; (ii) VH-CDR2 has the amino acid sequence of SEQ ID NO:18; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (g)(i) VH-CDR1 has the amino acid sequence of SEQ ID NO:64; (ii) VH-CDR2 has the amino acid sequence of SEQ ID NO:65; (iii) VH-CDR3 has the amino acid sequence of SEQ ID NO:66 or 80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; and (h)(i) VH-CDR1 has the amino acid sequence of SEQ ID NO:78; (ii) VH-CDR2 has the amino acid sequence of SEQ ID NO:79; (iii) VH-CDR3 has the amino acid sequence of SEQ ID NO:80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (i)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (j)(i) VH-CDR1 has the amino acid sequence of SEQ ID NO:58; (ii) VH-CDR2 has the amino acid sequence of SEQ ID NO:59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (k)(i) VH-CDR1 has the amino acid sequence of SEQ ID NO:85; (ii) VH-CDR2 has the amino acid sequence of SEQ ID NO:86; (iii) VH-CDR3 has the amino acid sequence of SEQ ID NO:87; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (l)(i) VH-CDR1 has the amino acid sequence of SEQ ID NO:99; (ii) VH-CDR2 has the amino acid sequence of SEQ ID NO:100; (iii) VH-CDR3 has the amino acid sequence of SEQ ID NO:101; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (m)(i) VH-CDR1 has the amino acid sequence of SEQ ID NO:106; (ii) VH-CDR2 has the amino acid sequence of SEQ ID NO:107, (iii) VH-CDR3 has the amino acid sequence of SEQ ID NO 108; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (n)(i) VH-CDR1 has the amino acid sequence of SEQ ID NO:113; (ii) VH-CDR2 has the amino acid sequence of SEQ ID NO:114; (iii) VH-CDR3 has the amino acid sequence of SEQ ID NO:115; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (o)(i) VH-CDR1 has the amino acid sequence of SEQ ID NO:113; (ii) VH-CDR2 has the amino acid sequence of SEQ ID NO:120; (iii) VH-CDR3 has the amino acid sequence of SEQ ID NO:121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (p)(i) VH-CDR1 has the amino acid sequence of SEQ ID NO:126; (ii) VH-CDR2 has the amino acid sequence of SEQ ID NO:127; (iii) VH-CDR3 has the amino acid sequence of SEQ ID NO:128; (iv) VL-CDR1 has the amino acid sequence of SEQ ID NO:133; (v) VL-CDR2 has the amino acid sequence of SEQ ID NO:134; and (vi) VL-CDR3 has the amino acid sequence of SEQ ID NO:135; and wherein the protein binds ActRIIA.

In some aspects, the ActRII-binding protein specifically binds ActRIIB and comprises a set of CDRs that has a total of one, two, three, four, five, six, seven, eight, nine, ten, fewer than ten, or zero, amino acid substitutions, deletions, and/or insertions from a reference set of CDRs in which (i) VH-CDR1 has the amino acid sequence of SEQ ID NO:145; (ii) VH-CDR2 has the amino acid sequence of SEQ ID NO:146; (iii) VH-CDR3 has the amino acid sequence of SEQ ID NO:147; (iv) VL-CDR1 has the amino acid sequence of SEQ ID NO:152; (v) VL-CDR2 has the amino acid sequence of SEQ ID NO:153; and (vi) VL-CDR3 has the amino acid sequence of SEQ ID NO:154.

In some aspects, the ActRII-binding protein specifically binds ActIIRA and ActRIIB and comprises a set of CDRs that has a total of one, two, three, four, five, six, seven, eight, nine, ten, fewer than ten, or zero, amino acid substitutions, deletions, and/or insertions from a reference set of CDRs in which (i) VH-CDR1 has the amino acid sequence of SEQ ID NO:166; (ii) VH-CDR2 has the amino acid sequence of SEQ ID NO:167; (iii) VH-CDR3 has the amino acid sequence of SEQ ID NO:168; (iv) VL-CDR1 has the amino acid sequence of SEQ ID NO:173; (v) VL-CDR2 has the amino acid sequence of SEQ ID NO:174; and (vi) VL-CDR3 has the amino acid sequence of SEQ ID NO:175.

In some aspects, the ActRII-binding protein specifically binds ActRII and comprises a VH and a VL pair selected from the group consisting of: (a)(i) a VH having at least 90%, 95%, 97%, 98%, or 99% sequence identity to SEQ ID NO:2, 16, 22, 28, 34, or 40, and (ii) a VL having at least 90%, 95%, 97%, 98%, or 99% sequence identity to SEQ ID NO:9, and wherein the protein binds ActRIIB; (b)(i) a VH having at least 90%, 95%, 97%, 98%, or 99% sequence identity to SEQ ID NO:45 or 57, and (ii) a VL having at least 90%, 95%, 97%, 98%, or 99% sequence identity to SEQ ID NO:50, and wherein the protein binds ActRIIB; (c)(i) a VH having at least 90%, 95%, 97%, 98%, or 99% sequence identity to SEQ ID NO:63 or 77, and (ii) a VL having at least 90%, 95%, 97%, 98%, or 99% sequence identity to SEQ ID NO:70, and wherein the protein binds ActRIIB; (d)(i) a VH having the amino acid sequence of SEQ ID NO:84, 98, 105, 112, or 119, and (ii) a VL having the amino acid sequence of SEQ ID NO:91, and wherein the protein binds ActRIIB and ActRIIA; and (e)(i) a VH having at least 90%, 95%, 97%, 98%, or 99% sequence identity to SEQ ID NO:125, and (ii) a VL having at least 90%, 95%, 97%, 98%, or 99% sequence identity to SEQ ID NO:132, and wherein the protein binds ActRIIA.

In some aspects, the ActRII-binding protein specifically binds ActRIIB and comprises a VH having at least 90%, 95%, 97%, 98%, or 99% sequence identity to SEQ ID NO:144, and a VL having at least 90%, 95%, 97%, 98%, or 99% sequence identity to SEQ ID NO:151.

In some aspects, the ActRII-binding protein specifically binds ActIIRA and ActRIIB and comprises a VH having at least 90%, 95%, 97%, 98%, or 99% sequence identity to SEQ ID NO:165, and a VL having at least 90%, 95%, 97%, 98%, or 99% sequence identity to SEQ ID NO:172.

In a further aspect, the ActRII-binding protein comprises a VH and a VL pair selected from the group consisting of: (a) a VH sequence of SEQ ID NO:2, 16, 22, 28, 34, or 40, and a VL sequence of SEQ ID NO:9; and wherein the protein binds ActRIIB; (b) a VH sequence of SEQ ID NO:45 or 57, and a VL sequence of SEQ ID NO:50; and wherein the protein binds ActRIIB; (c) a VH sequence of SEQ ID NO:63 or 77, and a VL sequence of SEQ ID NO:70; and wherein the protein binds ActRIIB; (d) a VH sequence of SEQ ID NO:84, 98, 105, 112, or 119, and a VL sequence of SEQ ID NO:91; and wherein the protein binds ActRIIB and ActRIIA; and (e) a VH sequence of SEQ ID NO:125, and a VL sequence of SEQ ID NO:132 and wherein the protein binds ActRIIA.

In additional aspects an ActRII-binding protein competes for binding to ActRII with an antibody comprising a VH and a VL sequence pair disclosed herein. In some aspects, an ActRII-binding protein binds to the same epitope as an ActRII-binding protein disclosed herein.

In some aspects, the ActRII-binding protein binds a polypeptide selected from the group consisting of: (a) amino acid residues NANWELERT (SEQ ID NO:157) of ActRIIB; (b) amino acid residues CCEGNFCNER (SEQ ID NO:159) of ActRIIB; (c) amino acid residues CCEGNMCNEK (SEQ ID NO:161) of ActRIIA; and (d) amino acid residues ECLFFNANWEKD (SEQ ID NO:162) of ActRIIA.

In a further aspect, the ActRII-binding protein comprises a VH sequence of SEQ ID NO:144, and a VL sequence of SEQ ID NO:151; and the protein binds ActRIIB.

In a further aspect, the ActRII-binding protein comprises a VH sequence of SEQ ID NO:165, and a VL sequence of SEQ ID NO:172; and the protein binds ActIIRA and ActRIIB.

In a further aspect, the ActRII-binding protein comprises a VH and a VL pair selected from the group consisting of: (a) a VH sequence of SEQ ID NO:2 and a VL sequence of SEQ ID NO:9; (b) a VH sequence of SEQ ID NO:16 and a VL sequence of SEQ ID NO:9; (c) a VH sequence of SEQ ID NO:22 and a VL sequence of SEQ ID NO:9; (d) a VH sequence of SEQ ID NO:28 and a VL sequence of SEQ ID NO:9; (e) a VH sequence of SEQ ID NO:34 and a VL sequence of SEQ ID NO:9; (f) a VH sequence of SEQ ID NO:40 and a VL sequence of SEQ ID NO:9; (g) a VH sequence of SEQ ID NO:45 and a VL sequence of SEQ ID NO:50; (h) a VH sequence of SEQ ID NO:57 and a VL sequence of SEQ ID NO:50; (i) a VH sequence of SEQ ID NO:63 and a VL sequence of SEQ ID NO:70; (j) a VH sequence of SEQ ID NO:77 and a VL sequence of SEQ ID NO:70; (k) a VH sequence of SEQ ID NO:84 and a VL sequence of SEQ ID NO:91; (l) a VH sequence of SEQ ID NO:98 and a VL sequence of SEQ ID NO:91; (m) a VH sequence of SEQ ID NO:105 and a VL sequence of SEQ ID NO:91; (n) a VH sequence of SEQ ID NO:112 and a VL sequence of SEQ ID NO:91; (o) VH sequence of SEQ ID NO:119 and a VL sequence of SEQ ID NO:91; and (p) VH sequence of SEQ ID NO:125 and a VL sequence of SEQ ID NO:132. In a further aspect, the ActRII-binding protein comprises a VH having a sequence of SEQ ID NO:144 and a VL having a sequence of SEQ ID NO:151. In a further aspect, the ActRII-binding protein comprises a VH having a sequence of SEQ ID NO:165 and a VL having a sequence of SEQ ID NO:172.

In some aspects, the ActRII-binding protein comprises a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:2, 16, 22, 28, 34, or 40, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:9, and wherein the protein binds ActRIIB; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:45 or 57, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:50, and wherein the protein binds ActRIIB; (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:63 or 77, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:70, and wherein the protein binds ActRIIB; (d)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:84, 98, 105, 112, or 119, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:91, and wherein the protein binds ActRIIB and ActRIIA; (e)(i) a VH sequence having a total of one, two, three, four, five, six, seven, eight, nine, ten, fewer than fifteen, or zero, amino acid substitutions, deletions, and/or insertions from a reference VH sequence of SEQ ID NO:125, and (ii) a VL sequence having a total of one, two, three, four, five, six, seven, eight, nine, ten, fewer than fifteen, or zero, amino acid substitutions, deletions, and/or insertions from a reference VL of SEQ ID NO:132, and wherein the protein binds ActRIIA.

In some aspects, the ActRII-binding protein comprises a VH sequence having a total of one, two, three, four, five, six, seven, eight, nine, ten, fewer than fifteen, or zero, amino acid substitutions, deletions, and/or insertions from a reference VH sequence of SEQ ID NO:144, and a VL sequence having a total of one, two, three, four, five, six, seven, eight, nine, ten, fewer than fifteen, or zero, amino acid substitutions, deletions, and/or insertions from a reference VL sequence of SEQ ID NO:151, and the protein binds ActRIIB.

In some aspects, the ActRII-binding protein comprises a VH sequence having a total of one, two, three, four, five, six, seven, eight, nine, ten, fewer than fifteen, or zero, amino acid substitutions, deletions, and/or insertions from a reference VH sequence of SEQ ID NO:165, and a VL sequence having a total of one, two, three, four, five, six, seven, eight, nine, ten, fewer than fifteen, or zero, amino acid substitutions, deletions, and/or insertions from a reference VL sequence of SEQ ID NO:172, and the protein binds ActIIRA and ActRIIB.

In a further aspect, the ActRII-binding protein comprises a VH and a VL pair wherein: (a) the VH sequence has a total of one, two, three, four, five, six, seven, eight, nine, ten, fewer than fifteen, or zero, amino acid substitutions, deletions, and/or insertions from a reference VH sequence of SEQ ID NO:2; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (b) the VH sequence has a total of one, two, three, four, five, six, seven, eight, nine, ten, fewer than fifteen, or zero, amino acid substitutions, deletions, and/or insertions from a reference VH sequence of SEQ ID NO:16; the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (c) the VH sequence has a total of one, two, three, four, five, six, seven, eight, nine, ten, fewer than fifteen, or zero, amino acid substitutions, deletions, and/or insertions from a reference VH sequence of SEQ ID NO:22; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (d) the VH sequence has a total of one, two, three, four, five, six, seven, eight, nine, ten, fewer than fifteen, or zero, amino acid substitutions, deletions, and/or insertions from a reference VH sequence of SEQ ID NO:28; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (e) the VH sequence has a total of one, two, three, four, five, six, seven, eight, nine, ten, fewer than fifteen, or zero, amino acid substitutions, deletions, and/or insertions from a reference VH sequence of SEQ ID NO:34; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (f) the VH sequence has a total of one, two, three, four, five, six, seven, eight, nine, ten, fewer than fifteen, or zero, amino acid substitutions, deletions, and/or insertions from a reference VH sequence of SEQ ID NO:40; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (g) the sequence has a total of one, two, three, four, five, six, seven, eight, nine, ten, fewer than fifteen, or zero, amino acid substitutions, deletions, and/or insertions from a reference VH sequence of SEQ ID NO:45; and the VL sequence has a total of one, two, three, four, five, six, seven, eight, nine, ten, fewer than fifteen, or zero, amino acid substitutions, deletions, and/or insertions from a reference VL sequence of SEQ ID NO:50; wherein the protein binds ActRIIB; (h) the VH sequence has a total of one, two, three, four, five, six, seven, eight, nine, ten, fewer than fifteen, or zero, amino acid substitutions, deletions, and/or insertions from a reference VH sequence of SEQ ID NO:57; and the VL sequence has a total of one, two, three, four, five, six, seven, eight, nine, ten, fewer than fifteen, or zero, amino acid substitutions, deletions, and/or insertions from a reference VL sequence of SEQ ID NO:50; wherein the protein binds ActRIIB; (i) the VH sequence has a total of one, two, three, four, five, six, seven, eight, nine, ten, fewer than fifteen, or zero, amino acid substitutions, deletions, and/or insertions from a reference VH sequence of SEQ ID NO:63; and the VL sequence has a total of one, two, three, four, five, six, seven, eight, nine, ten, fewer than fifteen, or zero, amino acid substitutions, deletions, and/or insertions from a reference VL sequence of SEQ ID NO:70; and wherein the protein binds ActRIIB; (j) the VH sequence has a total of one, two, three, four, five, six, seven, eight, nine, ten, fewer than fifteen, or zero, amino acid substitutions, deletions, and/or insertions from a reference VH sequence of SEQ ID NO:77; and the VL sequence has a total of one, two, three, four, five, six, seven, eight, nine, ten, fewer than fifteen, or zero, amino acid substitutions, deletions, and/or insertions from a reference VL sequence of SEQ ID NO:70; and wherein the protein binds ActRIIB; (k) the sequence has a total of one, two, three, four, five, six, seven, eight, nine, ten, fewer than fifteen, or zero, amino acid substitutions, deletions, and/or insertions from a reference VH sequence of SEQ ID NO:84; and the VL sequence has a total of one, two, three, four, five, six, seven, eight, nine, ten, fewer than fifteen, or zero, amino acid substitutions, deletions, and/or insertions from a reference VL sequence of SEQ ID NO:91; wherein the protein binds ActRIIB and ActRIIA; (l) the VH sequence has a total of one, two, three, four, five, six, seven, eight, nine, ten, fewer than fifteen, or zero, amino acid substitutions, deletions, and/or insertions from a reference VH sequence of SEQ ID NO:98; and the VL sequence has a total of one, two, three, four, five, six, seven, eight, nine, ten, fewer than fifteen, or zero, amino acid substitutions, deletions, and/or insertions from a reference VL sequence of SEQ ID NO:91; wherein the protein binds ActRIIB and ActRIIA; (m) the VH sequence has a total of one, two, three, four, five, six, seven, eight, nine, ten, fewer than fifteen, or zero, amino acid substitutions, deletions, and/or insertions from a reference VH sequence of SEQ ID NO:105; and the VL sequence has a total of one, two, three, four, five, six, seven, eight, nine, ten, fewer than fifteen, or zero, amino acid substitutions, deletions, and/or insertions from a reference VL sequence of SEQ ID NO:91; and wherein the protein binds ActRIIB and ActRIIA; (n) the VH sequence has a total of one, two, three, four, five, six, seven, eight, nine, ten, fewer than fifteen, or zero, amino acid substitutions, deletions, and/or insertions from a reference VH sequence of SEQ ID NO:112; and the VL sequence has a total of one, two, three, four, five, six, seven, eight, nine, ten, fewer than fifteen, or zero, amino acid substitutions, deletions, and/or insertions from a reference VL sequence of SEQ ID NO:91; and wherein the protein binds ActRIIB and ActRIIA; (o) the VH sequence has a total of one, two, three, four, five, six, seven, eight, nine, ten, fewer than fifteen, or zero, amino acid substitutions, deletions, and/or insertions from a reference VH sequence of SEQ ID NO:119; and the VL sequence has a total of one, two, three, four, five, six, seven, eight, nine, ten, fewer than fifteen, or zero, amino acid substitutions, deletions, and/or insertions from a reference VL sequence of SEQ ID NO:91; and wherein the protein binds ActRIIB and ActRIIA; or (p) the VH sequence has a total of one, two, three, four, five, six, seven, eight, nine, ten, fewer than fifteen, or zero, amino acid substitutions, deletions, and/or insertions from a reference VH sequence of SEQ ID NO:125; and the VL sequence has a total of one, two, three, four, five, six, seven, eight, nine, ten, fewer than fifteen, or zero, amino acid substitutions, deletions, and/or insertions from a reference VL sequence of SEQ ID NO:132; and wherein the protein binds ActRIIA.

In a further aspect, the ActRII-binding protein comprises a VH and a VL pair, wherein the VH sequence has a total of one, two, three, four, five, six, seven, eight, nine, ten, fewer than fifteen, or zero, amino acid substitutions, deletions, and/or insertions from a reference VH sequence of SEQ ID NO:144, and the VL sequence has a total of one, two, three, four, five, six, seven, eight, nine, ten, fewer than fifteen, or zero, amino acid substitutions, deletions, and/or insertions from a reference VL sequence of SEQ ID NO:151; and wherein the protein binds ActRIIB.

In a further aspect, the ActRII-binding protein comprises a VH and a VL pair, wherein the VH sequence has a total of one, two, three, four, five, six, seven, eight, nine, ten, fewer than fifteen, or zero, amino acid substitutions, deletions, and/or insertions from a reference VH sequence of SEQ ID NO:165, and the VL sequence has a total of one, two, three, four, five, six, seven, eight, nine, ten, fewer than fifteen, or zero, amino acid substitutions, deletions, and/or insertions from a reference VL sequence of SEQ ID NO:172; and wherein the protein binds ActRIIA and ActRIIB.

In some aspects, the ActRII-binding protein is an antibody that specifically binds ActRII. In additional aspects, the antibody is a monoclonal antibody, a recombinant antibody, a human antibody, a humanized antibody, a chimeric antibody, a bi-specific antibody, or a multi-specific antibody. Some aspects, the ActRII-binding protein is the ActRII-binding antibody fragment. In some aspects the antibody is an antibody fragment selected from the group consisting of a Fab, Fab', $F(ab')_2$, Fv, diabody, DART, and a single chain antibody molecule (e.g., a BiTE).

Nucleic acids and sets of nucleic acids encoding ActRII-binding proteins are also provided. Vectors and sets of vectors containing the nucleic acids and sets of nucleic acids, and host cells transformed with the nucleic acids and vectors are further provided. In some aspects, the host cell is a hybridoma or mammalian host cell such as, a NS0 murine myeloma cell, a PER.C6® human cell, or a Chinese hamster ovary (CHO) cell. Host cells including mammalian host cells and hybridomas that produce ActRII-binding proteins are also provided.

Methods for making an ActRII-binding protein are also provided. In some aspects, the method comprises culturing a host cell capable of expressing the ActRII-binding protein under suitable conditions for expressing the protein and optionally isolating the expressed ActRII-binding protein. ActRII-binding proteins prepared and/or isolated using methods disclosed herein or otherwise known in the art are also provided.

Pharmaceutical compositions comprising an ActRII-binding protein and a pharmaceutically acceptable carrier are further provided. In some aspects, the disclosure provides methods for treating and/or ameliorating a condition in a subject associated with elevated ActRII expression or ActRII-mediated signaling. In some aspects, the methods decrease ActRII-mediated signaling in the subject. Also provided is the use of an ActRII-binding protein provided herein (e.g., an anti-ActRIIB- and/or ActRIIA-binding antibody), in the manufacture or preparation of a medicament. In some embodiments, the medicament is for the treatment and/or amelioration of a condition in a subject associated with elevated ActRII expression or ActRII-mediated signaling. In an additional embodiment the disclosure provides the use of an ActRII-binding protein as provided herein in the manufacture of a medicament for the treatment of a disease or condition described herein.

Conditions that may be treated and/or ameliorated in a subject using the provided methods include, but are not limited to: muscle disorders such as degenerative muscle disease, muscular dystrophy, muscle atrophy, or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes insulin resistance, hyperglycemia, and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease such as osteoporosis; neurologic disease; neuromuscular disease, degenerative disease, wound healing; weight loss; and cancer (e.g., a carcinoma, myeloma, a bone-loss inducing cancer, pituitary cancer, and gastrointestinal cancer).

In some aspects, the disclosed methods include administering a pharmaceutical composition comprising an effective amount of an ActRII-binding protein to a subject in need thereof. In some aspects, the ActRII-binding protein is administered alone. In other aspects, the ActRII-binding protein is administered as a combination therapy. In further aspects, the ActRII-binding protein is administered as a combination therapy to the standard of care treatment/therapy.

Methods of blocking or reducing ActRII activity (e.g., ligand binding and/or signaling) are also provided. In some aspects the method comprises contacting an ActRII-binding protein and a cell that expresses the ActRII. In some instances the method comprises contacting an ActRII-binding protein and a cell that expresses the ActRII in the presence of an ActRII ligand (e.g., activin A). In some aspects, the method is performed in vivo. In other aspects, the method is performed in vitro. In some aspects the blocked or reduced ActRII activity is the phosphorylation of ActRI. In further aspects, the phosphorylated ActRI is ALK4 and/or ALK7. In additional aspects the blocked or reduced ActRII activity is the phosphorylation of Smads (e.g., Smad2 and/or Smad3). In some aspects, the disclosure provides a method of blocking or reducing ActRII activity in a subject that comprise administering an effective amount of an ActRII-binding protein to a subject in need thereof. In some aspects a method of reducing ActRIIA activity in a subject is provided that comprises administering an effective amount of an ActRIIA-binding protein to a subject in need thereof. In some aspects a method of reducing ActRIIB activity in a subject is provided that comprises administering an effective amount of an ActRIIB-binding protein to a subject in need thereof.

Also provided is a method of blocking or reducing ActRII activity in a pathological condition associated with increased ActRII expression and/or ActRII signaling, or in a pathological condition that can be treated and/or ameliorated by reducing or inhibiting the activity of an ActRII-ligand. In some instances, the method comprises administering an ActRII-binding protein to a subject having increased expression of ActRII or an ActRII-ligand. In some aspects the pathological condition is a muscle disorder. In further aspects, the muscle disorder is wasting or muscular dystrophy. In some aspects the pathological condition is a metabolic condition such as obesity or type II diabetes. In some aspects the pathological condition is a fibrotic condition of the lung, or liver. In additional aspects the pathological condition is a cancer. In further aspects, the cancer is myelofibrosis, myeloma (e.g., multiple myeloma), pituitary cancer, breast cancer, gastrointestinal cancer, or a carcinoma. In additional aspects the pathological condition is a bone-loss inducing cancer (e.g., prostate and breast cancer). In some aspects, the disclosure provides a method of blocking or reducing ActRII activity in a pathological condition associated with cancer treatment induced bone loss.

In some aspects, the disclosure provides a method of treating and/or ameliorating a muscle disorder. In some instances, the method comprises administering an ActRII-binding protein (e.g., an anti-ActRII antibody) to a subject having a muscle disorder. Further provided is use of an ActRII-binding protein as provided herein in the manufacture of a medicament for the treatment or amelioration of a muscle disorder. In further aspects the muscle disorder is wasting or muscular dystrophy. In other aspects, the subject is at risk of developing a muscle disorder. In further aspects the subject is at risk of developing wasting or muscular dystrophy.

In some aspects, the disclosure provides a method of treating and/or ameliorating a fibrotic condition. In some instances, the method comprises administering an ActRII-binding protein (e.g., in a pharmaceutical composition described herein) to a subject having a fibrotic condition. In other aspects, the subject is at risk of developing a fibrotic condition. In some aspects the fibrotic condition is chronic. Further provided is use of an ActRII-binding protein as provided herein in the manufacture of a medicament for the treatment or amelioration of a fibrotic condition.

In some aspects, the disclosure provides a method of decreasing fibrosis in a subject. In some instances, the method comprises administering an ActRII-binding protein (e.g., an anti-ActRII antibody such as a full-length ActRII-antibody or an ActRII-binding antibody fragment, and variants and derivatives thereof) to a subject having a fibrosis. In some aspects, the fibrosis is a hepatic or pulmonary fibrosis. Further provided is use of an ActRII-binding protein as provided herein in the manufacture of a medicament for the treatment or amelioration of fibrosis.

In another aspect, the disclosure provides a method of reducing the loss of hepatic or pulmonary function caused by fibrosis in a subject. In some aspects, the method comprises administering an ActRII-binding protein (e.g., an anti-ActRII antibody such as a full-length ActRII-antibody and an ActRII-binding fragment thereof) to a subject in need thereof In some aspects the method reduces the loss of hepatic function in a subject. In some aspects the method reduces the loss of pulmonary function in a subject.

BRIEF DESCRIPTION OF THE DRAWINGS/FIGURES

Figure 1D:
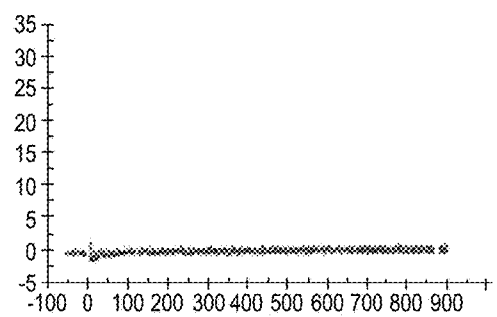
Figure 1E:
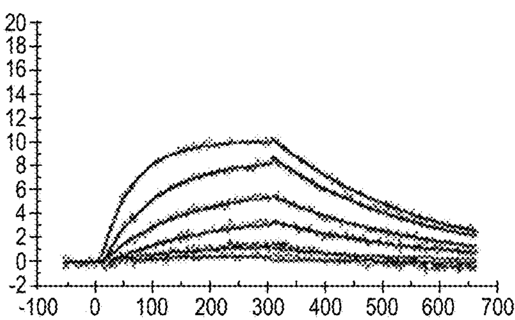
Figure 1F:
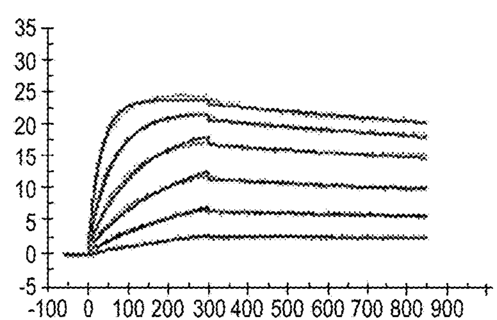
Figure 1G:
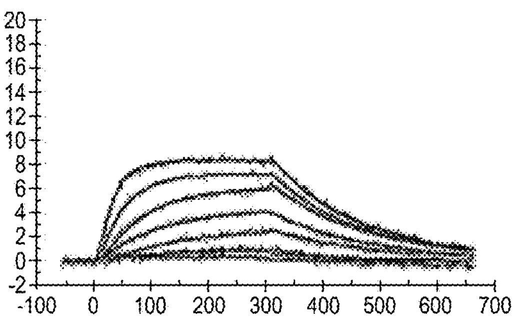
Figure 1H:
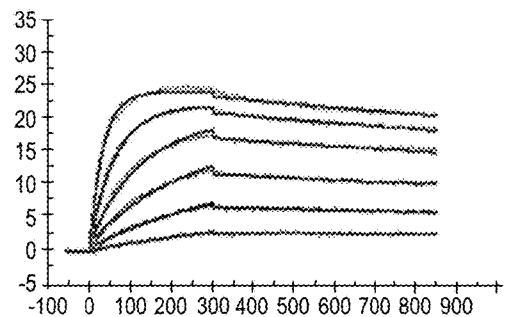
Figure 1I:
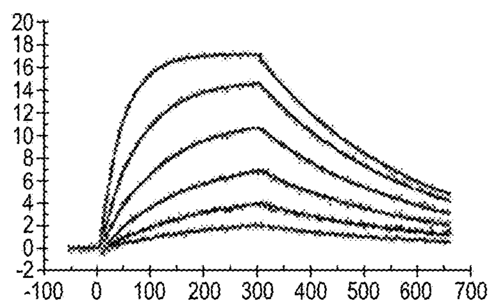
Figure 1J:
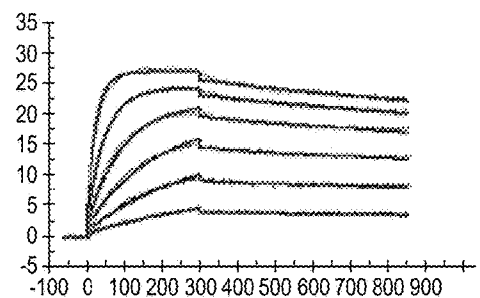
Figure 1K:
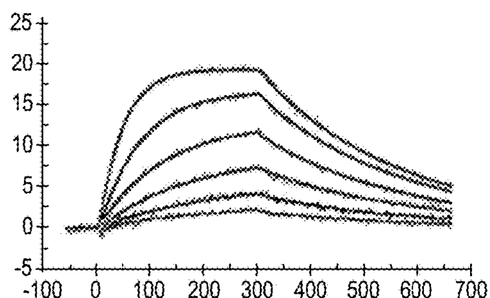
Figure 1L:
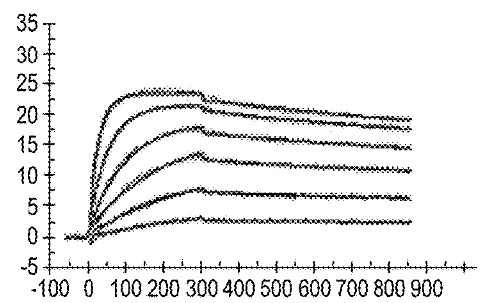
Figure 1M:
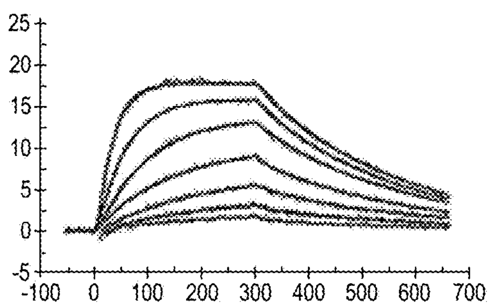
Figure 1N:
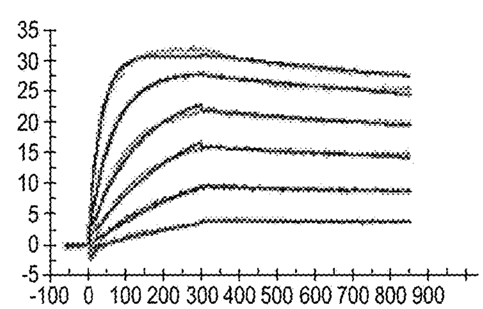

FIGS. 1A-1N depict kinetic characterization of A01 lineage antibodies binding to hActRIIB and hActRIIA as determined by BIACORE®-based analysis at 37° C. Monomeric or dimeric hActRIIB or hActRIIA was captured on a chip and then exposed to concentrations of A01 lineage antibodies. FIGS. 1A-1D depict characterization of antibody A01 (parent) binding to ActRIIB monomer (FIG. 1A), ActRIIB dimer (FIG. 1B), ActRIIA monomer (FIG. 1C), and ActRIIA dimer (FIG. 1D). FIGS. 1E and 1F depict characterization of antibody B01 binding to ActRIIB monomer (FIG. 1E) and ActRIIB dimer (FIG. 1F). FIGS. 1G-1H depict antibody C01 binding to ActRIIB monomer (FIG. 1G) and ActRIIB dimer (FIG. 1H). FIGS. 1I-1J depict antibody D01 binding to ActRIIB monomer (FIG. 1I) and ActRIIB dimer (FIG. 1J). FIGS. 1K-1L depict antibody E01 binding to ActRIIB monomer (FIG. 1K) and ActRIIB dimer (FIG. 1L). FIGS. 1M-1N depict antibody F01 binding to ActRIIB monomer (FIG. 1M) and ActRIIB dimer (FIG. 1N).

Figure 2:
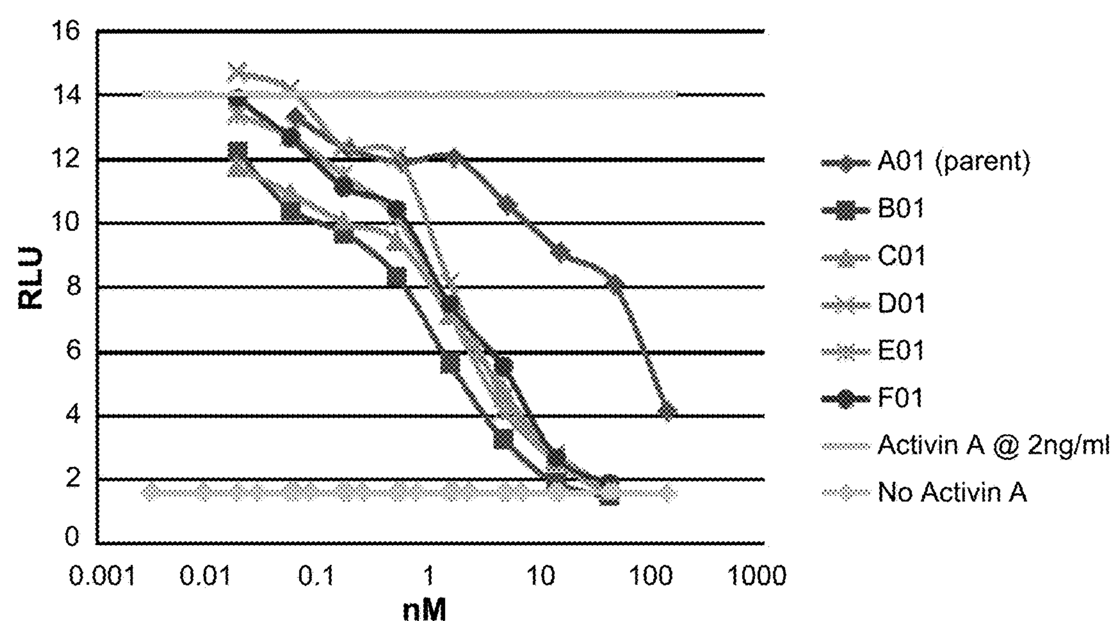

FIG. 2 depicts neutralizing activity of A01 lineage antibodies in a cell-based reporter gene assay. Included are assay responses with activin A alone (2 ng/ml), and activin A, combined with 50 ng/ml of A01 lineage antibodies A01, B01, C01, D01, E01, and F01.

Figure 3A:
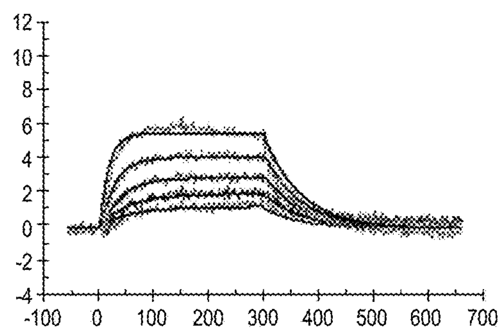
Figure 3B:
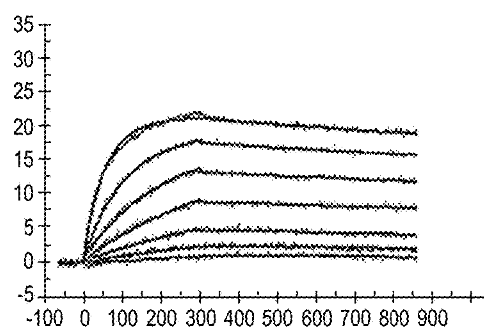
Figure 3C:
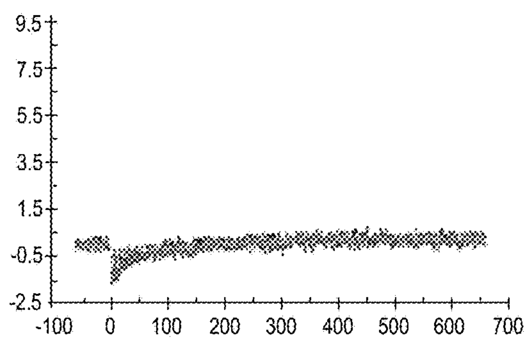
Figure 3D:
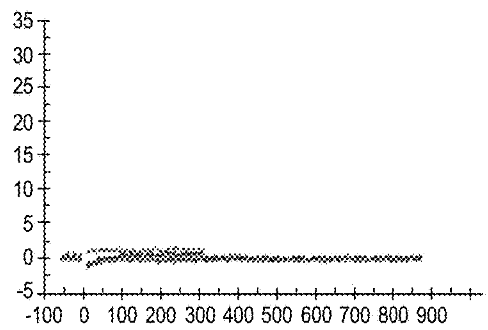
Figure 3E:
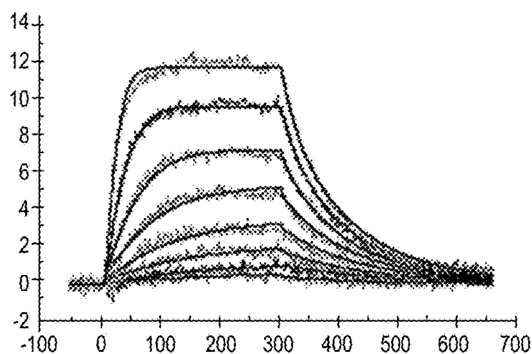
Figure 3F:
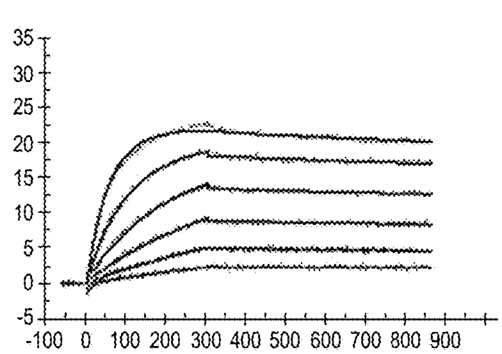

FIGS. 3A-3F depict kinetic characterization of G02 lineage antibodies binding to hActRIIB and hActRIIA as determined by BIACORE®-based analysis at 37° C. Monomeric or dimeric hActRIIB or hActRIIA was captured on a chip and then exposed G01 lineage. FIGS. 3A-3D depict characterization of antibody G01 binding to ActRIIB monomer (FIG. 3A), ActRIIB dimer (FIG. 3B), ActRIIA monomer (FIG. 3C), and ActRIIA dimer (FIG. 3D). FIGS. 1E and 1F depict characterization of antibody H01 binding to ActRIIB monomer (FIG. 3E) and ActRIIB dimer (FIG. 3F).

Figure 4:
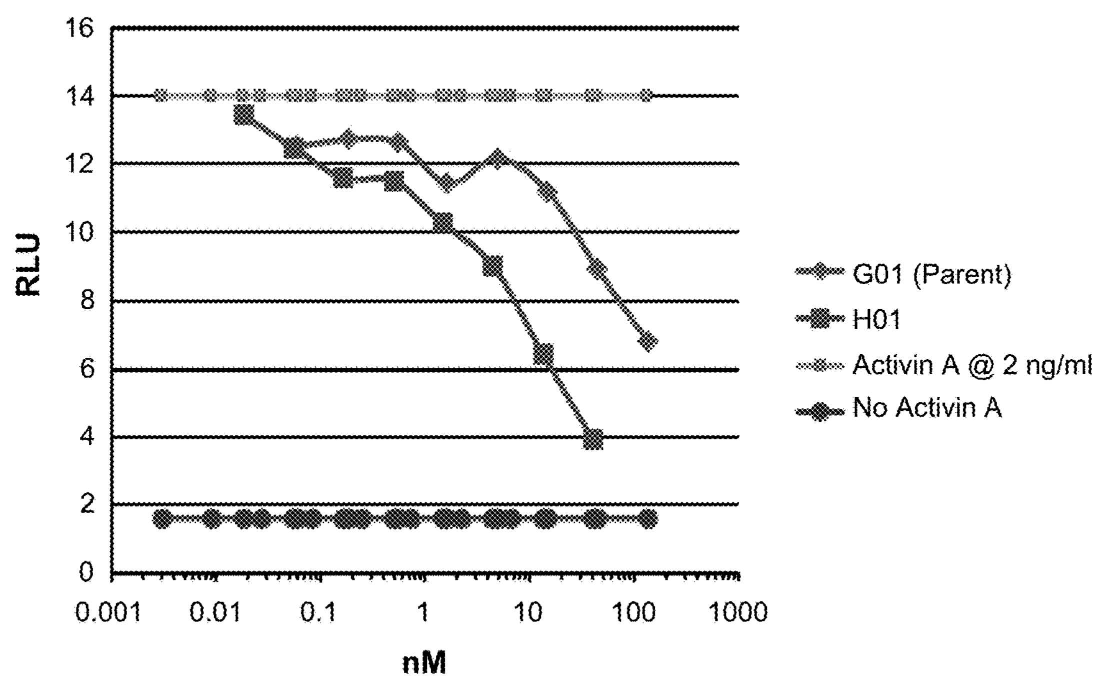

FIG. 4 depicts neutralizing activity of G01 parent and H01 optimized antibodies in a cell-based reporter gene assay. Included are assay responses in the absence of activin A, with activin A alone (2 ng/ml), and activin A, combined with 50 ng/ml of G01 lineage antibodies G01 or H01.

Figure 5A:
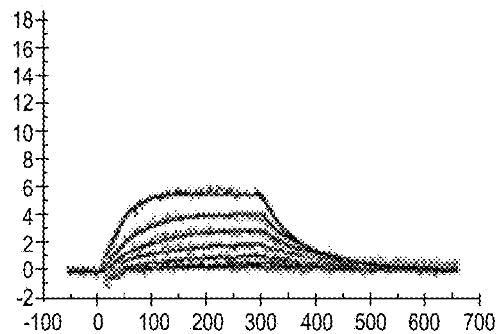
Figure 5B:
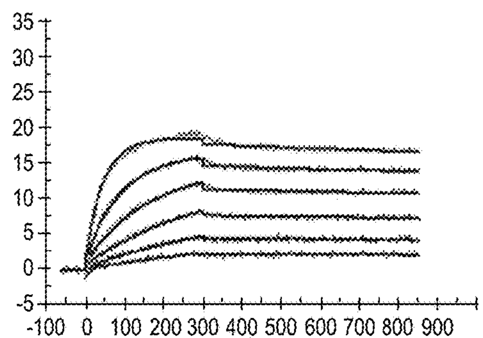
Figure 5C:
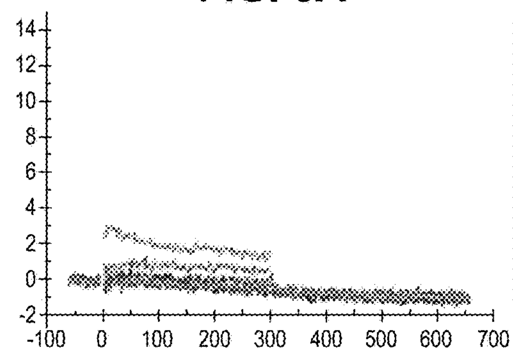
Figure 5D:
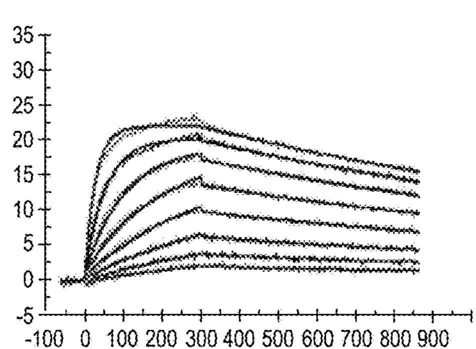
Figure 5E:
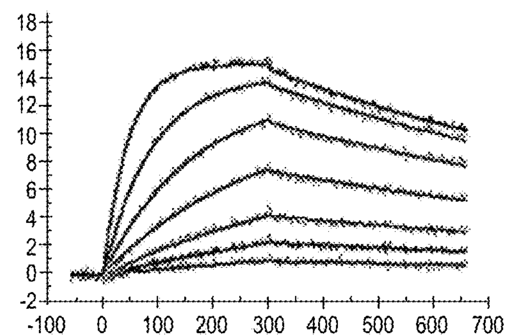
Figure 5F:
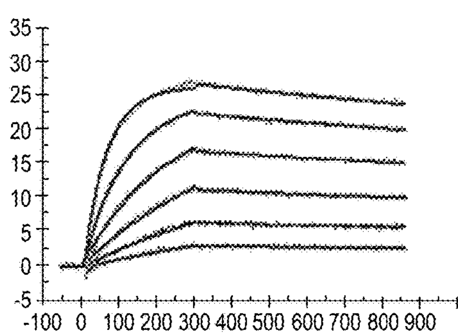
Figure 5G:
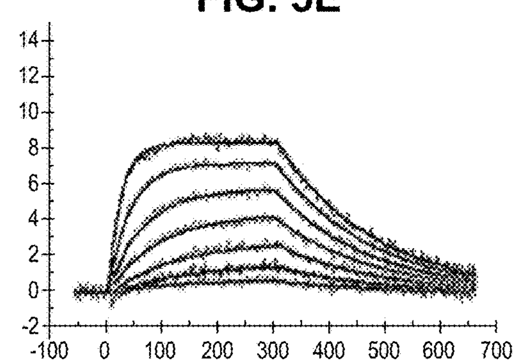
Figure 5H:
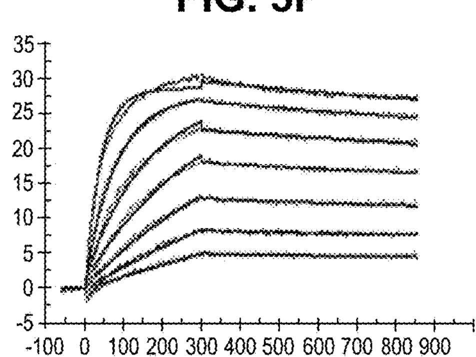
Figure 5I:
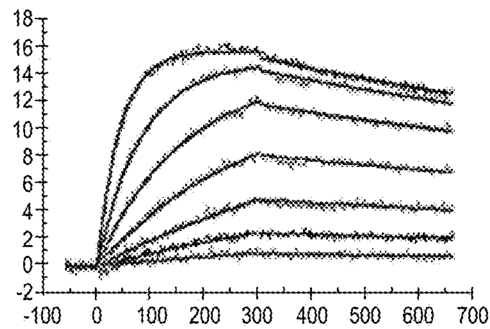
Figure 5J:
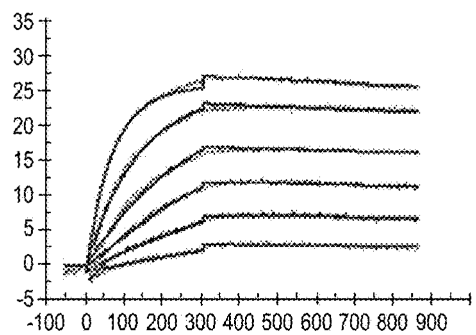
Figure 5K:
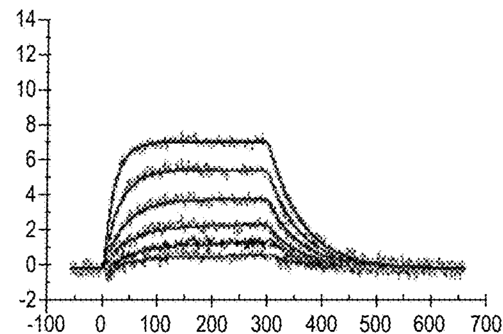
Figure 5L:
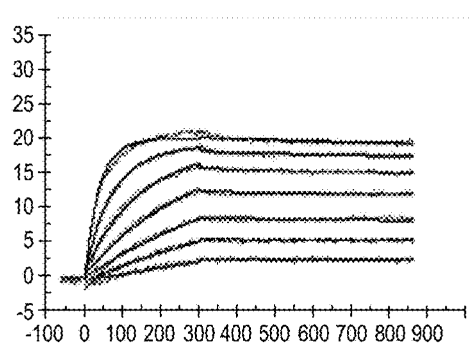
Figure 5M:
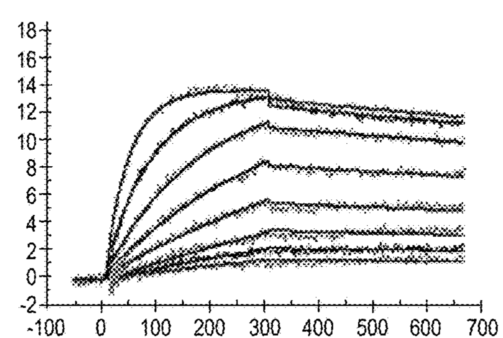
Figure 5N:
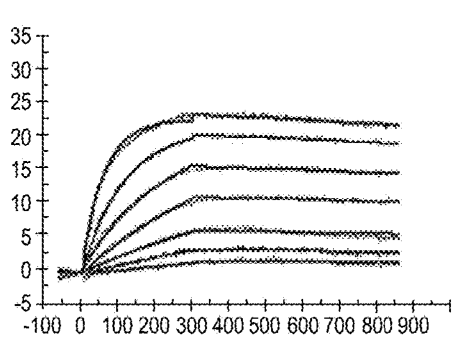
Figure 5O:
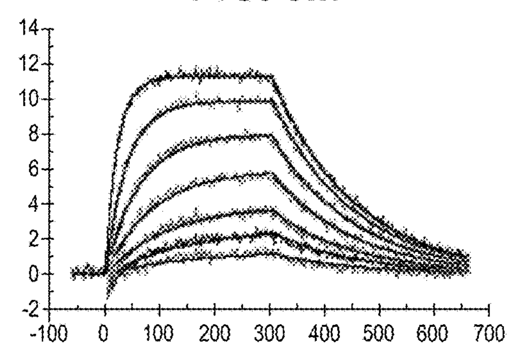
Figure 5P:
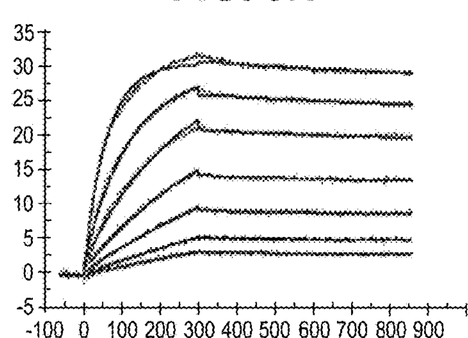
Figure 5Q:
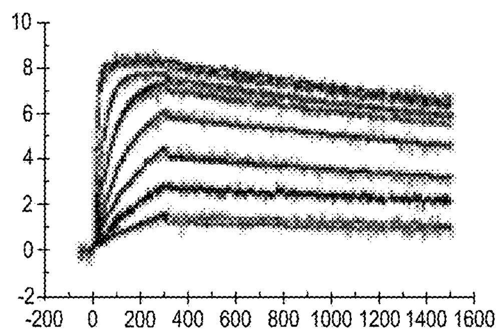
Figure 5R:
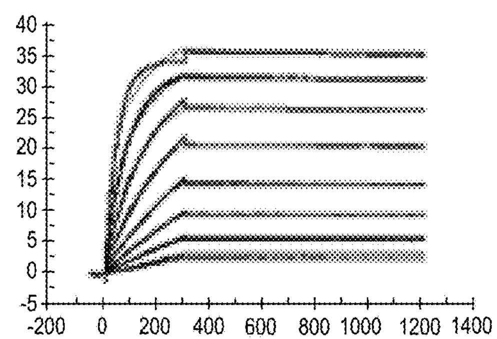
Figure 5S:
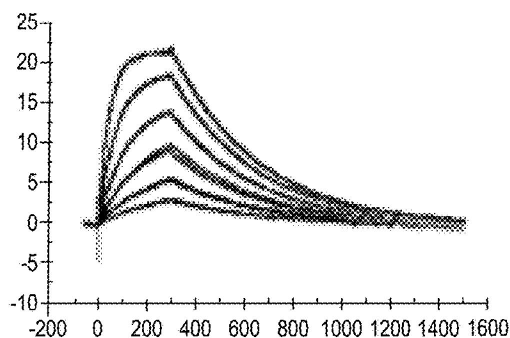
Figure 5T:
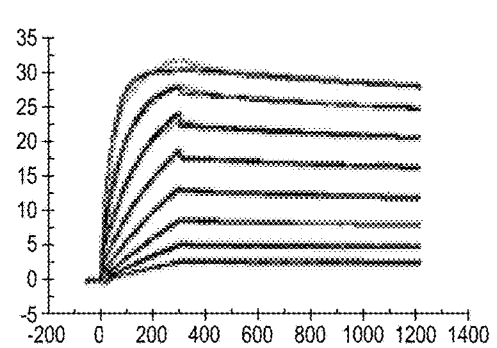

FIGS. 5A-5P depict kinetic characterization of A02 lineage antibodies binding to hActRIIB and hActRIIA as determined by BIACORE®-based analysis at 37° C. Monomeric or dimeric hActRIIB or hActRIIA was captured on a chip with and then exposed to A02 lineage antibodies. FIGS. 5A-5D depict characterization of antibody A02 (parent) binding to ActRIIB monomer (FIG. 5A), ActRIIB dimer (FIG. 5B), ActRIIA monomer (FIG. 5C), and ActRIIA dimer (FIG. 5D). FIGS. 5E-5H depict characterization of antibody B02 binding to ActRIIB monomer (FIG. 5E), ActRIIB dimer (FIG. 5F), ActRIIA monomer (FIG. 5G), and ActRIIA dimer (FIG. 5H). FIGS. 5I-5L depict characterization of antibody C02 binding to ActRIIB monomer (FIG. 5I), ActRIIB dimer (FIG. 5J), ActRIIA monomer (FIG. 5K), and ActRIIA dimer (FIG. 5L). FIGS. 5M-5P depict characterization of antibody D02 binding to ActRIIB monomer (FIG. 5M), ActRIIB dimer (FIG. 5N), ActRIIA monomer (FIG. 5O), and ActRIIA dimer (FIG. 5P). FIGS. 5Q-5T depict characterization of antibody D03 binding to ActRIIB monomer (FIG. 5Q), ActRIIB dimer (FIG. 5R), ActRIIA monomer (FIG. 5S), and ActRIIA dimer (FIG. 5T).

Figure 6A:
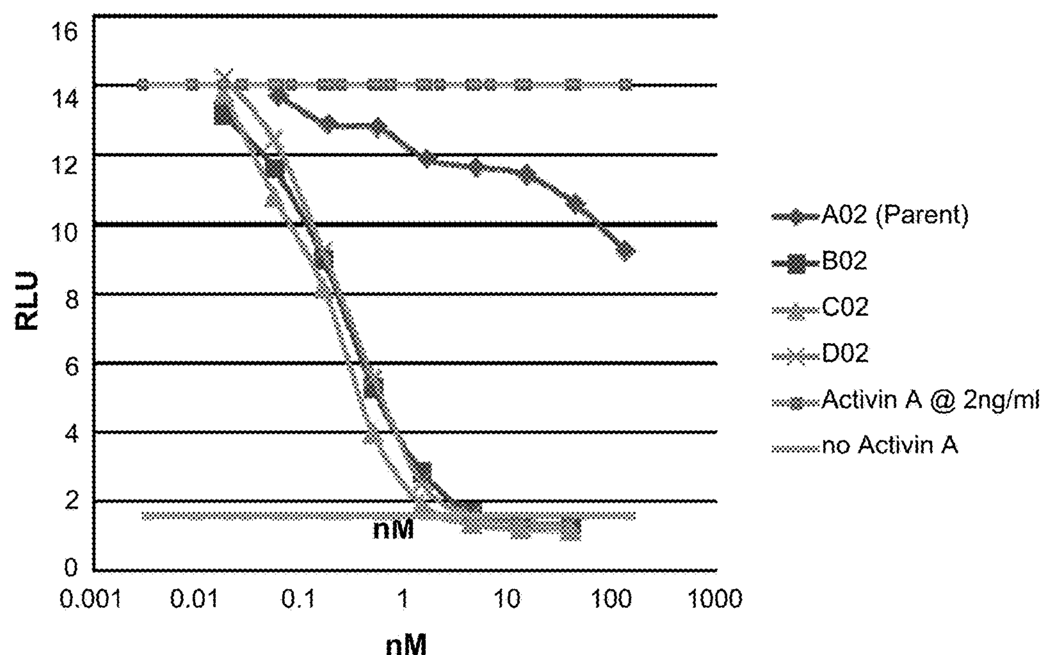
Figure 6B:
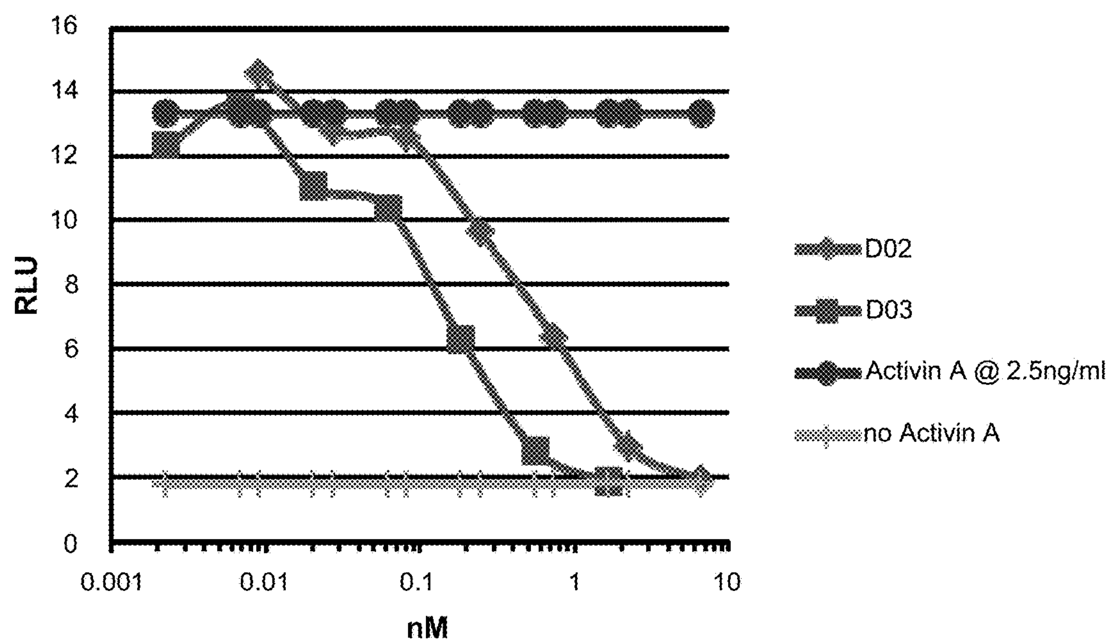

FIGS. 6A-6B depict neutralizing activity of A02 lineage antibodies in a cell-based reporter gene assay. Included are assay responses in the absence of activin A, with activin A alone (2 ng/ml), and activin A, combined with 50 ng/ml of A02 lineage antibodies. FIG. 6A depicts neutralizing activity of A02 (parent), B02, C02, and D02. FIG. 6B depicts neutralizing activity of D02 and D03.

Figure 7A:
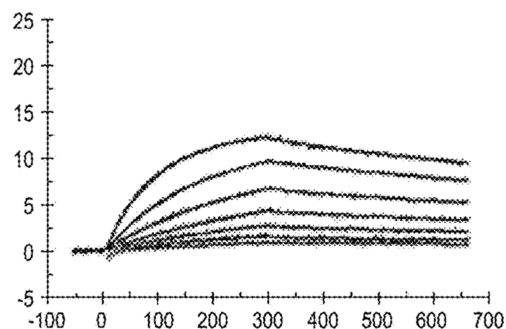
Figure 7B:
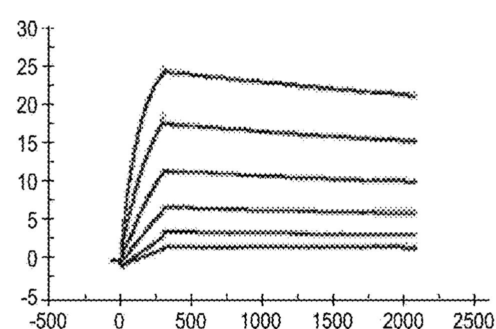
Figure 7C:
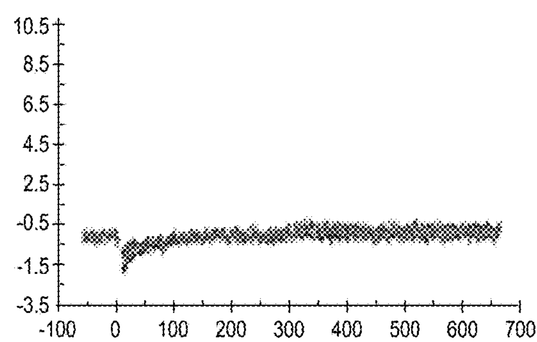
Figure 7D:
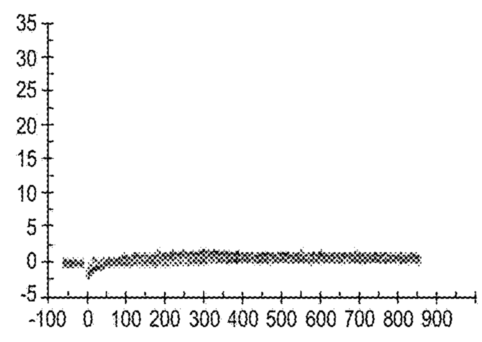
Figure 7E:
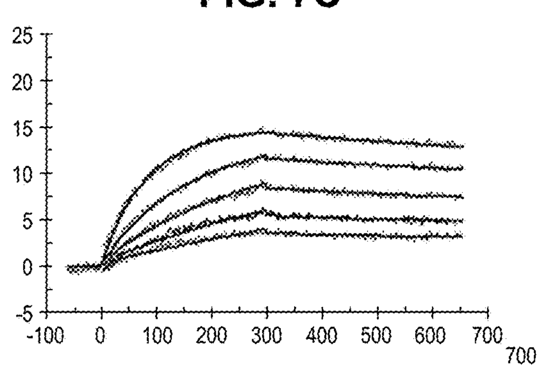
Figure 7F:
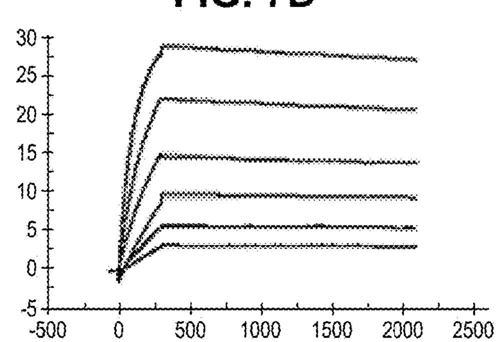

FIGS. 7A-7F depict kinetic characterization of E02 parent and F02 variant antibody binding to hActRIIB and hActRIIA as determined by BIACORE®-based analysis at 37° C. Monomeric or dimeric hActRIIB or hActRIIA was captured on a chip and then exposed to E02 and F02. FIGS. 7A-7D depict characterization of E02 parent binding to ActRIIB monomer (FIG. 7A), ActRIIB dimer (FIG. 7B), ActRIIA monomer (FIG. 7C), and ActRIIA dimer (FIG. 7D). FIGS. 7E AND 7F depict characterization of antibody F02 binding to ActRIIB monomer (FIG. 7E), and ActRIIB dimer (FIG. 7F).

Figure 8A:
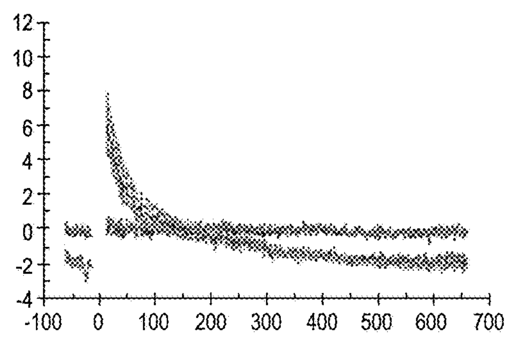
Figure 8B:
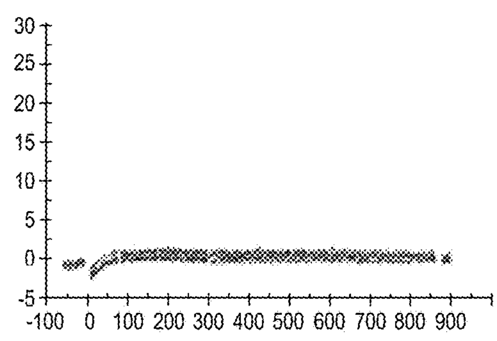
Figure 8C:
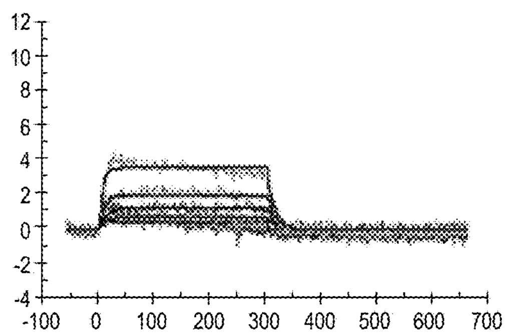
Figure 8D:
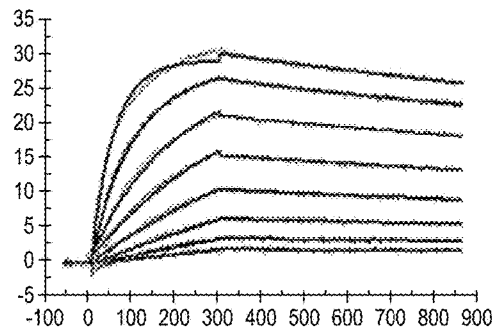

FIGS. 8A-8D depict kinetic characterization of antibody G02 binding to hActRIIB and hActRIIA as determined by BIACORE®-based analysis at 37° C. Monomeric or dimeric hActRIIB or hActRIIA was captured on a chip with and then exposed to the evaluated anti-hActRII antibodies. FIGS. 8A-8D depict characterization of antibody G02 binding to ActRIIB monomer (FIG. 8A), ActRIIB dimer (FIG. 8B), ActRIIA monomer (FIG. 8C), and ActRIIA dimer (FIG. 8D).

Figure 9:
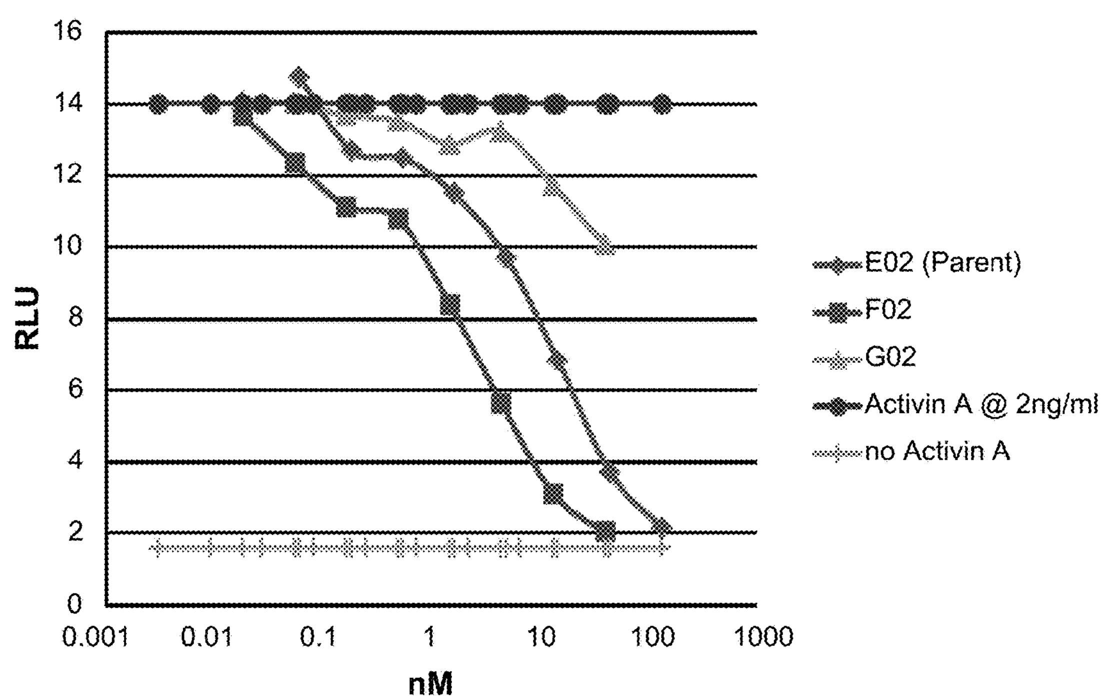

FIG. 9 depicts neutralizing activity of ActRIIB-binding E02 parent and F02 variant antibodies and ActRIIA-binding antibody G02 in a cell-based reporter gene assay. Included are assay responses in the absence of activin A, with activin A alone (2 ng/ml), and activin A, combined with 50 ng/ml of antibody E02, F02, or G02.

DETAILED DESCRIPTION

The disclosure provides isolated recombinant ActRII-binding proteins. In certain aspects the ActRII-binding proteins specifically bind ActRIIB and/or ActRIIA. In further aspects, the ActRII-binding proteins are anti-ActRII antibodies. Nucleic acids encoding the ActRII-binding proteins, vectors and host cells containing the nucleic acids, and methods of making and using the ActRII-binding proteins are also provided. The provided ActRII-binding proteins have uses in diagnosing, treating, and/or ameliorating diseases and conditions associated with increased ActRII expression and/or signaling. Such uses include but are not limited to, preventing, and/or ameliorating muscle disorders such as degenerative muscle disease muscular dystrophy, muscle atrophy or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease, neurologic disease, such as osteoporosis; wound healing; weight loss; and cancer (e.g., a carcinoma, myeloma, a bone-loss inducing cancer, pituitary cancer, and gastrointestinal cancer).

Definitions

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure. The headings provided herein are not limitations of the various aspects which can be had by reference to the specification as a whole. Moreover, the terms defined immediately below are more fully defined by reference to the specification in its entirety.

The terms "a," "an" and "the" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "comprise" is generally used in the sense of include, that is to say permitting the presence of one or more features or components. Wherever aspects are described herein with the language "comprising," otherwise analogous aspects described in terms of "consisting of," and/or "consisting essentially of" are also provided.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges are inclusive of the numbers defining the range.

An ActRII-binding protein refers to a protein that specifically binds to ActRII (i.e., ActRIIB and/or ActRIIA), preferrably binding to the extracellular domain of ActRII.

The terms "ActRII activin receptor type II, and "ActRII" are used interchangeably and refer to the activin receptor type IIA (ActRIIA) and/or activin receptor type IIB (ActRIIB) unless the context in which the term is used clearly dictates otherwise.

The terms "activin receptor type IIA," "ActRIIA receptor," and "ActRIIA" are used interchangeably herein, and refer to ActRIIA (also referred to as ACVR2A, ActRIIA, ActRII, and EC 2.7.11.30 in the literature). Reference sequence for human ActRIIA is provided in RefSeq NO:NP_001607.1. The provided ActRIIA-binding proteins bind the extracellular domain of ActRIIA corresponding to the amino acid sequence of SEQ ID NO:138.

The terms "activin receptor type IIB," "ActRIIB receptor," and "ActRIIB" are used interchangeably and refer to ActRIIB (also referred to as ACVR2B, ActRIIB, HTX4, ErbB3 receptor, and EC 2.7.11.30 in the literature). Reference sequence for human ActRIIB is provided in NCBI Reference Sequence NP_001097. The provided ActRIIB-binding proteins bind the extracellular domain of ActRIIB corresponding to the amino acid sequence of SEQ ID NO:139.

The term "compete" or "competes" when used in the context of ActRII-binding proteins (e.g., neutralizing antibodies) means competition between antigen binding proteins as determined by an assay in which the antigen binding protein (e.g., an anti-ActRII antibody or an ActRII-binding fragment thereof) under test prevents or inhibits specific binding of a reference antigen binding protein (e.g., a ligand, or a reference antibody) to a common antigen (e.g., an ActRIIA or ActRIIB extracellular domain or a fragment thereof). Numerous types of competitive binding assays can be used, for example: solid phase direct or indirect radioimmunoassay (RIA) (see, e.g., Moldenhauer et al., *Scand. J. Immunol.* 32:77-82 (1990) and Morel et al., *Molec. Immunol.* 25:7-15 (1988)), solid phase direct or indirect enzyme immunoassay (EIA), solid phase direct biotin-avidin EIA (see, e.g., Cheung, et al., *Virology* 176:546-552 (1990) and Kirkland et al., *J. Immunol.* 137:3614-3619 (1986)) and a sandwich competition assay (see, e.g., Stahli et al., *Methods in Enzymology* 92:242-253 (1983)). Typically, such an assay involves the use of purified antigen bound to a solid surface or cells bearing either of these, an unlabeled test antigen binding protein and a labeled reference antigen binding protein.

Competitive inhibition can be measured by determining the amount of label bound to the solid surface or cells in the presence of the test antigen binding protein. Usually the test antigen binding protein is present in excess. Antigen binding proteins identified by competition assay (competing antigen binding proteins) include ActRII-binding proteins that bind to the same epitope as the reference ActRII-binding protein as well as ActRII-binding proteins that bind to an adjacent epitope sufficiently proximal to the epitope bound by the reference ActRII-binding protein for steric hindrance to occur. Usually, when a competing ActRII (e.g., ActRIIA or ActRIIB) binding protein is present in excess, it will inhibit specific binding of a reference ActRII-binding protein ActRII (e.g., ActRIIA or ActRIIB) by at least 40%, 45%, 50%, 55%, 60%, 65%, 70% or 75%. In some instance, a competing antigen binding protein inhibits specific binding of a reference ActRII-binding protein by at least 80%, 85%, 90%, 91%, 92%, 93%, 94%, 95%, 96%, 97% 98%, or 99%.

The term "epitope" when used in context of an ActRII protein refers to an ActRII (e.g., human ActRIIA, human ActRIIB, murine ActRIIA or murine ActRIIA) protein determinant capable of binding to an ActRII-binding protein (e.g., an antibody) of the disclosure. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. The ActRII epitope bound by an ActRII-binding protein can readily be determined using techniques known in the art.

Antigen binding proteins such as the anti-ActRII-binding antibodies and ActRII-binding fragments, variants, or derivatives thereof disclosed herein, can be described or specified in terms of the epitope(s) or portion(s) of an antigen, e.g., a target polypeptide that they recognize or specifically bind. For example, the portion of ActRII that specifically interacts with the antigen binding domain of an ActRII-binding protein disclosed herein is an "epitope." Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. Epitope determinants may include chemically active surface groupings of molecules such as amino acids, sugar side chains, phosphoryl or sulfonyl groups, and may have specific three dimensional structural characteristics, and/or specific charge characteristics. An epitope typically includes at least 3, 4, 5, 6, 3, 4, 5, 6, 7, 8, 9, 10, 11, 12, 13, 14, 15, 16, 17, 18, 19, 20, 25, 30, 35 amino acids in a unique spatial conformation. Epitopes can routinely be determined using methods known in the art.

The terms "inhibit," "block," "reduce," "decrease," "suppress," "antagonize," and "neutralize" are used interchangeably and refer to any statistically significant decrease in activity (e.g., ActRII ligand binding and ActRII signaling), including full blocking of the activity. For example, "inhibition" or "suppression" can refer to a decrease of about 10%, 20%, 30%, 40%, 50%, 60%, 70%, 80%, 90% or 100% in activity compared to a control.

In some aspects, the term "decrease" may refer to the ability of an ActRII-binding protein such as an antibody or ActRII-binding fragment thereof, to statistically significantly (e.g., with a p value less than or equal to 0.05) decrease the phosphorylation of one or more Smads (e.g., Smad2 and/or Smad3) induced by contacting a cell expressing ActRII and a type I receptor with an ActRII ligand such as activin A, relative to the extent of Smad phosphorylation in the cell when not contacted with the ActRII-binding protein. The cell which expresses ActRII (e.g., ActRIIB and/or ActRIIA) can be a naturally occurring cell or a cell line, or can be recombinantly produced by introducing a nucleic acid encoding ActRII (e.g., ActRIIB and/or ActRIIA) into a host cell. In one aspect, the ActRII-binding protein, e.g., an ActRII antibody or ActRII-binding fragment thereof, decreases ActRII ligand mediated phosphorylation of one or more Smads (e.g., Smad2 and/or Smad3) by at least 10%, 20%, 30%, 40%, 50%, 60%, 70%, 80%, 90%, or 95%, or by about 100%, as determined, for example, by Western blotting followed by probing with an anti-phosphotyrosine antibody or by ELISA, using standard techniques and conditions described herein or otherwise known in the art.

In some aspects, an ActRIIA-binding protein decreases ActRIIA ligand (e.g., activin A) mediated phosphorylation of one or more Smads (e.g., Smad2 and/or Smad3) by at least 10%, 20%, 30%, 40%, 50%, 60%, 70%, 80%, 90%, or 95%, or by about 100%, as determined, for example, by Western blotting followed by probing with an anti-phosphotyrosine antibody or by ELISA (e.g., P-Smad ELISA) or a Smad dependent reporter gene assay using techniques described herein or otherwise known in the art.

In additional aspects, an ActRIIB-binding protein decreases ActRIIB ligand (e.g., activin A or GDF8)-mediated phosphorylation of one or more Smads (e.g., Smad2 and/or Smad3) by at least 10%, 20%, 30%, 40%, 50%, 60%, 70%, 80%, 90%, or 95%, or by about 100%, as determined, for example, by Western blotting followed by probing with an anti-phosphotyrosine antibody or by ELISA (e.g., a P-Smad ELISA) or a Smad dependent reporter gene assay using standard techniques and conditions described herein or otherwise known in the art.

The terms "antibody" and "immunoglobulin," are used interchangeably herein, and include whole (full-length) antibodies and antigen binding fragment or single chains thereof. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CHI, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. Exemplary antibodies include typical antibodies, scFvs, and combinations thereof where, for example, an scFv is covalently linked (for example, via peptidic bonds or via a chemical linker) to the N or C-terminus of either the heavy chain and/or the light chain of a typical antibody, or intercalated in the heavy chain and/or the light chain of a typical antibody.

The terms "antibody" and "immunoglobulin," encompass intact polyclonal antibodies, intact monoclonal antibodies, antibody fragments (such as Fab, Fab', F(ab')2, and Fv fragments), single chain Fv (scFv) derivatives and mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired binding activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. The term "IgG" refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3.

The terms "ActRII antibody," "an antibody that binds to ActRII," or "anti-ActRII antibody" refer to an antibody that is capable of binding ActRII (e.g., ActRIIB and/or ActRIIA) with sufficient affinity such that the antibody is useful as a therapeutic agent or diagnostic reagent in targeting ActRIIB and/or ActRIIA, respectively.

By "specifically binds" when used in the context of ActRII proteins, it is generally meant the ability of a binding protein such as an antibody, to bind to ActRII (e.g., ActRIIB and/or ActRIIA, preferably human ActRIIA and/or human ActRIIB, preferably an extracellular domain of ActRIIB and/or ActRIIA), with greater affinity than the binding protein binds to an unrelated control protein. In some aspects, the control protein is hen egg white lysozyme.

Preferably the binding protein binds ActRII with an affinity that is at least, 100, 500, or 1000 times greater than the affinity for a control protein. Preferably, the binding protein has a binding affinity for human ActRII of $\leq 1\times 10^{-7}$ M or $\leq 1\times 10^{-8}$ as measured using a binding assay known in the art. In some aspects, the binding affinity is measured using a radioimmunoassay (RIA) or BIACORE® (e.g., using ActRII (e.g., ActRIIB and/or ActRIIA) as the analyte and ActRII-binding protein as the ligand, or vice versa).

In some aspects, the extent of binding of an ActRII-binding protein (e.g., an anti-ActRII antibody) to an unrelated, non-ActRII protein is less than about 10% of the binding of the ActRII-binding protein to ActRII as measured, for example, by a radioimmunoassay (RIA), BIACORE® (using recombinant ActRII as the analyte and ActRII-binding protein as the ligand, or vice versa), kinetic exclusion assay (KINEXA®), or other binding assays known in the art. In certain aspects, the ActRII-binding protein is a full-length antibody or an ActRII-binding antibody fragment that has a dissociation constant ($K_D$) of ≤1 μM, ≤100 nM, ≤10 nM, ≤1 nM, ≤0.1 nM, ≤10 pM, ≤1 pM, or ≤0.1 pM.

The terms "antigen binding antibody fragment" (e.g., "ActRII-binding antibody fragment," "ActRIIA-binding antibody fragment" and "ActRIIB-binding antibody fragment") refer to a fragment containing all or a portion of an antigen binding variable region (e.g., CDR3) of an intact antibody. It is known that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from one or more antibody fragments. In some aspects the disclosure provides ActRII-binding antibody fragments wherein the antibody fragment is a Fab fragment, a Fab' fragment, a $F(ab')_2$ fragment, a Fv fragment, a diabody, or a single chain antibody molecule.

The Fc region includes polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, NIH, Bethesda, Md. (1991)). Fc may refer to this region in isolation, or this region in the context of a whole antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

A "monoclonal antibody" refers to a homogeneous antibody population involved in the highly specific recognition and binding of a single antigenic determinant or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, and Fv), single chain (scFv) mutants, and fusion proteins) comprising an antibody portion, and any other modified immunoglobulin molecule comprising an antigen recognition site. A monoclonal antibody may be made in any number of ways including, but not limited to, by hybridoma, phage selection, recombinant expression, and transgenic animals.

The term "chimeric antibody" refers to an antibody wherein the amino acid sequence of the immunoglobulin molecule is derived from two or more species. Typically, the variable region of both light and heavy chains corresponds to the variable region of antibodies derived from one species of mammal (e.g., mouse, rat, rabbit, etc.) with the desired antigen-binding specificity, affinity, and/or capability while the constant regions are homologous to the sequences in antibodies derived from another species (usually human) to avoid eliciting an immune response in that species.

The term "humanized antibody" refers to an antibody derived from a non-human (e.g., murine) immunoglobulin, which has been engineered to contain fewer preferably minimal non-human (e.g., murine) sequences. Typically, humanized antibodies are human immunoglobulins in which residues from the CDR are replaced by residues from the CDR of a non-human species (e.g., mouse, rat, rabbit, or hamster) that have the desired antigen-binding specificity, affinity, and/or capability (Jones, *Nature* 321:522-525 (1986); Riechmann, *Nature* 332:323-327 (1988); Verhoeyen, *Science* 239:1534-1536 (1988)). In some instances, the Fv framework region (FW) residues of a human immunoglobulin are replaced with the corresponding residues in an antibody from a non-human species that has the desired antigen-binding specificity, affinity, and/or capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

The term "human antibody" refers to an antibody produced by a human or an antibody having an amino acid sequence corresponding to an antibody produced by a human made using any technique known in the art. The term "human antibody" includes intact (full-length) antibodies, fragments thereof, and/or antibodies comprising at least one human heavy and/or light chain polypeptide such as, an antibody comprising murine light chain and human heavy chain polypeptides.

An "antagonist," "blocking," or "neutralizing" binding protein is one that inhibits or reduces activity of the antigen it binds, such as ActRIIB and/or ActRIIA. In some aspects, the antagonist ActRII-binding protein reduces or inhibits the binding to ActRIIA by an ActRIIA ligand such as activin A. In some aspects, the antagonist ActRII-binding protein reduces or inhibits the binding to ActRIIB by an ActRIIB ligand such as activin A. In certain aspects the antagonist ActRII-binding protein substantially or completely inhibits the activity of the ActRII. In some aspects, the ActRII activity is reduced by 10%, 20%, 30%, 50%, 70%, 80%, 90%, 95%, or 100%. In certain aspects the antagonist ActRII-binding protein is an anti-ActRIIA antibody, such as a full-length antibody or an ActRIIA-binding antibody fragment. In further aspects, the antagonist anti-ActRIIA antibody inhibits or reduces the activity of ActRIIA by at least 10%, 20%, 30%, 50%, 70%, 80%, 90%, 95%, or even 100%. In additional aspects, the antagonist ActRII-binding protein is an anti-ActRIIB antibody, such as a full-length antibody or an ActRIIB-binding antibody fragment. In further aspects, the antagonist anti-ActRIIB antibody inhibits or reduces the activity of ActRIIB by at least 10%, 20%, 30%, 50%, 70%, 80%, 90%, 95%, or even 100%.

"Binding affinity" generally refers to the strength of the sum total of non-covalent interactions between a single binding site of a molecule (e.g., an antibody) and its binding partner (e.g., an antigen). Unless indicated otherwise, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein and can be used for the purposes of the present disclosure.

"Potency" is a measure of pharmacological activity of a compound expressed in terms of the amount of the compound required to produce an effect of given intensity. It refers to the amount of the compound required to achieve a defined biological effect; the smaller the dose required, the more potent the drug. Potency is normally expressed as an $IC_{50}$ value, in nM unless otherwise stated. $IC_{50}$ is the median inhibitory concentration of an ActRII-binding protein (e.g., an anti-ActRIIA or anti-ActRIIB antibody). In functional assays, $IC_{50}$ is the concentration that reduces a biological response by 50% of its maximum. In ligand-receptor binding studies, $IC_{50}$ is the concentration that reduces ligand-receptor binding by 50% of maximal specific binding level. $IC_{50}$ can be calculated by any number of means known in the art. The fold improvement in potency for the antibodies or other binding protein provided herein as compared to a reference anti-ActRII antibody or other ActRII-binding protein can be at least 2-fold, 4-fold, 6-fold, 8-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, or at least 180-fold.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to specifically bind to an ActRII-bearing target cell will be able to effect cell-mediated cytotoxicity. For simplicity, the cell-mediated cytotoxicity resulting from the activity of an Fc fusion protein is also referred to herein as ADCC activity.

An ActRII-binding protein (e.g., an ActRII antibody, including an ActRII-binding fragment, variant, and derivative thereof), polynucleotide, vector, cell, or composition which is "isolated" is a protein (e.g., antibody), polynucleotide, vector, cell, or composition which is in a form not found in nature. Isolated proteins, polynucleotides, vectors, cells or compositions include those which have been purified to a degree that they are no longer in a form in which they are found in nature. In some aspects, a protein, polynucleotide, vector, cell, or composition which is isolated is substantially pure. Isolated proteins and isolated nucleic acid will be free or substantially free of material with which they are naturally associated such as other polypeptides or nucleic acids with which they are found in their natural environment, or the environment in which they are prepared (e.g., cell culture) when such preparation is by recombinant DNA technology practiced in vitro or in vivo. Proteins and nucleic acid may be formulated with diluents or adjuvants and still for practical purposes be isolated—for example the proteins will normally be mixed with gelatin or other carriers if used to coat microtitre plates for use in immunoassays, or will be mixed with pharmaceutically acceptable carriers or diluents when used in diagnosis or therapy.

The terms "subject," "individual," "animal," "patient," and "mammal," refer to any subject, particularly a mammalian subject, for whom diagnosis, prognosis, or therapy is desired. Mammalian subjects include but are not limited to humans, non-human primates, domestic animals, farm animals, rodents, and the like, which is to be the recipient of a particular treatment.

The term "pharmaceutical composition" refers to a preparation which is in such form as to permit the biological activity of the active ingredient to be effective, and which contains no additional components at concentrations that are unacceptably toxic to a subject to which the composition would be administered. Such composition can be sterile.

An "effective amount" of a polypeptide, e.g., an antigen binding protein including an antibody, as disclosed herein is an amount sufficient to carry out a specifically stated purpose. An "effective amount" can be determined empirically and in a routine manner, in relation to the stated purpose. The term "therapeutically effective amount" refers to an amount of a polypeptide, e.g., an antigen binding protein including an antibody, or other drug effective to "treat" a disease or condition in a subject (e.g., a mammal such as a human) and provides some improvement or benefit to a subject having the disease or condition. Thus, a "therapeutically effective" amount is an amount that provides some alleviation, mitigation, and/or decrease in at least one clinical symptom of the ActRII-mediated disease or condition. Clinical symptoms associated with the diseases or conditions that can be treated by the methods of the disclosure are well known. Further, therapeutic effects need not be complete or curative, as long as some benefit is provided to the subject. In some embodiments, the term "therapeutically effective" refers to an amount of a therapeutic agent that is capable of reducing ActRII activity in a patient in need thereof. The actual amount administered and rate and time-course of administration, will depend on the nature and severity of what is being treated. Prescription of treatment, e.g., decisions on dosage etc., is within the responsibility of general practitioners and other medical doctors. Appropriate doses of antibodies and antigen binding fragments thereof are generally known; see, Ledermann et al., *Int. J. Cancer* 47:659-664 (1991); Bagshawe et al., *Ant. Immun. and Radiophann.* 4:915-922 (1991).

A "sufficient amount" or "an amount sufficient to" achieve a particular result in a patient having an ActRII-mediated disease or condition refers to an amount of a therapeutic agent (e.g., an antigen binding protein including an antibody, as disclosed herein) that is effective to produce a desired effect, which is optionally a therapeutic effect (i.e., by administration of a therapeutically effective amount). In some embodiments, such particular result is a reduction in ActRII activity in a patient in need thereof.

The term "label" refers to a detectable compound or composition which is conjugated directly or indirectly to a moiety such as an anti-ActRII antibody so as to generate a "labeled" moiety. The label can be detectable by itself (e.g., radioisotope labels or fluorescent labels) or, in the case of an enzymatic label, can catalyze chemical alteration of a substrate compound or composition which is detectable.

Terms such as "treating," or "treatment," "to treat" or "ameliorating" and "to ameliorate" refer to both (a) therapeutic measures that cure, slow down, lessen symptoms of, and/or halt progression of a diagnosed pathologic condition or disorder and (b) prophylactic or preventative measures that prevent and/or slow the development of a targeted disease or condition. Thus, subjects in need of treatment include those already with the disease or condition; those at risk of developing the disease or condition; and those in whom the disease or condition is to be prevented. In certain aspects, a subject is successfully "treated" according to the methods provided herein if the subject shows, e.g., total, partial, or transient amelioration or elimination of a symptom associated with the disease or condition. In some aspects, the disclosure provides a method for treating a muscle disorder, such as muscle wasting due to disease or disuse. In additional aspects the disclosure provides a method for treating a disease or condition selected from muscle disorders such as degenerative muscle disease, muscular dystrophy, muscle atrophy, or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease, neurologic disease, such as osteoporosis; wound healing; weight loss; and cancer (e.g., a carcinoma, myeloma, a bone-loss inducing cancer, pituitary cancer, and gastrointestinal cancer). In further aspects the disclosure provides use of an ActRII-binding protein as provided herein in the manufacture of a medicament for the treatment or amelioration of one or more of the above diseases or conditions.

As used herein, "in combination with" or "combination therapies" refers to any form of administration such that additional therapies (e.g., second, third, fourth, etc.) are still effective in the body (e.g., multiple compounds are simultaneously effective in the subject, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, a subject that receives such treatment can benefit from a combined effect of different therapies. One or more ActRII-binding proteins of the disclosure can be administered concurrently with, prior to, or subsequent to, one or more other additional agents and/or supportive therapies. In general, each therapeutic agent will be administered at a dose and/or on a time schedule determined for that particular agent. The particular combination to employ in a regimen will take into account compatibility of the antagonist of the present disclosure with therapy and/or the desired outcome.

The methods and techniques of the present disclosure are generally performed according to known conventional methods and as described in various general and more specific references that are cited and discussed throughout the present disclosure unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), all of which are herein incorporated by reference.

The terms "cancer," "tumor," "cancerous," and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al., *Br. J. Cancer* 94:1057-1065 (2006)), colon cancer, colorectal cancer, endometrial carcinoma, myeloma (such as multiple myeloma), salivary gland carcinoma, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, and cholangiocarcinoma (liver). In a particular aspect, the cancer is myelofibrosis, myeloma (e.g., multiple myeloma), or pituitary cancer. In another aspect, the cancer is breast cancer, gastrointestinal cancer, or a carcinoma (e.g., basal and squamous cell carcinomas). In an additional aspect, the cancer is a bone-loss-inducing cancer.

The terms "polynucleotide" and "nucleic acid" are used interchangeably and are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, polynucleotides or nucleic acids can include regulatory elements such as promoters, enhancers, ribosome binding sites, or transcription termination signals.

The term "vector" means a construct, which is capable of delivering, and in some aspects expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "host cell" refers to a cell or a population of cells harboring or capable of harboring a recombinant nucleic acid. Host cells can be prokaryotic (e.g., *E. coli*), or eukaryotic. The host cells can be fungal cells including yeast such as *Saccharomyces cerevisiae, Pichia pastoris*, or *Schizosaccharomyces pombe*. The host cells also be any of various animal cells, such as insect cells (e.g., Sf-9) or mammalian cells (e.g., HEK293F, CHO, COS-7, NIH-3T3, NS0, PER.C6®, and hybridoma). In further aspects, the host cells is a CHO cell selected from the group consisting of CHO-K, CHO-0 CHO-Lec10, CHO-Lec13, CHO-Lec1, CHO Pro$^-$5, and CHO dhfr$^-$. In particular aspects, the host cell is a hybridoma.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because in some aspects the provided ActRII-binding proteins are based upon antibodies, the ActRII-binding proteins can occur as single chains or associated chains.

A "recombinant" polypeptide, protein or antibody refers to polypeptide, protein or antibody produced via recombinant DNA technology. Recombinantly produced polypeptides, proteins and antibodies expressed in host cells are considered isolated for the purpose of the present disclosure, as are native or recombinant polypeptides which have been separated, fractionated, or partially or substantially purified by any suitable technique.

Also included in the present disclosure are fragments, variants, or derivatives of polypeptides, and any combination thereof. The term "fragment" when referring to polypeptides and proteins include any polypeptides or proteins which retain at least some of the properties of the reference polypeptide or protein. Fragments of polypeptides include proteolytic fragments, as well as deletion fragments.

The term "variant" refers to an antibody or polypeptide sequence that differs from that of a parent antibody or polypeptide sequence by virtue of at least one amino acid modification. Variants of antibodies or polypeptides include fragments, and also antibodies or polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "derivatives" as applied to antibodies or polypeptides refers to antibodies or polypeptides which have been altered so as to exhibit additional features not found on the native antibody or polypeptide. An example of a "derivative" antibody is a fusion or a conjugate with a second polypeptide or another molecule (e.g., a polymer such as PEG, a chromophore, or a fluorophore) or atom (e.g., a radioisotope).

The term "amino acid substitution" refers to replacing an amino acid residue present in a parent sequence with another amino acid residue. An amino acid can be substituted in a parent sequence, for example, via chemical peptide synthesis or through known recombinant methods. Accordingly, references to a "substitution at position X" or "substitution at position X" refer to the substitution of an amino acid residue present at position X with an alternative amino acid residue. In some embodiments, substitution patterns can described according to the schema AXY, wherein A is the single letter code corresponding to the amino acid residue naturally present at position X, and Y is the substituting amino acid residue. In other aspects, substitution patterns can described according to the schema XY, wherein Y is the single letter code corresponding to the amino acid residue substituting the amino acid residue naturally present at position X.

A "conservative amino acid substitution" is one in which the amino acid residue is replaced with an amino acid residue having a similar side chain. Families of amino acid residues having similar side chains have been previously defined, including basic side chains (e.g., Lys, Arg, His), acidic side chains (e.g., Asp, Glu), uncharged polar side chains (e.g., Gly, Asp, Gln, Ser, Thr, Tyr, Cys), nonpolar side chains (e.g., Ala, Val, Leu, Ile, Pro, Phe, Met, Trp), beta-branched side chains (e.g., Thr, Val, Ile) and aromatic side chains (e.g., Tyr, Phe, Trp, His). Thus, if an amino acid residue in a polypeptide is replaced with another amino acid residue from the same side chain family, the substitution is considered to be conservative. In another aspect, a string of amino acid residues can be conservatively replaced with a structurally similar string that differs in order and/or composition of side chain family members.

Non-conservative substitutions include those in which (a) a residue having an electropositive side chain (e.g., Arg, His, or Lys) is substituted for, or by, an electronegative residue (e.g., Glu or Asp), (b) a hydrophilic residue (e.g., Ser or Thr) is substituted for, or by, a hydrophobic residue (e.g., Ala, Leu, Ile, Phe, or Val), (c) a Cys or Pro is substituted for, or by, any other residue, or (d) a residue having a bulky hydrophobic or aromatic side chain (e.g., Val, His, Ile, or Trp) is substituted for, or by, one having a smaller side chain (e.g., Ala or Ser) or no side chain (e.g., Gly).

Other substitutions can be readily identified. For example, for the amino acid alanine, a substitution can be taken from any one of D-Ala, Gly, beta-Ala, L-Cys and D-Cys. For lysine, a replacement can be any one of D-Lys, Arg, D-Arg, homo-Arg, Met, D-Met, omithine, or D-ornithine. Generally, substitutions in functionally important regions that can be expected to induce changes in the properties of isolated polypeptides are those in which (a) a polar residue (e.g., Ser or Thr) is substituted for (or by) a hydrophobic residue (e.g., Leu, Ile, Phe, or Ala); (b) a Cys residue is substituted for (or by) any other residue; (c) a residue having an electropositive side chain (e.g., Lys, Arg, or His), is substituted for (or by) a residue having an electronegative side chain (e.g., Glu or Asp); or (d) a residue having a bulky side chain (e.g., Phe) is substituted for (or by) one not having such a side chain (e.g., Gly). The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid residue can be inserted in a parent sequence, for example, via chemical peptide synthesis or through recombinant methods known in the art. Accordingly, the phrases "insertion between positions X and Y" or "insertion between Kabat positions X and Y," wherein X and Y correspond to amino acid residue positions (e.g., a cysteine amino acid residue insertion between positions 239 and 240), refers to the insertion of an amino acid residue between the X and Y positions, and also to the insertion in a nucleic acid sequence of a codon encoding an amino acid residue between the codons encoding the amino acid residues at positions X and Y.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software programs. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

The structure for carrying a CDR or a set of CDRs will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains and their CDRs can readily be determined by one skilled in the art using programs and known variable domain residue numbering systems such as Chothia, Chothia+, and Kabat can routinely be determined by reference to Kabat (Kabat et al., Sequences of Proteins of Immunological Interest. 4th Edition. U.S. DHHS. 1987, and tools available on the Internet (e.g., at bioinf.org.uk/abysis/sequence_input/key_annotation/key_annotation.html; and immuno.bme.nwu.edu)), herein incorporated by reference in its entirety.

CDRs can also be carried by other scaffolds such as fibronectin, cytochrome B, albumin (e.g., ALBUdAb (Domantis/GSK) and ALB-Kunitz (Dyax)), unstructured repeat sequences of 3 or 6 amino acids (e.g., PASylation® technology and XTEN® technology), and sequences containing elastin-like repeat domains (see, e.g., U.S. Pat. Appl. No. 61/442,106, which is herein incorporated by reference in its entirety).

A CDR amino acid sequence substantially as set out herein can be carried as a CDR in a human variable domain or a substantial portion thereof. The HCDR3 sequences substantially as set out herein represent embodiments of the present disclosure and each of these may be carried as a HCDR3 in a human heavy chain variable domain or a substantial portion thereof.

Variable domains employed in the present disclosure can be obtained from any germline or rearranged human variable domain, or can be a synthetic variable domain based on consensus sequences of known human variable domains. A CDR sequence (e.g., CDR3) can be introduced into a repertoire of variable domains lacking a CDR (e.g., CDR3), using recombinant DNA technology.

For example, Marks et al., (*Bio/Technology* 10:779-783 (1992); which is herein incorporated by reference in its entirety) provide methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al., further describe how this repertoire can be combined with a CDR3 of a particular antibody. Using analogous techniques, the CDR3-derived sequences of the present disclosure can be shuffled with repertoires of VH or VL domains lacking a CDR3, and the shuffled complete VH or VL domains combined with a cognate VL or VH domain to provide antigen binding proteins. The repertoire can then be displayed in a suitable host system such as the phage display system of Intl. Appl. Publ. No. WO92/01047 or any of a subsequent large body of literature, including Kay et al., (1996) Phage Display of Peptides and Proteins: A Laboratory Manual, San Diego: Academic Press, so that suitable antigen binding proteins may be selected. A repertoire can consist of from anything from 104 individual members upwards, for example from $10^6$ to $10^8$, or $10^{10}$, members. Other suitable host systems include yeast display, bacterial display, T7 display, and ribosome display. For a review of ribosome display for see Lowe et al., *Curr. Pharm. Biotech.* 517-527 (2004) and Intl. Appl. Publ. No. WO92/01047, each of which is herein incorporated by reference herein in its entirety. Analogous shuffling or combinatorial techniques are also disclosed by Stemmer (*Nature* 370:389-391 (1994), which is herein incorporated by reference in its entirety), which describes the technique in relation to a β-lactamase gene but observes that the approach may be used for the generation of antibodies.

An ActRII-binding protein (e.g., an anti-ActRIIA antibody and an anti-ActRIIB antibody) is said to "compete" with a reference molecule for binding to ActRII (e.g., ActRIIB and/or ActRIIA, respectively) if it binds to ActRII to the extent that it blocks, to some degree, binding of the reference molecule to ActRII. The ability of proteins to compete for binding to ActRII and thus to interfere with, block or "cross-block" one mothers binding to ActRII can be determined by any standard competitive binding assay known in the art including, for example, a competition ELISA assay, surface plasmon resonance (SPR; BIACORE®, Biosensor, Piscataway, N.J.) or according to methods described by Scatchard et al. (*Ann. N.Y. Acad. Sci.* 51:660-672 (1949)). An ActRII-binding protein may be said to competitively inhibit binding of the reference molecule to ActRII, for example, by at least 90%, at least 80%, at least 70%, at least 60%, or at least 50%. According to some aspects, the ActRII-binding protein competitively inhibits binding of the reference molecule to ActRIIA, by at least 90%, at least 80%, at least 70%, at least 60%, or at least 50%. According to other aspects, the ActRII-binding protein competitively inhibits binding of a reference molecule to ActRIIB, by at least 90%, at least 80%, at least 70%, at least 60%, or at least 50%.

ActRII-binding Proteins

Proteins that specifically bind ActRII are provided.

In some aspects, the ActRII-binding protein binds ActRII with an affinity that is at least, 100, 500, or 1000 times greater than the affinity of the ActRII-binding protein for a control protein that is not a TGF-beta receptor family member. In certain aspects, the ActRII-binding protein binds ActRII and has a dissociation constant ($K_D$) of <1 μM, <100 nM, <10 nM, <1 nM, <0.1 nM, <10 pM, <1 pM, or <0.1 pM. In some aspects, the ActRII-binding protein has a $K_D$ for human ActRII within the range of ≤1 μM and ≥0.1 pM, ≤100 μM and ≥0.1 pM, or ≤100 μM and ≥1 pM.

In some aspects, BIACORE® analysis is used to determine the ability of an ActRII-binding protein (e.g., an anti-ActRII antibody) to compete with/block the binding to ActRII protein by a reference ActRII-binding protein (e.g., an anti-ActRII antibody). In a further aspect in which a BIACORE® instrument (for example the BIACORE® 3000) is operated according to the manufacturer's recommendations, ActRII-Fc fusion protein is captured on a CM5 BIACORE® chip by previously attached anti-niFc IgG to generate an ActRII-coated surface. Typically 200-800 resonance units of ActRII-Fc (dimeric) would be coupled to the chip (an amount that gives easily measurable levels of binding but that is readily saturable by the concentrations of test reagent being used).

The two ActRII-binding proteins (termed A* and B*) to be assessed for their ability to compete with/block each other are mixed at a one to one molar ratio of binding sites in a suitable buffer to create a test mixture. When calculating the concentrations on a binding site basis the molecular weight of an ActRII-binding protein is assumed to be the total molecular weight of the ActRII-binding protein divided by the number of ActRII-binding sites on that ActRII-binding protein. The concentration of each ActRII-binding protein (i.e., A* and B*) in the test mixture should be high enough to readily saturate the binding sites for that ActRII-binding protein on the ActRII-Fc molecules captured on the BIACORE® chip. The A* and B* ActRII-binding proteins in the mixture are at the same molar concentration (on a binding basis) and that concentration would typically be between 1.00 and 1.5 micromolar (on a binding site basis). Separate solutions containing ActRII-binding protein A* alone and ActRII-binding protein B* alone are also prepared. ActRII-binding protein A* and ActRII-binding protein B* in these solutions should be in the same buffer and at the same concentration as in the test mixture. The test mixture is passed over the ActRII-Fc-coated BIACORE® chip and the total amount of binding recorded. The chip is then treated in such a way as to remove the bound ActRII-binding proteins without damaging the chip-bound ActRII-Fc. Typically, this is done by treating the chip with 30 mM HCl for 60 seconds. The solution of ActRII-binding protein A* alone is then passed over the ActRII-Fc-coated surface and the amount of binding recorded. The chip is again treated to remove the bound antibody without damaging the chip-bound ActRII-Fc. The solution of ActRII-binding protein B* alone is then passed over the ActRII-Fc-coated surface and the amount of binding recorded. The maximum theoretical binding of the mixture of ActRII-binding protein A* and ActRII-binding protein B* is next calculated, and is the sum of the binding of each ActRII-binding protein when passed over the ActRII surface alone. If the actual recorded binding of the mixture is less than this theoretical maximum then the two ActRII-binding proteins are competing with/blocking each other. Thus, in general, a blocking ActRII-binding protein is one which will bind to ActRII in the above BIACORE® blocking assay such that during the assay and in the presence of a second ActRII-binding protein the recorded binding is between 80% and 0.1% (e.g., 80%> to 4%) of the maximum theoretical binding, specifically between 75% and 0.1% (e.g., 75% to 4%) of the maximum theoretical binding, and more specifically between 70% and 0.1% (e.g., 70% to 4%) of maximum theoretical binding (as defined above) of the two ActRII-binding proteins in combination.

The BIACORE® assay described above is an exemplary assay used to determine if two ActRII-binding proteins such as anti-ActRII antibodies compete with/block each other for binding ActRII. On rare occasions, particular ActRII-binding proteins may not bind to ActRII-Fc coupled via anti-Fc IgG to a CM5 BIACORE® chip (this might occur when the relevant binding site on ActRII is masked or destroyed by ActRII linkage to Fc). In such cases, blocking can be determined using a tagged version of ActRII, for example C-terminal His-tagged ActRII. In this particular format, an anti-His antibody would be coupled to the BIACORE® chip and then the His-tagged ActRII would be passed over the surface of the chip and captured by the anti-His antibody. The cross-blocking analysis would be carried out essentially as described above, except that after each chip regeneration cycle, new His-tagged ActRII would be loaded back onto the surface coated with anti-His antibody. Moreover, various other known tags and tag binding protein combinations can be used for such a blocking analysis (e.g., HA tag with anti-HA antibodies; FLAG tag with anti-FLAG antibodies; biotin tag with streptavidin). The following generally describes an ELISA assay for determining whether an ActRII-binding protein blocks or is capable of blocking the binding of a reference ActRII-binding protein to ActRII.

In some aspects, an ELISA is used to determine the ability of an ActRII-binding protein (e.g., an anti-ActRII antibody) to compete for binding to the ActRII protein with a reference ActRII-binding protein (e.g., an anti-ActRII antibody or ActRII ligand). The general principle of such an assay is to have a reference ActRII-binding protein (e.g., an anti-ActRII antibody) coated onto the wells of an ELISA plate. An excess amount of a second potentially blocking, test ActRII-binding protein is added in solution (i.e., not bound to the ELISA plate). A limited amount of ActRII (or alternatively ActRII-Fc) is then added to the wells. The coated reference ActRII-binding protein and the test ActRII-binding protein in solution compete for binding of the limited number of ActRII (or ActRII-Fc) molecules. The plate is washed to remove ActRII that has not been bound by the coated reference ActRII-binding protein and to also remove the test, solution-phase ActRII-binding protein as well as any complexes formed between the test, solution-phase ActRII-binding protein and ActRII. The amount of bound ActRII is then measured using an appropriate ActRII detection reagent. A test ActRII-binding protein in solution that is able to block binding of the coated reference ActRII-binding protein to ActRII will be able to cause a decrease in the number of ActRII molecules that the coated reference ActRII-binding protein can bind relative to the number of ActRII molecules that the coated reference ActRII-binding protein can bind in the absence of the second, solution-phase test ActRII-binding protein. The background signal for the assay is defined as the signal obtained in wells with the coated reference ActRII-binding protein, solution-phase test ActRII-binding protein, ActRII buffer only (i.e., no ActRII) and ActRII detection reagents. The positive control signal for the assay is defined as the signal obtained in wells with the coated reference ActRII-binding protein, solution-phase test ActRII-binding protein buffer only (i.e., no solution-phase test ActRII-binding protein), ActRII and ActRII detection reagents. The ELISA assay is be run in such a manner so as to have the positive control signal at least 3 times the background signal. As a control for methodologic artifacts, the cross-blocking assay may be run in the format just described and also reversed, with the test ActRII-binding protein as the coated antibody and the reference ActRII-binding protein as the solution-phase antibody.

In some aspects, a reporter gene assay is used to determine the ability of an ActRII-binding protein (e.g., an anti-ActRII antibody) to neutralize ActRII (e.g., ActRIIB). In some aspects, the reporter gene assay is performed using recombinant A204 cells to determine the ability of an ActRII-binding protein (e.g., an anti-ActRII antibody) to neutralize ActRII (e.g., ActRIIB) activity. This assay is based on a human rhabdomyosarcoma cell line transfected with a pGL3(CAGA)12 plasmid containing a (CAGA)12 motif (see, e.g., Dennler et al., *EMBO* 17:3091-3100 (1998) and U.S. Pat. No. 8,765,385, each of which in herein incorporated by reference in its entirety) as well as a ReniUa reporter plasmid (pRLCMV) to control for transfection efficiency. The CAGA12 motif is present in TGF-beta responsive genes (PAI-1 gene), so this vector is of general use for factors signaling through Smad2 and Smad3. With respect to measuring the ActRIIB-binding activity of a candidate protein using this assay, since the A204 cell line expresses primarily ActRIIA rather than ActRIIB, it is not possible to directly test antibodies for potential ActRIIB neutralizing ability. Instead, this assay is designed to detect the ability of a test ActRII protein binding candidate to neutralize the inhibitory effect of the soluble fusion protein ActRIIB-Fc on activation of endogenous ActRIIA by ligands (such as activin A or GDF11) that can bind with high affinity to both ActRIIB and ActRIIA. Thus, in this assay, ligand-mediated activation of ActRIIA will occur despite the presence of ActRIIB-Fc if the ActRIIB-binding is neutralizing.

On the first day of the assay, A204 cells (ATCC HTB-82) are distributed in 48-well plates at $10^5$ cells per well. On the second day, a solution containing 10 μg pGL3(CAGA)12, 1 μg pRLCMV, 30 μl Fugene 6 (Roche Diagnostics), and 970 μl OptiMEM (Invitrogen) is preincubated for 30 minutes, then added to McCoy's growth medium, which is applied to the plated cells (500 μl/well) for incubation overnight at room temperature. On the third day, medium is removed, and cells are incubated for 6 hours at 37° C. with a mixture of ligands and inhibitors prepared as described below.

According to one aspect, the neutralizing potency of an ActRII-binding protein such as an anti-ActRII antibody, is evaluated whereby a serial dilution of the test protein is made in a 48-well plate in a 200 μl volume of assay buffer (McCoy's medium+0.1% BSA). For assays assessing the ability of a candidate protein to neutralize ActRIIB activity, an equal volume of ActRIIB-Fc (200 μg/ml) in assay buffer is then added. The test solutions are incubated at 37° C. for 30 minutes, then 400 μl of activin A (10 ng/ml) is added to all wells, and 350 μl of this mixture is added to each well of the 48-well plate of A204 cells. Each concentration of test protein is tested in duplicate. For assays assessing the ability of a candidate protein to neutralize ActRIIB activity, the final concentration of ActRIIB-Fc is 50 ng/ml (which is the $IC_{50}$ for this inhibitor of activin A signaling when the final concentration of activin A is 5 ng/ml). After incubation with test solutions for 6 hours, cells are rinsed with phosphate-buffered saline containing 0.1% BSA, then lysed with passive lysis buffer (Promega E1941) and stored overnight at −70° C. On the fourth and final day, plates are warmed to room temperature with gentle shaking. Cell lysates are transferred in duplicate to a chemoluminescence plate (96-well) and analyzed in a luminometer with reagents from a Dual-Luciferase Reporter Assay system (Promega E1980) to determine normalized luciferase activity.

Pharmacodynamic parameters dependent on ActRIIB signaling can be measured as endpoints for in vivo testing of ActRIIB-binding proteins in order to identify those binding proteins that are able to neutralize ActRIIB and provide a therapeutic benefit. An ActRIIB neutralizing binding agent is defined as one capable of causing a statistically significant change, as compared to vehicle-treated animals, in such a pharmacodynamic parameter. Such in vivo testing can be performed in any suitable mammal (e.g., mouse, rat, or monkey).

In some aspects, the ActRII-binding protein binds ActRIIA with an affinity that is at least, 100, 500, or 1000 times greater than the affinity of the ActRII-binding protein for a control protein that is not a TGF-beta receptor family member. In additional aspects, the ActRII-binding protein binds ActRIIA with an affinity that is at least, 100, 500, or 1000 times greater than the affinity of the ActRII-binding protein for a control protein that is not a TGF-beta receptor family member. In certain aspects, the ActRIIA-binding protein binds ActRIIA and has a dissociation constant ($K_D$) of <1 μM, <100 nM, <10 nM, <1 nM, <0.1 nM, <10 pM, <1 pM, or <0.1 pM. In some aspects, the ActRIIA-binding protein has a $K_D$ for human ActRIIA within the range of ≤1 μM and ≥0.1 pM, ≤100 μM and ≥0.1 pM, or ≤100 μM and ≥1 pM.

In some aspects, the ActRII-binding protein binds ActRIIB with an affinity that is at least, 100, 500, or 1000 times greater than the affinity of the ActRII-binding protein for a control protein that is not a TGF-beta family member. In additional aspects, the ActRII-binding protein binds ActRIIB with an affinity that is at least, 100, 500, or 1000 times greater than the affinity of the ActRII-binding protein for a control protein that is not a TGF-beta receptor family member. In certain aspects, the ActRIIB-binding protein binds ActRIIB and has a dissociation constant ($K_D$) of <1 μM, <100 nM, <10 nM, <1 nM, <0.1 nM, <10 pM, <1 pM, or <0.1 pM. In some aspects, the ActRIIB-binding protein has a $K_D$ for human ActRIIB within the range of ≤1 μM and ≥0.1 pM, ≤100 μM and ≥0.1 pM, or ≤100 μM and ≥1 pM.

In some aspects, the ActRII-binding protein binds ActRIIB and ActRIIA with an affinity that is at least, 100, 500, or 1000 times greater than the affinity of the ActRII-binding protein for a control protein that is not a TGF-beta family member. In additional aspects, the ActRII-binding protein binds ActRIIB and ActRIIA with an affinity that is at least, 100, 500, or 1000 times greater than the affinity of the ActRII-binding protein for a control protein that is not a TGF-beta receptor family member. In certain aspects, the ActRII-binding protein binds ActRIIB and ActRIIA and has a dissociation constant ($K_D$) of <1 μM, <100 nM, <10 nM, <1 nM, <0.1 nM, <10 pM, <1 pM, or <0.1 pM. In some aspects, the ActRIIA- and ActRIIB-binding protein has a $K_D$ for human ActRIIB and ActRIIA within the range of ≤1 μM and ≥0.1 pM, ≤100 μM and ≥0.1 pM, or ≤100 μM and ≥1 pM.

In some aspects, an ActRII-binding protein is an antibody that specifically binds ActRII. In additional aspects, the ActRII-binding protein is a full-length anti-ActRIIA antibody or a full-length anti-ActRIIB antibody. In additional aspects, the antibody is a monoclonal antibody, a recombinant antibody, a human antibody, a humanized antibody, a chimeric antibody, a bi-specific antibody, a multi-specific antibody, or an ActRII-binding antibody fragment thereof. In additional aspects, the antibody specifically binds ActRIIB and/or ActRIIA.

In some aspects, the ActRII-binding protein (e.g., an anti-ActRII antibody and an ActRII-binding antibody fragment) can bind to ActRII molecules across species.

The mature ActRIIA extracellular domain of human ActRIIA (SEQ ID NO:138) differs from that of the mouse ActRIIA ortholog (Ref. P27038) by only two conserved amino acid substitutions (i.e., K19R and V72I). In additional aspects, the ActRII-binding protein can bind to human ActRIIA (hActRIIA) and murine ActRIIA (murActRIIA). In certain aspects, the ActRII-binding protein is an anti-ActRIIA antibody (e.g., a full-length ActRIIA-antibody and an ActRIIA-binding antibody fragment, and a variant and derivative thereof) can specifically bind to ActRIIA (e.g., hActRIIA or murActRIIA) with a dissociation constant or $K_D$ of less than $10^{-8}$ M, than less than $10^{-9}$ M, or less than $10^{-10}$ M, as determined by BIACORE® or KINEXA®. In further aspects, the anti-ActRIIA antibody binds to ActRIIA with a $K_D$ of <1 nM (e.g., as determined by BIACORE® analysis). In a further aspect, the anti-ActRIIA antibody binds to ActRIIA with a $K_D$ within one order of magnitude of 1 nM or within two orders of magnitude of 1 nM. In some aspects, the ActRIIA-binding protein has a $K_D$ for human ActRIIA within the range of ≤1 μM and ≥0.1 pM, ≤100 μM and ≥0.1 pM, or ≤100 μM and ≥1 pM.

The mature extracellular domain of human ActRIIB (SEQ ID NO:139) differs from the corresponding sequence of the mouse ActRIIB ortholog (NCBI Ref. Seq. NP 031423) by one amino acid substitution (i.e., A95P). In certain aspects, the ActRII-binding protein is an anti-ActRIIB antibody (e.g., a full-length ActRIIB-antibody and an ActRIIB-binding antibody fragment, and a variant and derivative thereof) that specifically binds ActRIIB (e.g., hActRIIB and murActRIIB) with a dissociation constant or $K_D$ of less than $10^{-8}$ M, less than $10^{-9}$ M, or less than $10^{-10}$ M as determined by BIACORE® or KINEXA®. In further aspects, the anti-ActRIIB antibody binds to ActRIIB with a $K_D$ of <1 nM as determined by BIACORE® or KINEXA® analysis. In a further aspect, the anti-ActRIIB antibody binds ActRIIB with a $K_D$ within one order of magnitude of 1 nM or within two orders of magnitude of 1 nM. In some aspects, the ActRIIB-binding protein has a $K_D$ for human ActRIIB within the range of ≤1 μM and ≥0.1 pM, ≤100 μM and ≥0.1 pM, or ≤1 nM and ≥1 pM.

In some aspects, anti-ActRII antibody is an ActRII-binding antibody fragment. In some aspects, the ActRII-binding antibody fragment is a: Fab, Fab', $F(ab')_2$, Fv fragment, diabody, or single chain antibody molecule. In additional aspects, the ActRII-antibody is a Fd, single chain Fv(scFv), disulfide linked Fv, V-NAR domain, IgNar, intrabody, IgGΔCH2, minibody, $F(ab')_3$ tetrabody, triabody, diabody, single-domain antibody, DVD-Ig, Fcab, $mAb^2$, $(scFv)_2$, scFv-Fc or bis-scFv.

In additional aspects the ActRII-binding protein is an antibody that includes a VH and a VL. In some aspects the anti-ActRII antibody further includes a heavy chain constant region or fragment thereof. In some aspects, the antibody comprises a heavy chain immunoglobulin constant region selected from the group consisting of: (a) a human IgA constant region, or fragment thereof; (b) a human IgD constant region, or fragment thereof; (c) a human IgE constant domain, or fragment thereof; (d) a human IgG1 constant region, or fragment thereof; (e) a human IgG2 constant region, or fragment thereof; (f) a human IgG3 constant region, or fragment thereof; (g) a human IgG4 constant region, or fragment thereof; and (h) a human IgM constant region, or fragment thereof. In certain aspects an ActRII-binding protein comprises a heavy chain constant region or fragment thereof, e.g., a human IgG constant region or fragment thereof. In further aspects, the ActRII-binding protein comprises a heavy chain immunoglobulin constant domain that has, or has been mutated to have altered effector function and/or half-life.

In particular aspects, the ActRII-binding protein is an antibody that comprises an IgG1 heavy chain constant region containing a mutation that decreases effector function (see, e.g., Idusogie et al., *J. Immunol.* 166:2571-2575 (2001); Sazinsky et al., *PNAS USA* 105:20167-20172 (2008); Davis et al., *J. Rheumatol.* 34:2204-2210 (2007); Bolt et al., *Eur. J. Immunol.* 23:403-411 (1993); Alegre et al., *Transplantation* 57:1537-1543 (1994); Xu et al., *Cell Immunol.* 200:16-26 (2000); Cole et at, *Transplantation* 68:563-571 (1999); Hutchins et al., *PNAS USA* 92:11980-11984 (1995); Reddy et al., *J. Immunol.* 164:1925-1933 (2000); WO97/11971, and WO07/106585; U.S. Appl. Publ. 2007/0148167A1; McEarchern et al., *Blood* 109:1185-1192 (2007); Strohl, *Curr. Op. Biotechnol.* 20:685-691 (2009); and Kumagai et al., *J. Clin. Pharmacol.* 47:1489-1497 (2007), each of which is herein incorporated by reference in its entirety).

In some aspects, the heavy chain constant region or fragment thereof includes one or more amino acid substitutions relative to a wild-type IgG constant domain wherein the modified IgG has decreased ADCC compared to the half-life of an IgG having the wild-type IgG constant domain. Examples of Fc sequence engineering modifications contained in the provided antibodies that decrease ADCC include one or more modifications corresponding to: IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S, wherein the position numbering is according to the EU index as in Kabat.

In certain aspects an ActRII-binding protein comprises a heavy chain immunoglobulin constant domain that has, or has been mutated to have, reduced CDC activity. In particular aspects, the ActRII-binding protein is an antibody that comprises an IgG1 heavy chain constant region containing a mutation that decreases CDC activity (see, e.g., WO97/11971 and WO07/106585; U.S. Appl. Publ. 2007/0148167A1; McEarchern et al., *Blood* 109:1185-1192 (2007); Hayden-Ledbetter et al., *Clin. Cancer* 15:2739-2746

(2009); Lazar et al., *PNAS USA* 103:4005-4010 (2006); Bruckheimer et al., *Neoplasia* 11:509-517 (2009); Strohl, *Curr. Op. Biotechnol.* 20:685-691 (2009); and Sazinsky et al., *PNAS USA* 105:20167-20172 (2008); each of which is herein incorporated by reference in its entirety). Examples of Fc sequence engineering modifications contained in an anti-ActRII antibody that decrease CDC include one or more modifications corresponding to: IgG1-S239D, A330L, 1332E; IgG2 EU sequence 118-260; IgG4-EU sequence 261-447; IgG2-H268Q, V309L, A330S, A331S; IgG1-C226S, C229S, E233P, L234V, L235A; IgG1-L234F, L235E, P331S; and IgG1-C226S, P230S.

In further aspects, the heavy chain constant region or fragment thereof includes one or more amino acid substitutions relative to a wild-type IgG constant domain wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain aspects the IgG constant domain can contain one or more of a substitution of the amino acid at Kabat position 252 with Tyr, Phe, Trp, or Thr; a substitution of the amino acid at Kabat position 254 with Thr; a substitution of the amino acid at Kabat position 256 with Ser, Arg, Gln, Glu, Asp, or Thr; a substitution of the amino acid at Kabat position 257 with Leu; a substitution of the amino acid at Kabat position 309 with Pro; a substitution of the amino acid at Kabat position 311 with Ser; a substitution of the amino acid at Kabat position 428 with Thr, Leu, Phe, or Ser; a substitution of the amino acid at Kabat position 433 with Arg, Ser, Iso, Pro, or Gln; or a substitution of the amino acid at Kabat position 434 with Trp, Met, Ser, His, Phe, or Tyr. More specifically, the IgG constant domain can contain amino acid substitutions relative to a wild-type human IgG constant domain including a substitution of the amino acid at Kabat position 252 with Tyr, a substitution of the amino acid at Kabat position 254 with Thr, and a substitution of the amino acid at Kabat position 256 with Glu.

In additional aspects, the ActRII-binding protein is an antibody that comprises a light chain immunoglobulin constant region. In a further aspect, the antibody comprises a human Ig kappa constant region or a human Ig lambda constant region.

In some aspects, the ActRII-binding protein comprises a set of CDRs: VH-CDR1, VH-CDR2, VH-CDR3, VL-CDR1, VL-CDR2 and VL-CDR3, wherein the CDRs are present in a VH and a VL pair disclosed in Table 1. In further embodiments, the ActRII-binding protein comprises a set of CDRs wherein the CDRs are present in a VH and a VL pair selected from the group consisting of: (a) a VH sequence of SEQ ID NO:2, 16, 22, 28, 34, or 40, and a VL sequence of SEQ ID NO:9, and wherein the protein binds ActRIIB, (b) a VH sequence of SEQ ID NO:63 or 77, and a VL having the amino acid sequence of SEQ ID NO:70, and wherein the protein binds ActRIIB; (c) a VH sequence of SEQ ID NO:45 or 57, and a VL sequence of SEQ ID NO:50, and wherein the protein binds ActRIIB; (d) a VH sequence of SEQ ID NO:84, 98, 105, 112, or 119, and a VL sequence of SEQ ID NO:91, and wherein the protein binds ActRIIA, and (e) a VH sequence of SEQ ID NO:125, and a VL sequence of SEQ ID NO:132, and wherein the protein binds ActRIIA.

In further embodiments, the ActRII-binding protein comprises a set of CDRs wherein the CDRs are present in a VH and a VL pair having: (a) a VH sequence of SEQ ID NO:144, and a VL sequence of SEQ ID NO:151, and wherein the protein binds ActRIIB.

In further embodiments, the ActRII-binding protein comprises a set of CDRs wherein the CDRs are present in a VH and a VL pair having: (a) a VH sequence of SEQ ID NO:165, and a VL sequence of SEQ ID NO:172, and wherein the protein binds ActIIRA and ActRIIB.

In some aspects an ActRII-binding protein comprises a set of CDRs: (a) VH-CDR1, VH-CDR2, and VH-CDR3, or (b) VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs disclosed herein. In further aspects, the ActRII-binding protein comprises a set of CDRs, wherein the set of CDRs is identical to, or has a total of one, two, three, four, five, six, seven, eight, nine, ten, or fewer than ten, amino acid substitutions, deletions, and/or insertions from a reference set of CDRs in a VH or VL sequence disclosed in Table 1.

In some aspects an ActRII-binding protein comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs disclosed herein. In further aspects, the ActRII-binding protein comprises a set of CDRs, wherein the set of CDRs is identical to, or has a total of one, two, three, four, five, six, seven, eight, nine, ten, or fewer than ten, amino acid substitutions, deletions, and/or insertions from a reference set of CDRs in a VH and VL sequence pair disclosed in Table 1.

In additional aspects, the ActRII-binding protein specifically binds ActRII and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 has the amino acid sequence of SEQ ID NO:3, 17, 23, 29, 35 or 41; (ii) VH-CDR2 has the amino acid sequence of SEQ ID NO:4, 18, 24, 30, or 36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:64 or 78; (ii) VH-CDR2 has the amino acid sequence of SEQ ID NO:65 or 79; (iii) VH-CDR3 has the amino acid sequence of SEQ ID NO:66 or 80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (c)(i) VH-CDR1 has the amino acid sequence of SEQ ID NO:3 or 58; (ii) VH-CDR2 has the amino acid sequence of SEQ ID NO:4 or 59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (d)(i) VH-CDR1 has the amino acid sequence of SEQ ID NO:85, 99, 106, or 113; (ii) VH-CDR2 has the amino acid sequence of SEQ ID NO:86, 100, 107, 114, or 120; (iii) VH-CDR3 has the amino acid sequence of SEQ ID NO:87, 101, 108, 115, or 121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (e)(i) VH-CDR1 has the amino acid sequence of SEQ ID NO:126; (ii) VH-CDR2 has the amino acid sequence of SEQ ID NO:127; (iii) VH-CDR3 has the amino acid sequence of SEQ ID NO:128; (iv) VL-CDR1 has the amino acid sequence of SEQ ID NO:133; (v) VL-CDR2 has the amino acid sequence of SEQ ID NO:134; and (vi) VL-CDR3 has the amino acid sequence of SEQ ID NO:135; and wherein the protein binds ActRIIA. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In additional aspects, the ActRII-binding protein specifically binds ActRII and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which (i) VH-CDR1 has the amino acid sequence of SEQ ID NO:145; (ii) VH-CDR2 has the amino acid sequence of SEQ ID NO:146; (iii) VH-CDR3 has the amino acid sequence of SEQ ID NO:147; (iv) VL-CDR1 has the amino acid sequence of SEQ ID NO:152; (v) VL-CDR2 has the amino acid sequence of SEQ ID NO:153; and (vi) VL-CDR3 has the amino acid sequence of SEQ ID NO:154; and wherein the protein binds ActRIIB. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In additional aspects, the ActRII-binding protein specifically binds ActRII and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which (i) VH-CDR1 has the amino acid sequence of SEQ ID NO:166; (ii) VH-CDR2 has the amino acid sequence of SEQ ID NO:167; (iii) VH-CDR3 has the amino acid sequence of SEQ ID NO:168; (iv) VL-CDR1 has the amino acid sequence of SEQ ID NO:173; (v) VL-CDR2 has the amino acid sequence of SEQ ID NO:174; and (vi) VL-CDR3 has the amino acid sequence of SEQ ID NO:175; and wherein the protein binds ActIIRA and ActRIIB. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein specifically binds ActRII and comprises a set of CDRs that has a total of one, two, three, four, five, six, seven, eight, nine, ten, fewer than ten, or zero, amino acid substitutions, deletions, and/or insertions from a reference set of CDRs in which: (a)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:17; (ii) VH-CDR2 has the amino acid sequence of SEQ ID NO:18; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (c)(i) VH-CDR1 has the amino acid sequence of SEQ ID NO:23; (ii) VH-CDR2 has the amino acid sequence of SEQ ID NO:24; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (d)(i) VH-CDR1 has the amino acid sequence of SEQ ID NO:29; (ii) VH-CDR2 has the amino acid sequence of SEQ ID NO:30; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (e)(i) VH-CDR1 has the amino acid sequence of SEQ ID NO:35; (ii) VH-CDR2 has the amino acid sequence of SEQ ID NO:36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (f)(i) VH-CDR1 has the amino acid sequence of SEQ ID NO:41; (ii) VH-CDR2 has the amino acid sequence of SEQ ID NO:18; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (g)(i) VH-CDR1 has the amino acid sequence of SEQ ID NO:64; (ii) VH-CDR2 has the amino acid sequence of SEQ ID NO:65; (iii) VH-CDR3 has the amino acid sequence of SEQ ID NO:66; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; and (h)(i) VH-CDR1 has the amino acid sequence of SEQ ID NO:78; (ii) VH-CDR2 has the amino acid sequence of SEQ ID NO:79; (iii) VH-CDR3 has the amino acid sequence of SEQ ID NO:80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (i)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (j)(i) VH-CDR1 has the amino acid sequence of SEQ ID NO:58; (ii) VH-CDR2 has the amino acid sequence of SEQ ID NO:59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (k)(i) VH-CDR1 has the amino acid sequence of SEQ ID NO:85; (ii) VH-CDR2 has the amino acid sequence of SEQ ID NO:86; (iii) VH-CDR3 has the amino acid sequence of SEQ ID NO:87; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (l)(i) VH-CDR1 has the amino acid sequence of SEQ ID NO:99; (ii) VH-CDR2 has the amino acid sequence of SEQ ID NO:100; (iii) VH-CDR3 has the amino acid sequence of SEQ ID NO:101; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (m)(i) VH-CDR1 has the amino acid sequence of SEQ ID NO:106; (ii) VH-CDR2 has the amino acid sequence of SEQ ID NO:107, (iii) VH-CDR3 has the amino acid sequence of SEQ ID NO 108; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (n)(i) VH-CDR1 has the amino acid sequence of SEQ ID NO:113; (ii) VH-CDR2 has the amino acid sequence of SEQ ID NO:114; (iii) VH-CDR3 has the amino acid sequence of SEQ ID NO:115; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (o)(i) VH-CDR1 has the amino acid sequence of SEQ ID NO:113; (ii) VH-CDR2 has the amino acid sequence of SEQ ID NO:120; (iii) VH-CDR3 has the amino acid sequence of SEQ ID NO:121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (p)(i) VH-CDR1 has the amino acid sequence of SEQ ID NO:126; (ii) VH-CDR2 has the amino acid sequence of SEQ ID NO:127; (iii) VH-CDR3 has the amino acid sequence of SEQ ID NO:128; (iv) VL-CDR1 has the amino acid sequence of SEQ ID NO:133; (v) VL-CDR2 has the amino acid sequence of SEQ ID NO:134; and (vi) VL-CDR3 has the amino acid sequence of SEQ ID NO:135; and wherein the protein binds ActRIIA. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, an ActRII-binding protein specifically binds ActRIIB and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 has the amino acid sequence of SEQ ID NO:3, 17, 23, 29, 35, or 41; (ii) VH-CDR2 has the amino acid sequence of SEQ ID NO:4, 18, 24, 30, or 36; and (iii) VH-CDR3 has the amino acid sequence of SEQ ID NO:5; (b)(i) VH-CDR1 has the amino acid sequence of SEQ ID NO:3 or 58; (ii) VH-CDR2 has the amino acid sequence of SEQ ID NO:4 or 59; and (iii) VH-CDR3 has the amino acid sequence of SEQ ID NO:46; or (c)(i) VH-CDR1 has the amino acid sequence of SEQ ID NO:64 or 78; (ii) VH-CDR2 has the amino acid sequence of SEQ ID NO:65 or 79; and (iii) VH-CDR3 has the amino acid sequence of SEQ ID NO:66 or 80. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In some aspects, an ActRII-binding protein specifically binds ActRIIB and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:5; and wherein the protein binds ActRIIB; (b)(i) VH-CDR1 has the amino acid sequence of SEQ ID NO:17; (ii) VH-CDR2 has the amino acid sequence of SEQ ID NO:18; (iii) VH-CDR3 has the amino acid sequence of SEQ ID NO:5; and wherein the protein binds ActRIIB; (c)(i) VH-CDR1 has the amino acid sequence of SEQ ID NO:23; (ii) VH-CDR2 has the amino acid sequence of SEQ ID NO:24; (iii) VH-CDR3 has the amino acid sequence of SEQ ID NO:5; and wherein the protein binds ActRIIB; (d)(i) VH-CDR1 has the amino acid sequence of SEQ ID NO:29; (ii) VH-CDR2 has the amino acid sequence of SEQ ID NO:30; (iii) VH-CDR3 has the amino acid sequence of SEQ ID NO:5; and wherein the protein binds ActRIIB; (e)(i) VH-CDR1 has the amino acid sequence of SEQ ID NO:35; (ii) VH-CDR2 has the amino acid sequence of SEQ ID NO:36; (iii) VH-CDR3 has the amino acid sequence of SEQ ID NO:5; and wherein the protein binds ActRIIB; (f)(i) VH-CDR1 has the amino acid sequence of SEQ ID NO:41; (ii) VH-CDR2 has the amino acid sequence of SEQ ID NO:18; (iii) VH-CDR3 has the amino acid sequence of SEQ ID NO:5; and wherein the protein binds ActRIIB; (g)(i) VH-CDR1 has the amino acid sequence of SEQ ID NO:64; (ii) VH-CDR2 has the amino acid sequence of SEQ ID NO:65; (iii) VH-CDR3 has the amino acid sequence of SEQ ID NO:66; and wherein the protein binds ActRIIB; (h)(i) VH-CDR1 has the amino acid sequence of SEQ ID NO:78; (ii) VH-CDR2 has the amino acid sequence of SEQ ID NO:79; (iii) VH-CDR3 has the amino acid sequence of SEQ ID NO:80; and wherein the protein binds ActRIIB; (i)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:46; and wherein the protein binds ActRIIB; or (j)(i) VH-CDR1 has the amino acid sequence of SEQ ID NO:58; (ii) VH-CDR2 has the amino acid sequence of SEQ ID NO:59; (iii) VH-CDR3 has the amino acid sequence of SEQ ID NO:46; and wherein the protein binds ActRIIB. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In some aspects, an ActRII-binding protein specifically binds ActRIIB and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VL-CDR1 has the amino acid sequence of SEQ ID NO:10; (ii) VL-CDR2 has the amino acid sequence of SEQ ID NO:11; and (iii) VL-CDR3 has the amino acid sequence of SEQ ID NO:12; and wherein the protein binds ActRIIB; (b)(i) VL-CDR1 has the amino acid sequence of SEQ ID NO:71; (ii) VL-CDR2 has the amino acid sequence of SEQ ID NO:72; and (iii) VL-CDR3 has the amino acid sequence of SEQ ID NO:73; and wherein the protein binds ActRIIB; or (c)(i) VL-CDR1 has the amino acid sequence of SEQ ID NO:51; (ii) VL-CDR2 has the amino acid sequence of SEQ ID NO:52; and (iii) VL-CDR3 has the amino acid sequence of SEQ ID NO:53; and wherein the protein binds ActRIIB. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In some aspects, an ActRII-binding protein specifically binds ActRIIB and ActRIIA and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which VH-CDR1 has the amino acid sequence of SEQ ID NO:85, 99, 106, or 113; VH-CDR2 has the amino acid sequence of SEQ ID NO:86, 100, 107, 114, or 120; and VH-CDR3 has the amino acid sequence of SEQ ID NO:87, 101, 108, 115, or 121. In further aspects, the ActRIIB- and ActRIIA-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In some aspects, an ActRII-binding protein specifically binds ActRIIB and ActRIIA and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 has the amino acid sequence of SEQ ID NO:85; (ii) VH-CDR2 has the amino acid sequence of SEQ ID NO:86; (iii) VH-CDR3 has the amino acid sequence of SEQ ID NO:87; and wherein the protein binds ActRIIB and ActRIIA; (b)(i) VH-CDR1 has the amino acid sequence of SEQ ID NO:99; (ii) VH-CDR2 has the amino acid sequence of SEQ ID NO:100; (iii) VH-CDR3 has the amino acid sequence of SEQ ID NO:101; and wherein the protein binds ActRIIB and ActRIIA; (c)(i) VH-CDR1 has the amino acid sequence of SEQ ID NO:106; (ii) VH-CDR2 has the amino acid sequence of SEQ ID NO:107, (iii) VH-CDR3 has the amino acid sequence of SEQ ID NO 108; and wherein the protein binds ActRIIB and ActRIIA; (d)(i) VH-CDR1 has the amino acid sequence of SEQ ID NO:113; (ii) VH-CDR2 has the amino acid sequence of SEQ ID NO:114; (iii) VH-CDR3 has the amino acid sequence of SEQ ID NO:115; and wherein the protein binds ActRIIB and ActRIIA; or (e)(i) VH-CDR1 has the amino acid sequence of SEQ ID NO:113; (ii) VH-CDR2 has the amino acid sequence of SEQ ID NO:120; (iii) VH-CDR3 has the amino acid sequence of SEQ ID NO:121; and wherein the protein binds ActRIIB and ActRIIA. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In some aspects, an ActRII-binding protein specifically binds ActRIIB and ActRIIA and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which VL-CDR1 has the amino acid sequence of SEQ ID NO:92; (ii) VL-CDR2 has the amino acid sequence of SEQ ID NO:93; and (iii) VL-CDR3 has the amino acid sequence of SEQ ID NO:94; and wherein the protein binds ActRIIB and ActRIIA. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In some aspects, an ActRII-binding protein specifically binds ActRIIA and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which VH-CDR1 has the amino acid sequence of SEQ ID NO:126; VH-CDR2 has the amino acid sequence of SEQ ID NO:127; and VH-CDR3 has the amino acid sequence of SEQ ID NO:128. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In some aspects, the ActRII-binding protein specifically binds ActRIIA and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: VL-CDR1 has the amino acid sequence of SEQ ID NO:133 VL-CDR2 has the amino acid sequence of SEQ ID NO:134; and VL-CDR3 has the amino acid sequence of SEQ ID NO:135. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In additional aspects, the ActRII-binding protein specifically binds ActRIIB and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 has the amino acid sequence of SEQ ID NO:3, 17, 23, 29, 35, or 41; (ii) VH-CDR2 has the amino acid sequence of SEQ ID NO:4, 18, 24, 30, or 36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; or (vi) VL-CDR3 has the amino acid sequence of SEQ ID NO:12; (b)(i) VH-CDR1 has the amino acid sequence of SEQ ID NO:3 or 58; (ii) VH-CDR2 has the amino acid sequence of SEQ ID NO:4 or 59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; or (vi) VL-CDR3 has the amino acid sequence of SEQ ID NO:53; or (c)(i) VH-CDR1 has the amino acid sequence of SEQ ID NO:64 or 78; (ii) VH-CDR2 has the amino acid sequence of SEQ ID NO:65 or 79; (iii) VH-CDR3 has the amino acid sequence of SEQ ID NO:66, or 80; (iv) VL-CDR1 has the amino acid sequence of SEQ ID NO:71; (v) VL-CDR2 has the amino acid sequence of SEQ ID NO:72; or (vi) VL-CDR3 has the amino acid sequence of SEQ ID NO:73. In further aspects, the ActRIIB-binding protein comprises a VH and a VL. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In further aspects, the ActRII-binding protein specifically binds ActRIIB and comprises a set of CDRs: VH-CDR1, VH-CDR2, VH-CDR3, VL-CDR1, VL-CDR2, and VL-CDR3, wherein: (a)(i) VH-CDR1 has the amino acid sequence of SEQ ID NO:3, 17, 23, 29, 35, or 41; (ii) VH-CDR2 has the amino acid sequence of SEQ ID NO:4, 18, 24, 30, or 36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; or (vi) VL-CDR3 has the amino acid sequence of SEQ ID NO:12; (b)(i) VH-CDR1 has the amino acid sequence of SEQ ID NO:3 or 58; (ii) VH-CDR2 has the amino acid sequence of SEQ ID NO:4 or 59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; or (vi) VL-CDR3 has the amino acid sequence of SEQ ID NO:53; or (c)(i) VH-CDR1 has the amino acid sequence of SEQ ID NO:64 or 78; (ii) VH-CDR2 has the amino acid sequence of SEQ ID NO:65 or 79; (iii) VH-CDR3 has the amino acid sequence of SEQ ID NO:66, or 80; (iv) VL-CDR1 has the amino acid sequence of SEQ ID NO:71; (v) VL-CDR2 has the amino acid sequence of SEQ ID NO:72; or (vi) VL-CDR3 has the amino acid sequence of SEQ ID NO:73. In further aspects, the ActRIIB-binding protein comprises a VH and a VL. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In additional aspects, the ActRII-binding protein specifically binds ActRIIB and ActRIIA and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a) VH-CDR1 has the amino acid sequence of SEQ ID NO:85, 99, 106 or 113; (b) VH-CDR2 has the amino acid sequence of SEQ ID NO:86, 100, 107, 114, or 120; (c) VH-CDR3 has the amino acid sequence of SEQ ID NO:87, 101, 108, 115, or 121; (d) VL-CDR1 has the amino acid sequence of SEQ ID NO:92; (e) VL-CDR2 has the amino acid sequence of SEQ ID NO:93; or (f) VL-CDR3 has the amino acid sequence of SEQ ID NO:94. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In additional aspects, the ActRII-binding protein specifically binds ActRIIB and ActRIIA and comprises a set of CDRs: VH-CDR1, VH-CDR2, VH-CDR3, VL-CDR1, VL-CDR2, and VL-CDR3, wherein: (a) VH-CDR1 has the amino acid sequence of SEQ ID NO:85, 99, 106 or 113; (b) VH-CDR2 has the amino acid sequence of SEQ ID NO:86, 100, 107, 114, or 120; (c) VH-CDR3 has the amino acid sequence of SEQ ID NO:87, 101, 108, 115, or 121; (d) VL-CDR1 has the amino acid sequence of SEQ ID NO:92; (e) VL-CDR2 has the amino acid sequence of SEQ ID NO:93; or (f) VL-CDR3 has the amino acid sequence of SEQ ID NO:94. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In additional aspects, the ActRII-binding protein specifically binds ActRIIA and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a) VH-CDR1 has the amino acid sequence of SEQ ID NO:126; (b) VH-CDR2 has the amino acid sequence of SEQ ID NO:127; (c) VH-CDR3 has the amino acid sequence of SEQ ID NO:128; (d) VL-CDR1 has the amino acid sequence of SEQ ID NO:133; (e) VL-CDR2 has the amino acid sequence of SEQ ID NO:134; or (f) VL-CDR3 has the amino acid sequence of SEQ ID NO:135. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In further aspects, the ActRII-binding protein specifically binds ActRIIA and comprises a set of CDRs: VH-CDR1, VH-CDR2, VH-CDR3, VL-CDR1, VL-CDR2, and VL-CDR3, wherein: (a) VH-CDR1 has the amino acid sequence of SEQ ID NO:126; (b) VH-CDR2 has the amino acid sequence of SEQ ID NO:127; (c) VH-CDR3 has the amino acid sequence of SEQ ID NO:128; (d) VL-CDR1 has the amino acid sequence of SEQ ID NO:133; (e) VL-CDR2 has the amino acid sequence of SEQ ID NO:134; or (f) VL-CDR3 has the amino acid sequence of SEQ ID NO:135. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In some aspects, the ActRII-binding protein specifically binds ActRII and comprises a set of CDRs in which: (a)(i) VH-CDR1 has the amino acid sequence of SEQ ID NO:3, 17, 23, 29, 35 or 41; (ii) VH-CDR2 has the amino acid sequence of SEQ ID NO:4, 18, 24, 30, or 36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:64 or 78; (ii) VH-CDR2 has the amino acid sequence of SEQ ID NO:65 or 79; (iii) VH-CDR3 has the amino acid sequence of SEQ ID NO:66 or 80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (c)(i) VH-CDR1 has the amino acid sequence of SEQ ID NO:3 or 58; (ii) VH-CDR2 has the amino acid sequence of SEQ ID NO:4 or 59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (d)(i) VH-CDR1 has the amino acid sequence of SEQ ID NO:85, 99, 106, or 113; (ii) VH-CDR2 has the amino acid sequence of SEQ ID NO:86, 100, 107, 114, or 120; (iii) VH-CDR3 has the amino acid sequence of SEQ ID NO:87, 101, 108, 115, or 121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (e)(i) VH-CDR1 has the amino acid sequence of SEQ ID NO:126; (ii) VH-CDR2 has the amino acid sequence of SEQ ID NO:127; (iii) VH-CDR3 has the amino acid sequence of SEQ ID NO:128; (iv) VL-CDR1 has the amino acid sequence of SEQ ID NO:133; (v) VL-CDR2 has the amino acid sequence of SEQ ID NO:134; and (vi) VL-CDR3 has the amino acid sequence of SEQ ID NO:135; and wherein the protein binds ActRIIA.

In additional aspects, the ActRII-binding protein comprises a set of CDRs in which: (a)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (b)(i) VH-CDR1 has the amino acid sequence of SEQ ID NO:17; (ii) VH-CDR2 has the amino acid sequence of SEQ ID NO:18; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (c)(i) VH-CDR1 has the amino acid sequence of SEQ ID NO:23; (ii) VH-CDR2 has the amino acid sequence of SEQ ID NO:24; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (d)(i) VH-CDR1 has the amino acid sequence of SEQ ID NO:29; (ii) VH-CDR2 has the amino acid sequence of SEQ ID NO:30; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (e)(i) VH-CDR1 has the amino acid sequence of SEQ ID NO:35; (ii) VH-CDR2 has the amino acid sequence of SEQ ID NO:36; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (f)(i) VH-CDR1 has the amino acid sequence of SEQ ID NO:41; (ii) VH-CDR2 has the amino acid sequence of SEQ ID NO:18; (iii) VH-CDR3 has the amino acid sequence of SEQ ID NO:5; (iv) VL-CDR1 has the amino acid sequence of SEQ ID NO:10; (v) VL-CDR2 has the amino acid sequence of SEQ ID NO:11; and (vi) VL-CDR3 has the amino acid sequence of SEQ ID NO:12; and wherein the protein binds ActRIIB; (g)(i) VH-CDR1 has the amino acid sequence of SEQ ID NO:64; (ii) VH-CDR2 has the amino acid sequence of SEQ ID NO:65; (iii) VH-CDR3 has the amino acid sequence of SEQ ID NO:66; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; and (h)(i) VH-CDR1 has the amino acid sequence of SEQ ID NO:78; (ii) VH-CDR2 has the amino acid sequence of SEQ ID NO:79; (iii) VH-CDR3 has the amino acid sequence of SEQ ID NO:80; (iv) VL-CDR1 has the amino acid sequence of SEQ ID NO:71; (v) VL-CDR2 has the amino acid sequence of SEQ ID NO:72; and (vi) VL-CDR3 has the amino acid sequence of SEQ ID NO:73; and wherein the protein binds ActRIIB; (i)(i) VH-CDR1 has the amino acid sequence of SEQ ID NO:3; (ii) VH-CDR2 has the amino acid sequence of SEQ ID NO:4; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (j)(i) VH-CDR1 has the amino acid sequence of SEQ ID NO:58; (ii) VH-CDR2 has the amino acid sequence of SEQ ID NO:59; (iii) VH-CDR3 has the amino acid sequence of SEQ ID NO:46; (iv) VL-CDR1 has the amino acid sequence of SEQ ID NO:51; (v) VL-CDR2 has the amino acid sequence of SEQ ID NO:52; and (vi) VL-CDR3 has the amino acid sequence of SEQ ID NO:53; and wherein the protein binds ActRIIB; (k)(i) VH-CDR1 has the amino acid sequence of SEQ ID NO:85; (ii) VH-CDR2 has the amino acid sequence of SEQ ID NO:86; (iii) VH-CDR3 has the amino acid sequence of SEQ ID NO:87; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (l)(i) VH-CDR1 has the amino acid sequence of SEQ ID NO:99; (ii) VH-CDR2 has the amino acid sequence of SEQ ID NO:100; (iii) VH-CDR3 has the amino acid sequence of SEQ ID NO:101; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (m)(i) VH-CDR1 has the amino acid sequence of SEQ ID NO:106; (ii) VH-CDR2 has the amino acid sequence of SEQ ID NO:107, (iii) VH-CDR3 has the amino acid sequence of SEQ ID NO 108; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; (n)(i) VH-CDR1 has the amino acid sequence of SEQ ID NO:113; (ii) VH-CDR2 has the amino acid sequence of SEQ ID NO:114; (iii) VH-CDR3 has the amino acid sequence of SEQ ID NO:115; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA; or (o)(i) VH-CDR1 has the amino acid sequence of SEQ ID NO:113; (ii) VH-CDR2 has the amino acid sequence of SEQ ID NO:120; (iii) VH-CDR3 has the amino acid sequence of SEQ ID NO:121; (iv) VL-CDR1 has the amino acid sequence of SEQ ID NO:92; (v) VL-CDR2 has the amino acid sequence of SEQ ID NO:93; and (vi) VL-CDR3 has the amino acid sequence of SEQ ID NO:94; and wherein the protein binds ActRIIB and ActRIIA.

In some aspects an ActRII-binding protein comprises a VH-CDR3 or a VL-CDR3 sequence disclosed herein. In further aspects, the ActRII-binding protein comprises a VH-CDR3 or a VL-CDR3 sequence disclosed in Table 1. In some aspects an ActRII-binding protein comprises a VH-CDR3 and a VL-CDR3 sequence disclosed herein. In further aspects, the ActRII-binding protein comprises a VH-CDR3 and a VL-CDR3 sequence disclosed in Table 1.

In further aspects, the disclosure provides an ActRIIB-binding protein comprising a VH-CDR3 having the amino acid sequence of SEQ ID NO: 5, 46, 66, or 80. In some aspects, the ActRIIB-binding protein comprises a VH-CDR3 having the amino acid sequence of SEQ ID NO:5. In further aspects the ActRIIB-binding protein comprises a VH-CDR3 having the amino acid sequence of SEQ ID NO:5 and a VH-CDR2 having the amino acid sequence of SEQ ID NO:4, 18, 24, 30, or 36. In further aspects, the ActRIIB-binding protein comprises a VH-CDR3 having the amino acid sequence of SEQ ID NO:5, a VH-CDR2 having the amino acid sequence of SEQ ID NO:4, 18, 24, 30, or 36, and a VH-CDR1 having the amino acid sequence of SEQ ID NO:3, 17, 23, 29, 35, or 41. In some aspects, the ActRIIB-binding protein comprises a VH-CDR3 having the amino acid sequence of SEQ ID NO:46. In further aspects the ActRIIB-binding protein comprises a VH-CDR3 having the amino acid sequence of SEQ ID NO:46 and a VH-CDR2 having the amino acid sequence of SEQ ID NO:4 or 59. In further aspects, the ActRIIB-binding protein comprises a VH-CDR3 having the amino acid sequence of SEQ ID NO:46, a VH-CDR2 having the amino acid sequence of SEQ ID NO:4 or 59, and a VH-CDR1 having the amino acid sequence of SEQ ID NO:3 or 58. In some aspects, the ActRIIB-binding protein comprises a VH-CDR3 having the amino acid sequence of SEQ ID NO:66. In further aspects the ActRIIB-binding protein comprises a VH-CDR3 having the amino acid sequence of SEQ ID NO:66 and a VH-CDR2 having the amino acid sequence of SEQ ID NO:65. In further aspects, the ActRIIB-binding protein comprises a VH-CDR3 having the amino acid sequence of SEQ ID NO:66, a VH-CDR2 having the amino acid sequence of SEQ ID NO:65, and a VH-CDR1 having the amino acid sequence of SEQ ID NO:64. In some aspects, the ActRIIB-binding protein comprises a VH-CDR3 having the amino acid sequence of SEQ ID NO:80. In further aspects the ActRIIB-binding protein comprises a VH-CDR3 having the amino acid sequence of SEQ ID NO:80 and a VH-CDR2 having the amino acid sequence of SEQ ID NO:79. In further aspects, the ActRIIB-binding protein comprises a VH-CDR3 having the amino acid sequence of SEQ ID NO:80, a VH-CDR2 having the amino acid sequence of SEQ ID NO:79, and a VH-CDR1 having the amino acid sequence of SEQ ID NO:78. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In further aspects, the disclosure provides an ActRIIB-binding protein comprising a VL-CDR3 having the amino acid sequence of SEQ ID NO:12, 53, or 73. In some aspects, the ActRIIB-binding protein comprises a VL-CDR3 having the amino acid sequence of SEQ ID NO:12. In further aspects the ActRIIB-binding protein comprises a VL-CDR3 having the amino acid sequence of SEQ ID NO:12 and a VL-CDR2 having the amino acid sequence of SEQ ID NO:11. In further aspects, the ActRIIB-binding protein comprises a VL-CDR3 having the amino acid sequence of SEQ ID NO:12, a VL-CDR2 having the amino acid sequence of SEQ ID NO:11, and a VL-CDR1 having the amino acid sequence of SEQ ID NO:10. In some aspects, the ActRIIB-binding protein comprises a VL-CDR3 having the amino acid sequence of SEQ ID NO:53 In further aspects the ActRIIB-binding protein comprises a VL-CDR3 having the amino acid sequence of SEQ ID NO:53 and a VL-CDR2 having the amino acid sequence of SEQ ID NO:52. In further aspects, the ActRIIB-binding protein comprises a VL-CDR3 having the amino acid sequence of SEQ ID NO:53, a VL-CDR2 having the amino acid sequence of SEQ ID NO:52, and a VL-CDR1 having the amino acid sequence of SEQ ID NO:51. In some aspects, the ActRIIB-binding protein comprises a VL-CDR3 having the amino acid sequence of SEQ ID NO:73. In further aspects the ActRIIB-binding protein comprises a VL-CDR3 having the amino acid sequence of SEQ ID NO:73 and a VL-CDR2 having the amino acid sequence of SEQ ID NO:72. In further aspects, the ActRIIB-binding protein comprises a VL-CDR3 having the amino acid sequence of SEQ ID NO:73, a VL-CDR2 having the amino acid sequence of SEQ ID NO:72, and a VL-CDR1 having the amino acid sequence of SEQ ID NO:71. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In further aspects, the disclosure provides an ActRIIB- and/or ActRIIA-binding protein comprising a VH-CDR3 having the amino acid sequence of SEQ ID NO:87, 101, 108, 115, or 121. In further aspects, the ActRII-binding protein comprises a VH-CDR3 having the amino acid sequence of SEQ ID NO:87, 101, 108, 115, or 121, and a VH-CDR2 having the amino acid sequence of SEQ ID NO:86, 100, 107, 114, or 120. In further aspects, the ActRII-binding protein comprises a VH-CDR3 having the amino acid sequence of SEQ ID NO:87, 101, 108, 115, or 121, a VH-CDR2 having the amino acid sequence of SEQ ID NO:86, 100, 107, 114, or 120, and a VH-CDR1 having the amino acid sequence of SEQ ID NO:85, 99, 106 or 113. In some aspects, the ActRIIB- and/or ActRIIA binding protein comprises a VH-CDR3 having the amino acid sequence of SEQ ID NO:87. In further aspects the ActRIIB- and/or ActRIIA binding protein comprises a VH-CDR3 having the amino acid sequence of SEQ ID NO:87 and a VH-CDR2 having the amino acid sequence of SEQ ID NO:86. In further aspects, the ActRIIB- and/or ActRIIA-binding protein comprises a VH-CDR3 having the amino acid sequence of SEQ ID NO:87, a VH-CDR2 having the amino acid sequence of SEQ ID NO:86, and a VH-CDR1 having the amino acid sequence of SEQ ID NO:85. In some aspects, the ActRIIB- and/or ActRIIA-binding protein comprises a VH-CDR3 having the amino acid sequence of SEQ ID NO:101. In further aspects the ActRIIB- and/or ActRIIA-binding protein comprises a VH-CDR3 having the amino acid sequence of SEQ ID NO:101 and a VH-CDR2 having the amino acid sequence of SEQ ID NO:100. In further aspects, the ActRIIB- and/or ActRIIA-binding protein comprises a VH-CDR3 having the amino acid sequence of SEQ ID NO:101, a VH-CDR2 having the amino acid sequence of SEQ ID NO:100, and a VH-CDR1 having the amino acid sequence of SEQ ID NO:99. In some aspects, the ActRIIB- and/or ActRIIA-binding protein comprises a VH-CDR3 having the amino acid sequence of SEQ ID NO:108. In further aspects the ActRIIB- and/or ActRIIA-binding protein comprises a VH-CDR3 having the amino acid sequence of SEQ ID NO:108 and a VH-CDR2 having the amino acid sequence of SEQ ID NO:107. In further aspects, the ActRIIB- and/or ActRIIA-binding protein comprises a VH-CDR3 having the amino acid sequence of SEQ ID NO:108, a VH-CDR2 having the amino acid sequence of SEQ ID NO:107, and a VH-CDR1 having the amino acid sequence of SEQ ID NO:106. In some aspects, the ActRIIB- and/or ActRIIA-binding protein comprises a VH-CDR3 having the amino acid sequence of SEQ ID NO:115. In further aspects the ActRIIB- and/or ActRIIA-binding protein comprises a VH-CDR3 having the amino acid sequence of SEQ ID NO:115 and a VH-CDR2 having the amino acid sequence of SEQ ID NO:114. In further aspects, the ActRIIB- and/or ActRIIA-binding protein comprises a VH-CDR3 having the amino acid sequence of SEQ ID NO:115, a VH-CDR2 having the amino acid sequence of SEQ ID NO:114, and a VH-CDR1 having the amino acid sequence of SEQ ID NO:113. In further aspects, the ActRIIB- and/or ActRIIA-binding protein comprises a VH-CDR3 having the amino acid sequence of SEQ ID NO:121, a VH-CDR2 having the amino acid sequence of SEQ ID NO:120, and a VH-CDR1 having the amino acid sequence of SEQ ID NO:113. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In further aspects, the disclosure provides an ActRIIB- and/or ActRIIA-binding protein comprising a VL-CDR3 having the amino acid sequence of SEQ ID NO:94. In some aspects, the ActRIIB- and/or ActRIIA-binding protein comprises a VL-CDR3 having the amino acid sequence of SEQ ID NO:94 and a VL-CDR2 having the amino acid sequence of SEQ ID NO:93. In further aspects, the ActRIIB-binding protein comprises a VL-CDR3 having the amino acid sequence of SEQ ID NO:94, a VL-CDR2 having the amino acid sequence of SEQ ID NO:93, and a VL-CDR1 having the amino acid sequence of SEQ ID NO:92. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and/or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and/or ActRIIA-binding protein has 2, 3, or 4 of the above characteristics. In some aspects, the ActRIIB and/or ActRIIA-binding protein has at least 2 or at least 3 of the above characteristics.

In further aspects, the disclosure provides an ActRIIB- and/or ActRIIA-binding protein comprising a VH-antigen binding domain 3 (ABD3) having the amino acid sequence of SEQ ID NO:142. In further aspects, the ActRII-binding protein comprises a VH-ABD3 having the amino acid sequence of SEQ ID NO:142 and a VH-antigen binding domain 2 (VH-ABD2) having the amino acid sequence of SEQ ID NO:141. In further aspects, the ActRII-binding protein comprises a VH-ABD3 having the amino acid sequence of SEQ ID NO:133, a VH-ABD2 having the amino acid sequence of SEQ ID NO:141, and a VH-antigen binding domain 1 (VH-ABD1) having the amino acid sequence of SEQ ID NO:140. In further aspects, the ActRIIB- and ActRIIA-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB- and ActRIIA-binding protein has 2, 3, or 4 of the above characteristics. In some aspects, the ActRIIB- and ActRIIA-binding protein has at least 2 or at least 3 of the above characteristics.

In further aspects, the disclosure provides an ActRIIA-binding protein comprising a VH-CDR3 having the amino acid sequence of SEQ ID NO:128. In further aspects, the ActRII-binding protein comprises a VH-CDR3 having the amino acid sequence of SEQ ID NO:128 and a VH-CDR2 having the amino acid sequence of SEQ ID NO:127. In further aspects, the ActRII-binding protein comprises a VH-CDR3 having the amino acid sequence of SEQ ID NO:128, a VH-CDR2 having the amino acid sequence of SEQ ID NO:127, and a VH-CDR1 having the amino acid sequence of SEQ ID NO:126. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In further aspects, the disclosure provides an ActRIIA-binding protein comprising a VL-CDR3 having the amino acid sequence of SEQ ID NO:135. In further aspects, the ActRII-binding protein comprises a VL-CDR3 having the amino acid sequence of SEQ ID NO:135 and a VL-CDR2 having the amino acid sequence of SEQ ID NO:134. In further aspects, the ActRII-binding protein comprises a VL-CDR3 having the amino acid sequence of SEQ ID NO:135, a VL-CDR2 having the amino acid sequence of SEQ ID NO:134, and a VL-CDR1 having the amino acid sequence of SEQ ID NO:133. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In some aspects an ActRII-binding protein comprises a VH or a VL which has a total of one, two, three, four, five, six, seven, eight, nine, ten, fewer than fifteen, or zero, amino acid substitutions, deletions, and/or insertions compared to a reference VH or VL disclosed herein. In further aspects, the ActRII-binding protein comprises a VH or a VL which has a total of one, two, three, four, five, six, seven, eight, nine, ten, fewer than fifteen, or zero, amino acid substitutions, deletions, and/or insertions compared to a reference VH or VL disclosed in Table 1. In some aspects an ActRII-binding protein comprises a VH and a VL pair which has a total of one, two, three, four, five, six, seven, eight, nine, ten, fewer than fifteen, or zero, amino acid substitutions, deletions, and/or insertions compared to a reference VH and VL pair disclosed herein. In further aspects, the ActRII-binding protein comprises a VH and VL pair which has a total of one, two, three, four, five, six, seven, eight, nine, ten, fewer than fifteen, or zero, amino acid substitutions, deletions, and/or insertions compared to a reference VH and VL pair disclosed in Table 1.

In some aspects, the ActRII-binding protein comprises a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:2, 16, 22, 28, 34, or 40, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:9, and wherein the protein binds ActRIIB; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:45 or 57, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:50, and wherein the protein binds ActRIIB; (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:63 or 77, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:70, and wherein the protein binds ActRIIB; (d)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:84, 98, 105, 112, or 119, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:91, and wherein the protein binds ActRIIB and ActRIIA; and (e)(i) a VH sequence having a total of one, two, three, four, five, six, seven, eight, nine, ten, fewer than fifteen, or zero, amino acid substitutions, deletions, and/or insertions from a reference VH sequence of SEQ ID NO:125, and (ii) a VL sequence having a total of one, two, three, four, five, six, seven, eight, nine, ten, fewer than fifteen, or zero, amino acid substitutions, deletions, and/or insertions from a reference VL of SEQ ID NO:132, and wherein the protein binds ActRIIA.

In some aspects, the ActRII-binding protein comprises a VH and a VL pair having (i) a VH sequence having a total of one, two, three, four, five, six, seven, eight, nine, ten, fewer than fifteen, or zero, amino acid substitutions, deletions, and/or insertions from a reference VH sequence of SEQ ID NO:144, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:151, and the protein binds ActRIIB.

In some aspects, the ActRII-binding protein comprises a VH and a VL pair having (i) a VH sequence having a total of one, two, three, four, five, six, seven, eight, nine, ten, fewer than fifteen, or zero, amino acid substitutions, deletions, and/or insertions from a reference VH sequence of SEQ ID NO:165, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:172, and the protein binds ActIIRA and ActRIIB.

In a further aspect, the ActRII-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:2; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (b) the VH sequence has a total of one, two, three, four, five, six, seven, eight, nine, ten, fewer than fifteen, or zero, amino acid substitutions, deletions, and/or insertions from a reference VH sequence of SEQ ID NO:16; the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (c) the VH sequence has a total of one, two, three, four, five, six, seven, eight, nine, ten, fewer than fifteen, or zero, amino acid substitutions, deletions, and/or insertions from a reference VH sequence of SEQ ID NO:22; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (d) the VH sequence has a total of one, two, three, four, five, six, seven, eight, nine, ten, fewer than fifteen, or zero, amino acid substitutions, deletions, and/or insertions from a reference VH sequence of SEQ ID NO:28; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (e) the VH sequence has a total of one, two, three, four, five, six, seven, eight, nine, ten, fewer than fifteen, or zero, amino acid substitutions, deletions, and/or insertions from a reference VH sequence of SEQ ID NO:34; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (f) the VH sequence has a total of one, two, three, four, five, six, seven, eight, nine, ten, fewer than fifteen, or zero, amino acid substitutions, deletions, and/or insertions from a reference VH sequence of SEQ ID NO:40; and the VL sequence has a total of one, two, three, four, five, six, seven, eight, nine, ten, fewer than fifteen, or zero, amino acid substitutions, deletions, and/or insertions from a reference VL sequence of SEQ ID NO:9; and wherein the protein binds ActRIIB; (g) the sequence has a total of one, two, three, four, five, six, seven, eight, nine, ten, fewer than fifteen, or zero, amino acid substitutions, deletions, and/or insertions from a reference VH sequence of SEQ ID NO:45; and the VL sequence has a total of one, two, three, four, five, six, seven, eight, nine, ten, fewer than fifteen, or zero, amino acid substitutions, deletions, and/or insertions from a reference VL sequence of SEQ ID NO:50; wherein the protein binds ActRIIB; (h) the VH sequence has a total of one, two, three, four, five, six, seven, eight, nine, ten, fewer than fifteen, or zero, amino acid substitutions, deletions, and/or insertions from a reference VH sequence of SEQ ID NO:57; and the VL sequence has a total of one, two, three, four, five, six, seven, eight, nine, ten, fewer than fifteen, or zero, amino acid substitutions, deletions, and/or insertions from a reference VL sequence of SEQ ID NO:50; wherein the protein binds ActRIIB; (i) the VH sequence has a total of one, two, three, four, five, six, seven, eight, nine, ten, fewer than fifteen, or zero, amino acid substitutions, deletions, and/or insertions from a reference VH sequence of SEQ ID NO:63; and the VL sequence has a total of one, two, three, four, five, six, seven, eight, nine, ten, fewer than fifteen, or zero, amino acid substitutions, deletions, and/or insertions from a reference VL sequence of SEQ ID NO:70; and wherein the protein binds ActRIIB; (j) the VH sequence has a total of one, two, three, four, five, six, seven, eight, nine, ten, fewer than fifteen, or zero, amino acid substitutions, deletions, and/or insertions from a reference VH sequence of SEQ ID NO:77; and the VL sequence has a total of one, two, three, four, five, six, seven, eight, nine, ten, fewer than fifteen, or zero, amino acid substitutions, deletions, and/or insertions from a reference VL sequence of SEQ ID NO:70; and wherein the protein binds ActRIIB; (k) the sequence has a total of one, two, three, four, five, six, seven, eight, nine, ten, fewer than fifteen, or zero, amino acid substitutions, deletions, and/or insertions from a reference VH sequence of SEQ ID NO:84; and the VL sequence has a total of one, two, three, four, five, six, seven, eight, nine, ten, fewer than fifteen, or zero, amino acid substitutions, deletions, and/or insertions from a reference VL sequence of SEQ ID NO:91; wherein the protein binds ActRIIB and ActRIIA; (l) the VH sequence has a total of one, two, three, four, five, six, seven, eight, nine, ten, fewer than fifteen, or zero, amino acid substitutions, deletions, and/or insertions from a reference VH sequence of SEQ ID NO:98; and the VL sequence has a total of one, two, three, four, five, six, seven, eight, nine, ten, fewer than fifteen, or zero, amino acid substitutions, deletions, and/or insertions from a reference VL sequence of SEQ ID NO:91; wherein the protein binds ActRIIB and ActRIIA; (m) the VH sequence has a total of one, two, three, four, five, six, seven, eight, nine, ten, fewer than fifteen, or zero, amino acid substitutions, deletions, and/or insertions from a reference VH sequence of SEQ ID NO:105; and the VL sequence has a total of one, two, three, four, five, six, seven, eight, nine, ten, fewer than fifteen, or zero, amino acid substitutions, deletions, and/or insertions from a reference VL sequence of SEQ ID NO:91; and wherein the protein binds ActRIIB and ActRIIA; (n) the VH sequence has a total of one, two, three, four, five, six, seven, eight, nine, ten, fewer than fifteen, or zero, amino acid substitutions, deletions, and/or insertions from a reference VH sequence of SEQ ID NO:112; and the VL sequence has a total of one, two, three, four, five, six, seven, eight, nine, ten, fewer than fifteen, or zero, amino acid substitutions, deletions, and/or insertions from a reference VL sequence of SEQ ID NO:91; and wherein the protein binds ActRIIB and ActRIIA; (o) the VH sequence has a total of one, two, three, four, five, six, seven, eight, nine, ten, fewer than fifteen, or zero, amino acid substitutions, deletions, and/or insertions from a reference VH sequence of SEQ ID NO:119; and the VL sequence has a total of one, two, three, four, five, six, seven, eight, nine, ten, fewer than fifteen, or zero, amino acid substitutions, deletions, and/or insertions from a reference VL sequence of SEQ ID NO:91; and wherein the protein binds ActRIIB and ActRIIA; or (p) the VH sequence has a total of one, two, three, four, five, six, seven, eight, nine, ten, fewer than fifteen, or zero, amino acid substitutions, deletions, and/or insertions from a reference VH sequence of SEQ ID NO:125; and the VL sequence has a total of one, two, three, four, five, six, seven, eight, nine, ten, fewer than fifteen, or zero, amino acid substitutions, deletions, and/or insertions from a reference VL sequence of SEQ ID NO:132; and wherein the protein binds ActRIIA.

In a further aspect, the ActRII-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:144; and the VL sequence has a total of one, two, three, four, five, six, seven, eight, nine, ten, fewer than fifteen, or zero, amino acid substitutions, deletions, and/or insertions from a reference VL sequence of SEQ ID NO:151, and wherein the protein binds ActRIIB.

In a further aspect, the ActRII-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:165; and the VL sequence has a total of one, two, three, four, five, six, seven, eight, nine, ten, fewer than fifteen, or zero, amino acid substitutions, deletions, and/or insertions from a reference VL sequence of SEQ ID NO:172, and wherein the protein binds ActIIRA and ActRIIB.

In some aspects an ActRII-binding protein comprises a VH or a VL which has at least 90%, 95%, 97%, 98%, or 99% sequence identity to a reference VH or VL disclosed herein. In further aspects, the ActRII-binding protein comprises a VH or a VL which has at least 90%, 95%, 97%, 98%, or 99% sequence identity to a reference VH or VL disclosed in Table 1. In some aspects an ActRII-binding protein comprises a VH and VL which has at least 90%, 95%, 97%, 98%, or 99% sequence identity to a reference VH and VL disclosed herein. In further aspects, the ActRII-binding protein comprises a VH and VL which has at least 90%, 95%, 97%, 98%, or 99% sequence identity to a reference VH and VL disclosed in Table 1. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein specifically binds ActRII and comprises a VH and a VL pair selected from the group consisting of: (a)(i) a VH having at least 90%, 95%, 97%, 98%, or 99% sequence identity to SEQ ID NO:2, 16, 22, 28, 34, or 40, and (ii) a VL having at least 90%, 95%, 97%, 98%, or 99% sequence identity to SEQ ID NO:9, and wherein the protein binds ActRIIB; (b)(i) a VH having at least 90%, 95%, 97%, 98%, or 99% sequence identity to SEQ ID NO:45 or 57, and (ii) a VL having at least 90%, 95%, 97%, 98%, or 99% sequence identity to SEQ ID NO:50, and wherein the protein binds ActRIIB; (c)(i) a VH having at least 90%, 95%, 97%, 98%, or 99% sequence identity to SEQ ID NO:63 or 77, and (ii) a VL having at least 90%, 95%, 97%, 98%, or 99% sequence identity to SEQ ID NO:70, and wherein the protein binds ActRIIB; (d)(i) a VH having the amino acid sequence of SEQ ID NO:84, 98, 105, 112, or 119, and (ii) a VL having the amino acid sequence of SEQ ID NO:91, and wherein the protein binds ActRIIB and ActRIIA; and (e)(i) a VH having at least 90%, 95%, 97%, 98%, or 99% sequence identity to SEQ ID NO:125, and (ii) a VL having at least 90%, 95%, 97%, 98%, or 99% sequence identity to SEQ ID NO:132, and wherein the protein binds ActRIIA. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein binds ActRIIB and comprises a VH and VL pair selected from (i) a VH having at least 90%, 95%, 97%, 98%, or 99% sequence identity to SEQ ID NO:144, and (ii) a VL having at least 90%, 95%, 97%, 98%, or 99% sequence identity to SEQ ID NO:151, and the protein binds ActRIIB. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein binds ActRIIB and comprises a VH having at least 90%, 95%, 97%, 98%, or 99% sequence identity to SEQ ID NO:165, and (ii) a VL having at least 90%, 95%, 97%, 98%, or 99% sequence identity to SEQ ID NO:172, and the protein binds ActIIRA and ActRIIB. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In a further aspect, the ActRII-binding protein specifically binds ActRII and comprises a VH and a VL pair selected from the group consisting of: (a) a VH sequence of SEQ ID NO:2, 16, 22, 28, 34, or 40, and a VL sequence of SEQ ID NO:9; and wherein the protein binds ActRIIB; (b) a VH sequence of SEQ ID NO:45 or 57, and a VL sequence of SEQ ID NO:50; and wherein the protein binds ActRIIB; (c) a VH sequence of SEQ ID NO:63 or 77, and a VL sequence of SEQ ID NO:70; and wherein the protein binds ActRIIB; (d) a VH sequence of SEQ ID NO:84, 98, 105, 112, or 119, and a VL sequence of SEQ ID NO:91; and wherein the protein binds ActRIIB; and (e) a VH sequence of SEQ ID NO:125, and a VL sequence of SEQ ID NO:132 and wherein the protein binds ActRIIA. In a further aspect, the ActRII-binding protein comprises a VH and a VL pair selected from the group consisting of: (a) a VH sequence of SEQ ID NO:2 and a VL sequence of SEQ ID NO:9; (b) a VH sequence of SEQ ID NO:16 and a VL sequence of SEQ ID NO:9; (c) a VH sequence of SEQ ID NO:22 and a VL sequence of SEQ ID NO:9; (d) a VH sequence of SEQ ID NO:28 and a VL sequence of SEQ ID NO:9; (e) a VH sequence of SEQ ID NO:34 and a VL sequence of SEQ ID NO:9; (f) a VH sequence of SEQ ID NO:40 and a VL sequence of SEQ ID NO:9; (g) a VH sequence of SEQ ID NO:45 and a VL sequence of SEQ ID NO:50; (h) a VH sequence of SEQ ID NO:57 and a VL sequence of SEQ ID NO:50; (i) a VH sequence of SEQ ID NO:63 and a VL sequence of SEQ ID NO:70; (j) a VH sequence of SEQ ID NO:77 and a VL sequence of SEQ ID NO:70; (k) a VH sequence of SEQ ID NO:84 and a VL sequence of SEQ ID NO:91; (l) a VH sequence of SEQ ID NO:98 and a VL sequence of SEQ ID NO:91; (m) a VH sequence of SEQ ID NO:105 and a VL sequence of SEQ ID NO:91; (n) a VH sequence of SEQ ID NO:112 and a VL sequence of SEQ ID NO:91; (o) VH sequence of SEQ ID NO:119 and a VL sequence of SEQ ID NO:91; and (p) VH sequence of SEQ ID NO:125 and a VL sequence of SEQ ID NO:132.

In a further aspect, the ActRII-binding protein specifically binds ActRII and comprises a VH sequence of SEQ ID NO:144 and a VL sequence of SEQ ID NO:151, and the protein binds ActRIIB.

In a further aspect, the ActRII-binding protein specifically binds ActRII and comprises a VH sequence of SEQ ID NO:165 and a VL sequence of SEQ ID NO:172, and the protein binds ActIIRA and ActRIIB.

In some aspects, the ActRII-binding protein comprises a VH and VL pair selected from the group consisting of: (a) a VH having at least 90%, 95%, 97%, 98%, or 99% sequence identity to SEQ ID NO:2 and a VL having at least 90%, 95%, 97%, 98%, or 99% sequence identity to SEQ ID NO:9 and wherein the protein binds ActRIIB; (b) a VH having at least 90%, 95%, 97%, 98%, or 99% sequence identity to SEQ ID NO:16 and a VL having at least 90%, 95%, 97%, 98%, or 99% sequence identity to SEQ ID NO:9 and wherein the protein binds ActRIIB; (c) a VH having at least 90%, 95%, 97%, 98%, or 99% sequence identity to SEQ ID NO:22 and a VL having at least 90%, 95%, 97%, 98%, or 99% sequence identity to SEQ ID NO:9, and wherein the protein binds ActRIIB; (d) a VH having at least 90%, 95%, 97%, 98%, or 99% sequence identity to SEQ ID NO:28 and a VL having at least 90%, 95%, 97%, 98%, or 99% sequence identity to SEQ ID NO:9, and wherein the protein binds ActRIIB; (e) a VH having at least 90%, 95%, 97%, 98%, or 99% sequence identity to SEQ ID NO:34 and a VL having at least 90%, 95%, 97%, 98%, or 99% sequence identity to SEQ ID NO:9, and wherein the protein binds ActRIIB; (f) a VH having at least 90%, 95%, 97%, 98%, or 99% sequence identity to SEQ ID NO:40 and a VL having at least 90%, 95%, 97%, 98%, or 99% sequence identity to SEQ ID NO:9, and wherein the protein binds ActRIIB; (g) a VH having at least 90%, 95%, 97%, 98%, or 99% sequence identity to SEQ ID NO:45 and a VL having at least 90%, 95%, 97%, 98%, or 99% sequence identity to SEQ ID NO:50, and wherein the protein binds ActRIIB; (h) a VH having at least 90%, 95%, 97%, 98%, or 99% sequence identity to SEQ ID NO:57 and a VL having at least 90%, 95%, 97%, 98%, or 99% sequence identity to SEQ ID NO:50, wherein the protein binds ActRIIB; (i) a VH having at least 90%, 95%, 97%, 98%, or 99% sequence identity to SEQ ID NO:63 and a VL having at least 90%, 95%, 97%, 98%, or 99% sequence identity to SEQ ID NO:70, and wherein the protein binds ActRIIB; (j) a VH having at least 90%, 95%, 97%, 98%, or 99% sequence identity to SEQ ID NO:77 and a VL having at least 90%, 95%, 97%, 98%, or 99% sequence identity to SEQ ID NO:70; and wherein the protein binds ActRIIB; (k) a VH having at least 90%, 95%, 97%, 98%, or 99% sequence identity to SEQ ID NO:84 and a VL having at least 90%, 95%, 97%, 98%, or 99% sequence identity to SEQ ID NO:91, and wherein the protein binds ActRIIB and ActRIIA; (l) a VH having at least 90%, 95%, 97%, 98%, or 99% sequence identity to SEQ ID NO:98 and a VH having at least 90%, 95%, 97%, 98%, or 99% sequence identity to SEQ ID NO:91, and wherein the protein binds ActRIIB and ActRIIA; (m) a VH having at least 90%, 95%, 97%, 98%, or 99% sequence identity to SEQ ID NO:105 and a VL having at least 90%, 95%, 97%, 98%, or 99% sequence identity to SEQ ID NO:91, and wherein the protein binds ActRIIB and ActRIIA; (n) a VH having at least 90%, 95%, 97%, 98%, or 99% sequence identity to SEQ ID NO:112 and a VL having at least 90%, 95%, 97%, 98%, or 99% sequence identity to SEQ ID NO:91, and wherein the protein binds ActRIIB and ActRIIA; (o) a VH having at least 90%, 95%, 97%, 98%, or 99% sequence identity to SEQ ID NO:119 and a VL having at least 90%, 95%, 97%, 98%, or 99% sequence identity to SEQ ID NO:91, and wherein the protein binds ActRIIB and ActRIIA; and (p) a VH having at least 90%, 95%, 97%, 98%, or 99% sequence identity to SEQ ID NO:125 and a VL having at least 90%, 95%, 97%, 98%, or 99% sequence identity to SEQ ID NO:132, and wherein the protein binds ActRIIA. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein comprises a VH having at least 90%, 95%, 97%, 98%, or 99% sequence identity to SEQ ID NO:144 and a VL having at least 90%, 95%, 97%, 98%, or 99% sequence identity to SEQ ID NO:151; and the protein binds ActRIIB. In further aspects, the ActRIIB-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein comprises a VH having at least 90%, 95%, 97%, 98%, or 99% sequence identity to SEQ ID NO:165 and a VL having at least 90%, 95%, 97%, 98%, or 99% sequence identity to SEQ ID NO:172; and the protein binds ActIIRA and ActRIIB. In further aspects, the ActRII-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRII; (b) decreases the phosphorylation of Smads (e.g., Smad2 and/or Smad3) in cells expressing ActRII in the presence of an ActRII ligand (e.g., activin A or GDF8); (c) decreases the phosphorylation of ALK4 and/or ALK7 in cells expressing ActRII and ALK4 and/or ALK7 in the presence of an ActRII ligand; and (d) binds to ActRII with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein comprises a VH and VL pair selected from the group consisting of: (a) a VH sequence of SEQ ID NO:2 and a VL sequence of SEQ ID NO:9; (b) a VH sequence of SEQ ID NO:16 and a VL sequence of SEQ ID NO:9; (c) a VH sequence of SEQ ID NO:22 and a VL sequence of SEQ ID NO:9; (d) a VH sequence of SEQ ID NO:28 and a VL sequence of SEQ ID NO:9 (e) a VH sequence of SEQ ID NO:34 and a VL sequence of SEQ ID NO:9; (f) a VH sequence of SEQ ID NO:40 and a VL sequence of SEQ ID NO:9; (g) a VH sequence of SEQ ID NO:45 and a VL sequence of SEQ ID NO:50; (h) a VH sequence of SEQ ID NO:57 and a VL sequence of SEQ ID NO:50; (i) a VH sequence of SEQ ID NO:63 and a VL sequence of SEQ ID NO:70; (j) a VH sequence of SEQ ID NO:77 and a VL sequence of SEQ ID NO:70; (k) a VH sequence of SEQ ID NO:84 and a VL sequence of SEQ ID NO:91; (l) a VH sequence of SEQ ID NO:98 and a VL sequence of SEQ ID NO:91; (m) a VH sequence of SEQ ID NO:105 and a VL sequence of SEQ ID NO:91; (n) a VH sequence of SEQ ID NO:112 and a VL sequence of SEQ ID NO:91; (o) VH sequence of SEQ ID NO:119 and a sequence of SEQ ID NO:91; and (p) VH sequence of SEQ ID NO:125 and a sequence of SEQ ID NO:132.

In some aspects, the ActRII-binding protein comprises a VH sequence of SEQ ID NO:144 and a VL sequence of SEQ ID NO:151.

In some aspects, the ActRII-binding protein comprises a VH sequence of SEQ ID NO:165 and a VL sequence of SEQ ID NO:172.

In some aspects, the ActRII-binding protein specifically binds ActRIIB and comprises a VH having at least 90%, 95%, 97%, 98%, or 99% sequence identity to SEQ ID NO:2, 16, 22, 28, 34, 40, 45, 57, 63, or 77. In some aspects, the ActRII-binding protein comprises a VH having at least 90%, 95%, 97%, 98%, or 99% sequence identity to SEQ ID NO: 2. In some aspects, the ActRII-binding protein comprises a VH having at least 90%, 95%, 97%, 98%, or 99% sequence identity to SEQ ID NO:16. In some aspects, the ActRII-binding protein comprises a VH having at least 90%, 95%, 97%, 98%, or 99% sequence identity to SEQ ID NO: 22. In some aspects, the ActRII-binding protein comprises a VH having at least 90%, 95%, 97%, 98%, or 99% sequence identity to SEQ ID NO: 28. In some aspects, the ActRII-binding protein comprises a VH having at least 90%, 95%, 97%, 98%, or 99% sequence identity to SEQ ID NO: 34. In some aspects, the ActRII-binding protein comprises a VH having at least 90%, 95%, 97%, 98%, or 99% sequence identity to SEQ ID NO: 40. In some aspects, the ActRII-binding protein comprises a VH having at least 90%, 95%, 97%, 98%, or 99% sequence identity to SEQ ID NO: 45. In some aspects, the ActRII-binding protein comprises a VH having at least 90%, 95%, 97%, 98%, or 99% sequence identity to SEQ ID NO: 57. In some aspects, the ActRII-binding protein comprises a VH having at least 90%, 95%, 97%, 98%, or 99% sequence identity to SEQ ID NO:63. In some aspects, the ActRII-binding protein comprises a VH having at least 90%, 95%, 97%, 98%, or 99% sequence identity to SEQ ID NO:77. In some aspects, the ActRII-binding protein specifically binds ActRIIB and comprises a VL having at least 90%, 95%, 97%, 98%, or 99% sequence identity to SEQ ID NO:9, 50, or 70. In further aspects, the ActRII-binding protein specifically binds ActRIIB and comprises a VH having at least 90%, 95%, 97%, 98%, or 99% sequence identity to SEQ ID NO:2, 16, 22, 28, 34, or 40, and a VL having at least 90%, 95%, 97%, 98%, or 99% sequence identity to SEQ ID NO:9. In further aspects, the ActRII-binding protein specifically binds ActRIIB and comprises a VH having at least 90%, 95%, 97%, 98%, or 99% sequence identity to SEQ ID NO: 45 or 57. In some aspects, the ActRII-binding protein specifically binds ActRIIB and comprises a VL having at least 90%, 95%, 97%, 98%, or 99% sequence identity to SEQ ID NO:50. In further aspects, the ActRII-binding protein specifically binds ActRIIB and comprises a VH having at least 90%, 95%, 97%, 98%, or 99% sequence identity to SEQ ID NO: 45 or 57, and a VL having at least 90%, 95%, 97%, 98%, or 99% sequence identity to SEQ ID NO:50. In some aspects, the ActRII-binding protein specifically binds ActRIIB and comprises a VH and a VL, wherein, the VH has at least 90%, 95%, 97%, 98%, or 99% sequence identity to SEQ ID NO: 63 or 77; and the VL has at least 90%, 95%, 97%, 98%, or 99% sequence identity to SEQ ID NO:70. In further aspects, the ActRII-binding protein specifically binds ActRIIB and comprises a VH having at least 90%, 95%, 97%, 98%, or 99% sequence identity to SEQ ID NO: 63 or 77, and a VL having at least 90%, 95%, 97%, 98%, or 99% sequence identity to SEQ ID NO:70. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In some aspects, the ActRII-binding protein specifically binds ActRIIB and comprises a VH having at least 90%, 95%, 97%, 98%, or 99% sequence identity to SEQ ID NO:144. In some aspects, the ActRII-binding protein specifically binds ActRIIB and comprises a VL having at least 90%, 95%, 97%, 98%, or 99% sequence identity to SEQ ID NO:151. In some aspects, the ActRII-binding protein specifically binds ActRIIB and comprises a VH and a VL, wherein, the VH has at least 90%, 95%, 97%, 98%, or 99% sequence identity to SEQ ID NO:144; and the VL has at least 90%, 95%, 97%, 98%, or 99% sequence identity to SEQ ID NO:151. In further aspects, the ActRII-binding protein specifically binds ActRIIB and comprises a VH having the amino acid sequence of SEQ ID NO:144 and a VL having the amino acid sequence of SEQ ID NO:151. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In some aspects, the ActRII-binding protein specifically binds ActIIRA and ActRIIB and comprises a VH having at least 90%, 95%, 97%, 98%, or 99% sequence identity to SEQ ID NO:165. In some aspects, the ActRII-binding protein specifically binds ActIIRA and ActRIIB and comprises a VL having at least 90%, 95%, 97%, 98%, or 99% sequence identity to SEQ ID NO:172. In some aspects, the ActRII-binding protein specifically binds ActIIRA and ActRIIB and comprises a VH and a VL, wherein, the VH has at least 90%, 95%, 97%, 98%, or 99% sequence identity to SEQ ID NO:165; and the VL has at least 90%, 95%, 97%, 98%, or 99% sequence identity to SEQ ID NO:172. In further aspects, the ActRII-binding protein specifically binds ActIIRA and ActRIIB and comprises a VH having the amino acid sequence of SEQ ID NO:165 and a VL having the amino acid sequence of SEQ ID NO:172. In further aspects, the ActRII-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIA and/or ActRIIB; (b) decreases the phosphorylation of Smads (e.g., Smad2 and/or Smad3) in cells expressing ActRIIA and/or ActRIIB in the presence of an ActRIIA and/or ActRIIB ligand (e.g., activin A or GDF8); (c) decreases the phosphorylation of ALK4 and/or ALK7 in cells expressing ActRIIA and/or ActRIIB and ALK4 and/or ALK7 in the presence of an ActRIIA and/or ActRIIB ligand; and (d) binds to each of ActRIIA and ActRIIB with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics.

In some aspects, the ActRII-binding protein specifically binds ActRIIB and ActRIIA and comprises a VH having at least 90%, 95%, 97%, 98%, or 99% sequence identity to SEQ ID NO: SEQ ID NO:84, 98, 105, 112, or 119. In some aspects, the ActRII-binding protein specifically binds ActRIIB and ActRIIA and comprises a VH having at least 90%, 95%, 97%, 98%, or 99% sequence identity to SEQ ID NO:84. In some aspects, the ActRII-binding protein specifically binds ActRIIB and ActRIIA and comprises a VH having at least 90%, 95%, 97%, 98%, or 99% sequence identity to SEQ ID NO: SEQ ID NO: 98. In some aspects, the ActRII-binding protein specifically binds ActRIIB and ActRIIA and comprises a VH having at least 90%, 95%, 97%, 98%, or 99% sequence identity to SEQ ID NO: SEQ ID NO:105. In some aspects, the ActRII-binding protein specifically binds ActRIIB and ActRIIA and comprises a VH having at least 90%, 95%, 97%, 98%, or 99% sequence identity to SEQ ID NO: SEQ ID NO:112. In some aspects, the ActRII-binding protein specifically binds ActRIIB and ActRIIA and comprises a VH having at least 90%, 95%, 97%, 98%, or 99% sequence identity to SEQ ID NO: SEQ ID NO:119. In some aspects, the ActRII-binding protein specifically binds ActRIIB and ActRIIA and comprises a VL having at least 90%, 95%, 97%, 98%, or 99% sequence identity to SEQ ID NO:91. In further aspects, the ActRII-binding protein specifically binds ActRIIB and ActRIIA and comprises a VH having at least 90%, 95%, 97%, 98%, or 99% sequence identity to SEQ ID NO:84, 98, 105, 112, or 119, and a VL having at least 90%, 95%, 97%, 98%, or 99% sequence identity to SEQ ID NO:91. In further aspects, the ActRII-binding protein specifically binds ActRIIB and ActRIIA and comprises a VH having at least 90%, 95%, 97%, 98%, or 99% sequence identity to SEQ ID NO:84, and a VL having at least 90%, 95%, 97%, 98%, or 99% sequence identity to SEQ ID NO:91. In further aspects, the ActRII-binding protein specifically binds ActRIIB and ActRIIA and comprises a VH having at least 90%, 95%, 97%, 98%, or 99% sequence identity to SEQ ID NO: 98 and a VL having at least 90%, 95%, 97%, 98%, or 99% sequence identity to SEQ ID NO:91. In further aspects, the ActRII-binding protein specifically binds ActRIIB and ActRIIA and comprises a VH having at least 90%, 95%, 97%, 98%, or 99% sequence identity to SEQ ID NO:105 and a VL having at least 90%, 95%, 97%, 98%, or 99% sequence identity to SEQ ID NO:91. In further aspects, the ActRII-binding protein specifically binds ActRIIB and/or ActRIIA and comprises a VH having at least 90%, 95%, 97%, 98%, or 99% sequence identity to SEQ ID NO: 112 and a VL having at least 90%, 95%, 97%, 98%, or 99% sequence identity to SEQ ID NO:91. In further aspects, the ActRII-binding protein specifically binds ActRIIB and ActRIIA and comprises a VH having at least 90%, 95%, 97%, 98%, or 99% sequence identity to SEQ ID NO:119, and a VL having at least 90%, 95%, 97%, 98%, or 99% sequence identity to SEQ ID NO:91. In further aspects, the ActRIIB- and ActRIIA-binding protein has at least one characteristic selected from the group consisting of: (a) competes with an ActRII ligand (e.g., activin A, activin B, GDF1, GDF3, GDF8 (myostatin), GDF11, BMP6, BMP7, BMP9, or BMP10) for binding to ActRIIB and ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A or GDF8); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB and ActRIIA-binding protein has 2, 3, or 4 of the above characteristics. In some aspects, the ActRIIB and ActRIIA-binding protein has at least 2 or at least 3 of the above characteristics.

In some aspects, the ActRII-binding protein specifically binds ActRIIA and comprises a VH having at least 90%, 95%, 97%, 98%, or 99% sequence identity to SEQ ID NO:125. In some aspects, the ActRII-binding protein specifically binds ActRIIA and comprises a VL having at least 90%, 95%, 97%, 98%, or 99% sequence identity to SEQ ID NO:132. In some aspects, the ActRII-binding protein specifically binds ActRIIA and comprises a VH and a VL, wherein, the VH has at least 90%, 95%, 97%, 98%, or 99% sequence identity to SEQ ID NO:125; and the VL has at least 90%, 95%, 97%, 98%, or 99% sequence identity to SEQ ID NO:132. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In additional aspects an ActRII-binding protein competes for binding to ActRII with an antibody comprising a VH and a VL sequence pair disclosed herein. In additional aspects an ActRII-binding protein competes for binding to ActRII with an antibody comprising a VH and a VL sequence pair disclosed in Table 1. In certain aspects, an ActRII-binding protein binds to the same epitope as an ActRII-binding protein disclosed herein. In additional aspects, an ActRII-binding protein binds to the same epitope as an ActRII-binding protein disclosed in Table 1. The ability of an ActRII-binding protein to compete for binding with and/or bind the same epitope of ActRII as a reference ActRII-binding protein can readily be determined using techniques disclosed herein or otherwise known in the art.

In some aspects, the ActRII-binding protein specifically binds ActRIIB and comprises a VH of SEQ ID NO:2, 16, 22, 28, 34, 40, 45, 57, 63, or 77. In additional aspects, the ActRII-binding protein specifically binds ActRIIB and comprises a VL of SEQ ID NO:9, 50, or 70. In further aspects, the ActRII-binding protein specifically binds ActRIIB and comprises a VH of SEQ ID NO:2, 16, 22, 28, 34, 40, 45, 57, 63, or 77; and a VL of SEQ ID NO:9, 50, or 70. In some aspects, the ActRII-binding protein specifically binds ActRIIB and comprises a VH of SEQ ID NO:144. In additional aspects, the ActRII-binding protein specifically binds ActRIIB and comprises a VL of SEQ ID NO:151. In further aspects, the ActRII-binding protein specifically binds ActRIIB and comprises a VH of SEQ ID NO:144 and a VL of SEQ ID NO:151. In further aspects, the ActRII-binding protein specifically binds ActRIIB but does not specifically bind ActRIIA. In some aspects, the ActRII-binding protein specifically binds ActRIIA and ActRIIB and comprises a VH of SEQ ID NO:165. In additional aspects, the ActRII-binding protein specifically binds ActRIIA and ActRIIB and comprises a VL of SEQ ID NO:172. In further aspects, the ActRII-binding protein specifically binds ActRIIA and ActRIIB and comprises a VH of SEQ ID NO:165 and a VL of SEQ ID NO:172. In further aspects, the ActRII-binding protein specifically binds ActRIIA and ActRIIB.

In some aspects, the ActRII-binding protein binds amino acid residues NANWELERT (SEQ ID NO:157) of ActRIIB. In some aspects, the ActRII-binding protein binds amino acid residues NANWELERT (SEQ ID NO:157) of ActRIIB, but does not bind AcRIIA. In some aspects, the ActRII-binding protein binds amino acid residues VKKGCWLDD (SEQ ID NO:158) of ActRIIB, but does not bind AcRIIA. In some aspects, the ActRII-binding protein binds amino acid residues NANWELERT (SEQ ID NO:157) and amino acid residues VKKGCWLDD (SEQ ID NO:158) of ActRIIB. In further aspects, the ActRII-binding protein binds amino acid residues NANWELERT (SEQ ID NO:157) and amino acid residues VKKGCWLDD (SEQ ID NO:158) of ActRIIB, but does not bind ActRIIA.

In some aspects, the ActRII-binding protein binds a polypeptide selected from the group consisting of: (a) amino acid residues NANWELERT (SEQ ID NO:157) of ActRIIB; (b) amino acid residues CCEGNFCNER (SEQ ID NO:159) of ActRIIB; (c) amino acid residues CCEGNMCNEK (SEQ ID NO:161) of ActRIIA; and (d) amino acid residues ECLFFNANWEKD (SEQ ID NO:162) of ActRIIA.

In some aspects, the ActRII-binding protein binds a polypeptide or a set of polypeptides selected from the group consisting of: (a) amino acid residues NANWELERT (SEQ ID NO:157) and amino acid residues CCEGNFCNER (SEQ ID NO:159) of ActRIIB; (b) amino acid residues NANWELERT (SEQ ID NO:157) and amino acid residues VKKGCWLDD (SEQ ID NO:158) of ActRIIB; (c) amino acid residues NANWELERT (SEQ ID NO:157), amino acid residues CCEGNFCNER (SEQ ID NO:159), and amino acid residues GCWLDDFNCYDR (SEQ ID NO:160) of ActRIIB; (d) amino acid residues NANWELERT (SEQ ID NO:157) of ActRIIB and amino acid residues ECLFFNANWEKD (SEQ ID NO:162) of ActRIIA; (e) amino acid residues NANWELERT (SEQ ID NO:157), amino acid residues GCWLDDFNCYDR (SEQ ID NO:160), and amino acid residues VKKGCWLDD (SEQ ID NO:158) of ActRIIB; (f) amino acid residues CCEGNFCNER (SEQ ID NO:159) of ActRIIB and amino acid residues CCEGNMCNEK (SEQ ID NO:161) of ActRIIA; (g) amino acid residues CCEGNMCNEK (SEQ ID NO:161), amino acid residues ECLFFNANWEKD (SEQ ID NO:162), and amino acid residues CWLDDI NCYDRT (SEQ ID NO:163) of ActRIIA; (h) amino acid residues NANWELERT (SEQ ID NO:157), amino acid residues CCEGNFCNER (SEQ ID NO:159), and amino acid residues GCWLDDFNCYDR (SEQ ID NO:160) of ActRIIB, and amino acid residues CCEG NMCNEK (SEQ ID NO:161), amino acid residues ECLFFNANWEKD (SEQ ID NO:162), and amino acid residues CWLDDINCYDRT (SEQ ID NO:163) of ActRIIA.

In some aspects, the ActRII-binding protein competes for binding to ActRIIB with an antibody comprising a VH of SEQ ID NO:2, 16, 22, 28, 34, 40, 45, 57, 63, 77, or 144, and a VL of SEQ ID NO:9, 50, 70, or 151. In further aspects, the ActRII-binding protein binds the same epitope of ActRIIB and/or ActRIIA as an antibody comprising a VH of SEQ ID NO:2, 16, 22, 28, 34, 40, 45, 57, 63, 77, or 144, and a VL of SEQ ID NO:9, 50, 70, or 151.

In some aspects, the ActRIIB-binding protein (e.g., an anti-ActRIIB antibody) comprises a VH of SEQ ID NO:2 and a VL of SEQ ID NO:9. In some aspects, an ActRIIB-binding protein competes for binding to ActRIIB with an antibody comprising a VH of SEQ ID NO:2 and a VL of SEQ ID NO:9. In further aspects, the ActRII-binding protein binds the same epitope of ActRIIB as an antibody comprising a VH of SEQ ID NO:2 and a VL of SEQ ID NO:9.

In some aspects, the ActRIIB-binding protein comprises a VH of SEQ ID NO:16 and a VL of SEQ ID NO:9. In some aspects, an ActRIIB-binding protein competes for binding to ActRIIB with an antibody comprising a VH of SEQ ID NO:16 and a VL of SEQ ID NO:9. In further aspects, the ActRII-binding protein binds the same epitope of ActRIIB as an antibody comprising a VH of SEQ ID NO:16 and a VL of SEQ ID NO:9.

In some aspects, the ActRIIB-binding protein comprises a VH of SEQ ID NO:22 and a VL of SEQ ID NO:9. In some aspects, an ActRIIB-binding protein competes for binding to ActRIIB with an antibody comprising a VH of SEQ ID NO:22 and a VL of SEQ ID NO:9. In further aspects, the ActRII-binding protein binds the same epitope of ActRIIB as an antibody comprising a VH of SEQ ID NO:22 and a VL of SEQ ID NO:9.

In some aspects, the ActRIIB-binding protein comprises a VH of SEQ ID NO:28 and a VL of SEQ ID NO:9. In some aspects, an ActRIIB-binding protein competes for binding to ActRIIB with an antibody comprising a VH of SEQ ID NO:28 and a VL of SEQ ID NO:9. In further aspects, the ActRII-binding protein binds the same epitope of ActRIIB as an antibody comprising a VH of SEQ ID NO:28 and a VL of SEQ ID NO:9.

In some aspects, the ActRIIB-binding protein comprises a VH of SEQ ID NO:34 and a VL of SEQ ID NO:9. In some aspects, an ActRIIB-binding protein competes for binding to ActRIIB with an antibody comprising a VH of SEQ ID NO:34 and a VL of SEQ ID NO:9. In further aspects, the ActRII-binding protein binds the same epitope of ActRIIB as an antibody comprising a VH of SEQ ID NO:34 and a VL of SEQ ID NO:9.

In some aspects, the ActRIIB-binding protein comprises a VH of SEQ ID NO:40 and a VL of SEQ ID NO:9. In some aspects, an ActRIIB-binding protein competes for binding to ActRIIB with an antibody comprising a VH of SEQ ID NO:40 and a VL of SEQ ID NO:9. In further aspects, the ActRII-binding protein binds the same epitope of ActRIIB as an antibody comprising a VH of SEQ ID NO:40 and a VL of SEQ ID NO:9.

In some aspects, the ActRIIB-binding protein comprises a VH of SEQ ID NO:45 and a VL of SEQ ID NO:50. In some aspects, an ActRIIB-binding protein competes for binding to ActRIIB with an antibody comprising a VH of SEQ ID NO:45 and a VL of SEQ ID NO:50. In further aspects, the ActRII-binding protein binds the same epitope of ActRIIB as an antibody comprising a VH of SEQ ID NO:45 and a VL of SEQ ID NO:50.

In some aspects, the ActRIIB-binding protein comprises a VH of SEQ ID NO:57 and a VL of SEQ ID NO:50. In some aspects, an ActRIIB-binding protein competes for binding to ActRIIB with an antibody comprising a VH of SEQ ID NO:57 and a VL of SEQ ID NO:50. In further aspects, the ActRII-binding protein binds the same epitope of ActRIIB as an antibody comprising a VH of SEQ ID NO:57 and a VL of SEQ ID NO:50.

In some aspects, the ActRIIB-binding protein comprises a VH of SEQ ID NO:63 and a VL of SEQ ID NO:70. In some aspects, an ActRIIB-binding protein competes for binding to ActRIIB with an antibody comprising a VH of SEQ ID NO:63 and a VL of SEQ ID NO:70. In further aspects, the ActRII-binding protein binds the same epitope of ActRIIB as an antibody comprising a VH of SEQ ID NO:63 and a VL of SEQ ID NO:70.

In some aspects, the ActRIIB-binding protein comprises a VH of SEQ ID NO:77 and a VL of SEQ ID NO:70. In some aspects, an ActRIIB-binding protein competes for binding to ActRIIB with an antibody comprising a VH of SEQ ID NO:77 and a VL of SEQ ID NO:70. In further aspects, the ActRII-binding protein binds the same epitope of ActRIIB as an antibody comprising a VH of SEQ ID NO:77 and a VL of SEQ ID NO:70.

In some aspects, the ActRIIB-binding protein comprises a VH of SEQ ID NO:144 and a VL of SEQ ID NO:151. In some aspects, an ActRIIB-binding protein competes for binding to ActRIIB with an antibody comprising a VH of SEQ ID NO:144 and a VL of SEQ ID NO:151. In further aspects, the ActRII-binding protein binds the same epitope of ActRIIB as an antibody comprising a VH of SEQ ID NO:144 and a VL of SEQ ID NO:151.

In some aspects, the ActRII-binding protein comprises a VH of SEQ ID NO:165 and a VL of SEQ ID NO:172. In some aspects, an ActRIIB-binding protein competes for binding to ActRIIB with an antibody comprising a VH of SEQ ID NO:165 and a VL of SEQ ID NO:172. In further aspects, the ActRII-binding protein binds the same epitope of ActRIIB as an antibody comprising a VH of SEQ ID NO:165 and a VL of SEQ ID NO:172.

In some aspects, the ActRII-binding protein comprises a VH of SEQ ID NO:165 and a VL of SEQ ID NO:172. In some aspects, an ActRIIA-binding protein competes for binding to ActRIIA with an antibody comprising a VH of SEQ ID NO:165 and a VL of SEQ ID NO:172. In further aspects, the ActRII-binding protein binds the same epitope of ActRIIA as an antibody comprising a VH of SEQ ID NO:165 and a VL of SEQ ID NO:172.

In some aspects, the ActRIIB-binding protein competes for binding to amino acid residues NANWELERT (SEQ ID NO:157) of ActRIIB with an antibody comprising a VH of SEQ ID NO:144 and a VL of SEQ ID NO:151. In some aspects, the ActRIIB-binding protein competes for binding to amino acid residues VKKGCWLDD (SEQ ID NO:158) of ActRIIB with an antibody comprising a VH of SEQ ID NO:144 and a VL of SEQ ID NO:151. In some aspects, the ActRIIB-binding protein competes for binding to amino acid residues NANWELERT (SEQ ID NO:157) and amino acid residues VKKGCWLDD (SEQ ID NO:158) of ActRIIB, with an antibody comprising a VH of SEQ ID NO:144 and a VL of SEQ ID NO:151. In further aspects, the ActRIIB-binding protein does not specifically bind ActRIIA.

In some aspects, the ActRII-binding protein competes for binding to ActRIIB and/or ActRIIA with an antibody comprising a VH of SEQ ID NO:84, 98, 105, 112, or 119 and a VL of SEQ ID NO:91. In further aspects, the ActRII-binding protein binds the same epitope of ActRIIB and/or ActRIIA as an antibody comprising a VH of SEQ ID NO:84, 98, 105, 112, or 119; and a VL of SEQ ID NO:91.

In some aspects, the ActRII-binding protein binds amino acid residues CCEGNFCNER (SEQ ID NO:159) of ActRIIB.

In some aspects, the ActRII-binding protein binds amino acid residues GCWLDDFNCYDR (SEQ ID NO:160) of ActRIIB.

In some aspects, the ActRII-binding protein binds amino acid residues NANWELERT (SEQ ID NO:157) of ActRIIB. In some aspects, the ActRII-binding protein binds amino acid residues NANWELERT (SEQ ID NO:157) and amino acid residues GCWLDDFNCYDR (SEQ ID NO:160) of ActRIIB. In some embodiments, the ActRII-binding protein binds amino acid residues NANWELERT (SEQ ID NO:157) and amino acid residues CCEGNFCNER (SEQ ID NO:159) of ActRIIB. In further embodiments, the ActRII-binding protein binds amino acid residues NANWELERT (SEQ ID NO:157), amino acid residues CCEGNFCNER (SEQ ID NO:159), and amino acid residues GCWLDDFNCYDR (SEQ ID NO:160) of ActRIIB.

In some aspects, the ActRII-binding protein binds amino acid residues CCEGNMCNEK (SEQ ID NO:161) of ActRIIA.

In some aspects, the ActRII-binding protein binds amino acid residues ECLFFNANWEKD (SEQ ID NO:162) of ActRIIA. In further aspects, the ActRII-binding protein binds amino acid residues CCEGNMCNEK (SEQ ID NO:161) and amino acid residues ECLFFNANWEKD (SEQ ID NO:162) of ActRIIA.

In some aspects, the ActRII-binding protein binds amino acid residues CWLDDINCYDRT (SEQ ID NO:163) of ActRIIA. In further embodiments, the ActRII-binding protein binds amino acid residues CCEGNMCNEK (SEQ ID NO:161), amino acid residues ECLFFNANWEKD (SEQ ID NO:162), and amino acid residues CWLDDINCYDRT (SEQ ID NO:163) of ActRIIA.

In some aspects, the ActRII-binding protein binds amino acid residues CCEGNFCNER (SEQ ID NO:159) of ActRIIB and amino acid residues CCEGNMCNEK (SEQ ID NO:161) of ActRIIA.

In some aspects, the ActRII-binding protein binds amino acid residues NANWELERT (SEQ ID NO:157) of ActRIIB and amino acid residues ECLFFNANWEKD (SEQ ID NO:162) of ActRIIA. In further aspects, the ActRII-binding protein binds amino acid residues CCEGNFCNER (SEQ ID NO:159) and amino acid residues NANWELERT (SEQ ID NO:157) of ActRIIB and amino acid residues CCEGNMCNEK (SEQ ID NO:161) and amino acid residues ECLFFNANWEKD (SEQ ID NO:162) of ActRIIA. In further aspects, the ActRII-binding protein binds amino acid residues CCEGNFCNER (SEQ ID NO:159), amino acid residues NANWELERT (SEQ ID NO:157) and amino acid residues GCWLDDFNCYDR (SEQ ID NO:160) of ActRIIB and amino acid residues CCEGNMCNEK (SEQ ID NO:161), amino acid residues ECLFFNANWEKD (SEQ ID NO:162), and amino acid residues CWLDDINCYDRT (SEQ ID NO:163) of ActRIIA.

In some aspects, the ActRIIB- and ActRIIA-binding protein comprises a VH of SEQ ID NO:84 and a VL of SEQ ID NO:91. In some aspects, an ActRIIB-binding protein competes for binding to ActRIIB and ActRIIA with an antibody comprising a VH of SEQ ID NO:84 and a VL of SEQ ID NO:91. In further aspects, the ActRII-binding protein binds the same epitope of ActRIIB and ActRIIA as an antibody comprising a VH of SEQ ID NO:84 and a VL of SEQ ID NO:91.

In some aspects, the ActRIIB- and ActRIIA-binding protein comprises a VH of SEQ ID NO:165 and a VL of SEQ ID NO:172. In some aspects, an ActRIIB-binding protein competes for binding to ActRIIB and ActRIIA with an antibody comprising a VH of SEQ ID NO:165 and a VL of SEQ ID NO:172. In further aspects, the ActRII-binding protein binds the same epitope of ActRIIB and ActRIIA as an antibody comprising a VH of SEQ ID NO:165 and a VL of SEQ ID NO:172.

In some aspects, the ActRIIB- and ActRIIA-binding protein competes for binding to amino acid residues CCEGNFCNER (SEQ ID NO:159) of ActRIIB with an antibody comprising a VH of SEQ ID NO:84 and a VL of SEQ ID NO:91. In some aspects, the ActRIIB and ActRIIA-binding protein competes for binding to amino acid residues NANWELERT (SEQ ID NO:157) of ActRIIB with an antibody comprising a VH of SEQ ID NO:84 and a VL of SEQ ID NO:91. In further aspects, the ActRIIB- and ActRIIA-binding protein competes for binding to amino acid residues CCEGNFCNER (SEQ ID NO:159) and amino acid residues NANWELERT (SEQ ID NO:157) of ActRIIB with an antibody comprising a VH of SEQ ID NO:84 and a VL of SEQ ID NO:91.

In some aspects, the ActRIIB- and ActRIIA-binding protein competes for binding to amino acid residues CCEGNFCNER (SEQ ID NO:159) of ActRIIB with an antibody comprising a VH of SEQ ID NO:165 and a VL of SEQ ID NO:172. In some aspects, the ActRIIB and ActRIIA-binding protein competes for binding to amino acid residues NANWELERT (SEQ ID NO:157) of ActRIIB with an antibody comprising a VH of SEQ ID NO:165 and a VL of SEQ ID NO:172. In further aspects, the ActRIIB- and ActRIIA-binding protein competes for binding to amino acid residues CCEGNFCNER (SEQ ID NO:159) and amino acid residues NANWELERT (SEQ ID NO:157) of ActRIIB with an antibody comprising a VH of SEQ ID NO:165 and a VL of SEQ ID NO:172.

In some aspects, the ActRIIB- and ActRIIA-binding protein competes for binding to amino acid residues GCWLDDFNCYDR (SEQ ID NO:160) of ActRIIB with an antibody comprising a VH of SEQ ID NO:84 and a VL of SEQ ID NO:91.

In some aspects, the ActRIIB- and ActRIIA-binding protein competes for binding to amino acid residues GCWLDDFNCYDR (SEQ ID NO:160) of ActRIIB with an antibody comprising a VH of SEQ ID NO:165 and a VL of SEQ ID NO:172.

In some aspects, the ActRIIB- and ActRIIA-binding protein competes for binding to amino acid residues CCEGNFCNER (SEQ ID NO:159), amino acid residues NANWELERT (SEQ ID NO:157), and amino acid residues GCWLDDFNCYDR (SEQ ID NO:160) of ActRIIB with an antibody comprising a VH of SEQ ID NO:84 and a VL of SEQ ID NO:91.

In some aspects, the ActRIIB- and ActRIIA-binding protein competes for binding to amino acid residues CCEGNFCNER (SEQ ID NO:159), amino acid residues NANWELERT (SEQ ID NO:157), and amino acid residues GCWLDDFNCYDR (SEQ ID NO:160) of ActRIIB with an antibody comprising a VH of SEQ ID NO:165 and a VL of SEQ ID NO:172.

In some aspects, the ActRII-binding protein specifically binds ActRIIB and ActRIIA and comprises a VH of SEQ ID NO:84, 98, 105, 112, or 119. In additional aspects, the ActRII-binding protein specifically binds ActRIIB and ActRIIA and comprises a VL of SEQ ID NO:91. In further aspects, the ActRII-binding protein specifically binds ActRIIB and ActRIIA and comprises a VH of SEQ ID NO:84, 98, 105, 112, or 119; and a VL of SEQ ID NO:91.

In some aspects, the ActRII-binding protein specifically binds ActRIIB and ActRIIA and comprises a VH of SEQ ID NO:165. In additional aspects, the ActRII-binding protein specifically binds ActRIIB and ActRIIA and comprises a VL of SEQ ID NO:172. In further aspects, the ActRII-binding protein specifically binds ActRIIB and ActRIIA and comprises a VH of SEQ ID NO:165; and a VL of SEQ ID NO:172.

In some aspects, the ActRIIB- and ActRIIA-binding protein comprises a VH of SEQ ID NO:84 and a VL of SEQ ID NO:91. In further aspects, the ActRII-binding protein binds the same epitope of ActRIIB and ActRIIA as an antibody comprising a VH of SEQ ID NO:84 and a VL of SEQ ID NO:91.

In some aspects, the ActRIIB- and ActRIIA-binding protein comprises a VH of SEQ ID NO:98 and a VL of SEQ ID NO:91. In some aspects, an ActRIIB-binding protein competes for binding to ActRIIB and ActRIIA with an antibody comprising a VH of SEQ ID NO:98 and a VL of SEQ ID NO:91. In further aspects, the ActRII-binding protein binds the same epitope of ActRIIB and ActRIIA as an antibody comprising a VH of SEQ ID NO:98 and a VL of SEQ ID NO:91.

In some aspects, the ActRIIB- and ActRIIA-binding protein comprises a VH of SEQ ID NO:105 and a VL of SEQ ID NO:91. In some aspects, an ActRIIB-binding protein competes for binding to ActRIIB and ActRIIA with an antibody comprising a VH of SEQ ID NO:105 and a VL of SEQ ID NO:91. In further aspects, the ActRII-binding protein binds the same epitope of ActRIIB and ActRIIA as an antibody comprising a VH of SEQ ID NO:105 and a VL of SEQ ID NO:91.

In some aspects, the ActRIIB- and ActRIIA-binding protein comprises a VH of SEQ ID NO:112 and a VL of SEQ ID NO:91. In some aspects, an ActRIIB-binding protein competes for binding to ActRIIB and ActRIIA with an antibody comprising a VH of SEQ ID NO:112 and a VL of SEQ ID NO:91. In further aspects, the ActRII-binding protein binds the same epitope of ActRIIB and ActRIIA as an antibody comprising a VH of SEQ ID NO:112 and a VL of SEQ ID NO:91.

In some aspects, the ActRIIB- and ActRIIA-binding protein comprises a VH of SEQ ID NO:119 and a VL of SEQ ID NO:91. In some aspects, an ActRIIB-binding protein competes for binding to ActRIIB and ActRIIA with an antibody comprising a VH of SEQ ID NO:119 and a VL of SEQ ID NO:91. In further aspects, the ActRII-binding protein binds the same epitope of ActRIIB and ActRIIA as an antibody comprising a VH of SEQ ID NO:119 and a VL of SEQ ID NO:91.

In some aspects, the ActRIIA-binding protein comprises a VH of SEQ ID NO:125 and a VL of SEQ ID NO:132. In some aspects, an ActRIIA-binding protein competes for binding to ActRIIA with an antibody comprising a VH of SEQ ID NO:125 and a VL of SEQ ID NO:132. In further aspects, the ActRII-binding protein binds the same epitope of ActRIIA as an antibody comprising a VH of SEQ ID NO:125 and a VL of SEQ ID NO:132.

In some aspects, the ActRII-binding protein specifically binds ActRIIB and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a) VH-CDR1 has the amino acid sequence of SEQ ID NO:3 or 58; (b) VH-CDR2 has the amino acid sequence of SEQ ID NO:4 or 59; or (c) VH-CDR3 has the amino acid sequence of SEQ ID NO:46. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In some aspects, the ActRII-binding protein specifically binds ActRIIB and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a) VL-CDR1 has the amino acid sequence of SEQ ID NO:51; (b) VL-CDR2 has the amino acid sequence of SEQ ID NO:52; or (c) VL-CDR3 has the amino acid sequence of SEQ ID NO:53. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In additional aspects, the ActRII-binding protein specifically binds ActRIIB and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a) VH-CDR1 has the amino acid sequence of SEQ ID NO:3 or 58; (b) VH-CDR2 has the amino acid sequence of SEQ ID NO:4 or 59; (c) VH-CDR3 has the amino acid sequence of SEQ ID NO:46; (d) VL-CDR1 has the amino acid sequence of SEQ ID NO:51; (e) VL-CDR2 has the amino acid sequence of SEQ ID NO:52; or (f) VL-CDR3 has the amino acid sequence of SEQ ID NO:53. In further aspects, the ActRIIB-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB; (b) decreases the phosphorylation of Smads (e.g., Smad2 and/or Smad3) in cells expressing ActRIIB in the presence of an ActRIIB ligand (e.g., activin A or GDF8); (c) decreases the phosphorylation of ALK4 and/or ALK7 in cells expressing ActRIIB and ALK4 and/or ALK7 in the presence of an ActRIIB ligand; and (d) binds to ActRIIB with a $K_D$ of ≤1 nM and ≥1 pM (e.g., as determined by BIACORE® analysis). In some aspects, the ActRIIB-binding protein has 2, 3, or 4 of the above characteristics. In some aspects, the ActRIIB-binding protein has at least 2 or at least 3 of the above characteristics.

In further aspects, the ActRII-binding protein specifically binds ActRIIB and ActRIIA and comprises a set of VH antigen binding domains (ABDs): VH-ABD1, VH-ABD2, VH-ABD3, VL-ABD1, VL-ABD2, and VL-ABD3, wherein: (a) VH-ABD1 has the amino acid sequence of SEQ ID NO:140; (b) VH-ABD2 has the amino acid sequence of SEQ ID NO:141; (c) VH-ABD3 has the amino acid sequence of SEQ ID NO:142; (d) VL-ABD1 has the amino acid sequence of SEQ ID NO:92; (e) VL-ABD2 has the amino acid sequence of SEQ ID NO:93; or (f) VL-ABD3 has the amino acid sequence of SEQ ID NO:94. In further aspects, the ActRIIB-binding protein comprises a VH and a VL. In further aspects, the ActRIIB- and ActRIIA-binding protein has at least one characteristic selected from the group consisting of (a) competes with an ActRII ligand (e.g., activin A, activin B, GDF1, GDF3, GDF8 (myostatin), GDF11, BMP6, BMP7, BMP9, or BMP10) for binding to ActRIIB or ActRIIA; (b) decreases the phosphorylation of Smads (e.g., Smad2 and/or Smad3) in cells expressing ActRIIB and/or ActRIIA in the presence of an ActRIIB and/or ActRIIA ligand (e.g., activin A); (c) decreases the phosphorylation of ALK4 and/or ALK7 in cells expressing ActRIIB and/or ActRIIA and ALK4 and/or ALK7 in the presence of an ActRIIB and/or ActRIIA ligand; and (d) binds to ActRIIB and/or ActRIIA with a $K_D$ of ≤1 nM and ≥1 pM (e.g., as determined by BIACORE® analysis). In some aspects, the ActRIIB- and ActRIIA-binding protein has 2, 3, or 4 of the above characteristics. In some aspects, the ActRIIB- and ActRIIA-binding protein has at least 2 or at least 3 of the above characteristics.

In some aspects, the ActRII-binding protein specifically binds ActRIIA and comprises a VH and a VL wherein the VH sequence is identical to, or has a total of one, two, three, four, five, six, seven, eight, nine, ten, fewer than fifteen, or zero, amino acid substitutions, deletions, and/or insertions from a reference VH sequence of SEQ ID NO:125, and wherein the VL sequence is identical to, or has a total of one, two, three, four, five, six, seven, eight, nine, ten, fewer than fifteen, or zero, amino acid substitutions, additions and/or deletions from a reference VL sequence of SEQ ID NO:132. In further aspects, the ActRIIA-binding protein has at least one characteristic selected from the group consisting of (a) competes with an ActRIIA ligand (e.g., activin A, activin B, GDF1, GDF3, or Nodal); (b) decreases the phosphorylation of Smads (e.g., Smad2 and/or Smad3) in cells expressing ActRIIA in the presence of an ActRIIA ligand (e.g., activin A); (c) decreases the phosphorylation of ALK4 and/or ALK7 in cells expressing ActRIIA and ALK4 and/or ALK7 in the presence of an ActRIIA ligand; and (d) binds to ActRIIA with a $K_D$ of ≤1 nM and ≥1 pM (e.g., as determined by BIACORE® analysis). In some aspects, the ActRIIA-binding protein has 2, 3, or 4 of the above characteristics. In some aspects, the ActRIIA-binding protein has at least 2 or at least 3 of the above characteristics.

In some aspects, the ActRII-binding protein is an antibody that specifically binds ActRII. In some aspects, the anti-ActRII specifically binds ActRIIB and/or ActRIIA. In some aspects, the anti-ActRII antibody is a murine antibody, a humanized antibody, a chimeric antibody, a monoclonal antibody, a polyclonal antibody, a recombinant antibody, a multispecific antibody, or any combination thereof. In some aspects the anti-ActRII antibody is an Fv fragment, an Fab fragment, an F(ab')2 fragment, an Fab' fragment, a dsFv fragment, an scFv fragment, or an sc(Fv)2 fragment.

In some aspects, the ActRII-binding protein specifically binds ActRII (e.g., ActRIIA and/or ActRIIB) and blocks an activity of an ActRII-ligand (e.g., GDF8 (myostatin) and/or activin). In some aspects the ActRII-binding protein specifically binds ActRII (e.g., and decreases the inhibition of muscle formation or the increase in fat formation associated with the activity of an ActRII ligand (e.g., GDF8 (myostatin and/or activin). In some aspects the ActRII-binding protein specifically binds ActRII and treats or ameliorates one or more conditions associated with a muscle disorder or a metabolic disorder. In some aspects, the muscle disorder is muscle wasting due to disease or disuse. In some aspects, the metabolic disorder is diabetes, obesity, hyperglycemia, or bone loss.

In particular aspects, the ActRIIB-binding protein (e.g., an anti-ActRIIB antibody or an anti-ActRIIB and ActRIIA antibody) inhibits or decreases the binding of ActRIIB by GDF8 (myostatin) or GDF8-mediated ActRIIB Smad signaling. In another aspect, the ActRIIB-binding protein decreases the inhibition of muscle formation or the increase in fat formation. In some aspects the ActRIIB-binding protein binds ActRIIB and inhibits or decreases one or more conditions associated with a muscle disorder or a metabolic disorder. In some aspects, the muscle disorder is muscle wasting, due to disease or disuse. In some aspects, the metabolic disorder is diabetes, obesity, hyperglycemia, or bone loss increases muscle mass or strength in a subject.

In certain aspects, the blocking of ActRII (e.g., ActRIIB and/or ActRIIA) activity by an ActRII-binding protein (e.g., an anti-ActRIIB antibody and an anti-ActRIIA antibody) described herein, inhibits or decreases one or more conditions associated with a muscle disorder, such as muscle wasting. In further aspects the blocking of ActRII inhibits or decreases one or more conditions associated with muscle wasting due to disease or disuse. In particular aspects, the ActRII-binding protein (e.g., an anti-ActRIIB antibody or an anti-ActRIIB and ActRIIA antibody) inhibits or decreases the binding to ActRIIB by GDF8. In another aspect the ActRIIB-binding protein inhibits or decreases the inhibition of muscle differentiation by a Smad-dependent pathway.

In some aspects, the ActRII-binding protein specifically binds ActRIIB and blocks an ActRIIB ligand-mediated activity. Some ActRIIB ligands such as GDF-8 are known to be a negative regulator of skeletal muscle tissue and myostatin signaling is known to lead to muscle mass. ActRIIB ligand-mediated signalling can also modulate the production of muscle-specific enzymes (e.g., creatine kinase), stimulate myoblast proliferation, and modulate preadipocyte differentiation to adipocytes. Increased myostatin activity has been associated with muscle wasting disorders, muscle loss due to inactivity, and metabolic disorders including diabetes, obesity, hyperglycemia, and bone loss. Increased ActRIIB ligand-mediated activity has also been associated with age-related increases in fat to muscle ratios, and age-related muscular atrophy. In some aspects the ActRII-binding protein specifically binds ActRIIB and decreases the inhibition of muscle formation or the increase in fat formation associated with the activity of some ActRIIB ligands-. In some aspects the ActRII-binding protein specifically binds ActRIIB and treats or ameliorates one or more conditions associated with a muscle disorder or a metabolic disorder. In some aspects, the muscle disorder is muscle wasting due to disease or disuse. In some aspects, the metabolic disorder is diabetes, obesity, hyperglycemia, or bone loss. ActRIIB ligand-mediated activity can be determined using art-recognized methods, such as those described herein.

In certain aspects, the blocking of ActRII (e.g., ActRIIB and/or ActRIIA) activity by an ActRII-binding protein (e.g., an anti-ActRIIB antibody and an anti-ActRIIA antibody) described herein, reduces one or more conditions associated with fibrosis. In particular aspects, the ActRIIB-binding protein inhibits or decreases ActRIIB-mediated development of fibrotic lesions, weight loss or other clinical symptoms, and/or altered expression of biological molecules (e.g., mRNA or protein expression) associated with the development of a fibrotic condition. In particular aspects, the ActRIIA-binding protein inhibits or decreases ActRIIA-mediated development of fibrotic lesions, weight loss or other clinical symptoms, and/or altered expression of biological molecules (e.g., mRNA or protein expression) associated with the development of a fibrotic condition.

As noted above, an anti-ActRII antibody (e.g., a full-length ActRIIB-antibody and an ActRII-binding antibody fragment, and a variant and derivative thereof) containing a VH and/or VL amino acid sequence that binds ActRII can have at least 85%, 90%, 95%, 96%, 97%, 98% or 99% sequence identity to a sequence set forth herein. In some aspects, the VH and/or VL amino acid sequence(s) that binds ActRII comprise 8, 7, 6, 5, 4, 3, 2, 1 amino acid additions, substitutions (e.g., conservative substitutions) or deletions relative to a sequence set forth herein. In additional aspects, the VH and/or VL amino acid sequence that binds ActRII comprise 1, 2, 3, 4, 5 or more amino acid additions, substitutions (e.g., conservative substitutions) or deletions relative to a sequence set forth herein. An anti-ActRII antibody containing VH and VL regions having a certain percent similarity to a VH region or VL region, or having one or more substitutions, deletions and/or insertions (e.g., conservative substitutions) can be obtained by mutagenesis (e.g., site-directed or PCR-mediated mutagenesis) of nucleic acid molecules encoding VH and/or VL regions described herein, followed by testing of the encoded altered antibody for binding to ActRII and optionally testing for retained function using the functional assays described herein or an assay known in the art that can routinely be modified to test the retained function.

The affinity or avidity of an ActRII-binding protein such as, an anti-ActRIIB antibody (e.g., a full-length ActRIIB-antibody and an ActRII-binding antibody fragment, and a variant and derivative thereof), for hActRIIB, murActRIIB, can be determined experimentally using any suitable method known in the art, e.g., flow cytometry, enzyme-linked immunosorbent assay (ELISA), or radioimmunoassay (RIA), or kinetics (e.g., BIACORE® or KINEXA® analysis). Direct binding assays and competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein.) The measured affinity of a particular antibody-antigen interaction can vary if measured under different conditions (e.g., salt concentration, pH, temperature). Thus, measurements of affinity and other ActRII-binding parameters (e.g., $K_D$ or Kd, $K_{on}$, $K_{off}$) are made with standardized solutions of ActRII-binding proteins and ActRII and the measurements are performed using standardized conditions and methods, as described herein or otherwise known in the art.

The disclosure further provides an ActRII-binding protein such as, an anti-ActRIIB antibody and/or an Anti-ActRIIA antibody as described herein, where the ActRII-binding protein is conjugated to a heterologous agent. In certain aspects the heterologous agent is an antimicrobial agent, a therapeutic agent, a prodrug, a peptide, a protein, an enzyme, a lipid, a biological response modifier, a pharmaceutical agent, a lymphokine, a heterologous antibody or antibody fragment, a detectable label, or a polyethylene glycol (PEG). Heteroconjugate ActRII-binding proteins are discussed in more detail elsewhere herein.

In certain aspects, the ActRII-binding protein is not an anti-ActRII antibody. A variety of methods for identifying and producing non-antibody polypeptides that bind with high affinity to a protein target are known in the art. See, e.g., Skerra, Curr. *Opin. Biotech.* 18:295-304 (2007); Hosse et al., *Protein Science* 15:14-27 (2006); Gill et al., *Curr. Opin. Biotechnol.* 17:653-658 (2006); Nygren, *FEBSJ.* 275:2668-2676 (2008); and Skerra, *FEBS J.* 275:2677-2683 (2008), each of which is incorporated by reference herein in its entirety. In some aspects, phage display technology can been used to identify/produce an ActRII-binding protein. In some aspects, the ActRII-binding protein comprises a protein scaffold based on a type selected from the group consisting of VASP polypeptides, avian pancreatic polypeptide (aPP), tetranectin (based on CTLD3), affilin (based on γB-crystallin/ubiquitin), a knottin, an SH3 domain, a PDZ domain, tendamistat, transferrin, an ankyrin consensus repeat domain (e.g., DARPins), a lipocalin protein fold (e.g., anticalins and Duocalins), a Protein Epitope Mimetic (PEM), a maxybody/avimer, a domain antibody a fibronectin domain (e.g., 10 Fn3, see, e.g., U.S. Appl. Publ. Nos. 2003/0170753 and 20090155275, each of which is herein incorporated by reference in its entirety), a domain of protein A (e.g., Affibodies), and thioredoxin.

In some aspects the disclosure provides an ActRIIA-binding protein (e.g., an anti-ActRIIA antibody such as, a full-length anti-ActRIIA antibody and an ActRIIA-binding antibody fragment) that competes for binding ActRIIA with an anti-ActRIIA antibody provided herein. In some aspects the disclosure provides an ActRIIA-binding protein that binds to the same epitope of ActRIIA as an ActRIIA-binding protein provided herein.

In some aspects the disclosure provides an ActRIIB-binding protein (e.g., an anti-ActRIIB antibody such as, a full-length anti-ActRIIB antibody and an ActRIIB-binding antibody fragment) that competes for binding ActRIIB with an anti-ActRIIB antibody provided herein. In some aspects the disclosure provides an ActRIIB-binding protein that binds to the same epitope of ActRIIB as an ActRIIB-binding protein provided herein. The ability of a test ActRII-binding protein to inhibit the binding of, for example, a reference binding protein such as an antibody comprising a VH sequence of SEQ ID NO:40 and a VL sequence of SEQ ID NO:9, or a VH sequence of SEQ ID NO:119 and a VL sequence of SEQ ID NO:91, to ActRIIB demonstrates that the test ActRII-binding protein can compete with the reference antibody for binding to ActRIIB. Such an ActRIIB-binding protein can, according to non-limiting theory, bind to the same or a related (e.g., a structurally similar or spatially proximal) epitope on ActRIIB as the ActRIIB-reference antibody with which it competes. In one aspect, the ActRIIB-binding protein binds to the same epitope on ActRIIB as an antibody comprising a VH sequence of SEQ ID NO:40 and a VL sequence of SEQ ID NO:9.

ActRII receptors such as, ActRIIB and ActRIIA, are known to phosphorylate ActRI coreceptors (e.g., Alk4 and Alk7) and to signal through the phosphorylation of Smads (e.g., Smad2 and/or Smad3). In some aspects, an ActRII-binding protein (e.g., an anti-ActRIIB antibody and an anti-ActRIIA antibody) can decrease ActRII-mediated phosphorylation of its cognate ActRI receptor. In some aspects, an ActRIIB-binding protein (e.g., an anti-ActRIIB antibody) can decrease ActRIIB-mediated phosphorylation of ALK4 and/or ALK7. In some aspects, an ActRIIA-binding protein (e.g., an anti-ActRIIA antibody) can decrease ActRIIA-mediated phosphorylation of ALK4 and/or ALK7. In some aspects, an ActRII-binding protein can inhibit ActRII-mediated Smads (e.g., Smad2 and/or Smad3) phosphorylation in ActRII2-expressing cells. In some aspects, an ActRIIB-binding protein (e.g., an anti-ActRIIB antibody) can decrease ActRIIB-mediated Smads (e.g., Smad2 and/or Smad3) phosphorylation in cell expressing ActRIIB. In some aspects, an ActRIIA-binding protein (e.g., an anti-ActRIIA antibody) can decrease ActRIIA-mediated Smads (e.g., Smad2 and/or Smad3) phosphorylation in cell expressing ActRIIA. In some aspects the ActRII receptor expressing cells are human.

In some aspects, an ActRII-binding protein has at least one characteristic selected from: (a) competing with activin A for binding to ActRIIA and/or ActRIIB; (b) decreasing the phosphorylation of Smads (e.g., Smad2 and/or Smad3) in cells expressing ActRIIA and/or ActRIIB in the presence of an ActRIIA and/or ActRIIB ligand (e.g., activin A); (c) decreasing the phosphorylation of ALK4 and/or ALK7 in cells expressing ActRIIA and/or ActRIIB and ALK4 and/or ALK7 in the presence of an ActRIIB and/or ActRIIA ligand; and (d) binding to ActRIIA and/or ActRIIB with a $K_D$ of ≤1 nM and ≥1 pM as determined by BIACORE® or by KINEXA®.

In some aspects, an ActRII-binding protein (e.g., an anti-ActRII antibody) suppresses ActRII-mediated phosphorylation of an ActRI receptor (e.g., ALK4 and/or ALK7), or the phosphorylation of Smads (e.g., Smad2 and/or Smad3) in cells expressing ActRII as measured using a cell-based assay. In some aspects, an ActRII-binding protein suppresses ActRII-mediated phosphorylation with an $IC_{50}$ lower than 500 pM, lower than 350 pM, lower than 250 pM, lower than 150 pM, lower than 100 pM, lower than 75 pM, lower than 60 pM, lower than 50 pM, lower than 40 pM, lower than 30 pM, lower than 20 pM, lower than 15 pM, lower than 10 pM, or lower than 5 pM, as measured using a cell-based assay.

Preparation of ActRII-binding Proteins

In some aspects, the ActRII-binding protein binds the extracellular domain of ActRII (e.g., ActRIIB and ActRIIA). In further aspects, the ActRII-binding protein is an anti-ActRIIA antibody and/or an anti-ActRIIB antibody such as, a full-length anti-ActRIIA antibody and a full-length anti-ActRIIB antibody and an ActRII-binding antibody fragment, and variants, and derivatives thereof.

ActRII-binding proteins can be readily prepared using known techniques. Monoclonal anti-ActRII (e.g., ActRIIB and ActRIIA) antibodies can be prepared using techniques known in the art, including hybridoma methods, such as those described by Kohler and Milstein, *Nature* 256:495-497 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line to form hybridoma cells that can then be selected away from unfused lymphocytes and myeloma cells. Hybridomas that produce monoclonal antibodies directed specifically against ActRII such as hActRIIB and hActRIIA, as determined by immunoprecipitation, immunoblotting, or by an in vitro binding assay (e.g., radioimmunoassay (RIA); enzyme-linked immunosorbent assay (ELISA)) can then be propagated either in in vitro culture using standard methods (see, e.g., Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

The provided monoclonal antibodies can also be made using recombinant DNA methods as described in U.S. Pat. No. 4,816,567, wherein the polynucleotides encoding a monoclonal antibody are isolated from mature B-cells or a hybridoma cell, such as by RT-PCR using oligonucleotide primers that specifically amplify the genes encoding the heavy and light chains of the antibody, and their sequence is determined using known procedures. The isolated polynucleotides encoding the heavy and light chains are then cloned into suitable expression vectors, which when transfected into host cells such as *E. coli* cells, simian COS cells, Chinese hamster ovary (CHO) cells, Per.C6 cells, or myeloma cells (e.g., NS0 cells) that do not otherwise produce immunoglobulin protein, monoclonal antibodies are generated by the host cells. Recombinant anti-ActRII monoclonal antibodies can also readily be isolated from phage display libraries expressing CDRs of the desired species using known techniques (see, e.g., McCafferty et al., *Nature* 348:552-554 (1990); Clackson et al., *Nature* 352:624-628 (1991); and Marks et al., *J. Mol. Biol.* 222:581-597 (1991)).

The anti-ActRII antibodies can optionally be humanized, resurfaced, and engineered to display high affinity for the ActRII antigen (e.g., ActRIIB and ActRIIA) and other favorable biological properties. For example, a humanized (or human) anti-ActRII antibody, can readily be designed and prepared using commonly available three-dimensional immunoglobulin modeling and known procedures for selecting framework (FW) residues, consensus sequences, and germline sequences to provide a desired antibody characteristic, such as increased affinity for ActRII.

Affinity maturation strategies and chain shuffling strategies are known in the art and can be employed to generate high affinity anti-ActRII (e.g., anti-ActRIIA and/or anti-ActRIIB) antibodies as well as derivatives and variants of the ActRII-binding proteins disclosed herein. See, e.g., Marks et al., *Bio/Technology* 10:779-783 (1992), which is herein incorporated by reference in its entirety. An additional strategy for generating high affinity anti-ActRII (e.g., anti-ActRIIA and/or anti-ActRIIB) antibodies as well as derivatives and variants of the ActRII-binding proteins disclosed herein is to generate novel VH or VL regions carrying CDR-derived sequences of the disclosure using random mutagenesis of one or more selected VH and/or VL genes to generate mutations within the entire variable domain. Such a technique that uses error-prone PCR is described by Gram et al. (*PNAS USA* 89:3576-3580 (1992)). In some embodiments, one or two amino acid substitutions are made within a set of VH CDRs and/or VL CDRs. A further strategy used direct mutagenesis to CDR regions of VH or VL genes encoding anti-ActRII antibodies disclosed herein. Examples of such techniques are disclosed by Barbas et al. (*PNAS USA* 91:3809-3813 (1994)) and Schier et al. (*J. Mol. Biol.* 263: 551-567 (1996)).

Humanization, resurfacing or engineering of anti-ActRII antibodies of the disclosure can be performed using any known method including, but not limited to, those described in Jones et al., *Nature* 321:522 (1986); Riechmann et al., *Nature* 332:323 (1988); Verhoeyen et al., *Science* 239:1534 (1988)), Sims et al., *J. Immunol.* 151: 2296 (1993); Chothia et al., *J. Mol. Biol.* 196:901 (1987), Carter et al., *PNAS USA* 89:4285 (1992); Presta et al., *J. Immunol.* 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; Intl. Appl. Nos. PCT/US98/16280; PCT/US96/18978; PCT/US91/09630; PCT/US91/05939; PCT/US94/01234; PCT/GB89/01334; PCT/GB91/01134; PCT/GB92/01755; Intl. Appl. Publ. Nos. WO90/14443; WO90/14424; WO90/14430; and EP Pat. Publ. No. EP 229246; each of which is herein incorporated by reference in is entirely. Likewise, known assays are available for readily selecting ActRII-antibodies displaying desirable features e.g., assays for determining binding affinity to ActRII; cross-blocking assays such as the BIACORE®-based human ActRII-binding protein competition binding assays described herein).

Methods for engineering, humanizing or resurfacing non-human or human antibodies can also be used and are known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. Preferably, part or all of the non-human or human CDR sequences are maintained while the non-human sequences of the variable and constant regions can be replaced with human or other amino acids.

The nucleic acid(s) encoding an ActRII-binding protein, such as a full-length anti-ActRIIA or anti-ActRIIB antibody can further be modified in a number of different manners using recombinant DNA technology to generate alternative antibodies. In some aspects, nucleic acid(s) encoding the constant domains of the light and heavy chains of, for example, a mouse monoclonal antibody can be substituted (a) for those coding regions of, for example, a human antibody to generate a chimeric antibody or (b) for non-immunoglobulin encoding nucleic acid(s) to generate a fusion antibody. In some aspects, the constant regions are truncated or removed to generate the desired antibody fragment of a monoclonal antibody. Site-directed or high-density mutagenesis of the variable region coding sequence can be used to optimize specificity, affinity, etc. of a monoclonal antibody.

Anti-ActRII human antibodies can be directly prepared using any of the numerous techniques known in the art. (See, e.g., Cole et al., Monoclonal Antibodies and Cancer Therapy, Alan R. Liss, p. 77 (1985); Boemer et al., *J. Immunol.* 147(1):86-95 (1991); and U.S. Pat. No. 5,750,373). Similarly, human anti-ActRII antibodies can readily be obtained from immortalized human B lymphocyte immunized in vitro or isolated from an immunized individual that produces an antibody directed against ActRII (e.g., ActRIIB and ActRIIA).

Human anti-ActRII antibodies can also be selected from a phage library that expresses human antibodies, as described, for example, in Vaughan et al., *Nat. Biotech.* 14:309-314 (1996), Sheets et al., *PNAS* 95:6157-6162 (1998), Hoogenboom and Winter, *J. Mol. Biol.* 227:381 (1991), and Marks et al., *J. Mol. Biol.* 222:581 (1991). Techniques for the generating and screening antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., *J. Mol. Biol.* 376(4):1182-1200 (2008)(each of which is herein incorporated by reference in its entirety).

Human anti-ActRII antibodies can also be made in transgenic mice containing human immunoglobulin loci that are capable upon immunization of producing human antibodies in the absence of endogenous immunoglobulin production. This approach is described for example, in U.S. Pat. Nos. 5,545,807; 5,545,806; 5,569,825; 5,625,126; 5,633,425; and 5,661,016.

Human anti-ActRII antibodies can also be selected and/or isolated from yeast-based antibody presentation libraries, as disclosed in, for example, WO012/009568; WO09/036379; WO10/105256; WO03/074679 and U.S. Appl. Publ. No. US2002/0177170, the contents of each of which is herein incorporated by reference in its entirety. Such libraries are designed in silico to be reflective of the diversity afforded by the human preimmune repertoire.

Alternatively, anti-ActRII antibodies may be selected from a yeast-displayed antibody library see, for example: Blaise et al., *Gene* 342(2):211-218 (2004); Boder et al., *Nat Biotechnol.* 15(6):553-557 (1997); Kuroda et al., *Biotechnol. Lett.* 33(1):1-9 (2011). Review; Lauer et al., *J. Pharm. Sci.* 101(1):102-15 (2012); Orcutt K. D. and Wittrup K. D. Antibody Engineering, yeast display and selectios (2010), 207-233; Rakestraw et al., *Protein Eng. Des. Sel.* 24(6):525-30 (2011); and U.S. Pat. Nos. 6,423,538; 6,696,251; and 6,699,658.

Various techniques are known for the production of antigen-binding antibody fragments. Traditionally, these fragments are derived via proteolytic digestion of intact antibodies (see, e.g., Morimoto et al., *J. Biochem. Biophys. Meth.* 24:107-117 (1993); and Brennan et al., *Science* 229: 81 (1985)). In certain aspects an ActRII-binding antibody fragments produced recombinantly. Fab, Fv, and scFv antibody fragments can all be expressed in and secreted from *E. coli* or other host cells, thus allowing the production of large amounts of these fragments. Such an ActRII-binding antibody fragment can additionally be isolated from the antibody phage libraries discussed above. In some aspects, the ActRII-binding antibody fragment is a linear antibody as described in U.S. Pat. No. 5,641,870. Other techniques for the production of antigen-binding antibody fragments are known in the art.

Known techniques can be readily adapted for the production of single-chain antibodies that bind ActRII (see, e.g., U.S. Pat. No. 4,946,778). In addition, known methods can routinely be adapted for the construction of Fab expression libraries (see, e.g., Huse et al., *Science* 246:1275-1281 (1989)) to allow rapid and effective identification of monoclonal Fab fragments with the desired specificity for ActRII. ActRII-binding antibody fragment can be produced by techniques known in the art including, but not limited to: (a) a F(ab')2 fragment produced by pepsin digestion of an antibody; (b) a Fab fragment generated by reducing the disulfide bridges of an F(ab')2 fragment, (c) a Fab fragment generated by the treatment of the anti-ActRII antibody with papain and a reducing agent, and (d) Fv fragments.

In certain aspects, an ActRII-binding protein (e.g., an anti-ActRIIA antibody and/or an anti-ActRIIB antibody) can be modified in order to increase its serum half-life. This can be achieved, for example, by incorporation of a salvage receptor binding epitope into the ActRII-binding protein by mutation of an appropriate region in the ActRII-binding protein or by incorporating the salvage receptor epitope into a peptide tag that is then fused to the ActRIIB-binding protein at either end or in the middle (e.g., by DNA or peptide synthesis). Other methods to increase the serum half-life of an ActRII-binding protein, e.g., conjugation to a heterologous molecule such as PEG are known in the art.

Heteroconjugate ActRII-binding proteins (e.g., anti-ActRIIB antibodies, such as a full-length anti-ActRIIB antibodies and ActRIIB-binding antibody fragments, and variants and derivatives thereof) are also within the scope of the disclosure. Heteroconjugate ActRII-binding proteins are composed of two covalently joined proteins. It is contemplated that the heteroconjugate ActRII-binding proteins can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

ActRII-binding proteins can comprise any type of variable region that provides for the association of the antibody with ActRII (e.g., ActRIIB and ActRIIA). Such variable region can comprise or be derived from any mammal that can be induced to mount a humoral response and generate immunoglobulins against the ActRII antigen. The variable region of an anti-ActRII antibody can be, for example, of human, murine, non-human primate (e.g., cynomolgus monkeys, macaques, etc.) or lupine origin. In some aspects both the variable and constant regions of the modified anti-ActRII antibodies are human. In other aspects the variable regions of compatible antibodies (usually derived from a non-human source) can be engineered or specifically tailored to improve the binding properties or reduce the immunogenicity of the molecule. In this respect, variable regions useful according to the disclosure can be humanized or otherwise altered through the inclusion of imported amino acid sequences using affinity maturation, mutagenesis procedures, chain shuffling strategies and/or other methods described herein or otherwise know in the art.

In certain aspects, the variable domains in both the heavy and light chains of an anti-ActRII antibody are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain aspects from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. It is well within the competence of those of ordinary skill in the art, to routinely obtain a functional antibody with reduced immunogenicity. See, e.g., U.S. Pat. Nos. 5,585,089, 5,693,761 and 5,693,762.

Alterations to the variable region notwithstanding, those of ordinary skill in the art will appreciate that the modified anti-ActRII of the disclosure will comprise antibodies in which at least a fraction of one or more of the constant region domains has been deleted or otherwise altered so as to provide desired biochemical characteristics such as decreased ADCC or increased serum half-life when compared with an antibody of approximately the same immunogenicity comprising a native or unaltered constant region. In some aspects, the constant region of the modified anti-ActRII antibodies comprise a human constant region. Modifications to the constant region can include additions, deletions or substitutions of one or more amino acids in one or more domains. The modified anti-ActRII antibodies disclosed herein can comprise alterations or modifications to one or more of the three heavy chain constant domains (CH1, CH2 or CH3) and/or to the light chain constant domain (CL). In some aspects, the modified anti-ActRII antibodies comprise constant regions wherein one or more domains are partially or entirely deleted are contemplated. In some aspects, the modified anti-ActRII antibodies comprise domain deleted constructs or variants wherein the entire CH2 domain has been removed (ΔCH2 constructs). In some aspects, the omitted constant region domain can be replaced by a short amino acid spacer (e.g., 10 residues) that provides some of the molecular flexibility typically imparted by the absent constant region.

It is generally understood that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain aspects, an anti-ActRII antibody has an altered effector function that, in turn, affects the biological profile of the administered anti-ActRII antibody. For example, the deletion or inactivation (through point mutations or other means) of a constant region domain can reduce Fc receptor binding of the circulating modified antibody. In other cases the constant region modifications, can moderate complement binding and thus reduce the serum half-life and non-specific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using biochemical or molecular engineering techniques known to those of ordinary skill in the art.

In some aspects, an ActRIIB-binding protein provided herein is an ActRII antibody that does not have one or more effector functions. For instance, in some aspects, the anti-ActRII antibody has no antibody-dependent cellular cytoxicity (ADCC) activity and/or no complement-dependent cytoxicity (CDC) activity. In certain aspects, the anti-ActRII antibody does not bind to an Fc receptor and/or complement factors. In certain aspects, the anti-ActRII antibody has no effector function. Examples of Fc sequence engineering modifications that reduce or eliminate ADCC and/or CDC activity and Fc receptor and/or complement factor binding are described herein or otherwise know in the art, as are assays and procedures for testing the same.

In some aspects, an anti-ActRII antibody is engineered to fuse the CH3 domain directly to the hinge region of the respective modified antibody. In other constructs a peptide spacer is inserted between the hinge region and the modified CH2 and/or CH3 domains. For example, compatible constructs can be expressed in which the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. Accordingly, in certain aspects, any spacer added to the construct can be relatively non-immunogenic, or even omitted altogether, so as to maintain the desired biochemical qualities of the modified anti-ActRII.

In additional aspects anti-ActRII antibodies are modified by the partial deletion or substitution of a few or even a single amino acid in a constant region. For example, the mutation of a single amino acid in selected areas of the CH2 domain can be enough to substantially reduce Fc binding and thereby. Similarly one or more constant region domains that control the effector function (e.g., complement C1Q binding) can be fully or partially deleted. Such partial deletions of the constant regions can improve selected characteristics of the anti-ActRII antibody (e.g., serum half-life) while leaving other desirable functions associated with the corresponding constant region domain intact. In some aspects the constant regions of the anti-ActRII antibodies are modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified anti-ActRII antibody. The disclosure also provides an anti-ActRII antibody that contains the addition of one or more amino acids to the constant region to enhance desirable characteristics such, as decreasing or increasing effector function or providing attachments sites for one or more cytotoxin, labeling or carbohydrate moieties. In such aspects it can be desirable to insert or replicate specific sequences derived from selected constant region domains.

The disclosure also provides an ActRII-binding protein that is a variant to the ActRIIB and ActRIIA-binding proteins provided herein (e.g., murine, chimeric, humanized and human ActRII-binding proteins). In particular aspects, the variant ActRII-binding protein has at least one characteristic selected from the group consisting of: (a) competing with activin A for binding to ActRIIB and/or ActRIIA; (b) decreasing the phosphorylation of Smads (e.g., Smad2 and/or Smad3) in cells expressing ActRIIB and/or ActRIIA in the presence of an ActRIIB and/or ActRIIA ligand (e.g., activin A); (c) decreasing the phosphorylation of ALK4 and/or ALK7 in cells expressing ActRIIB and/or ActRIIA and ALK4 and/or ALK7 in the presence of an ActRIIB and/or ActRIIA ligand; and (d) binding to ActRIIB or ActRIIA with a $K_D$ of ≤1 nM and ≥1 pM (e.g., as determined by BIACORE® analysis). In some aspects, the ActRII-binding protein has 2, 3, or 4 of the above characteristics. In some aspects, the ActRII-binding protein has at least 2 or at least 3 of the above characteristics. In further aspects, the variant contains conservative amino acid residue substitution mutations compared to an ActRII-binding protein provided herein.

The provided ActRII-binding proteins, such as anti-ActRII antibodies, can be derivatized to contain additional chemical moieties known in the art for improving for example, the solubility, biological half-life, bioavailability, and to otherwise improve the stability, formulation and/or therapeutic properties of the ActRII-binding protein. A non-exhaustive overview for such moieties can be found for example, in Remington's Pharmaceutical Sciences, 20th ed., Mack Publishing Co., Easton, Pa. (2000).

Nucleic Acids Encoding ActRII-Binding Proteins and their Expression

Nucleic acid molecules and combinations of nucleic acid molecules that encode an ActRII-binding protein are also provided. In some aspects, the nucleic acids molecules encode an anti-ActRII antibody, such as a full-length anti-ActRII antibody and an ActRII-binding antibody fragment. In further aspects, the disclosure provides nucleic acid molecules that encode a variant or derivative of a full-length anti-ActRII antibody or an ActRII-binding antibody fragment provided herein.

The nucleic acid molecules disclosed herein can be in the form of RNA or in the form of DNA. DNA includes cDNA, genomic DNA, and synthetic DNA; and can be double-stranded or single-stranded, and if single stranded can be the coding strand/or non-coding (anti-sense) strand. In certain aspects, the nucleic acid molecule is isolated. In additional aspects, a nucleic acid molecule is substantially pure. In some aspects the nucleic acid is cDNA or is derived from cDNA. In some aspects the nucleic acid is be recombinantly produced.

In some aspects, the nucleic acid molecule comprises an ActRII-binding protein coding sequence operably linked to a control sequence that controls the expression of the coding sequence in a host cell or in vitro. In particular aspects, the coding sequence is a cDNA. The disclosure also relates to vectors containing nucleic acid molecules comprises an ActRII-binding protein coding sequence operably linked to a control sequence that controls the expression of the coding sequence in a host cell or in vitro.

In some aspects, the nucleic acid molecule comprises a coding sequence for a mature ActRII-binding protein that is fused in the same reading frame to a heterologous polynucleotide sequence. In some aspects, the heterologous polynucleotide sequence encodes a leader peptide sequence that facilitates the secretion of the expressed protein from the host cell transformed with the ActRII-binding protein encoding nucleic acid molecule(s). A protein containing a leader sequence is referred to as a preprotein and can have the leader sequence cleaved by the host cell to form the mature form of the ActRII-binding protein. Such leader peptide sequences and their use facilitating the secretion of recombinant proteins in host cells is generally known in the art. In additional aspects, the heterologous polynucleotide sequence encodes additional 5' amino acid residues that can function for example, to facilitate purification, add or improve protein stability and/or therapeutic or diagnostic properties of the recombinantly expressed ActRII-binding protein.

In some aspects the disclosure provides isolated nucleic acids such as an ActRII-binding protein encoding cDNA fragments, sufficient for use as a hybridization probe, PCR primer or sequencing primer.

In some aspects, the nucleic acid molecules encode an ActRII-binding protein that has at least one characteristic selected from the group consisting of: (a) competes with an ActRII ligand for binding to the ActRII; (b) decreases the phosphorylation of ALK4 and/or ALK7 in cells expressing an ActRII and a cognate ActRI in the presence of an ActRII ligand; (c) decreases the phosphorylation of one or more Smads in cells expressing ActRII in the presence of an ActRII ligand; and (d) binds to ActRII with a $K_D$ of ≤1 nM and ≥1 pM (e.g., as determined by BIACORE® analysis). In some aspects, the encoded ActRII-binding protein has 2, 3, or 4 of the above characteristics. In some aspects, the encoded ActRII-binding protein has at least 2 or at least 3 of the above characteristics. In some aspects, the encoded ActRII-binding protein competes for binding to ActRII with an antibody having an ActRII-binding VH and VL pair disclosed herein. In additional aspects, the encoded ActRII-binding protein binds to the same epitope of ActRII as an antibody disclosed herein.

In some aspects, the nucleic acid molecules encode an ActRII-binding protein that specifically binds ActRIIA and has at least one characteristic selected from the group consisting of: (a) competes with an ActRIIA ligand (e.g., activin A, activin B, GDF1, GDF3, or Nodal); (b) decreases the phosphorylation of ALK4 and/or ALK7 in cells expressing ActRIIA and ALK4 and/or ALK7 in the presence of an ActRIIA ligand (e.g., activin A); (c) decreases the phosphorylation of one or more Smads in cells expressing ActRIIA in the presence of an ActRIIA ligand; and (d) binds to ActRIIA with a $K_D$ of ≤1 nM and ≥1 pM (e.g., as determined by BIACORE® analysis). In some aspects, the encoded ActRIIA-binding protein has 2, 3, or 4 of the above characteristics. In some aspects, the encoded ActRIIA-binding protein has at least 2 or at least 3 of the above characteristics. In some aspects, the encoded ActRIIA-binding protein competes for binding to ActRIIA with an antibody having an ActRIIA-binding VH and VL pair disclosed herein. In additional aspects, the encoded ActRIIA-binding protein binds to the same epitope of ActRIIA as an antibody disclosed herein. In further aspects, the nucleic acid molecules encode an ActRIIA-binding protein that specifically binds ActRII and comprises a VH and a VL.

In some aspects, the nucleic acid molecules encode an ActRII-binding protein that specifically binds ActRIIB and has at least one characteristic selected from the group consisting of: (a) competes with activin A and/or GDF8 for binding to ActRIIB; (b) decreases the phosphorylation of ALK4 and/or ALK7 in cells expressing ActRIIB and ALK4 and/or ALK7 in the presence of an ActRIIB ligand (e.g., activin A and/or GDF8); (c) decreases the phosphorylation of one or more Smads in cells expressing ActRIIB in the presence of an ActRIIB ligand; and (d) binds to ActRIIB with a $K_D$ of ≤1 nM and ≥1 pM (e.g., as determined by BIACORE® analysis). In some aspects, the encoded ActRIIB-binding protein has 2, 3, or 4 of the above characteristics. In some aspects, the encoded ActRIIB-binding protein has at least 2 or at least 3 of the above characteristics. In some aspects, the encoded ActRIIB-binding protein competes for binding to ActRIIB with an antibody having an ActRIIB-binding VH and VL pair disclosed herein. In additional aspects, the encoded ActRIIB-binding protein binds to the same epitope of ActRIIB as an antibody disclosed herein. In further aspects, the nucleic acid molecules encode an ActRIIB-binding protein that specifically binds ActRIIB and comprises a VH and a VL In some aspects, the nucleic acid molecules encode an ActRII-binding protein that specifically binds ActRIIB and ActRIIA and has at least one characteristic selected from the group consisting of: (a) competes with activin A and/or GDF8 for binding to ActRIIB and ActRIIA; (b) decreases the phosphorylation of ALK4 and/or ALK7 in cells expressing ActRIIA and/or ActRIIB and ALK4 and/or ALK7 in the presence of an ActRIIA and/or ActRIIB ligand (e.g., activin A and/or GDF8); (c) decreases the phosphorylation of one or more Smads in cells expressing ActRIIA and/or ActRIIB in the presence of an ActRIIA and/or ActRIIB ligand; and (d) binds to ActRIIA or ActRIIB with a $K_D$ of ≤1 nM and ≥1 pM (e.g., as determined by BIACORE® analysis). In some aspects, the encoded ActRIIB and ActRIIA-binding protein has 2, 3, or 4 of the above characteristics. In some aspects, the encoded ActRIIB-binding protein has at least 2 or at least 3 of the above characteristics. In some aspects, the encoded ActRIIB and ActRIIA-binding protein competes for binding to ActRIIB and ActRIIA with an antibody having an ActRIIB and ActRIIA-binding VH and VL pair disclosed herein. In additional aspects, the encoded ActRIIB-binding protein binds to the same epitope of ActRIIA or ActRIIB as an antibody disclosed herein. In further aspects, the nucleic acid molecules encode an ActRIIB and ActRIIA-binding protein that specifically binds ActRIIB and ActRIIA and comprises a VH and a VL.

The disclosure also provides vectors and sets of vectors containing nucleic acids and sets of nucleic acids encoding the ActRIIB-binding proteins provided herein. Host cells transformed with these nucleic acids, sets of nucleic acids, vectors, and sets of vectors are also provided, as are methods of making an using the ActRII-binding proteins.

In some aspects, the disclosure provides a host cell comprising a nucleic acid molecule or combination of nucleic acid molecules or a vector as provided above, where the host cell can, in some instances express an ActRII-binding protein (e.g., an anti-ActRII antibody such as, a full-length ActRIIB-antibody and an ActRII-binding antibody fragment), that specifically binds to ActRII. In further aspects, the disclosure provides a host cell transformed with a nucleic acid molecule or combination of nucleic acid molecules or a vector as provided above, where the host cell can, in some instances express an ActRII-binding protein that specifically binds to ActRII. Such host cells can be utilized in a method of making an ActRII-binding protein as provided herein, where the method includes (a) culturing the host cell and (b) isolating the ActRII-binding proteins expressed from the host cell.

The disclosure also provides a method for making an ActRII-binding protein comprising culturing a host cell (e.g., a hybridoma or transformed mammalian host cell) capable of expressing the ActRII-binding protein under suitable conditions and optionally provides a method for isolating the ActRII-binding protein secreted from the host cell. And the disclosure additionally provides the ActRII-binding protein isolated using the disclosed methods.

In certain aspects the polynucleotides comprise the coding sequence(s) for the mature ActRII-binding protein(s) (e.g., an ActRII-antibody, such as a full-length antibody and an ActRII-binding antibody fragment) fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Nucleic acid variants encoding an ActRII-binding protein such as, an anti-ActRII antibody and an ActRII-binding antibody fragment, are also provided. Nucleic acid variants can contain alterations in the coding regions, non-coding regions, or both. In some aspects the nucleic acid variants contain alterations that produce silent substitutions, additions, or deletions, but do not alter the properties or activities of the encoded polypeptide. In some aspects, the nucleic acid variants are produced by silent substitutions due to the degeneracy of the genetic code. Nucleic acid variants can be produced for a variety of reasons, e.g., to optimize codon expression for a particular host (change codons in the human mRNA to those preferred by a bacterial host such as *E. coli*). Vectors and cells comprising the nucleic acids described herein are also provided.

In some aspects a nucleic acid sequence encoding an ActRII-binding protein (e.g., an anti-ActRII antibody such as a full-length antibody and an ActRII-binding antibody fragment) is constructed by chemical synthesis using an oligonucleotide synthesizer. Such oligonucleotides can be designed based on the amino acid sequence of the desired polypeptide and codon optimization based on the host cell preferences. Standard methods can routinely be applied to synthesize an isolate polynucleotide sequences encoding ActRII-binding proteins.

Once assembled (by synthesis, site-directed mutagenesis or another method), the nucleic acid sequences encoding ActRII-binding proteins can routinely be operably linked to a control sequence appropriate for expression of the ActRII-binding proteins in a desired host. In some aspects, the nucleic acid sequences encoding ActRII-binding proteins is inserted into an expression vector and operably linked to a control sequence appropriate for expression of the protein in a desired host. In order to obtain high expression levels of a transfected gene in a host, the gene can be operably linked to or associated with transcriptional and translational expression control sequences that are functional in the chosen expression host.

In certain aspects, recombinant expression vectors are used to amplify and express DNA encoding an ActRII-binding protein, such as, an anti-ActRIIB antibody, an anti-ActRIIA antibody, an ActRIIB-binding antibody fragment, or an ActRIIA-binding antibody fragment. Recombinant expression vectors are replicable DNA constructs which have synthetic or cDNA-derived DNA fragments encoding a polypeptide chain of an ActRII-binding protein operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final protein. In certain aspects, the disclosure provides a composition, e.g., a pharmaceutical composition, comprising a nucleic acid or vector of as described above or elsewhere herein, optionally further comprising one or more carriers, diluents, excipients, or other additives.

Also provided is a host cell transformed with the nucleic acid molecule or cDNA molecules and/or the vectors disclosed herein. The disclosure also provides host cells transformed with the disclosed nucleic acid molecule or molecules operably linked to a control sequence and optionally inserted into a vector. In some aspects, the host cell is a mammalian host cell. In further aspects, the mammalian host cell is a NS0 murine myeloma cell, a PER.C6® human cell, or a Chinese hamster ovary (CHO) cell. In other aspects, the host cell is a hybridoma.

In additional aspects, the disclosure provides a method of making an ActRII-binding protein (e.g., an anti-ActRII antibody such as, a full-length ActRII-antibody and an ActRII-binding antibody fragment, and variants and derivatives thereof) provided herein comprising culturing a transformed host cell or a hybridoma disclosed herein under suitable conditions for producing the ActRII-binding protein. The disclosure optionally provides isolating the ActRII-binding protein secreted from the host cell. The disclosure also optionally provides the ActRII-binding protein produced using this method and pharmaceutical compositions comprising the ActRII-binding protein and a pharmaceutically acceptable carrier.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives, and also wider host range plasmids, such as M13 and filamentous single-stranded DNA phages.

Suitable host cells for expression of an ActRII-binding protein, include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Appl. Publ. No. 2008/0187954, U.S. Pat.

Nos. 6,413,746 and 6,660,501, and Intl. Appl. Publ. No. WO04/009823, each of which is herein incorporated by reference in its entirety.

Various mammalian or insect cell culture systems can also be advantageously employed to express recombinant ActRII-binding proteins (e.g., an anti-ActRII antibody such as, a full-length ActRII-antibody and an ActRII-binding antibody fragment, and variants and derivatives thereof). Expression of recombinant ActRII-binding proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (*Cell* 23:175 (1981)), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *BioTechnology* 6:47 (1988).

ActRII-binding proteins produced by a transformed host cell or hybridoma can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. ActRII-binding proteins can also be physically characterized using such techniques as proteolysis, nuclear magnetic resonance and x-ray crystallography.

For example, supernatants from systems that secrete recombinant ActRII-binding proteins into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an ActRII-binding protein. Some or all of the foregoing purification steps, in various combinations, can also routinely be employed to provide a homogeneous recombinant ActRII-binding proteins.

A recombinant ActRII-binding protein (e.g., an anti-ActRII antibody such as, a full-length ActRII-antibody and an ActRII-binding antibody fragment and variants and derivatives thereof) produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying target binding proteins such as full-length antibodies and antigen-binding antibody fragments also include, for example, those described in U.S. Appl. Publ. Nos. 2008/0312425, 2008/0177048, and 2009/0187005, each of which is incorporated herein by reference herein in its entirety.

In certain aspects, the ActRII-binding protein is not an antibody. A variety of methods are known for identifying and producing non-antibody polypeptides that bind with high affinity to a protein target. See, e.g., Skerra, *Curr. Opin. Biotechnol.* 18:295-304 (2007), Hosse et al., *Protein Science* 15:14-27 (2006), Gill et al., *Curr. Opin. Biotechnol.* 17:653-658 (2006), Nygren, *FEES J.* 275:2668-2676 (2008), and Skerra, *FEBS J.* 275:2677-2683 (2008), each of which is herein incorporated by reference in its entirety. In certain embodiments, phage display technology is used to identify/produce the ActRII-binding protein. In certain embodiments, the polypeptide comprises a protein scaffold of a type selected from the group consisting of protein A, a lipocalin, a fibronectin domain (e.g., Fibronectin type III (Fn3)), an ankyrin consensus repeat domain, and thioredoxin.

Methods of Use and Pharmaceutical Compositions

The provided ActRII-binding proteins (including antibodies, immunoconjugates, and polypeptides) are useful in a variety of applications including, but not limited to, diagnostic methods and methods of treating and/or ameliorating various diseases and conditions with an ActRII-binding protein (e.g., an anti-ActRIIB and an ActRIIA antibody). Methods are provided for the use of an ActRII-binding protein (e.g., an anti-ActRII antibody such as, a full-length antibody that specifically binds ActRII and an ActRII-binding antibody fragment, and variants and derivatives thereof) to treat subjects having a disease or condition associated with ActRII (e.g., ActRIIB and/or ActRIIA) signaling and/or increased ActRII expression. In additional aspects, the disclosure provides a pharmaceutical composition containing an ActRII-binding protein provided herein and a pharmaceutically acceptable carrier. In some aspects, the disclosure provides a pharmaceutical composition containing an ActRII-binding protein provided herein and a pharmaceutically acceptable carrier, for use as a medicament. The disclosure also provides the use of the pharmaceutical compositions disclosed herein for treating and/or ameliorating a disease or condition associated with ActRII, increased ActRII expression and/or increased ActRII signaling. In some aspects, the disease or condition treated using the pharmaceutical composition provided herein is a muscle disorder, such as muscle wasting due to disease or disuse. In additional aspects the disease or condition treated using the pharmaceutical compositions provided herein is a fibrotic condition (e.g., a hepatic, pulmonary, vascular and/or ocular fibrotic condition); an inflammatory, cardiovascular, pulmonary, musculoskeletal, neurologic, or metabolic disease or condition; wound healing; or cancer.

In some aspects, a pharmaceutical composition contains an ActRII-binding protein (e.g., a full-length antibody that specifically binds ActRIIB and a full-length antibody that specifically binds ActRIIA) and a pharmaceutically acceptable carrier, and further comprises a labeling group or an effector group. A "label" refers to one or more elements, isotopes, or chemical compounds attached to enable the detection in a screen. Labels generally fall into three classes: (a) isotopic labels, which may be radioactive or heavy isotopes, (b) small molecule labels, which may include fluorescent and colorimetric dyes, or molecules such as biotin that enable other labeling methods, and (c) immune labels, which may be an epitope incorporated as a fusion partner that is recognized by an antibody, "Labeling group" refers to any detectable label. In some aspects, the labeling group is coupled to the ActRII-binding protein via a spacer (e.g., a peptide spacer) to reduce potential steric hindrance. Labels may be incorporated into the compound at any position and may be incorporated in vitro or in vivo during protein expression. Various methods for labeling proteins are known in the art and may be used in performing the provided methods. In additional aspects, the labeling group is selected from the group consisting of: isotopic labels, magnetic labels, redox active moieties, optical dyes, biotinylated groups and polypeptide epitopes recognized by a secondary reporter. In some aspects, the labeling group is a fluorescent protein such as a Green Fluorescent Protein or derivative thereof (e.g., enhanced GFP, blue fluorescent protein or derivative thereof (e.g., EBFP (Enhanced Blue Fluorescent Protein), EBFP2, Azurite, mKalama1, cyan fluorescent protein or derivative thereof (e.g., ECFP (Enhanced Cyan Fluorescent Protein), Cerulean, CyPet), yellow fluorescent protein or derivative thereof (e.g., YFP, Citrine, Venus, YPet). In some aspects, the polypeptide epitope is a member selected from a biotin signaling peptide, histidine peptide (his), hemagglutinin (HA), Flag, gold binding peptide. In additional aspects the effector group is selected from the group consisting of a radioisotope, radionucleotide, a toxin, a therapeutic and a chemotherapeutic agent.

The ActRII-binding proteins of the present disclosure have applications in in vitro and in vivo diagnostic and therapeutic utilities. For example, the ActRII-binding proteins can be administered to cells in culture, e.g., in vitro or in vivo, or in a subject, to treat, prevent or diagnose a variety of diseases or conditions. In some aspects, the ActRII-binding proteins are human antibodies, murine antibodies, or humanized antibodies.

Also provided are methods of blocking ActRII activity. In some aspects, the method comprises contacting ActRII with an ActRII-binding protein. In some instances the method is performed in vivo. In other instances, the method is performed in vitro. In some aspects the blocked ActRII activity is selected from (a) binding by an ActRII ligand (e.g., activin A, activin B, GDF8 (myostatin), GDF11, BMP6, GDF3, BMP9, or BMP10); (b) phosphorylation of one or more Smads in cells expressing ActRII in the presence of activin A; (c) phosphorylation of ALK4 and/or ALK7 in cells expressing ActRII, and ALK4 and/or ALK7 in the presence of an ActRII ligand.

In some aspects a method of blocking ActRIIA activity is provided. In further aspects, the method comprises contacting ActRIIA with an ActRIIA-binding protein. In some instances the method is performed in vivo. In other instances, the method is performed in vitro. In some aspects the blocked ActRIIA activity is selected from (a) binding by an ActRIIA ligand (e.g., activin A, activin B, GDF1, GDF3, or Nodal); (b) phosphorylation of one or more Smads in cells expressing ActRIIA in the presence of activin A; (c) phosphorylation of ALK4 and/or ALK7 in cells expressing ActRIIA, and ALK4 and/or ALK7 in the presence of an ActRIIA ligand.

In some aspects a method of blocking ActRIIB activity is provided. In further aspects, the method comprises contacting ActRIIB with an ActRIIB-binding protein. In some instances the method is performed in vivo. In other instances, the method is performed in vitro. In some aspects the blocked ActRIIB activity is selected from (a) binding by an ActRIIB ligand (e.g., activin A, activin B, GDF8 (myostatin), GDF11, BMP6, GDF3, BMP9, or BMP10); (b) phosphorylation of one or more Smads in cells expressing ActRIIA in the presence of activin A; (c) phosphorylation of ALK4 and/or ALK7 in cells expressing ActRIIA, and ALK4 and/or ALK7 in the presence of an ActRIIB ligand.

In one aspect, the disclosure provides for the treatment, prevention and/or amelioration of a disease or condition that comprises administering an ActRII-binding protein (e.g., a full-length antibody that specifically binds ActRIIB and a full-length antibody that specifically binds ActRIIA) to a subject that has a disease or condition, or is at risk of developing a disease or condition, associated with ActRII expression and/or elevated ActRII signaling. In another aspect the treatment includes the administration of an ActRII-binding protein to an isolated tissue or cells from a subject, where the subject has a disease or condition, or is at risk of developing a disease or condition, associated with ActRII expression or ActRII signaling. Further provided is use of an ActRII-binding protein as provided herein in the manufacture of a medicament for the treatment of a disease or condition associated with ActRII expression or ActRII signaling.

The disclosure provides pharmaceutical compositions comprising an ActRII-binding protein and a pharmaceutically acceptable carrier. Also provided are methods for treating and/or ameliorating conditions associated with an ActRII (e.g., ActRIIA or ActRIIB)-mediated activity in a subject, comprising administering to a subject in need thereof an effective amount of a pharmaceutical composition comprising an ActRII-binding protein provided herein. In some aspects, the ActRII-binding protein is administered alone. In other aspects, the ActRII-binding protein is administered as a combination therapy. Also provided are methods of reducing ActRII activity in a subject comprising administering an effective amount of an ActRII-binding protein to a subject in need thereof.

The disclosure also provides methods for treating and/or ameliorating a disease or condition associated with a muscle disorder. In some aspects, the muscle disorder is wasting. In further aspects the wasting is due to disease or disuse. In some aspects, the method comprises administering to a subject in need thereof, an effective amount of a pharmaceutical composition comprising an ActRII-binding protein (e.g., an antibody that specifically binds ActRIIB an antibody that specifically binds ActRIIA, or an antibody that specifically binds ActRIIB and ActRIIA). In additional aspects, the ActRII-binding protein is administered alone or as a combination therapy.

According to some aspects, the disclosure provides a method of inducing the formation of skeletal muscle in a subject. In some aspects, the method comprises administering an ActRIIB-binding protein (e.g., an anti-ActRIIB antibody such as, a full-length ActRIIB-antibody and an ActRIIB-binding antibody fragment) to a subject in need thereof. In some aspects the method increases muscle mass or strength in the subject.

The disclosure also provides methods for treating and/or ameliorating a disease or condition associated with muscle disorders such as degenerative muscle disease, muscular dystrophy, muscle atrophy, or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes insulin resistance, hyperglycemia, and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease such as osteoporosis; neurologic disease; wound healing; weight loss; and cancer (e.g., a carcinoma, myeloma, a bone-loss inducing cancer, pituitary cancer, and gastrointestinal cancer), in a subject. In some aspects, the method comprises administering to a subject in need thereof, an effective amount of a pharmaceutical composition comprising an ActRII-binding protein (e.g., an antibody that specifically binds ActRIIB, an antibody that specifically binds ActRIIA, or an antibody that specifically binds ActRIIB and ActRIIA). In additional aspects, the ActRII-binding protein is administered alone or as a combination therapy. Further provided is use of disease or condition, or is at risk of developing a disease or condition, associated with ActRII expression or ActRII signaling.

The disclosure also provides methods of reducing ActRII (e.g., ActRIIA or ActRIIB) activity such as signaling in a subject. In some aspects, the method comprises administering to a subject in need thereof (e.g., a subject diagnosed with muscle wasting; a fibrotic condition (e.g., a hepatic, pulmonary, vascular and/or ocular fibrotic condition); an inflammatory, cardiovascular, pulmonary, musculoskeletal (i.e., bone and/or muscular), neurologic, or metabolic disease or condition; wound healing; or cancer) an effective amount of an ActRII-binding protein (e.g., an antibody that specifically binds ActRIIB, an antibody that specifically binds ActRIIA, or an antibody that specifically binds ActRIIB and ActRIIA) or an effective amount of a pharmaceutical composition comprising an ActRII-binding protein.

In one aspect, the disclosure provides methods of treating and/or ameliorating a muscle disorder in a subject. In some instances, the method comprises administering an ActRII-binding protein (e.g., an antibody that specifically binds ActRIIB, an antibody that specifically binds ActRIIA, or an antibody that specifically binds ActRIIB and ActRIIA) to a subject having a muscle disorder. In other aspects, the subject is at risk of developing a muscle disorder. In some aspects the muscle disorder or condition is muscle atrophy. In further aspects, the muscle atrophy is a condition associated with glucocorticoid treatment such as, treatment with cortisol, dexamethasone, betamethasone, prednisone, methylprednisolone, or prednisolone. In additional aspects, the muscle atrophy is a condition associated with nerve trauma or a result of a degenerative, metabolic, or inflammatory neuropathy (e.g., Guillian-Barré syndrome, peripheral neuropathy, or exposure to environmental toxins or drugs). In additional aspects, the muscle atrophy is a condition associated with an adult motor neuron disease, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland disorder, diabetes, benign congenital hypotonia, central core disease, burn injury, chronic obstructive pulmonary disease, liver diseases (examples such as fibrosis, cirrhosis), sepsis, congestive heart failure, aging, space travel or time spent in a zero gravity environment.

In some aspects the treated and/or ameliorated muscle disorder is muscle atrophy associated with a myopathy. In further aspects the myopathy is selected from the group consisting of: mitochondrial myopathy; a metabolic myopathy, such as caused by a glycogen or lipid storage disease a congenital myopathy, including nemalene myopathy, multi/minicore myopathy and myotubular (centronuclear) myopathy; myotonia; familial periodic paralysis; and inflammatory myopathy. In additional aspects, the myopathy is a condition associated with a muscular dystrophy syndrome, such as Duchenne, Becker, myotonic, fascioscapulohumeral, Fukuyama, limb girdle, scapulohumeral, Emery-Dreifuss, oculopharyngeal, Charcot-Marie-Tooth disease (CMT), a congenital muscular dystrophy, or hereditary distal myopathy. The provided ActRII-binding proteins may be used to treat inclusion body myositis, myoglobinurias, rhabdomyolysis, myositis ossificans, polymyositis, or dermatomyositis. In addition, the provided ActRII-binding proteins may treat or prevent muscle atrophy arising from glucocorticoid treatment, sarcopenia, prolonged bed rest, skeletal immobilization, sepsis, or congestive heart failure In another aspect, the disclosure provides methods of treating and/or ameliorating muscular dystrophy. The term "muscular dystrophy" refers to a group of degenerative muscle diseases characterized by gradual weakening and deterioration of skeletal muscles and sometimes the heart and respiratory muscles. Exemplary muscular dystrophies that can be treated and/or ameliorated with the ActRII-binding proteins and pharmaceutical compositions provided herein include: Duchenne muscular dystrophy (DMD), Becker muscular dystrophy (BMD), Emery-Dreifuss muscular dystrophy (EDMD), limb-girdle muscular dystrophy (LGMD), fascioscapulohumeral muscular dystrophy (FSH or FSHD) (also known as Landouzy-Dejerine), myotonic muscular dystrophy (MMD) (also known as Steinert's Disease), oculopharyngeal muscular dystrophy (OPMD), distal muscular dystrophy (DD), congenital muscular dystrophy (CMD), and scapulohumeral muscular dystrophy (SMD).

In another aspect, the disclosure provides methods of treating and/or ameliorating a fibrotic condition (e.g., a fibrosis). In some instances, the method comprises administering an ActRII-binding protein (e.g., an antibody that specifically binds ActRIIB, an antibody that specifically binds ActRIIA, or an antibody that specifically binds ActRIIB and ActRIIA) to a subject having a fibrotic condition. In other aspects, the subject is at risk of developing a fibrotic condition. In further aspects the fibrotic condition is DN. In some aspects, the treated fibrotic condition is a primary fibrosis. In one aspect, the treated fibrotic condition is idiopathic. In some aspects the fibrotic condition is chronic. In some aspects, the treated fibrotic condition is systemic. In other aspects, the treated fibrotic disease or condition is a condition associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); or a medical treatment (e.g., surgical incision, chemotherapy or radiation).

Fibrotic conditions that can be treated and/or ameliorated with the ActRII-binding proteins provided herein include, but are not limited to, fibrosis, hepatic injury (e.g., liver injury caused by alcohol, and viral infection such as, Hepatitis B and C infection), pulmonary fibrosis (e.g., cystic fibrosis, IPF or lung fibrosis caused by cigarette smoking, environmental hazards and chemotherapeutic drugs such as, bleomycin), radiation induced fibrosis, injection fibrosis, vascular fibrosis, atherosclerosis, pancreatic fibrosis, musculoskeletal fibrosis (e.g., muscle fibrosis), cardiac fibrosis, skin fibrosis, scleroderma, ophthalmic fibrosis (e.g., age-related macular degeneration, diabetic macular edema, diabetic retinopathy, and dry eye disease), progressive systemic sclerosis (PSS), chronic graft-versus-host disease, Peyronie's disease, post-cystoscopic urethral stenosis, retroperitoneal fibrosis, mediastinal fibrosis, progressive massive fibrosis, proliferative fibrosis, neoplastic fibrosis, Dupuytren's disease, strictures, pleural fibrosis, sarcoidosis, spinal cord injury/fibrosis, and myelofibrosis.

Also provided are methods of decreasing fibrosis in a subject. In some aspects, the disclosure provides a method of decreasing fibrosis in a subject that comprises administering an ActRII-binding protein (e.g., in a pharmaceutical composition described herein) to a subject having a fibrosis. Such decreased fibrosis can be reflected in for example, reduced fibrosis and decreases signs or conditions associated with fibrosis including for example, decreased development of fibrotic lesions, a decrease in weight loss or other clinical symptoms, and/or an altered expression of biological molecules (e.g., mRNA or protein expression) associated with development of the fibrotic condition being treated. In some aspects, the fibrosis is a hepatic, muscle, or pulmonary fibrosis. Further provided is use of an ActRII-binding protein as provided herein in the manufacture of a medicament for the treatment of fibrosis.

In another aspect, the disclosure provides methods of reducing fibrosis in cells or tissues. The methods include contacting a fibrotic cell or tissue with an ActRII-binding protein (e.g., as a single agent or in combination with another agent or therapeutic modality) in an amount sufficient to decrease or inhibit the fibrosis. These methods can be carried out in vitro or in vivo. In one aspect, the method is carried out in vivo, for example, in a mammalian subject (e.g., an animal model). In one aspect the subject is a human. In some aspects, reducing fibrosis includes: (a) reducing or inhibiting the formation or deposition of tissue fibrosis; (b) reducing the size, cellularity (e.g., fibroblast or immune cell numbers), composition; or cellular content, of a fibrotic lesion; (c) reducing the collagen or hydroxyproline content, of a fibrotic lesion; (d) reducing expression or activity of one or more fibrogenic proteins; and/or (e) reducing fibrosis associated with an inflammatory response. In some aspects, reducing fibrosis includes: (a) reducing or inhibiting the formation or deposition of tissue fibrosis; (b) reducing the size, cellularity (e.g., fibroblast or immune cell numbers), composition; or cellular content, of a fibrotic lesion; (c) reducing the collagen or hydroxyproline content, of a fibrotic lesion; (d) reducing expression or activity of one or more fibrogenic proteins; and/or (e) reducing fibrosis associated with inflammation.

According to some aspects, the disclosure provides methods of reducing the loss of hepatic or pulmonary function in a subject. In some aspects, the method comprises administering an ActRII-binding protein (e.g., an anti-ActRII antibody such as, a full-length ActRII-antibody and an ActRII-binding antibody fragment) to a subject in need thereof. In some aspects the method reduces the loss of hepatic function in a subject. In further aspects, the method reduces the loss of hepatic function in a subject through reducing hepatic fibrosis. In some aspects the method reduces the loss of pulmonary function in a subject. In some aspects the method reduces the loss of pulmonary function in a subject through reducing pulmonary fibrosis. In some aspects the methods reduces the loss of pulmonary function and/or pulmonary fibrosis in a subject having or at risk of developing idiopathic pulmonary fibrosis (IPF).

Additionally provided are methods of improving hepatic or pulmonary function by reducing fibrosis in a subject. In some instances, the method comprises administering an ActRII-binding protein e.g., an anti-ActRII antibody such as, a full-length ActRII-antibody and an ActRII-binding antibody fragment, and variants and derivatives thereof) or pharmaceutical composition provided herein to a subject in need thereof. In some aspects, reducing the loss of, or improving, hepatic or pulmonary function includes: (a) reducing or inhibiting the formation or deposition of tissue fibrosis in the corresponding organ; (b) reducing the size, cellularity (e.g., fibroblast or immune cell numbers), composition; or cellular content, of a fibrotic lesion in the corresponding organ; (c) reducing the collagen or hydroxyproline content, of a fibrotic lesion in the corresponding organ; (d) reducing expression or activity of one or more fibrogenic proteins (e.g., fibrinogen and collagen) in the corresponding organ; (d) reducing expression extracellular matrix and/or EMT in the corresponding organ; and/or (e) reducing fibrosis associated with an inflammatory response in the corresponding organ.

The human body responds to trauma and injury by scarring. Fibrosis, a type of disorder characterized by excessive scarring, occurs when the normal wound healing response is disturbed. During fibrosis, the wound healing response continues causing an excessive production and deposition of collagen. In another aspect, the disclosure provides a method for treating fibrosis comprising administering to a subject in need thereof a therapeutically effective amount of ActRII-binding protein (e.g., an antibody that specifically binds ActRIIB or an antibody that specifically binds ActRIIA).

In some aspects, the disclosure provides methods of reducing the loss of, or improving, hepatic or pulmonary function. In some aspects, the method results in: (a) reducing or inhibiting the formation or deposition of tissue fibrosis in the corresponding organ; (b) reducing the size, cellularity (e.g., fibroblast or immune cell numbers), composition; or cellular content, of a fibrotic lesion in the corresponding organ; (c) reducing the collagen or hydroxyproline content, of a fibrotic lesion in the corresponding organ; (d) reducing expression or activity of one or more fibrogenic proteins (e.g., fibrinogen and collagen) in the corresponding organ; (d) reducing expression extracellular matrix and/or EMT in the corresponding organ; and/or (e) reducing fibrosis associated with an inflammatory response in the corresponding organ.

The disclosure also provides methods of treating and/or ameliorating a fibrotic condition of the lung. In some aspects, the method comprises administering an ActRII-binding protein (e.g., an anti-ActRII antibody such as, an antibody that specifically binds ActRII, and fragments and variants and derivatives thereof) to a subject having or at risk of developing, a fibrotic condition of the lung. In some aspects, the pulmonary fibrosis is idiopathic, pharmacologically-induced, radiation-induced, chronic obstructive pulmonary disease (COPD), or chronic asthma. Fibrotic conditions of the lung that can be treated include one or more members of the group consisting of: usual interstitial pneumonitis (UIP), interstitial lung disease, cryptogenic fibrosing alveolitis (CFA), and bronchiectasis. In some aspects the treated fibrotic condition of the lung is a condition associated with an inflammatory disorder of the lung, e.g., asthma, and/or chronic obstructive pulmonary disease (COPD).

In particular aspects, the disclosure provides a method of treating and/or ameliorating a pulmonary fibrosis that comprises administering an ActRII-binding protein to a subject having or at risk of developing, pulmonary fibrosis. Further provided is use of an ActRII-binding protein as provided herein in the manufacture of a medicament for the treatment or amelioration of pulmonary fibrosis.

In some aspects, the fibrotic condition of the lung treated with an ActRII-binding protein (e.g., and anti-ActRIIA antibody and an anti-ActRIIB antibody) is a member selected from the group consisting of: acute respiratory distress syndrome, chronic asthma, acute lung syndrome, bronchopulmonary dysplasia, pulmonary hypertension (e.g., idiopathic pulmonary hypertension (IPH)), histiocytosis X pneumoconiosis, Caplan's disease, rheumatoid disease, and systemic sclerosis.

In some aspects, the fibrotic condition of the lung treated with an ActRII-binding protein (e.g., and anti-ActRIIA antibody and an anti-ActRIIB antibody) provided herein is a condition associated with an autoimmune connective tissue disorder. In some aspects, the autoimmune connective tissue disorder is selected from the group consisting of: sarcoidosis rheumatoid arthritis, scleroderma and systemic lupus erythematosus (SLE). In additional aspects, the fibrotic condition of the lung is a condition associated with a disease, a toxin, an insult, or a medical treatment. Thus, in some aspects, the fibrotic condition of the lung is a condition associated with one or more members of the group consisting of: exposure to toxins and irritants including, inhaled workplace hazards (e.g., dust, asbestos, silica, bauxite, iron, cotton, talc, and coal dust), toxins (e.g., amiodarone, carmustine, chloramphenicol, hexamethonium), cigarette smoke, and environmental pollutants. In additional aspects, the treated fibrotic condition of the lung is a condition associated with an infectious disease. In particular aspects the infectious disease is a condition associated with a chronic infection.

In additional aspects, the treated fibrotic condition of the lung is a condition associated with a medical treatment. In particular aspects the medical treatment is selected from surgery, radiation therapy, and drug therapy. In further aspects, the drug therapy is chemotherapy. In further aspects, the chemotherapy involves the administration of a chemotherapeutic agent selected from the group consisting of bleomycin, methotrexate, amiodarone, busulfan, nitrosourea, and nitrofurantoin.

Also provided are methods of treating and/or ameliorating pulmonary hypertension or idiopathic pulmonary fibrosis (IPF). In some instances, the method comprises administering an ActRII-binding protein (e.g., an anti-ActRII antibody such as, a full-length ActRII-antibody and an ActRII-binding antibody fragment, and variants and derivatives thereof) to a subject having or at risk of developing pulmonary hypertension or IPF. In some instances, the ActRII-binding protein or the pharmaceutical composition comprising an ActRII-binding-protein is administered to treat prevent, and/or ameliorate pulmonary hypertension. In some instances, the ActRII-binding protein or the pharmaceutical composition comprising an ActRII-binding protein is administered to treat, prevent, and/or ameliorate IPF. In some aspects, the ActRII-binding protein or the pharmaceutical composition comprising an ActRII-binding protein is administered to a subject having or at risk of developing pulmonary hypertension or IPF.

The disclosure also provides methods of treating and/or ameliorating fibrotic condition of the liver. In some aspects, the method comprises administering an ActRII-binding protein or an effective amount of a pharmaceutical composition comprising an ActRII-binding protein to a subject having or at risk of developing, a fibrotic condition of the liver. Further provided is use of an ActRII-binding protein as provided herein in the manufacture of a medicament for the treatment or amelioration of a fibrotic condition of the liver. Fibrotic conditions of the liver that can be treated using ActRII-binding proteins provided herein include one or more members of the group consisting of: steatosis (e.g., nonalcoholic steatohepatitis (NASH), fatty liver disease, cholestatic liver disease (e.g., primary biliary cirrhosis (PBC)), liver cirrhosis, alcohol induced liver fibrosis, infection-induced liver fibrosis, biliary duct injury, biliary fibrosis, congenital hepatic fibrosis, autoimmune hepatitis, and a cholangiopathy. In further aspects, the infection-induced liver fibrosis is bacterial-induced or viral-induced.

In an additional aspect, the fibrotic condition of the liver that can be treated with an ActRII-binding protein provided herein is one or more members of the group consisting of: hepatic fibrosis associated with viral infection (e.g., hepatitis (hepatitis C, B and D), autoimmune hepatitis, non-alcoholic fatty liver disease (NAFLD), progressive massive fibrosis, alcoholism, and exposure to toxins or irritants (e.g., alcohol, pharmaceutical drugs and environmental toxins).

The disclosure also provides methods of treating and/or ameliorating cardiac fibrosis. In some aspects, the method comprises administering an ActRII-binding protein or an effective amount of a pharmaceutical composition comprising an ActRII-binding protein to a subject having or at risk of developing, a fibrotic condition of the cardiovascular system. In some embodiments, the cardiac fibrosis is endomyocardial fibrosis or idiopathic myocardiopathy. In some embodiments, the skin fibrosis is scleroderma, post-traumatic, operative cutaneous scarring, keloids, or cutaneous keloid formation. In some embodiments, the eye fibrosis is glaucoma, sclerosis of the eyes, conjunctival scarring, corneal scarring, or pterygium. In some embodiments, the retroperitoneal fibrosis is idiopathic, pharmacologically-induced or radiation-induced. In some embodiments, the cystic fibrosis is cystic fibrosis of the pancreas or cystic fibrosis of the lungs. In some embodiments, the injection fibrosis occurs as a complication of an intramuscular injection. Further provided is use of an ActRII-binding protein as provided herein in the manufacture of a medicament for the treatment or amelioration of a fibrotic condition of the fibrotic condition of the cardiovascular system.

Also provided are methods of treating and/or ameliorating an ocular disease or condition comprising administering an ActRII-binding protein to a subject in need thereof. In particular aspects the ocular disease or condition is glaucoma. In some aspects, the ocular disease is retinopathy. In further aspects, the ocular disease is diabetic retinopathy.

In additional aspects, the disclosure provides methods of treating and/or ameliorating a fibrotic condition of the eye (e.g., fibrosis of the eye, ophthalmic fibroses, and fibrosis associated with retinal dysfunction). Thus, in some instances, the method comprises administering an ActRII-binding protein to a subject having or at risk for developing a fibrotic condition of the eye. Further provided is use of an ActRII-binding protein as provided herein in the manufacture of a medicament for the treatment or amelioration of a fibrotic condition of the fibrotic condition of the cardiovascular system.

Fibrotic conditions of the eye that can be treated according to the methods provided herein can occur in response to injury, such as mechanical wound (e.g., fibrosis associated with alkali burn) or various metabolic malfunctions (including, e.g., responses to inflammation, ischemia, and degenerative disease). In some aspects, the disclosure provides methods for treating fibrosis associated with ocular surgery.

In further aspects, the fibrosis is a condition associated with postoperative scarring in an ocular condition. In further aspects, the postoperative scarring is a condition associated with surgery involving, retinal reattachment, cataract extraction or a drainage procedure.

In some aspects, the disclosure provides a method of treating and/or ameliorating a fibrotic condition of the eye associated with one or more members of the group consisting of: macular edema (e.g., diabetic macular edema), dry eye disease, fibrosis of the lens, fibrosis of the corneal stroma or endothelium, scarring in the cornea and conjunctiva, fibrovascular scarring, retinal fibrosis, and retinal gliosis.

In some aspects, the disclosure provides a method for treating a fibrotic condition of the eye associated with macular degeneration. In some embodiments, the treated fibrotic condition is a condition associated with age-related macular degeneration. In some embodiments the treated condition is a condition associated with wet macular degeneration. In other embodiments the treated condition is a condition associated with dry macular degeneration.

In some aspects, the disclosure provides a method for treating and/or ameliorating an inflammatory disease or condition that comprises administering an ActRII-binding protein to a subject in need thereof. Further provided is use of an ActRII-binding protein as provided herein in the manufacture of a medicament for the treatment or amelioration of inflammatory disease or condition. In some aspects, the inflammatory disease or condition is inflammatory cancer, inflammation associated with fibrosis, inflammation associated with atherosclerosis, asthma or an autoimmune disorder.

Additionally provided are methods of treating and/or ameliorating a cardiovascular disease or condition. Further provided is use of an ActRII-binding protein as provided herein in the manufacture of a medicament for the treatment or amelioration of a cardiovascular disease or condition. In some instances, the method comprises treating or ameliorating a cardiovascular disease or condition by administering an ActRII-binding protein to a subject in need thereof. In some aspects, the cardiovascular disease or condition is anemia, congestive heart failure, ventricular dysfunction, vascular calcification, pulmonary hypertension, arterial restenosis, or myocardial fibrosis.

In some aspects, the disclosure provides a method for treating and/or ameliorating a pulmonary disease or condition that comprises administering an ActRII-binding protein to a subject in need thereof. Further provided is use of an ActRII-binding protein as provided herein in the manufacture of a medicament for the treatment or amelioration of a pulmonary disease or condition.

In some aspects, the disclosure provides a method for treating and/or ameliorating a musculoskeletal disease or condition that comprises administering an effective dose of ActRII-binding protein to a subject in need thereof. Further provided is use of an ActRII-binding protein as provided herein in the manufacture of a medicament for the treatment or amelioration of a musculoskeletal disease or condition. Exemplary ActRIIB-associated conditions that can be treated and/or ameliorated by administering an effective dose of an ActRII-binding protein (e.g., anti-ActRIIB antibody) include neuromuscular disorders (e.g., muscular dystrophy and muscle atrophy), congestive obstructive pulmonary disease or pulmonary emphysema (and associated muscle wasting), muscle wasting syndrome, sarcopenia, cachexia, adipose tissue disorders (e.g., obesity), type 2 diabetes, and bone degenerative disease (e.g., osteoporosis). The use of an ActRII-binding protein as provided herein in the manufacture of a medicament for the treatment or amelioration of each of these diseases or conditions is provided herein.

Other exemplary ActRII-associated conditions that can be treated and/or ameliorated by administering an effective dose of an ActRII-binding protein (e.g., anti-ActRIIB antibody) include musculodegenerative and neuromuscular disorders, and osteoporosis.

The provided ActRII-binding proteins provide an effective means to increase muscle mass in other neuromuscular diseases or conditions that are in need of muscle growth. For example, in amyotrophic lateral sclerosis (ALS). Other neuromuscular diseases in which ActRII-binding proteins may be useful include paralysis due to spinal cord injury or stroke; denervation due to trauma or degenerative, metabolic, or inflammatory neuropathy; adult motor neuron disease; autoimmune motor neuropathy with multifocal conductor block; and infantile or juvenile spinal muscular atrophy.

In other aspects, the disclosure provides methods of inducing bone and/or cartilage formation, preventing bone loss, increasing bone mineralization or preventing the demineralization of bone. For example, the provided ActRII-binding proteins have use in treating osteoporosis and the healing of bone fractures and cartilage defects in a subject (e.g., humans and other animals). In some aspects, the disclosure provides a method for healing bone fractures or cartilage in a subject. In another aspect, the provided methods and compositions are administered to treat a condition causing bone loss such as osteoporosis, hyperparathyroidism, Cushing's disease, thyrotoxicosis, chronic diarrheal state or malabsorption, or anorexia nervosa.

In additional aspects, the disclosure provides a method for treating a neurological disorder or condition that comprises administering an ActRII-binding protein to a subject in need thereof. Further provided is use of an ActRII-binding protein as provided herein in the manufacture of a medicament for the treatment or amelioration of a neurological disorder or condition. In some aspects, the neurological disorder or condition is associated with neuronal death. In some aspects, the neurological disorder or condition is Parkinson's Disease, ALS; brain atrophy, or dementia.

In additional aspects, the disclosure provides a method for treating a metabolic disorder or condition that comprises administering an ActRII-binding protein to a subject in need thereof. Further provided is use of an ActRII-binding protein as provided herein in the manufacture of a medicament for the treatment or amelioration of a metabolic disorder or condition. In some aspects, the metabolic disorder or condition is a condition associated with diabetes. In some aspects the metabolic disorder or condition is obesity. In further aspects the metabolic disorder or condition is hypertrophic obesity. In some aspects, the metabolic disorder or condition is cancer cachexia or muscle wasting.

In other aspects, the disclosure provides positions and methods for regulating body fat content in a subject and for treating or preventing conditions related thereto, and particularly, health-compromising conditions related thereto.

As provided herein, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). According to one aspect, the disclosure provides a method of regulating body weight by administering to a subject (e.g., a human) in need thereof an ActRII-binding protein provided herein. In one aspect, the disclosure provides a method for reducing body weight and/or reducing weight gain in an subject, and more particularly, for treating or ameliorating obesity in a patient at risk for or suffering from obesity. In another aspect, the disclosure provides a method and compounds for treating a subject that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. The provided ActRIIB-binding proteins may further be used as a therapeutic agent for slowing or preventing the development of type II diabetes and metabolic syndrome.

In particular aspects, the disclosure provides a method of treating and/or ameliorating a condition associated with diabetes that comprises administering an ActRII-binding protein to a subject having or at risk of developing, diabetes and/or a condition associated with diabetes. Further provided is use of an ActRII-binding protein as provided herein in the manufacture of a medicament for the treatment or amelioration of diabetes or a condition associated with diabetes. In one aspect, the condition associated with diabetes is diabetic neuropathy, diabetic retinopathy, diabetic nephropathy, diabetic vasculopathy or diabetic microangiopathy.

In additional aspects, the disclosure provides a method for promoting wound healing that comprises administering an ActRII-binding protein to a subject in need thereof. In some aspects the ActRII-binding protein is administered to a subject to reduce scar formation associated with wound healing. In some aspects the ActRII-binding protein is administered to a subject at risk of developing a hypertrophic scar or keloid.

Additionally provided are methods of antagonizing ActRII activity in a pathological condition associated with ActRII expression and/or ActRII signaling. In some instances, the method comprises administering an ActRII-binding protein (e.g., an anti-ActRII antibody such as, a full-length anti-ActRII-antibody or an ActRII-binding antibody fragment) to a subject in need thereof. In some aspects the pathological condition is a musculoskeletal disease or disorder, such as muscle atrophy. In some aspects the pathological condition is a fibrotic disease of, for example, the lung or liver. In further aspects, the pathological condition is diabetes. In some aspects, the pathological condition is obesity (e.g., hypertrophic obesity). In additional aspects, the pathological condition is pulmonary hypertension or idiopathic pulmonary fibrosis (IPF). In some aspects the pathological condition is an ocular disease such as, diabetic retinopathy. In some aspects the pathological condition is a cancer, such as a carcinoma (e.g., basal and squamous cell carcinomas of the skin, head and neck carcinomas, and renal cell carcinoma), myeloma (e.g., multiple myeloma), colorectal cancer, or a bone-loss inducing cancer.

Methods of antagonizing ActRIIB activity in a pathological condition associated with ActRIIB expression and/or increased ActRIIB signaling are also provided. In some instances, the method comprises administering an ActRII-binding protein (e.g., an anti-ActRII antibody such as, a full-length anti-ActRIIB-antibody and an ActRIIB-binding antibody fragment, and variants and derivatives thereof) to a subject in need thereof. In some aspects the pathological condition is a musculoskeletal disease or disorder, such as muscle atrophy. In some aspects the pathological condition is a fibrotic disease of, for example, the lung or liver. In further aspects, the pathological condition is diabetes. In some aspects, the pathological condition is obesity (e.g., hypertrophic obesity). In additional aspects, the pathological condition is pulmonary hypertension or idiopathic pulmonary fibrosis (IPF). In some aspects the pathological condition is an ocular disease such as, diabetic retinopathy. In some aspects the pathological condition is a cancer, such as a carcinoma (e.g., basal and squamous cell carcinomas of the skin, and head and neck carcinomas), myeloma, renal cell carcinoma, colorectal cancer, or a bone-loss inducing cancer.

Additionally provided are methods of antagonizing ActRIIA activity in a pathological condition associated with ActRIIA expression and/or increased ActRIIA signaling. In some instances, the method comprises administering an ActRII-binding protein (e.g., an anti-ActRII antibody such as, a full-length anti-ActRIIA-antibody or an ActRIIA-binding antibody fragment) to a subject in need thereof. In some aspects the pathological condition is a musculoskeletal disease or disorder, such as muscle atrophy. In one aspect the pathological condition is a fibrotic disease. In some aspects the pathological condition is a fibrotic disease of, for example, the lung or liver. In a further aspect the pathological condition is a fibrotic disease of lung or liver. In further aspects, the pathological condition is diabetes. In some aspects, the pathological condition is obesity (e.g., hypertrophic obesity). In additional aspects, the pathological condition is pulmonary hypertension or idiopathic pulmonary fibrosis (IPF). In some aspects the pathological condition is an ocular disease such as, diabetic retinopathy. In some aspects the pathological condition is a cancer, such as a carcinoma (e.g., basal and squamous cell carcinomas of the skin, head and neck carcinomas), myeloma (e.g., multiple myeloma), colorectal cancer, or a bone-loss inducing cancer.

Additionally provided are methods of antagonizing ActRIIB and ActRIIA activity in a pathological condition associated with ActRIIB and/or ActRIIA expression, and/or increased ActRIIB and/or ActRIIA signaling. In some instances, the method comprises administering an ActRII-binding protein (e.g., an anti-ActRII antibody such as, a full-length anti-ActRII-antibody or an ActRII-binding antibody fragment) to a subject in need thereof. In some aspects the pathological condition is a musculoskeletal disease or disorder, such as muscle atrophy. In one aspect the pathological condition is a fibrotic disease. In some aspects the pathological condition is a fibrotic disease of, for example, the lung, or liver. In a further aspect the pathological condition is a fibrotic disease of the lung, or liver. In further aspects, the pathological condition is diabetes. In some aspects, the pathological condition is obesity (e.g., hypertrophic obesity). In additional aspects, the pathological condition is pulmonary hypertension or idiopathic pulmonary fibrosis (IPF). In some aspects the pathological condition is an ocular disease such as, diabetic retinopathy. In some aspects the pathological condition is a cancer, such as a carcinoma (e.g., basal and squamous cell carcinomas of the skin, head and neck carcinomas), myeloma (e.g., multiple myeloma), colorectal cancer, or a bone-loss inducing cancer.

In additional aspects, the disclosure provides methods of treating and/or ameliorating cancer or a condition associated with cancer or the treatment thereof, that comprises administering an ActRII-binding protein (e.g., an anti-ActRII antibody or ActRII-binding fragment thereof) to a subject in need thereof. In some aspects the ActRII-binding protein is an anti-ActRIIB antibody or an ActRIIB-binding fragment thereof. Further provided is use of an ActRII-binding protein as provided herein in the manufacture of a medicament for the treatment or amelioration of cancer or a condition associated with cancer. In some aspects the ActRII-binding protein is an anti-ActRIIA antibody or an ActRIIA-binding fragment thereof. In some aspects the ActRII-binding protein is an antibody that binds ActRIIB and ActRIIA or an ActRIIB and ActRIIA ActRIIB-binding fragment thereof. In some aspects, the subject has a cancer selected from the group consisting of a: melanoma, uterine cancer, lung cancer, ovarian cancer, breast cancer, colon cancer, pancreatic cancer and a sarcoma. In particular aspects, the subject has a carcinoma (e.g., basal and squamous cell carcinomas of the skin, and head and neck carcinoma), myeloma, colorectal cancer, or a bone-loss inducing cancer.

In some aspects, the method comprises contacting a cancer cell, tumor associated-stromal cell, or endothelial cell expressing ActRII (e.g., ActRIIB and/or ActRIIA), with an ActRII-binding protein that specifically binds the ActRII. In some instances, the method comprises contacting activin A with an ActRII-binding protein. In additional aspects the tumor cell is from a cancer selected from the group consisting of: myelofibrosis, myeloma (e.g., multiple myeloma), pituitary cancer. In another aspect, the cancer is breast cancer, gastrointestinal cancer, or a carcinoma (e.g., basal and squamous cell carcinomas). In an additional aspect, the cancer is a bone-loss-inducing cancer. In some aspects the tumor cell is from a cancer line.

The disclosure provides methods that comprise administering a therapeutically effective amount of a ActRII-binding protein, alone or in combination with one or more additional therapies (e.g., one or more additional therapeutic agents) to a subject having, or at risk for developing, a fibrotic condition. The disclosure additionally provides compositions for use of an ActRII-binding protein alone or in combination with another agent for preparation of one or more medicaments for use in treating (e.g., preventing), and/or ameliorating a ActRII-mediated disease and/or condition (e.g., muscle disorders such as degenerative muscle disease, muscular dystrophy, muscle atrophy, or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes insulin resistance, hyperglycemia, and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease such as osteoporosis; neurologic disease; wound healing; weight loss; and cancer (e.g., a carcinoma, myeloma, a bone-loss inducing cancer, pituitary cancer, and gastrointestinal cancer)).

Also provided is the use of an ActRII-binding protein provided herein for diagnostic monitoring of protein levels (e.g., ActRIIB and/or ActRIIA levels) in blood or tissue as part of a clinical testing procedure, e.g., to determine the efficacy of a given treatment regimen. For example, detection can be facilitated by coupling an ActRII-binding protein to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Pharmaceutical Compositions and Administration Methods

Methods of preparing and administering an ActRII-binding protein to a subject in need thereof are known to or are readily determined by those of ordinary skill in the art. The route of administration of the ActRII-binding proteins can be, for example, oral, parenteral, by inhalation or topical. The term parenteral includes, e.g., intravenous, intraarterial, intraperitoneal, intramuscular, intraocular, subcutaneous, rectal, or vaginal administration. While all these forms of administration are clearly contemplated as being within the scope of the disclosure, another example of a form for administration would be a solution for injection, in particular for intravenous or intraarterial injection or drip. Usually, a suitable pharmaceutical composition can comprise a buffer (e.g., acetate, phosphate or citrate buffer), a surfactant (e.g., polysorbate), optionally a stabilizer agent (e.g., human albumin), etc. In other methods compatible with the teachings herein, ActRII-binding proteins as provided herein can be delivered directly to the organ and/or site of a fibrosis or tumor, thereby increasing the exposure of the diseased tissue to therapeutic agent. In one aspect, the administration is directly to the airway, e.g., by inhalation or intranasal administration.

As discussed herein, ActRII-binding proteins can be administered in a pharmaceutically effective amount for the in vivo treatment of ActRII-mediated diseases and conditions including but not limited to, muscle disorders such as degenerative muscle disease, muscular dystrophy, muscle atrophy, or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes insulin resistance, hyperglycemia, and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease such as osteoporosis; neurologic disease; wound healing; weight loss; and cancer (e.g., a carcinoma, myeloma, a bone-loss inducing cancer, pituitary cancer, and gastrointestinal cancer. In this regard, it will be appreciated that the disclosed ActRII-binding proteins can be formulated so as to facilitate administration and promote stability of the active agent. Pharmaceutical compositions in accordance with the disclosure can comprise a pharmaceutically acceptable, non-toxic, sterile carrier such as physiological saline, non-toxic buffers, preservatives and the like. For the purposes of the instant application, a pharmaceutically effective amount of a ActRII-binding protein, conjugated or unconjugated, means an amount sufficient to achieve effective binding to ActRII and to achieve a benefit, e.g., to ameliorate symptoms of a disease or condition or to detect a substance or a cell. Suitable formulations for use in therapeutic methods disclosed herein are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an ActRII-binding protein (e.g., an antibody that specifically binds ActRIIB and/or ActRIIA) that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

ActRII-binding proteins provided herein can be administered to a human or other subject in accordance with the aforementioned methods of treatment in an amount sufficient to produce a therapeutic effect. The ActRII-binding proteins provided herein can be administered to such human or other animal in a conventional dosage form prepared by combining the ActRII-binding proteins with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables. A cocktail comprising one or more different ActRII-binding proteins can also be used.

Therapeutically effective doses of ActRII-binding compositions for treatment of an ActRII-mediated disease or condition such as degenerative muscle disease, muscular dystrophy, muscle atrophy, or muscle wasting disorders; a fibrotic condition; an inflammatory, autoimmune, cardiovascular, pulmonary, musculoskeletal, skeletal, ocular, neurologic, or metabolic disease or condition; obesity; wound healing; and cancer, vary depending upon many different factors, including means of administration, target site, physiological state of the subject, whether the subject is human or an animal, other medications administered, and whether treatment is prophylactic or therapeutic. Usually, the subject is a human, but non-human mammals including transgenic mammals can also be treated. Treatment dosages can be titrated using routine methods known to those of ordinary skill in the art to optimize safety and efficacy.

To ameliorate the symptoms of a particular disease or condition by administration of an ActRII-binding protein refers to any lessening, whether permanent or temporary, lasting or transient that can be attributed to or associated with administration of the ActRII-binding.

The disclosure also provides for the use of an ActRII-binding protein, such as, an anti-ActRII antibody in the manufacture of a medicament for example, for treating or degenerative muscle disease, muscular dystrophy, muscle atrophy, or muscle wasting disorders; a fibrotic condition; an inflammatory, autoimmune, cardiovascular, pulmonary, musculoskeletal, skeletal, ocular, neurologic, or metabolic disease or condition; obesity; wound healing; and cancer.

Combination Therapies

In some aspects, an ActRII-binding protein (e.g., an anti-ActRII antibody such as, a full-length ActRII-antibody and an ActRII-binding antibody fragment, and variants and derivatives thereof) is administered in combination with one or more other therapies. Such therapies include additional therapeutic agents as well as other medical interventions. Exemplary therapeutic agents that can be administered in combination with the ActRII-binding proteins provided herein include, but are not limited to, anti-SDI-fibrotics, corticosteroids, anti-inflammatories, angiotensin converting enzyme inhibitors, angiotensin receptor blockers, diuretics, antidiabetics, immune suppressants, chemotherapeutic agents, anti-metabolites, and immunomodulators. In various aspects, an ActRII-binding protein is administered to a subject before, during, and/or after a surgical excision/removal procedure.

Diagnostics

The disclosure also provides a diagnostic method useful during diagnosis of ActRII-mediated diseases and conditions (e.g., muscle disorders such as degenerative muscle disease, muscular dystrophy, muscle atrophy, or muscle wasting disorders; a fibrotic condition (e.g., a hepatic, pulmonary, vascular and/or ocular fibrotic condition, such as myocardial fibrosis, and idiopathic pulmonary fibrosis (IPF)); metabolic disease (e.g., type II diabetes insulin resistance, hyperglycemia, and obesity); inflammatory disease or conditions, autoimmune disease, cardiovascular disease (e.g., congestive heart failure, and hypertension); ocular disease such as age-related macular degeneration; pulmonary disease, musculoskeletal disease, skeletal disease such as osteoporosis; neurologic disease; wound healing; weight loss; and cancer e.g., a carcinoma, myeloma, a bone-loss inducing cancer, pituitary cancer, and gastrointestinal cancer)), which involves measuring the expression level of ActRII (e.g., ActRIIA or ActRIIB) protein tissue or body fluid from an individual and comparing the measured expression level with a standard ActRII (e.g., ActRIIA or ActRIIB) expression level in normal tissue or body fluid, whereby an increase in ActRII expression level compared to the standard is indicative of a disorder treatable by an ActRII-binding protein provided herein, such as a full-length anti-ActRIIB antibody and antigen-binding antibody fragment as provided herein.

The ActRII-binding proteins provided herein such as, anti-ActRII antibodies (e.g., full-length ActRII-antibodies and ActRII-binding antibody fragment, and variants and derivatives thereof) can be used to assay ActRII (e.g., ActRIIB and ActRIIA) levels in a biological sample using classical immunohistological methods known to those of skill in the art (see, e.g., Jalkanen, et al., *J. Cell. Biol.* 101:976-985 (1985); Jalkanen et al., *J. Cell Biol.* 105:3087-3096 (1987)). Other antibody-based methods useful for detecting ActRII protein (e.g., ActRIIB and ActRIIA) expression include immunoassays, such as the enzyme linked immunosorbent assay (ELISA), immunoprecipitation, or Western blotting.

By "assaying the expression level of ActRII protein" is intended qualitatively or quantitatively measuring or estimating the level of ActRII protein in a first biological sample either directly (e.g., by determining or estimating absolute protein level) or relatively (e.g., by comparing to the disease associated polypeptide level in a second biological sample). The ActRII protein expression level in the first biological sample can be measured or estimated and compared to a standard ActRII protein level, the standard being taken from a second biological sample obtained from an individual not having the disorder or being determined by averaging levels from a population of individuals not having the disorder. As will be appreciated in the art, once the "standard" ActRII protein level is known, it can be used repeatedly as a standard for comparison.

By "biological sample" is intended any biological sample obtained from an individual, cell line, tissue culture, or other source of cells potentially expressing ActRII. Methods for obtaining tissue biopsies and body fluids from mammals are known in the art.

Kits Comprising ActRII-binding Proteins

This disclosure further provides kits that include an ActRII-binding protein (e.g., an antibody that specifically binds ActRII such as, a full-length ActRII-antibody and an ActRII-binding antibody fragment, and variants and derivatives thereof) in suitable packaging, and written material and that can be used to perform the methods described herein. The written material can include any of the following information: instructions for use, discussion of clinical studies, listing of side effects, scientific literature references, package insert materials, clinical trial results, and/or summaries of these and the like. The written material can indicate or establish the activities and/or advantages of the composition, and/or describe dosing, administration, side effects, drug interactions, or other information useful to the health care provider. Such information can be based on the results of various studies, for example, studies using experimental animals involving in vivo models and/or studies based on human clinical trials. The kit can further contain another therapy (e.g., another agent) and/or written material such as that described above that serves to provide information regarding the other therapy (e.g., the other agent).

In certain aspects, a kit comprises at least one purified ActRII-binding protein in one or more containers. In some aspects, the kits contain all of the components necessary and/or sufficient to perform a detection assay, including all controls, directions for performing assays, and any necessary software for analysis and presentation of results.

Immunoassays

ActRII-binding proteins (e.g., antibodies that specifically bind ActRII, and ActRII-binding fragments of antibodies that specifically bind ActRII, and variants, or derivatives thereof) can be assayed for immunospecific binding by any method known in the art. The immunoassays that can be used include, but are not limited to, competitive and non-competitive assay systems using techniques such as Western blots, radioimmunoassays (REA), ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, or protein A immunoassays. Such assays are routine and known in the art (see, e.g., Ausubel et al., eds, (1994) Current Protocols in Molecular Biology (John Wiley & Sons, Inc., NY) Vol. 1, which is herein incorporated by reference in its entirety).

ActRII-binding proteins (e.g., antibodies that specifically binds ActRII and ActRII-binding fragments of antibodies that specifically bind ActRII, and variants, or derivatives thereof) provided herein can be employed histologically, as in immunofluorescence, immunoelectron microscopy or non-immunological assays, for in situ detection of ActRII (e.g., ActRIIB and ActRIIA) or conserved variants or peptide fragments thereof. In situ detection can be accomplished according to methods known in the art. Those of ordinary skill in the art will be able to determine operative and optimal assay conditions for each determination by employing routine experimentation. Methods suitable for determination of binding characteristics of an ActRII-binding protein are described herein or otherwise known in the art. Equipment and software designed for such kinetic analyses are commercially available (e.g., BIACORE®, BIAevaluation® software, GE Healthcare; KINEXA® Software, Sapidyne Instruments).

Unless otherwise indicated, the practice of the disclosure employs conventional techniques of cell biology, cell culture, molecular biology, transgenic biology, microbiology, recombinant DNA, and immunology, which are within the skill of the art.

The following examples are offered by way of illustration and not by way of limitation.

EXAMPLES

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

Example 1.

Selection, Characterization and Production of ActRII-Binding Antibodies

A multi-round selection procedure was used to select for human IgG antibodies that bind ActRII with high affinity and compete with activin A for binding human ActRII, which is detailed below.

Materials and Methods

Antigens (ActRIIA, ActRIIB, ActRIIA-Fc, and ActRIIB-Fc) were biotinylated using the EZ-Link Sulfo-NHS-Biotinylation Kit from Pierce. Goat anti-human $F(ab')_2$ kappa-FITC (LC-FITC), Extravidin-PE (EA-PE) and streptavidin-633 (SA-633) were obtained from Southern Biotech, Sigma and Molecular Probes, respectively. Streptavidin MicroBeads and MACS LC separation columns were purchased from Miltenyi Biotec.

Naïve Discovery

Eight naïve human synthetic yeast libraries each of ~$10^9$ diversity were propagated as described previously (see, e.g., WO09/036379; WO10/105256; WO12/009568). For the first two rounds of selection, a magnetic bead sorting technique utilizing the Miltenyi MACs system was performed, as described (see, e.g., Siegel et al., *J. Immunol. Meth.* 286(1-2):141-153 (2004)). Briefly, yeast cells (~$10^{10}$ cells/library) were incubated with 3 ml of 10 nM biotinylated monomeric ActRII-Fc antigen (ActRIIB-Fc or ActRIIA-Fc) for 15 minute at room temperature in FACS wash buffer (phosphate-buffered saline (PBS)/0.1% bovine serum albumin (BSA)). After washing once with 50 ml ice-cold wash buffer, the cell pellet was resuspended in 40 mL wash buffer, and Streptavidin MicroBeads (500 μl) were added to the yeast and incubated for 15 minutes at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately $1\times10^8$ yeast were pelleted, washed three times with wash buffer, and incubated with decreasing concentrations of biotinylated monomeric or ActRII-Fc fusion antigen (100 to 1 nM) under equilibrium conditions at room temperature. Yeast were then washed twice and stained with LC-FITC (diluted 1:100) and either SA-633 (diluted 1:500) or EA-PE (diluted 1:50) secondary reagents for 15 minutes at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were assigned to select for specific binders relative to a background control. Subsequent rounds of selection were employed in order to reduce the number non-specific reagent binders utilizing soluble membrane proteins from CHO cells (See, e.g., WO14/179363 and Xu et al., *Protein Eng. Des. Sel.* 26(10): 663-670 (2013)), and to identify binders with improved affinity to ActRII (ActRIIB or ActRIIA) using the ActRII-Fc (ActRIIB-Fc and ActRIIA-Fc antigen, respectively). After the final round of sorting, yeast were plated and individual colonies were picked for characterization and for nomination of clones for affinity maturation.

Affinity Maturation

Binding optimization of naïve clones was carried out utilizing three maturation strategies: light chain diversification; diversification of CDRH and/CDRH2; and performing sequential VH and VL mutagenesis.

Light chain diversification: Heavy chain plasmids were extracted naïve outputs (described above) and transformed into a light chain library with a diversity of $1\times10^6$. Selections were performed as described above with one round of MACS sorting and two rounds of FACS sorting using 10 nM or 1 nM biotinylated ActRII-Fc antigen (ActRIIB-Fc or ActRIIA-Fc) for respective rounds.

CDRH1 and CDRH2 selection: The CDRH3s from clones selected from the light chain diversification procedure of was recombined into a premade library with CDRH1 and CDRH2 variants of a diversity of $1\times10^8$ and parallel selections were performed using ActRIIB and ActRIIA antigen, respectively. As described above. Affinity pressures were applied by incubating the biotinylated antigen-antibody yeast complex with unbiotinylated antigen for different amounts of time to select for the highest affinity antibodies.

VHmut/VKmut selection: Clones obtained from the CDRH1 and CDRH2 selection procedure were subject to additional rounds of affinity maturation via error prone PCR-based mutagenesis of the heavy chain and/or light chain. Selections were performed using ActRIIB or ActRIIA as antigen generally as described above but with the addition of employing FACS sorting for all selection rounds. Antigen concentration was reduced and cold antigen competition times were increased to pressure further for optimal affinity.

Antibody Production and Purification

In order to produce sufficient amounts of selected antibodies for further characterization, the yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

ForteBio $K_D$ Measurements

ForteBio affinity measurements of selected antibodies were performed generally as previously described (see, e.g., Estep et al., *Mabs,* 5(2):270-278 (2013)). Briefly, ForteBio affinity measurements were performed by loading IgGs on-line onto AHQ sensors. Sensors were equilibrated off-line in assay buffer for 30 minutes and then monitored on-line for 60 seconds for baseline establishment. Sensors with loaded IgGs were exposed to 100 nM antigen for 5 minutes, afterwards they were transferred to assay buffer for 5 minutes for off-rate measurement. Kinetics were analyzed using the 1:1 binding model.

MSD-SET $K_D$ Measurements

Equilibrium affinity measurements of selected antibodies were performed generally as previously described (Estep et al., *Mabs* 5(2):270-278 (2013)). Briefly, solution equilibrium titrations (SET) were performed in PBS+0.1% IgG-Free BSA (PBSF) with antigen (ActRIIB monomer or ActRIIA monomer) held constant at 10-100 pM and incubated with 3- to 5-fold serial dilutions of Fab or mAbs starting at 10 pM-10 nM. Antibodies (20 nM in PBS) were coated onto standard bind MSD-ECL plates overnight at 4° C. or at room temperature for 30 minutes. Plates were then blocked by BSA for 30 minutes with shaking at 700 rpm, followed by three washes with wash buffer (PBSF+0.05% Tween 20). SET samples were applied and incubated on the plates for 150 s with shaking at 700 rpm followed by one wash. Antigen captured on a plate was detected with 250 ng/mL sulfotag-labeled streptavidin in PBSF by incubation on the plate for 3 minutes. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Octet Red384 Epitope Binning/Ligand Blocking

Epitope binning/ligand blocking of selected antibodies was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Data was processed using ForteBio's Data Analysis Software 7.0. Additional binding by the second antibody or ligand after antigen association indicates an unoccupied epitope (non-competitor), while no binding indicates epitope blocking (competitor or ligand blocking).

Size Exclusion Chromatography

A TSKgel SuperSW mAb HTP column (22855) was used for fast SEC analysis of yeast-produced mAbs at 0.4 mL/minute with a cycle time of 6 min/run. 200 mM Sodium Phosphate and 250 mM Sodium Chloride was used as the mobile phase.

Dynamic Scanning Fluorimetry 10 uL of 20× Sypro Orange was added to 20 uL of 0.2-1 mg/mL mAb or Fab solution. An RT-PCR instrument (Bio-Rad CFX96 RT PCR) was used to ramp the sample plate temperature from 40° to 95° C. at 0.5° C. increment, with a 2 minute equilibration at each temperature. The negative of the first derivative for the raw data was used to extract Tm.

Based on the foregoing analyses, the sequences of 8 naïve ActRII-binding antibodies with preferred characteristics were confirmed and chosen for binding optimization using the maturation strategies described above.

Example 2.

Characterization of ActRII-binding Naïve and Optimized Antibodies

Exemplary naïve and binding optimized ActRII-binding proteins generated according to the previous example were further characterized by sequence, SPR, and cell-based reporter assay analyses.

Sequences of exemplary naïve and binding optimized ActRII-binding antibodies generated according to the methods described in Example 1 are presented in Table 1 (exemplary CDR sequences are underscored).

TABLE 1

| Exemplary ActRII-binding proteins | |
|---|---|
| ActRIIB-binding Antibodies<br>A01 | |
| VH | CAGCTGCAGCTGCAGGAGTCGGGCCCAGGACTGGTGAAGCCTTCGGAGACCCTGTCCCTCACCTG<br>CACTGTCTCTGGTGGCTCCATCAGCAGTAGTAGTTACGCATGGGGCTGGATCCGCCAGCCCCCAGG<br>GAAGGGGCTGGAGTGGATTGGGAGTATCTATTATAGTGGGAGCACCTACTACAACCCGTCCCTCA<br>AGAGTCGAGTCACCATATCCGTAGACACGTCCAAGAACCAGTTCTCCCTGAAGCTGAGTTCTGTGA<br>CCGCCGCAGACACGGCGGTGTACTACTGCGCCAGAGACTCAGGAATAGGATACAGCTACGCCTCA<br>TCACATGGCTACTACTACTACATGGACGTATGGGGCAAGGGTACAACTGTCACCGTCTCCTCA<br>(SEQ ID NO: 1) |
| VH | QLQLQESGPGLVKPSETLSLTCTVSGGSISSSSYAWGWIRQPPGKGLEWIGSIYYSGSTYYNPSLKSRVTI<br>SVDTSKNQFSLKLSSVTAADTAVYYCARDSGIGYSYASSHGYYYYMDVWGKGTTVTVSS (SEQ ID<br>NO: 2)<br>CDR1: GGSISSSSY (SEQ ID NO: 3; nucleotides 26-34 of SEQ ID NO: 2)<br>CDR2: YYSGS (SEQ ID NO: 4; amino acid residues 54-58 of SEQ ID NO: 2)<br>CDR3: DSGIGYSYASSHGYYYYMDV (SEQ ID NO: 5; amino acid residues 100-119 of SEQ ID NO: 2) |
| H | CAGCTGCAGCTGCAGGAGTCGGGCCCAGGACTGGTGAAGCCTTCGGAGACCCTGTCCCTCACCTG<br>CACTGTCTCTGGTGGCTCCATCAGCAGTAGTAGTTACGCATGGGGCTGGATCCGCCAGCCCCCAGG<br>GAAGGGGCTGGAGTGGATTGGGAGTATCTATTATAGTGGGAGCACCTACTACAACCCGTCCCTCA<br>AGAGTCGAGTCACCATATCCGTAGACACGTCCAAGAACCAGTTCTCCCTGAAGCTGAGTTCTGTGA<br>CCGCCGCAGACACGGCGGTGTACTACTGCGCCAGAGACTCAGGAATAGGATACAGCTACGCCTCA<br>TCACATGGCTACTACTACTACATGGACGTATGGGGCAAGGGTACAACTGTCACCGTCTCCTCAGCT<br>AGCACAAAAGGACCAAGCGTGTTTCCACTGGCACCTAGCAGCAAATCCACCAGCGGCGGAACAGC<br>AGCCCTCGGGTGCCTGGTGAAGGATTACTTCCCTGAGCCAGTCACAGTGTCCTGGAACTCCGGAGC<br>CCTGACATCCGGCGTGCACACCTTCCCCGCTGTGCTGCAATCCAGCGGACTGTATAGCCTCAGCTC<br>CGTCGTGACAGTCCCTTCCAGCAGCCTGGGCACACAGACTTACATTTGCAACGTGAACCACAAACC<br>TTCCAACACTAAGGTGGACAAAAAGGTGGAACCCAAATCCTGTGATAAGACCCATACATGCCCAC<br>CTTGTCCCGCTCCTGAGCTGCTGGGGGGACCTTCCGTCTTTCTGTTTCCTCCAAAACCAAAAGACA<br>CACTCATGATCAGCCGGACCCCCGAAGTCACCTGTGTGGTGGTGGACGTCAGCCACGAAGATCCA<br>GAGGTCAAGTTCAATTGGTACGTGGATGGAGTGGAAGTCCACAACGCAAAAACCAAACCTAGAGA<br>AGAACAGTACAATAGCACATACAGGGTGGTGTCCGTCCTGACAGTGCTCCACCAGGACTGGCTCA<br>ATGGCAAAGAGTATAAGTGCAAGGTGAGCAACAAGGCCCTGCCTGCACCAATTGAGAAAACAATT<br>AGCAAGGCAAAGGGGCAGCCACGGGAACCCCAGGTGTATACCCTGCCCCCAAGCCGGGATGAAC<br>TGACCAAAAACCAGGTCAGCCTGACATGCCTGGTGAAAGGGTTTTACCCAAGCGATATTGCCGTC<br>GAGTGGGAGAGCAACGGACAGCCAGAAAACAATTACAAAACCACCCCACCTGTGCTGGACTCCG<br>ATGGGAGCTTTTTCCTGTACAGCAAGCTCACAGTGGACAAGTCCAGATGGCAACAGGGCAACGTG<br>TTTTCCTGCTCCGTGATGCACGAGGCCCTCCACAACCACTATACACAAAAGTCCCTCTCCCTCAGC<br>CCAGGAAAG (SEQ ID NO: 6) |
| H | QLQLQESGPGLVKPSETLSLTCTVSGGSISSSSYAWGWIRQPPGKGLEWIGSIYYSGSTYYNPSLKSRVTI<br>SVDTSKNQFSLKLSSVTAADTAVYYCARDSGIGYSYASSHGYYYYMDVWGKGTTVTVSSASTKGPSV<br>FPLAPSSKSTSGGTAALGCLVKDYFPEPVTVSWNSGALTSGVHTFPAVLQSSGLYSLSSVVTVPSSSLGT<br>QTYICNVNHKPSNTKVDKKVEPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK (SEQ ID NO: 7) |
| VL | GAAATAGTGTTGACGCAGTCTCCAGCCACCCTGTCTGTGTCTCCAGGGGAAAGAGCCACCCTCTCC<br>TGCAGGGCCAGTCAGAGTGTTGGCAGCAACTTAGCCTGGTACCAGCAGAAACCTGGCCAGGCTCC<br>CAGGCTCCTCATCTATGGTGCATCCACCAGGGCCACTGGTATCCCAGCCAGGTTCAGTGGCAGTGG<br>GTCTGGGACAGAGTTCACTCTCACCATCAGCAGCCTGCAGTCTGAAGATTTTGCAGTTTATTACTG<br>TCAGCAGTACTTCCACTTCCCTCTCACTTTTGGCGGAGGGACCAAGGTTGAGATCAAA (SEQ ID<br>NO: 8) |
| VL | EIVLTQSPATLSVSPGERATLSCRASQSVGSNLAWYQQKPGQAPRLLIYGASTRATGIPARFSGSGSGTE<br>FTLTISSLQSEDFAVYYCQQYFHFPLTFGGGTKVEIK (SEQ ID NO: 9)<br>CDR1: RASQSVGSNLA (SEQ ID NO: 10; amino acid residues 24-34 of SEQ ID NO: 9)<br>CDR2: GASTRAT (SEQ ID NO: 11; amino acid residues 50-56 of SEQ ID NO: 9)<br>CDR3: QQYFHFPLT (SEQ ID NO: 12; amino acid residues 89-97 of SEQ ID NO: 9) |
| L | GAAATAGTGTTGACGCAGTCTCCAGCCACCCTGTCTGTGTCTCCAGGGGAAAGAGCCACCCTCTCC<br>TGCAGGGCCAGTCAGAGTGTTGGCAGCAACTTAGCCTGGTACCAGCAGAAACCTGGCCAGGCTCC<br>CAGGCTCCTCATCTATGGTGCATCCACCAGGGCCACTGGTATCCCAGCCAGGTTCAGTGGCAGTGG<br>GTCTGGGACAGAGTTCACTCTCACCATCAGCAGCCTGCAGTCTGAAGATTTTGCAGTTTATTACTG<br>TCAGCAGTACTTCCACTTCCCTCTCACTTTTGGCGGAGGGACCAAGGTTGAGATCAAACGTACGGT<br>GGCTGCACCTTCCGTCTTTATCTTTCCACCTTCCGATGAGCAGCTGAAGAGCGGAACAGCAAGCGT<br>GGTGTGTCTGCTGAACAACTTTTATCCCCGGGAGGCAAAGGTGCAGTGGAAAGTCGACAATGCTC<br>TCCAGTCCGGCAATTCCCAAGAGAGCGTGACAGAGCAAGATTCCAAGGACTCCACTTACAGCCTG<br>TCCAGCACCCTCACACTGAGCAAGGCTGATTACGAGAAACACAAAGTGTACGCTTGTGAAGTCAC<br>CCACCAAGGCCTGAGCAGCCCAGTCACTAAGTCCTTTAACCGGGGCGAATGT (SEQ ID NO: 13) |
| L | EIVLTQSPATLSVSPGERATLSCRASQSVGSNLAWYQQKPGQAPRLLIYGASTRATGIPARFSGSGSGTE<br>FTLTISSLQSEDFAVYYCQQYFHFPLTFGGGTKVEIKRTVAAPSVFIFPPSDEQLKSGTASVVCLLNNFYP<br>REAKVQWKVDNALQSGNSQESVTEQDSKDSTYSLSSTLTLSKADYEKHKVYACEVTHQGLSSPVTKS<br>FNRGEC (SEQ ID NO: 14) |
| E01 | |
| VH | CAGGTGCAGCTGCAGGAGTCGGGCCCAGGACTGGTGAAGCCTTCACAGACCCTGTCCCTCACCTGT<br>ACTGTCTCTGGTGGCTCCATCGGGAGTGGTGGTTACTACTGGAGCTGGATCCGCCAGCACCCAGGG<br>AAGGGCCTGGAGTGGATTGGGGGATCTATGGTAGTGGGAGCACCTACTACAACCCGTCCCTCAAG |

TABLE 1-continued

Exemplary ActRII-binding proteins

AGTCGAGTTACCATATCAGTAGACACGTCTAAGAACCAGTTCTCCCTGAAGCTGAGTTCTGTGACCG
CCGCAGACACGGCGGTGTACTACTGCGCCAGAGACTCAGGAATAGGATACAGCTACGCCTCATCAC
ATGGCTACTACTACTACATGGACGTATGGGGCAAGGGTACAACTGTCACCGTCTCCTCA (SEQ ID NO: 15)

VH QVQLQESGPGLVKPSQTLSLTCTVSGGSIGSGGYYWSWIRQHPGKGLEWIGGIYGSGSTYYNPSLKSRVT
ISVDTSKNQFSLKLSSVTAADTAVYYCARDSGIGYSYASSHGYYYYMDVWGKGTTVTVSS (SEQ ID NO: 16)
CDR1: GGSIGSGGY (SEQ ID NO: 17; amino acid residues 26-34 of SEQ ID NO: 16)
CDR2: YGSG (SEQ ID NO: 18; amino acid residues 54-57 of SEQ ID NO: 16)
CDR3: DSGIGYSYASSHGYYYYMDV (SEQ ID NO: 5; amino acid residues 100-119 of SEQ ID NO: 16)

H CAGGTGCAGCTGCAGGAGTCGGGCCCAGGACTGGTGAAGCCTTCACAGACCCTGTCCCTCACCTGT
ACTGTCTCTGGTGGCTCCATCGGGAGTGGTGGTTACTACTGGAGCTGGATCCGCCAGCACCCAGGG
AAGGGCCTGGAGTGGATTGGGGGGATCTATGGTAGTGGGAGCACCTACTACAACCCGTCCCTCAA
GAGTCGAGTTACCATATCAGTAGACACGTCTAAGAACCAGTTCTCCCTGAAGCTGAGTTCTGTGAC
CGCCGCAGACACGGCGGTGTACTACTGCGCCAGAGACTCAGGAATAGGATACAGCTACGCCTCAT
CACATGGCTACTACTACTACATGGACGTATGGGGCAAGGGTACAACTGTCACCGTCTCCTCAGCTA
GCACAAAAGGACCAAGCGTGTTTCCACTGGCACCTAGCAGCAAATCCACCAGCGGCGGAACAGCA
GCCCTCGGGTGCCTGGTGAAGGATTACTTCCCTGAGCCAGTCACAGTGTCCTGGAACTCCGGAGCC
CTGACATCCGGCGTGCACACCTTCCCCGCTGTGCTGCAATCCAGCGGACTGTATAGCCTCAGCTCC
GTCGTGACAGTCCCTTCCAGCAGCCTGGGCACACAGACTTACATTTGCAACGTGAACCACAAACCT
TCCAACACTAAGGTGGACAAAAAGGTGGAACCCAAATCCTGTGATAAGACCCATACATGCCCACC
TTGTCCCGCTCCTGAGCTGCTGGGGGGACCTTCCGTCTTTCTGTTTCCTCCAAAACCAAAAGACACA
CTCATGATCAGCCGGACCCCCGAAGTCACCTGTGTGGTGGTGGACGTCAGCCACGAAGATCCAGA
GGTCAAGTTCAATTGGTACGTGGATGGAGTGGAAGTCCACAACGCAAAAACCAAACCTAGAGAAG
AACAGTACAATAGCACATACAGGGTGGTGTCCGTCCTGACAGTGCTCCACCAGGACTGGCTCAAT
GGCAAAGAGTATAAGTGCAAGGTGAGCAACAAGGCCCTGCCTGCACCAATTGAGAAAACAATTAG
CAAGGCAAAGGGGCAGCCACGGGAACCCCAGGTGTATACCCTGCCCCCAAGCCGGGATGAACTGA
CCAAAAACCAGGTCAGCCTGACATGCCTGGTGAAAGGGTTTTACCCAAGCGATATTGCCGTCGAGT
GGGAGAGCAACGGACAGCCAGAAAACAATTACAAAACCACCCCACCTGTGCTGGACTCCGATGGG
AGCTTTTTCCTGTACAGCAAGCTCACAGTGGACAAGTCCAGATGGCAACAGGGCAACGTGTTTTCC
TGCTCCGTGATGCACGAGGCCCTCCACAACCACTATACACAAAAGTCCCTCTCCCTCAGCCCAGGA
AAG (SEQ ID NO: 19)

H QVQLQESGPGLVKPSQTLSLTCTVSGGSIGSGGYYWSWIRQHPGKGLEWIGGIYGSGSTYYNPSLKSRV
TISVDTSKNQFSLKLSSVTAADTAVYYCARDSGIGYSYASSHGYYYYMDVWGKGTTVTVSSASTKGPS
VFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO: 20)

VL SEQ ID NO: 8

VL EIVLTQSPATLSVSPGERATLSCRASQSVGSNLAWYQQKPGQAPRLLIYGASTRATGIPARFSGSGSGTE
FTLTISSLQSEDFAVYYCQQYFHFPLTFGGGTKVEIK (SEQ ID NO: 9)
CDR1: RASQSVGSNLA (SEQ ID NO: 10; amino acid residues 24-34 of SEQ ID NO: 9)
CDR2: GASTRAT (SEQ ID NO: 11; amino acid residues 50-56 of SEQ ID NO: 9)
CDR3: QQYFHFPLT (SEQ ID NO: 12; amino acid residues 89-97 of SEQ ID NO: 9)

L SEQ ID NO: 13

L SEQ ID NO: 14

F01

VH CAGGTGCAGCTGCAGGAGTCGGGCCCAGGACTGGTGAAGCCTTCACAGACCCTGTCCCTCACCTG
TACTGTCTCTGGTGGCTCCATCAAGAGTGGTGGGTACTACTGGAGCTGGATCCGCCAGCACCCAGG
GAAGGGCCTGGAGTGGATTGGGGGGATCTATCCGAGTGGGAGCACCTACTACAACCCGTCCCTCA
AGAGTCGAGTTACCATATCAGTAGACACGTCTAAGAACCAGTTCTCCCTGAAGCTGAGTTCTGTGA
CCGCCGCAGACACGGCGGTGTACTACTGCGCCAGAGACTCAGGAATAGGATACAGCTACGCCTCA
TCACATGGCTACTACTACTACATGGACGTATGGGGCAAGGGTACAACTGTCACCGTCTCCTCA
(SEQ ID NO: 21)

VH QVQLQESGPGLVKPSQTLSLTCTVSGGSIKSGGYYWSWIRQHPGKGLEWIGGIYPSGSTYYNPSLKSRVT
ISVDTSKNQFSLKLSSVTAADTAVYYCARDSGIGYSYASSHGYYYYMDVWGKGTTVTVSS (SEQ ID NO: 22)
CDR1: GGSIKSGGY (SEQ ID NO: 23; amino acid residues 26-34 of SEQ ID NO: 22)
CDR2: WIGGIYPSGSTYY (SEQ ID NO: 24; amino acid residues 49-61 of SEQ ID NO: 22)
CDR3: DSGIGYSYASSHGYYYYMDV (SEQ ID NO: 5; amino acid residues 100-119 of SEQ ID NO: 22)

H CAGGTGCAGCTGCAGGAGTCGGGCCCAGGACTGGTGAAGCCTTCACAGACCCTGTCCCTCACCTG
TACTGTCTCTGGTGGCTCCATCAAGAGTGGTGGGTACTACTGGAGCTGGATCCGCCAGCACCCAGG
GAAGGGCCTGGAGTGGATTGGGGGGATCTATCCGAGTGGGAGCACCTACTACAACCCGTCCCTCA
AGAGTCGAGTTACCATATCAGTAGACACGTCTAAGAACCAGTTCTCCCTGAAGCTGAGTTCTGTGA
CCGCCGCAGACACGGCGGTGTACTACTGCGCCAGAGACTCAGGAATAGGATACAGCTACGCCTCA
TCACATGGCTACTACTACTACATGGACGTATGGGGCAAGGGTACAACTGTCACCGTCTCCTCAGCT
AGCACAAAAGGACCAAGCGTGTTTCCACTGGCACCTAGCAGCAAATCCACCAGCGGCGGAACAGC
AGCCCTCGGGTGCCTGGTGAAGGATTACTTCCCTGAGCCAGTCACAGTGTCCTGGAACTCCGGAGC
CCTGACATCCGGCGTGCACACCTTCCCCGCTGTGCTGCAATCCAGCGGACTGTATAGCCTCAGCTC
CGTCGTGACAGTCCCTTCCAGCAGCCTGGGCACACAGACTTACATTTGCAACGTGAACCACAAACC
TTCCAACACTAAGGTGGACAAAAAGGTGGAACCCAAATCCTGTGATAAGACCCATACATGCCCAC
CTTGTCCCGCTCCTGAGCTGCTGGGGGGACCTTCCGTCTTTCTGTTTCCTCCAAAACCAAAAGACA
CACTCATGATCAGCCGGACCCCCGAAGTCACCTGTGTGGTGGTGGACGTCAGCCACGAAGATCCA
GAGGTCAAGTTCAATTGGTACGTGGATGGAGTGGAAGTCCACAACGCAAAAACCAAACCTAGAGA
AGAACAGTACAATAGCACATACAGGGTGGTGTCCGTCCTGACAGTGCTCCACCAGGACTGGCTCA

TABLE 1-continued

| Exemplary ActRII-binding proteins | |
|---|---|
| | ATGGCAAAGAGTATAAGTGCAAGGTGAGCAACAAGGCCCTGCCTGCACCAATTGAGAAAACAATT |
| | AGCAAGGCAAAGGGGCAGCCACGGGAACCCCAGGTGTATACCCTGCCCCCAAGCCGGGATGAAC |
| | TGACCAAAAACCAGGTCAGCCTGACATGCCTGGTGAAAGGGTTTTACCCAAGCGATATTGCCGTC |
| | GAGTGGGAGAGCAACGGACAGCCAGAAAACAATTACAAAACCACCCCACCTGTGCTGGACTCCG |
| | ATGGGAGCTTTTTCCTGTACAGCAAGCTCACAGTGGACAAGTCCAGATGGCAACAGGGCAACGTG |
| | TTTTCCTGCTCCGTGATGCACGAGGCCCTCCACAACCACTATACACAAAAGTCCCTCTCCCTCAGC |
| | CCAGGAAAG (SEQ ID NO: 25) |
| H | QVQLQESGPGLVKPSQTLSLTCTVSGGSIKSGGYYWSWIRQHPGKGLEWIGGIYPSGSTYYNPSLKSR |
| | VTISVDTSKNQFSLKLSSVTAADTAVYYCARDSGIGYSYASSHGYYYYMDVWGKGTTVTVSSASTKG |
| | PSVFPLAPSSKSTSGGTAALGCLVKDYFPEPVTVSWNSGALTSGVHTFPAVLQSSGLYSLSSVVTVPSS |
| | SLGTQTYICNVNHKPSNTKVDKKVEPKSCDKTHTCPPCPAPELLGGPSVFLFPPKPKDTLMISRTPEVT |
| | CVVVDVSHEDPEVKFNWYVDGVEVHNAKTKPREEQYNSTYRVVSVLTVLHQDWLNGKEYKCKVSN |
| | KALPAPIEKTISKAKGQPREPQVYTLPPSRDELTKNQVSLTCLVKGFYPSDIAVEWESNGQPENNYKTT |
| | PPVLDSDGSFFLYSKLTVDKSRWQQGNVFSCSVMHEALHNHYTQKSLSLSPGK (SEQ ID NO: 26) |
| VL | SEQ ID NO: 8 |
| VL | EIVLTQSPATLSVSPGERATLSCRASQSVGSNLAWYQQKPGQAPRLLIYGASTRATGIPARFSGSGSGTEF |
| | TLTISSLQSEDFAVYYCQQYFHFPLTFGGGTKVEIK (SEQ ID NO: 9) |
| | CDR1: RASQSVGSNLA (SEQ ID NO: 10; amino acid residues 24-34 of SEQ ID NO: 9) |
| | CDR2: GASTRAT (SEQ ID NO: 11; amino acid residues 50-56 of SEQ ID NO: 9) |
| | CDR3: QQYFHFPLT (SEQ ID NO: 12; amino acid residues 89-97 of SEQ ID NO: 9) |
| L | SEQ ID NO: 13 |
| L | SEQ ID NO: 14 |
| **B01** | |
| VH | CAGGTGCAGCTGCAGGAGTCGGGCCCAGGACTGGTGAAGCCTTCACAGACCCTGTCCCTCACCTG |
| | TACTGTCTCTGGTGGCTCCATCGAGAGCGGTGGTTACTACTGGAGCTGGATCCGCCAGCACCCAG |
| | GGAAGGGCCTGGAGTGGATTGGGGGTATCTATGGGAGTGGGAGCACCTACTACAACCCGTCCCTC |
| | AAGAGTCGAGTTACCATATCAGTAGACACGTCTAAGAACCAGTTCTCCCTGAAGCTGAGTTCTGT |
| | GACCGCCGCAGACACGGCGGTGTACTACTGCGCCAGAGACTCAGGAATAGGATACAGCTACGCC |
| | TCATCACATGGCTACTACTACTACATGGACGTATGGGGCAAGGGTACAACTGTCACCGTCTCCTC |
| | A (SEQ ID NO: 27) |
| VH | QVQLQESGPGLVKPSQTLSLTCTVSGGSILSGGYYWSWIRQHPGKGLEWIGGIYYSGKTYYNPSLKSR |
| | VTISVDTSKNQFSLKLSSVTAADTAVYYCARDSGIGYSYASSHGYYYYMDVWGKGTTVTVSS (SEQ |
| | ID NO: 28) |
| | CDR1: GGSILSGGY (SEQ ID NO: 29; amino acid residues 26-34 of SEQ ID NO: 28) |
| | CDR2: YYSGK (SEQ ID NO: 30; amino acid residues 54-58 of SEQ ID NO: 28) |
| | CDR3: DSGIGYSYASSHGYYYYMDV (SEQ ID NO: 5; amino acid residues 100-119 of SEQ ID NO: 28) |
| H | CAGGTGCAGCTGCAGGAGTCGGGCCCAGGACTGGTGAAGCCTTCACAGACCCTGTCCCTCACCTG |
| | TACTGTCTCTGGTGGCTCCATCGAGAGCGGTGGTTACTACTGGAGCTGGATCCGCCAGCACCCAG |
| | GGAAGGGCCTGGAGTGGATTGGGGGTATCTATGGGAGTGGGAGCACCTACTACAACCCGTCCCTC |
| | AAGAGTCGAGTTACCATATCAGTAGACACGTCTAAGAACCAGTTCTCCCTGAAGCTGAGTTCTGT |
| | GACCGCCGCAGACACGGCGGTGTACTACTGCGCCAGAGACTCAGGAATAGGATACAGCTACGCC |
| | TCATCACATGGCTACTACTACTACATGGACGTATGGGGCAAGGGTACAACTGTCACCGTCTCCTC |
| | AGCTAGCACAAAAGGACCAAGCGTGTTTCCACTGGCACCTAGCAGCAAATCCACCAGCGGCGGA |
| | ACAGCAGCCCTCGGGTGCCTGGTGAAGGATTACTTCCCTGAGCCAGTCACAGTGTCCTGGAACTC |
| | CGGAGCCCTGACATCCGGCGTGCACACCTTCCCCGCTGTGCTGCAATCCAGCGGACTGTATAGCC |
| | TCAGCTCCGTCGTGACAGTCCCTTCCAGCAGCCTGGGCACACAGACTTACATTTGCAACGTGAAC |
| | CACAAACCTTCCAACACTAAGGTGGACAAAAAGGTGGAACCCAAATCCTGTGATAAGACCCATA |
| | CATGCCCACCTTGTCCCGCTCCTGAGCTGCTGGGGGGACCTTCCGTCTTTCTGTTTCCTCCAAAAC |
| | CAAAAGACACACTCATGATCAGCCGGACCCCCGAAGTCACCTGTGTGGTGGTGGACGTCAGCCAC |
| | GAAGATCCAGAGGTCAAGTTCAATTGGTACGTGGATGGAGTGGAAGTCCACAACGCAAAAACCA |
| | AACCTAGAGAAGAACAGTACAATAGCACATACAGGGTGGTGTCCGTCCTGACAGTGCTCCACCA |
| | GGACTGGCTCAATGGCAAAGAGTATAAGTGCAAGGTGAGCAACAAGGCCCTGCCTGCACCAATT |
| | GAGAAAACAATTAGCAAGGCAAAGGGGCAGCCACGGGAACCCCAGGTGTATACCCTGCCCCCAA |
| | GCCGGGATGAACTGACCAAAAACCAGGTCAGCCTGACATGCCTGGTGAAAGGGTTTTACCCAAG |
| | CGATATTGCCGTCGAGTGGGAGAGCAACGGACAGCCAGAAAACAATTACAAAACCACCCCACCT |
| | GTGCTGGACTCCGATGGGAGCTTTTTCCTGTACAGCAAGCTCACAGTGGACAAGTCCAGATGGCA |
| | ACAGGGCAACGTGTTTTCCTGCTCCGTGATGCACGAGGCCCTCCACAACCACTATACACAAAAGT |
| | CCCTCTCCCTCAGCCCAGGAAAG (SEQ ID NO: 31) |
| H | QVQLQESGPGLVKPSQTLSLTCTVSGGSIESGGYYWSWIRQHPGKGLEWIGGIYGSGSTYYNPSLKSR |
| | VTISVDTSKNQFSLKLSSVTAADTAVYYCARDSGIGYSYASSHGYYYYMDVWGKGTTVTVSSASTKG |
| | PSVFPLAPSSKSTSGGTAALGCLVKDYFPEPVTVSWNSGALTSGVHTFPAVLQSSGLYSLSSVVTVPSS |
| | SLGTQTYICNVNHKPSNTKVDKKVEPKSCDKTHTCPPCPAPELLGGPSVFLFPPKPKDTLMISRTPEVT |
| | CVVVDVSHEDPEVKFNWYVDGVEVHNAKTKPREEQYNSTYRVVSVLTVLHQDWLNGKEYKCKVSN |
| | KALPAPIEKTISKAKGQPREPQVYTLPPSRDELTKNQVSLTCLVKGFYPSDIAVEWESNGQPENNYKTT |
| | PPVLDSDGSFFLYSKLTVDKSRWQQGNVFSCSVMHEALHNHYTQKSLSLSPGK (SEQ ID NO: 32) |
| VL | SEQ ID NO: 8 |
| VL | EIVLTQSPATLSVSPGERATLSCRASQSVGSNLAWYQQKPGQAPRLLIYGASTRATGIPARFSGSGSGTEF |
| | TLTISSLQSEDFAVYYCQQYFHFPLTFGGGTKVEIK (SEQ ID NO: 9) |
| | CDR1: RASQSVGSNLA (SEQ ID NO: 10; amino acid residues 24-34 of SEQ ID NO: 9) |
| | CDR2: GASTRAT (SEQ ID NO: 11; amino acid residues 50-56 of SEQ ID NO: 9) |
| | CDR3: QQYFHFPLT (SEQ ID NO: 12; amino acid residues 89-97 of SEQ ID NO: 9) |
| L | SEQ ID NO: 13 |
| L | SEQ ID NO: 14 |

TABLE 1-continued

Exemplary ActRII-binding proteins

C01

VH CAGGTGCAGCTGCAGGAGTCGGGCCCAGGACTGGTGAAGCCTTCACAGACCCTGTCCCTCACCTG
TACTGTCTCTGGTGGCTCCATCTCTAGTGGTGGTTACTTTTGGAGCTGGATCCGCCAGCACCCAGG
GAAGGGCCTGGAGTGGATTGGGGGGATCTATTACAGTGGGCGGACCTACTACAACCCGTCCCTCA
AGAGTCGAGTTACCATATCAGTAGACACGTCTAAGAACCAGTTCTCCCTGAAGCTGAGTTCTGTG
ACCGCCGCAGACACGGCGGTGTACTACTGCGCCAGAGACTCAGGAATAGGATACAGCTACGCCTC
ATCACATGGCTACTACTACTACATGGACGTATGGGGCAAGGGTACAACTGTCACCGTCTCCTCA
(SEQ ID NO: 33)

VH QVQLQESGPGLVKPSQTLSLTCTVSGGSISSGGYFWSWIRQHPGKGLEWIGGIYYSGRTYYNPSLKSRV
TISVDTSKNQFSLKLSSVTAADTAVYYCARDSGIGYSYASSHGYYYYMDVWGKGTTVTVSS (SEQ ID
NO: 34)
CDR1: GGSISSGGY (SEQ ID NO: 35; amino acid residues 26-34 of SEQ ID NO: 34)
CDR2: YYSGRT (SEQ ID NO: 36; amino acid residues 54-58 of SEQ ID NO: 34)
CDR3: DSGIGYSYASSHGYYYYMDV (SEQ ID NO: 5; amino acid residues 100-119 of SEQ ID NO: 34)

H CAGGTGCAGCTGCAGGAGTCGGGCCCAGGACTGGTGAAGCCTTCACAGACCCTGTCCCTCACCTG
TACTGTCTCTGGTGGCTCCATCTCTAGTGGTGGTTACTTTTGGAGCTGGATCCGCCAGCACCCAGG
GAAGGGCCTGGAGTGGATTGGGGGGATCTATTACAGTGGGCGGACCTACTACAACCCGTCCCTCA
AGAGTCGAGTTACCATATCAGTAGACACGTCTAAGAACCAGTTCTCCCTGAAGCTGAGTTCTGTG
ACCGCCGCAGACACGGCGGTGTACTACTGCGCCAGAGACTCAGGAATAGGATACAGCTACGCCTC
ATCACATGGCTACTACTACTACATGGACGTATGGGGCAAGGGTACAACTGTCACCGTCTCCTCAG
CTAGCACAAAAGGACCAAGCGTGTTTCCACTGGCACCTAGCAGCAAATCCACCAGCGGCGGAACA
GCAGCCCTCGGGTGCCTGGTGAAGGATTACTTCCCTGAGCCAGTCACAGTGTCCTGGAACTCCGG
AGCCCTGACATCCGGCGTGCACACCTTCCCCGCTGTGCTGCAATCCAGCGGACTGTATAGCCTCAG
CTCCGTCGTGACAGTCCCTTCCAGCAGCCTGGGCACACAGACTTACATTTGCAACGTGAACCACA
AACCTTCCAACACTAAGGTGGACAAAAAGGTGGAACCCAAATCCTGTGATAAGACCCATACATGC
CCACCTTGTCCCGCTCCTGAGCTGCTGGGGGGACCTTCCGTCTTTCTGTTTCCTCCAAAACCAAAA
GACACACTCATGATCAGCCGGACCCCCGAAGTCACCTGTGTGGTGGTGGACGTCAGCCACGAAGA
TCCAGAGGTCAAGTTCAATTGGTACGTGGATGGAGTGGAAGTCCACAACGCAAAAACCAAACCTA
GAGAAGAACAGTACAATAGCACATACAGGGTGGTGTCCGTCCTGACAGTGCTCCACCAGGACTGG
CTCAATGGCAAAGAGTATAAGTGCAAGGTGAGCAACAAGGCCCTGCCTGCACCAATTGAGAAAA
CAATTAGCAAGGCAAAGGGGCAGCCACGGGAACCCCAGGTGTATACCCTGCCCCCAAGCCGGGA
TGAACTGACCAAAAACCAGGTCAGCCTGACATGCCTGGTGAAAGGGTTTTACCCAAGCGATATTG
CCGTCGAGTGGGAGAGCAACGGACAGCCAGAAAACAATTACAAAACCACCCCACCTGTGCTGGA
CTCCGATGGGAGCTTTTTCCTGTACAGCAAGCTCACAGTGGACAAGTCCAGATGGCAACAGGGCA
ACGTGTTTTCCTGCTCCGTGATGCACGAGGCCCTCCACAACCACTATACACAAAAGTCCCTCTCCC
TCAGCCCAGGAAAG (SEQ ID NO: 37)

H QVQLQESGPGLVKPSQTLSLTCTVSGGSISSGGYFWSWIRQHPGKGLEWIGGIYYSGRTYYNPSLKSRV
TISVDTSKNQFSLKLSSVTAADTAVYYCARDSGIGYSYASSHGYYYYMDVWGKGTTVTVSSASTKGP
SVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO: 38)

VL SEQ ID NO: 8

VL EIVLTQSPATLSVSPGERATLSCRASQSVGSNLAWYQQKPGQAPRLLIYGASTRATGIPARFSGSGSGTE
FTLTISSLQSEDFAVYYCQQYFHFPLTFGGGTKVEIK (SEQ ID NO: 9)
CDR1: RASQSVGSNLA (SEQ ID NO: 10; amino acid residues 24-34 of SEQ ID NO: 9)
CDR2: GASTRAT (SEQ ID NO: 11; amino acid residues 50-56 of SEQ ID NO: 9)
CDR3: QQYFHFPLT (SEQ ID NO: 12; amino acid residues 89-97 of SEQ ID NO: 9)

L SEQ ID NO: 13

L SEQ ID NO: 14

D01

VH CAGGTGCAGCTGCAGGAGTCGGGCCCAGGACTGGTGAAGCCTTCACAGACCCTGTCCCTCACCTGT
ACTGTCTCTGGTGGCTCCATCGAGAGCGGTGGTTACTACTGGAGCTGGATCCGCCAGCACCCAGGG
AAGGGCCTGGAGTGGATTGGGGGTATCTATGGGAGTGGGAGCACCTACTACAACCCGTCCCTCAA
GAGTCGAGTTACCATATCAGTAGACACGTCTAAGAACCAGTTCTCCCTGAAGCTGAGTTCTGTGAC
CGCCGCAGACACGGCGGTGTACTACTGCGCCAGAGACTCAGGAATAGGATACAGCTACGCCTCAT
CACATGGCTACTACTACTACATGGACGTATGGGGCAAGGGTACAACTGTCACCGTCTCCTCA)
(SEQ ID NO: 39)

VH QVQLQESGPGLVKPSQTLSLTCTVSGGSIESGGYYWSWIRQHPGKGLEWIGGIYGSGSTYYNPSLKSRV
TISVDTSKNQFSLKLSSVTAADTAVYYCARDSGIGYSYASSHGYYYYMDVWGKGTTVTVSS (SEQ ID
NO: 40)
CDR1: GGSIESGGY (SEQ ID NO: 41; amino acid residues 26-34 of SEQ ID NO: 40)
CDR2: YGSGS (SEQ ID NO: 18; amino acid residues 54-58 of SEQ ID NO: 40)
CDR3: DSGIGYSYASSHGYYYYMDV (SEQ ID NO: 5; amino acid residues 100-119 of SEQ ID NO: 40)

H CAGGTGCAGCTGCAGGAGTCGGGCCCAGGACTGGTGAAGCCTTCACAGACCCTGTCCCTCACCTGT
ACTGTCTCTGGTGGCTCCATCGAGAGCGGTGGTTACTACTGGAGCTGGATCCGCCAGCACCCAGGG
AAGGGCCTGGAGTGGATTGGGGGTATCTATGGGAGTGGGAGCACCTACTACAACCCGTCCCTCAA
GAGTCGAGTTACCATATCAGTAGACACGTCTAAGAACCAGTTCTCCCTGAAGCTGAGTTCTGTGAC
CGCCGCAGACACGGCGGTGTACTACTGCGCCAGAGACTCAGGAATAGGATACAGCTACGCCTCAT
CACATGGCTACTACTACTACATGGACGTATGGGGCAAGGGTACAACTGTCACCGTCTCCTCAGCTA
GCACAAAAGGACCAAGCGTGTTTCCACTGGCACCTAGCAGCAAATCCACCAGCGGCGGAACAGCA
GCCCTCGGGTGCCTGGTGAAGGATTACTTCCCTGAGCCAGTCACAGTGTCCTGGAACTCCGGAGCC
CTGACATCCGGCGTGCACACCTTCCCCGCTGTGCTGCAATCCAGCGGACTGTATAGCCTCAGCTCC

TABLE 1-continued

| | Exemplary ActRII-binding proteins |
|---|---|
| | GTCGTGACAGTCCCTTCCAGCAGCCTGGGCACACAGACTTACATTTGCAACGTGAACCACAAACCT<br>TCCAACACTAAGGTGGACAAAAAGGTGGAACCCAAATCCTGTGATAAGACCCATACATGCCCACC<br>TTGTCCCGCTCCTGAGCTGCTGGGGGGACCTTCCGTCTTTCTGTTTCCTCCAAAACCAAAAGACACA<br>CTCATGATCAGCCGGACCCCCGAAGTCACCTGTGTGGTGGTGGACGTCAGCCACGAAGATCCAGA<br>GGTCAAGTTCAATTGGTACGTGGATGGAGTGGAAGTCCACAACGCAAAAACCAAACCTAGAGAAG<br>AACAGTACAATAGCACATACAGGGTGGTGTCCGTCCTGACAGTGCTCCACCAGGACTGGCTCAAT<br>GGCAAAGAGTATAAGTGCAAGGTGAGCAACAAGGCCCTGCCTGCACCAATTGAGAAAACAATTAG<br>CAAGGCAAAGGGGCAGCCACGGGAACCCCAGGTGTATACCCTGCCCCCAAGCCGGGATGAACTGA<br>CCAAAAACCAGGTCAGCCTGACATGCCTGGTGAAAGGGTTTTACCCAAGCGATATTGCCGTCGAGT<br>GGGAGAGCAACGGACAGCCAGAAAACAATTACAAAACCACCCCACCTGTGCTGGACTCCGATGGG<br>AGCTTTTTCCTGTACAGCAAGCTCACAGTGGACAAGTCCAGATGGCAACAGGGCAACGTGTTTTCC<br>TGCTCCGTGATGCACGAGGCCCTCCACAACCACTATACACAAAAGTCCCTCTCCCTCAGCCCAGGA<br>AAG (SEQ ID NO: 42) |
| H | QVQLQESGPGLVKPSQTLSLTCTVSGGSIESGGYYWSWIRQHPGKGLEWIGGIYGSGSTYYNPSLKSRV<br>TISVDTSKNQFSLKLSSVTAADTAVYYCARDSGIGYSYASSHGYYYYMDVWGKGTTVTVSSASTKGPS<br>VFPLAPSSKSTSGGTAALGCLVKDYFPEPVTVSWNSGALTSGVHTFPAVLQSSGLYSLSSVVTVPSSSLG<br>TQTYICNVNHKPSNTKVDKKVEPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPGK (SEQ ID NO: 43) |
| VL | SEQ ID NO: 8 |
| VL | EIVLTQSPATLSVSPGERATLSCRASQSVGSNLAWYQQKPGQAPRLLIYGASTRATGIPARFSGSGSGTE<br>FTLTISSLQSEDFAVYYCQQYFHFPLTFGGGTKVEIK (SEQ ID NO: 9)<br>CDR1: RASQSVGSNLA (SEQ ID NO: 10; amino acid residues 24-34 of SEQ ID NO: 9)<br>CDR2: GASTRAT (SEQ ID NO: 11; amino acid residues 50-56 of SEQ ID NO: 9)<br>CDR3: QQYFHFPLT (SEQ ID NO: 12; amino acid residues 89-97 of SEQ ID NO: 9) |
| L | SEQ ID NO: 13 |
| L | SEQ ID NO: 14 |
| | G01 |
| VH | CAGCTGCAGCTGCAGGAGTCGGGCCCAGGACTGGTGAAGCCTTCGGAGACCCTGTCCCTCACCTGC<br>ACTGTCTCTGGTGGCTCCATCAGCAGTAGTAGTTACGCATGGGGCTGGATCCGCCAGCCCCCAGGGA<br>AGGGGCTGGAGTGGATTGGGAGTATCTATTATAGTGGGAGCACCTACTACAACCCGTCCCTCAAGA<br>GTCGAGTCACCATATCCGTAGACACGTCCAAGAACCAGTTCTCCCTGAAGCTGAGTTCTGTGACCGC<br>CGCAGACACGGCGGTGTACTACTGCGCCAGAGCTGGAAAATACCGATGGCACGGAATGGACGTATG<br>GGGCCAGGGAACAACTGTCACCGTCTCCTCA (SEQ ID NO: 44) |
| VH | QLQLQESGPGLVKPSETLSLTCTVSGGSISSSSYAWGWIRQPPGKGLEWIGSIYYSGSTYYNPSLKSRVTIS<br>VDTSKNQFSLKLSSVTAADTAVYYCARAGKYRWHGMDVWGQGTTVTVSS (SEQ ID NO: 45)<br>CDR1: GGSISSSSY (SEQ ID NO: 3; amino acid residues 26-34 of SEQ ID NO: 45)<br>CDR2: YYSGS (SEQ ID NO: 4; amino acid residues 54-58 of SEQ ID NO: 45)<br>CDR3: AGKYRWHGMDV (SEQ ID NO: 46; amino acid residues 100-110 of SEQ ID NO: 45) |
| H | CAGCTGCAGCTGCAGGAGTCGGGCCCAGGACTGGTGAAGCCTTCGGAGACCCTGTCCCTCACCTGC<br>ACTGTCTCTGGTGGCTCCATCAGCAGTAGTAGTTACGCATGGGGCTGGATCCGCCAGCCCCCAGGGA<br>AGGGGCTGGAGTGGATTGGGAGTATCTATTATAGTGGGAGCACCTACTACAACCCGTCCCTCAAGA<br>GTCGAGTCACCATATCCGTAGACACGTCCAAGAACCAGTTCTCCCTGAAGCTGAGTTCTGTGACCGC<br>CGCAGACACGGCGGTGTACTACTGCGCCAGAGCTGGAAAATACCGATGGCACGGAATGGACGTATG<br>GGGCCAGGGAACAACTGTCACCGTCTCCTCAGCTAGCACAAAAGGACCAAGCGTGTTTCCACTGGC<br>ACCTAGCAGCAAATCCACCAGCGGCGGAACAGCAGCCCTCGGGTGCCTGGTGAAGGATTACTTCCC<br>TGAGCCAGTCACAGTGTCCTGGAACTCCGGAGCCCTGACATCCGGCGTGCACACCTTCCCCGCTGTG<br>CTGCAATCCAGCGGACTGTATAGCCTCAGCTCCGTCGTGACAGTCCCTTCCAGCAGCCTGGGCACAC<br>AGACTTACATTTGCAACGTGAACCACAAACCTTCCAACACTAAGGTGGACAAAAAGGTGGAACCCA<br>AATCCTGTGATAAGACCCATACATGCCCACCTTGTCCCGCTCCTGAGCTGCTGGGGGGACCTTCCGT<br>CTTTCTGTTTCCTCCAAAACCAAAAGACACACTCATGATCAGCCGGACCCCCGAAGTCACCTGTGTG<br>GTGGTGGACGTCAGCCACGAAGATCCAGAGGTCAAGTTCAATTGGTACGTGGATGGAGTGGAAGTC<br>CACAACGCAAAAACCAAACCTAGAGAAGAACAGTACAATAGCACATACAGGGTGGTGTCCGTCCTG<br>ACAGTGCTCCACCAGGACTGGCTCAATGGCAAAGAGTATAAGTGCAAGGTGAGCAACAAGGCCCTG<br>CCTGCACCAATTGAGAAAACAATTAGCAAGGCAAAGGGGCAGCCACGGGAACCCCAGGTGTATAC<br>CCTGCCCCCAAGCCGGGATGAACTGACCAAAAACCAGGTCAGCCTGACATGCCTGGTGAAAGGGTT<br>TTACCCAAGCGATATTGCCGTCGAGTGGGAGAGCAACGGACAGCCAGAAAACAATTACAAAACCAC<br>CCCACCTGTGCTGGACTCCGATGGGAGCTTTTTCCTGTACAGCAAGCTCACAGTGGACAAGTCCAGA<br>TGGCAACAGGGCAACGTGTTTTCCTGCTCCGTGATGCACGAGGCCCTCCACAACCACTATACACAAA<br>AGTCCCTCTCCCTCAGCCCAGGAAAG (SEQ ID NO: 47) |
| H | QLQLQESGPGLVKPSETLSLTCTVSGGSISSSSYAWGWIRQPPGKGLEWIGSIYYSGSTYYNPSLKSRVTIS<br>VDTSKNQFSLKLSSVTAADTAVYYCARAGKYRWHGMDVWGQGTTVTVSSASTKGPSVFPLAPSSKSTS<br>GGTAALGCLVKDYFPEPVTVSWNSGALTSGVHTFPAVLQSSGLYSLSSVVTVPSSSLGTQTYICNVNHKP<br>SNTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLYSKLTVD<br>KSRWQQGNVFSCSVMHEALHNHYTQKSLSLSPGK (SEQ ID NO: 48) |
| VL | GACATCCAGATGACCCAGTCTCCATCTTCCGTGTCTGCATCTGTAGGAGACAGAGTCACCATCACTT<br>GTCGGGCGAGTCAGGGTATTAGCAGCTGGTTAGCCTGGTATCAGCAGAAACCAGGGAAAGCCCCTA<br>AGCTCCTGATCTATGCTGCATCCAATTTGCAAAGTGGGGTCCCATCAAGGTTCAGCGGCAGTGGATC<br>TGGGACAGATTTCACTCTCACCATCAGCAGCCTGCAGCCTGAAGATTTTGCAACTTATTACTGTCAG<br>CAGGCACCCGACCTCCCTATCACTTTTGGCGGAGGGACCAAGGTTGAGATCAAA (SEQ ID NO: 49) |

TABLE 1-continued

| Exemplary ActRII-binding proteins | |
|---|---|
| VL | DIQMTQSPSSVSASVGDRVTITCRASQGISSWLAWYQQKPGKAPKLLIYAASNLQSGVPSRFSGSGSGTD<br>FTLTISSLQPEDFATYYCQQAPDLPITFGGGTKVEIK (SEQ ID NO: 50)<br>CDR1: RASQGISSWLA (SEQ ID NO: 51; amino acid residues 24-34 of SEQ ID NO: 50)<br>CDR2: AASNLQS (SEQ ID NO: 52; amino acid residues 50-56 of SEQ ID NO: 50)<br>CDR3: QQAPDLPIT (SEQ ID NO: 53; amino acid residues 89-97 of SEQ ID NO: 50) |
| L | GACATCCAGATGACCCAGTCTCCATCTTCCGTGTCTGCATCTGTAGGAGACAGAGTCACCATCACT<br>TGTCGGGCGAGTCAGGGTATTAGCAGCTGGTTAGCCTGGTATCAGCAGAAACCAGGGAAAGCCCC<br>TAAGCTCCTGATCTATGCTGCATCCAATTTGCAAAGTGGGGTCCCATCAAGGTTCAGCGGCAGTGG<br>ATCTGGGACAGATTTCACTCTCACCATCAGCAGCCTGCAGCCTGAAGATTTTGCAACTTATTACTGT<br>CAGCAGGCACCCGACCTCCCTATCACTTTTGGCGGAGGGACCAAGGTTGAGATCAAACGTACGGT<br>GGCTGCACCTTCCGTCTTTATCTTTCCACCTTCCGATGAGCAGCTGAAGAGCGGAACAGCAAGCGT<br>GGTGTGTCTGCTGAACAACTTTTATCCCCGGGAGGCAAAGGTGCAGTGGAAAGTCGACAATGCTCT<br>CCAGTCCGGCAATTCCCAAGAGAGCGTGACAGAGCAAGATTCCAAGGACTCCACTTACAGCCTGT<br>CCAGCACCCTCACACTGAGCAAGGCTGATTACGAGAAACACAAAGTGTACGCTTGTGAAGTCACC<br>CACCAAGGCCTGAGCAGCCCAGTCACTAAGTCCTTTAACCGGGGCGAATGT (SEQ ID NO: 54) |
| L | DIQMTQSPSSVSASVGDRVTITCRASQGISSWLAWYQQKPGKAPKLLIYAASNLQSGVPSRFSGSGSGT<br>DFTLTISSLQPEDFATYYCQQAPDLPITFGGGTKVEIKRTVAAPSVFIFPPSDEQLKSGTASVVCLLNNFY<br>PREAKVQWKVDNALQSGNSQESVTEQDSKDSTYSLSSTLTLSKADYEKHKVYACEVTHQGLSSPVTKS<br>FNRGEC (SEQ ID NO: 55) |
| H01 | |
| VH | CAGGTGCAGCTGCAGGAGTCGGGCCCAGGACTGGTGAAGCCTTCGGAGACCCTGTCCCTCACCTGC<br>GCTGTCTCTGGTTACTCCATCAGCAGTGGTGTTTACTGGATGTGGATCCGGCAGCCCCCAGGGAAGG<br>GGCTGGAGTGGATTGGGAGTATCGTTCATAGTGGGCATACCTACTACAACCCGTCCCTCAAGAGTCG<br>AGTCACCATATCAGTAGACACGTCCAAGAACCAGTTCTCCCTGAAGCTGAGTTCTGTGACCGCCGCA<br>GACACGGCGGTGTACTACTGCGCCAGAGCTGGAAAATACCGATGGCACGGAATGGACGTATGGGGC<br>CAGGGAACAACTGTCACCGTCTCCTCA (SEQ ID NO: 56) |
| VH | QVQLQESGPGLVKPSETLSLTCAVSGYSISSGVYWMWIRQPPGKGLEWIGSIVHSGHTYYNPSLKSRVTIS<br>VDTSKNQFSLKLSSVTAADTAVYYCARAGKYRWHGMDVWGQGTTVTVSS (SEQ ID NO: 57)<br>CRD1: GYSISSGV (SEQ ID NO: 58; amino acid residues 26-33 of SEQ ID NO: 57)<br>CDR2: VHSGH (SEQ ID NO: 59; amino acid residues 53-57 of SEQ ID NO: 57)<br>CDR3: AGKYRWHGMDV (SEQ ID NO: 46; amino acid residues 99-109 of SEQ ID NO: 57) |
| H | CAGGTGCAGCTGCAGGAGTCGGGCCCAGGACTGGTGAAGCCTTCGGAGACCCTGTCCCTCACCTGC<br>GCTGTCTCTGGTTACTCCATCAGCAGTGGTGTTTACTGGATGTGGATCCGGCAGCCCCCAGGGAAGG<br>GGCTGGAGTGGATTGGGAGTATCGTTCATAGTGGGCATACCTACTACAACCCGTCCCTCAAGAGTCG<br>AGTCACCATATCAGTAGACACGTCCAAGAACCAGTTCTCCCTGAAGCTGAGTTCTGTGACCGCCGCA<br>GACACGGCGGTGTACTACTGCGCCAGAGCTGGAAAATACCGATGGCACGGAATGGACGTATGGGGC<br>CAGGGAACAACTGTCACCGTCTCCTCAGCTAGCACAAAAGGACCAAGCGTGTTTCCACTGGCACCT<br>AGCAGCAAATCCACCAGCGGCGGAACAGCAGCCCTCGGGTGCCTGGTGAAGGATTACTTCCCTGAG<br>CCAGTCACAGTGTCCTGGAACTCCGGAGCCCTGACATCCGGCGTGCACACCTTCCCCGCTGTGCTGC<br>AATCCAGCGGACTGTATAGCCTCAGCTCCGTCGTGACAGTCCCTTCCAGCAGCCTGGGCACACAGAC<br>TTACATTTGCAACGTGAACCACAAACCTTCCAACACTAAGGTGGACAAAAAGGTGGAACCCAAATC<br>CTGTGATAAGACCCATACATGCCCACCTTGTCCCGCTCCTGAGCTGCTGGGGGGACCTTCCGTCTTT<br>CTGTTTCCTCCAAAACCAAAAGACACACTCATGATCAGCCGGACCCCCGAAGTCACCTGTGTGGTGG<br>TGGACGTCAGCCACGAAGATCCAGAGGTCAAGTTCAATTGGTACGTGGATGGAGTGGAAGTCCACA<br>ACGCAAAAACCAAACCTAGAGAAGAACAGTACAATAGCACATACAGGGTGGTGTCCGTCCTGACA<br>GTGCTCCACCAGGACTGGCTCAATGGCAAAGAGTATAAGTGCAAGGTGAGCAACAAGGCCCTGCCT<br>GCACCAATTGAGAAAACAATTAGCAAGGCAAAGGGGCAGCCACGGGAACCCCAGGTGTATACCCT<br>GCCCCCAAGCCGGGATGAACTGACCAAAAACCAGGTCAGCCTGACATGCCTGGTGAAAGGGTTTTA<br>CCCAAGCGATATTGCCGTCGAGTGGGAGAGCAACGGACAGCCAGAAAACAATTACAAAACCACCC<br>CACCTGTGCTGGACTCCGATGGGAGCTTTTTCCTGTACAGCAAGCTCACAGTGGACAAGTCCAGATG<br>GCAACAGGGCAACGTGTTTTCCTGCTCCGTGATGCACGAGGCCCTCCACAACCACTATACACAAAA<br>GTCCCTCTCCCTCAGCCCAGGAAAG (SEQ ID NO: 60) |
| H | QVQLQESGPGLVKPSETLSLTCAVSGYSISSGVYWMWIRQPPGKGLEWIGSIVHSGHTYYNPSLKSRVTIS<br>VDTSKNQFSLKLSSVTAADTAVYYCARAGKYRWHGMDVWGQGTTVTVSSASTKGPSVFPLAPSSKSTS<br>GGTAALGCLVKDYFPEPVTVSWNSGALTSGVHTFPAVLQSSGLYSLSSVVTVPSSSLGTQTYICNVNHKP<br>SNTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLYSKLTVD<br>KSRWQQGNVFSCSVMHEALHNHYTQKSLSLSPGK (SEQ ID NO: 61) |
| VL | SEQ ID NO: 49 |
| VL | DIQMTQSPSSVSASVGDRVTITCRASQGISSWLAWYQQKPGKAPKLLIYAASNLQSGVPSRFSGSGSGTD<br>FTLTISSLQPEDFATYYCQQAPDLPITFGGGTKVEIK (SEQ ID NO: 50)<br>CDR1: RASQGISSWLA (SEQ ID NO: 51; amino acid residues 24-34 of SEQ ID NO: 50)<br>CDR2: AASNLQS (SEQ ID NO: 52; amino acid residues 50-56 of SEQ ID NO: 50)<br>CDR3: QQAPDLPIT (SEQ ID NO: 53; amino acid residues 89-97 of SEQ ID NO: 50) |
| L | SEQ ID NO: 54 |
| L | SEQ ID NO: 55 |
| E02 | |
| VH | GAGGTGCAGCTGTTGGAGTCTGGGGGAGGCTTGGTACAGCCTGGGGGGTCCCTGAGACTCTCCTGT<br>GCAGCCTCTGGATTCACCTTTAGCAGCTATGCCATGAGCTGGGTCCGCCAGGCTCCAGGGAAGGGG<br>CTGGAGTGGGTCTCAGGAATTAGTGGTAGTGGTGGTAGCACATACTACGCAGACTCCGTGAAGGG<br>CCGGTTCACCATCTCCAGAGACAATTCCAAGAACACGCTGTATCTGCAAATGAACAGCCTGAGAG<br>CCGAGGACACGGCGGTGTACTACTGCGCCAAGGACCCTTTGTCTCTACTTCTAGGCTACTTTGACT<br>ACTGGGGACAGGGTGCATTGGTCACCGTCTCCTCA (SEQ ID NO: 62) |

TABLE 1-continued

| Exemplary ActRII-binding proteins | |
|---|---|
| VH | EVQLLESGGGLVQPGGSLRLSCAASGFTFSSYAMSWVRQAPGKGLEWVSGISGSGGSTYYADSVKGRF TISRDNSKNTLYLQMNSLRAEDTAVYYCAKDPLSLLLGYFDYWGQGALVTVSS (SEQ ID NO: 63)<br>CDR1: GFTFSSY (SEQ ID NO: 64; amino acid residues 26-32 of SEQ ID NO: 63)<br>CDR2: SGSGGS (SEQ ID NO: 65; amino acid residues 52-57 of SEQ ID NO: 63)<br>CDR3: DPLSLLLGYFDY (SEQ ID NO: 66; amino acid residues 99-110 of SEQ ID NO: 63) |
| H | GAGGTGCAGCTGTTGGAGTCTGGGGGAGGCTTGGTACAGCCTGGGGGGTCCCTGAGACTCTCCTGT GCAGCCTCTGGATTCACCTTTAGCAGCTATGCCATGAGCTGGGTCCGCCAGGCTCCAGGGAAGGGG CTGGAGTGGGTCTCAGGAATTAGTGGTAGTGGTGGTAGCACATACTACGCAGACTCCGTGAAGGG CCGGTTCACCATCTCCAGAGACAATTCCAAGAACACGCTGTATCTGCAAATGAACAGCCTGAGAG CCGAGGACACGGCGGTGTACTACTGCGCCAAGGACCCTTTGTCTCTACTTCTAGGCTACTTTGACT ACTGGGGACAGGGTGCATTGGTCACCGTCTCCTCAGCTAGCACAAAGGACCAAGCGTGTTTCCAC TGGCACCTAGCAGCAAATCCACCAGCGGCGGAACAGCAGCCCTCGGGTGCCTGGTGAAGGATTAC TTCCCTGAGCCAGTCACAGTGTCCTGGAACTCCGGAGCCCTGACATCCGGCGTGCACACCTTCCCC GCTGTGCTGCAATCCAGCGGACTGTATAGCCTCAGCTCCGTCGTGACAGTCCCTTCCAGCAGCCTG GGCACACAGACTTACATTTGCAACGTGAACCACAAACCTTCCAACACTAAGGTGGACAAAAAGGT GGAACCCAAATCCTGTGATAAGACCCATACATGCCCACCTTGTCCCGCTCCTGAGCTGCTGGGGGG ACCTTCCGTCTTTCTGTTTCCTCCAAAACCAAAAGACACACTCATGATCAGCCGGACCCCCGAAGT CACCTGTGTGGTGGTGGACGTCAGCCACGAAGATCCAGAGGTCAAGTTCAATTGGTACGTGGATG GAGTGGAAGTCCACAACGCAAAAACCAAACCTAGAGAAGAACAGTACAATAGCACATACAGGGT GGTGTCCGTCCTGACAGTGCTCCACCAGGACTGGCTCAATGGCAAAGAGTATAAGTGCAAGGTGA GCAACAAGGCCCTGCCTGCACCAATTGAGAAAACAATTAGCAAGGCAAAGGGGCAGCCACGGGA ACCCCAGGTGTATACCCTGCCCCCAAGCCGGGATGAACTGACCAAAAACCAGGTCAGCCTGACAT GCCTGGTGAAAGGGTTTTACCCAAGCGATATTGCCGTCGAGTGGGAGAGCAACGGACAGCCAGAA AACAATTACAAAACCACCCCACCTGTGCTGGACTCCGATGGGAGCTTTTTCCTGTACAGCAAGCTC ACAGTGGACAAGTCCAGATGGCAACAGGGCAACGTGTTTTCCTGCTCCGTGATGCACGAGGCCCTC CACAACCACTATACACAAAAGTCCCTCTCCCTCAGCCCAGGAAAG (SEQ ID NO: 67) |
| H | EVQLLESGGGLVQPGGSLRLSCAASGFTFSSYAMSWVRQAPGKGLEWVSGISGSGGSTYYADSVKGRF TISRDNSKNTLYLQMNSLRAEDTAVYYCAKDPLSLLLGYFDYWGQGALVTVSSASTKGPSVFPLAPSS KSTSGGTAALGCLVKDYFPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYKTTPPVLDSDGSFFL YSKLTVDKSRWQQGNVFSCSVMHEALHNHYTQKSLSLSPGK (SEQ ID NO: 68) |
| VL | GACATCCAGATGACCCAGTCTCCTTCCACCCTGTCTGCATCTGTAGGAGACAGAGTCACCATCACT TGCCGGGCCAGTCAGAGTATTAGTAGCTGGTTGGCCTGGTATCAGCAGAAACCAGGGAAAGCCCC TAAGCTCCTGATCTATGATGCCTCCAGTTTGGAAAGTGGGGTCCCATCAAGGTTCAGCGGCAGTGG ATCTGGGACAGAATTCACTCTCACCATCAGCAGCCTGCAGCCTGATGATTTTGCAACTTATTACTG CCAGCAGTACAATCGCCACTCTCCTACTTTTGGCGGAGGGACCAAGGTTGAGATCAAA (SEQ ID NO: 69) |
| VL | DIQMTQSPSTLSASVGDRVTITCRASQSISSWLAWYQQKPGKAPKLLIYDASSLESGVPSRFSGSGSGTE FTLTISSLQPDDFATYYCQQYNRHSPTFGGGTKVEIK (SEQ ID NO: 70)<br>CDR1: RASQSISSWLA (SEQ ID NO: 71; amino acid residues 24-34 of SEQ ID NO: 70)<br>CDR2: DASSLES (SEQ ID NO: 72; amino acid residues 50-56 of SEQ ID NO: 70)<br>CDR3: QQYNRHSPT (SEQ ID NO: 73; amino acid residues 89-97 of SEQ ID NO: 70) |
| L | GACATCCAGATGACCCAGTCTCCTTCCACCCTGTCTGCATCTGTAGGAGACAGAGTCACCATCACT TGCCGGGCCAGTCAGAGTATTAGTAGCTGGTTGGCCTGGTATCAGCAGAAACCAGGGAAAGCCCC TAAGCTCCTGATCTATGATGCCTCCAGTTTGGAAAGTGGGGTCCCATCAAGGTTCAGCGGCAGTGG ATCTGGGACAGAATTCACTCTCACCATCAGCAGCCTGCAGCCTGATGATTTTGCAACTTATTACTG CCAGCAGTACAATCGCCACTCTCCTACTTTTGGCGGAGGGACCAAGGTTGAGATCAAACGTACGGT GGCTGCACCTTCCGTCTTTATCTTTCCACCTTCCGATGAGCAGCTGAAGAGCGGAACAGCAAGCGT GGTGTGTCTGCTGAACAACTTTTATCCCCGGGAGGCAAAGGTGCAGTGGAAAGTCGACAATGCTCT CCAGTCCGGCAATTCCCAAGAGAGCGTGACAGAGCAAGATTCCAAGGACTCCACTTACAGCCTGT CCAGCACCCTCACACTGAGCAAGGCTGATTACGAGAAACACAAAGTGTACGCTTGTGAAGTCACC CACCAAGGCCTGAGCAGCCCAGTCACTAAGTCCTTTAACCGGGGCGAATGT (SEQ ID NO: 74) |
| L | DIQMTQSPSTLSASVGDRVTITCRASQSISSWLAWYQQKPGKAPKLLIYDASSLESGVPSRFSGSGSGTE FTLTISSLQPDDFATYYCQQYNRHSPTFGGGTKVEIKRTVAAPSVFIFPPSDEQLKSGTASVVCLLNNFYP REAKVQWKVDNALQSGNSQESVTEQDSKDSTYSLSSTLTLSKADYEKHKVYACEVTHQGLSSPVTKSF NRGEC (SEQ ID NO: 75) |

| F02 | |
|---|---|
| VH | GAGGTGCAGCTGTTGGAGTCTGGGGGAGGCTTGGTACAGCCTGGGGGGTCCCTGAGACTCTCCTGT GCAGCCTCTGGATTCACCTTTAGCCGTTATGCCATGTCGTGGGTCCGCCAGGCTCCAGGGAAGGGG CTGGAGTGGGTCTCAGGTATTAGTGGAAGTGGTGGTGCGACATACTACGCAGACTCCGTGAAGGG CCGGTTCACCATCTCCAGAGACAATTCCAAGAACACGCTGTATCTGCAAATGAACAGCCTGAGAG CCGAGGACACGGCGGTGTACTACTGCGCCAAGGACCCTTTGTCTCTACTTCTAGGCTACTTTGACT ACTGGGGACAGGGTGCATTGGTCACCGTCTCCTCA (SEQ ID NO: 76) |
| VH | EVQLLESGGGLVQPGGSLRLSCAASGFTFSRYAMSWVRQAPGKGLEWVSGISGSGGATYYADSVKGR FTISRDNSKNTLYLQMNSLRAEDTAVYYCAKDPLSLLLGYFDYWGQGALVTVSS (SEQ ID NO: 77)<br>CDR1: GFTFSRY (SEQ ID NO: 78; amino acid residues 26-32 of SEQ ID NO: 77)<br>CDR2: SGSGGA (SEQ ID NO: 79; amino acid residues 52-57 of SEQ ID NO: 77)<br>CDR3: DPLSLLLGYFDY (SEQ ID NO: 80; amino acid residues 99-110 of SEQ ID NO: 77) |
| H | GAGGTGCAGCTGTTGGAGTCTGGGGGAGGCTTGGTACAGCCTGGGGGGTCCCTGAGACTCTCCTGT GCAGCCTCTGGATTCACCTTTAGCCGTTATGCCATGTCGTGGGTCCGCCAGGCTCCAGGGAAGGGG CTGGAGTGGGTCTCAGGTATTAGTGGAAGTGGTGGTGCGACATACTACGCAGACTCCGTGAAGGG CCGGTTCACCATCTCCAGAGACAATTCCAAGAACACGCTGTATCTGCAAATGAACAGCCTGAGAG CCGAGGACACGGCGGTGTACTACTGCGCCAAGGACCCTTTGTCTCTACTTCTAGGCTACTTTGACT ACTGGGGACAGGGTGCATTGGTCACCGTCTCCTCAGCTAGCACAAAGGACCAAGCGTGTTTCCAC |

TABLE 1-continued

Exemplary ActRII-binding proteins

TGGCACCTAGCAGCAAATCCACCAGCGGCGGAACAGCAGCCCTCGGGTGCCTGGTGAAGGATTAC
TTCCCTGAGCCAGTCACAGTGTCCTGGAACTCCGGAGCCCTGACATCCGGCGTGCACACCTTCCCC
GCTGTGCTGCAATCCAGCGGACTGTATAGCCTCAGCTCCGTCGTGACAGTCCCTTCCAGCAGCCTG
GGCACACAGACTTACATTTGCAACGTGAACCACAAACCTTCCAACACTAAGGTGGACAAAAAGGT
GGAACCCAAATCCTGTGATAAGACCCATACATGCCCACCTTGTCCCGCTCCTGAGCTGCTGGGGGG
ACCTTCCGTCTTTCTGTTTCCTCCAAAACCAAAAGACACACTCATGATCAGCCGGACCCCCGAAGT
CACCTGTGTGGTGGTGGACGTCAGCCACGAAGATCCAGAGGTCAAGTTCAATTGGTACGTGGATG
GAGTGGAAGTCCACAACGCAAAAACCAAACCTAGAGAAGAACAGTACAATAGCACATACAGGGT
GGTGTCCGTCCTGACAGTGCTCCACCAGGACTGGCTCAATGGCAAAGAGTATAAGTGCAAGGTGA
GCAACAAGGCCCTGCCTGCACCAATTGAGAAAACAATTAGCAAGGCAAAGGGGCAGCCACGGGA
ACCCCAGGTGTATACCCTGCCCCCAAGCCGGGATGAACTGACCAAAAACCAGGTCAGCCTGACAT
GCCTGGTGAAAGGGTTTTACCCAAGCGATATTGCCGTCGAGTGGGAGAGCAACGGACAGCCAGAA
AACAATTACAAAACCACCCCACCTGTGCTGGACTCCGATGGGAGCTTTTTCCTGTACAGCAAGCTC
ACAGTGGACAAGTCCAGATGGCAACAGGGCAACGTGTTTTCCTGCTCCGTGATGCACGAGGCCCTC
CACAACCACTATACACAAAAGTCCCTCTCCCTCAGCCCAGGAAAG (SEQ ID NO: 81)

H EVQLLESGGGLVQPGGSLRLSCAASGFTFSRYAMSWVRQAPGKGLEWVSGISGSGGATYYADSVKGR
FTISRDNSKNTLYLQMNSLRAEDTAVYYCAKDPLSLLLGYFDYWGQGALVTVSSASTKGPSVFPLAPSS
KSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK (SEQ ID NO: 82)

VL SEQ ID NO: 69

VL DIQMTQSPSTLSASVGDRVTITCRASQSISSWLAWYQQKPGKAPKLLIYDASSLESGVPSRFSGSGSGTE
FTLTISSLQPDDFATYYCQQYNRHSPTFGGGTKVEIK (SEQ ID NO: 70)
CDR1: RASQSISSWLA (SEQ ID NO: 71; amino acid residues 24-34 of SEQ ID NO: 70)
CDR2: DASSLES (SEQ ID NO: 72; amino acid residues 50-56 of SEQ ID NO: 70)
CDR3: QQYNRHSPT (SEQ ID NO: 73; amino acid residues 89-97 of SEQ ID NO: 70)

L SEQ ID NO: 74

L SEQ ID NO: 75

I01

VH GAGGTGCAGCTGTTGGAGTCTGGGGGAGGCTTGGTACAGCCTGGGGGGTCCCTGAGACTCTCCTGT
GCAGCCTCTGGATTCACCTTTGGGAGCTATGGCATGACTTGGGTCCGCCAGGCTCCAGGGAAGGGG
CTGGAGTGGGTCTCAGTTATTAGTGGAAGTGGTGGTGGGACATACTACGCAGACTCCGTGAAGGG
CCGGTTCACCATCTCCAGAGACAATTCCAAGAACACGCTGTATCTGCAAATGAACAGCCTGAGAG
CCGAGGACACGGCGGTGTACTACTGCGCCAAGGGTCCTAGAATAGTGGGCATGGATGTGTGGGGC
CAGGGAACAACTGTCACCGTCTCCTCA (SEQ ID NO: 143)

VH EVQLLESGGGLVQPGGSLRLSCAASGFTFGSYGMTWVRQAPGKGLEWVSVISGSGGGTYYADSVKGR
FTISRDNSKNTLYLQMNSLRAEDTAVYYCAKGPRIVGMDVWGQGTTVTVS (SEQ ID NO: 144)
CDR1: SYGMT (SEQ ID NO: 145; amino acid residues 31-35 of SEQ ID NO: 144)
CDR2: VISGSGGGTYYADSVKG (SEQ ID NO: 146; amino acid residues 50-65 of SEQ ID NO: 144)
CDR3: GPRIVGMDV (SEQ ID NO: 147; amino acid residues 95-102 of SEQ ID NO: 144)

H GAGGTGCAGCTGTTGGAGTCTGGGGGAGGCTTGGTACAGCCTGGGGGGTCCCTGAGACTCTCCTGT
GCAGCCTCTGGATTCACCTTTGGGAGCTATGGCATGACTTGGGTCCGCCAGGCTCCAGGGAAGGGG
CTGGAGTGGGTCTCAGTTATTAGTGGAAGTGGTGGTGGGACATACTACGCAGACTCCGTGAAGGG
CCGGTTCACCATCTCCAGAGACAATTCCAAGAACACGCTGTATCTGCAAATGAACAGCCTGAGAG
CCGAGGACACGGCGGTGTACTACTGCGCCAAGGGTCCTAGAATAGTGGGCATGGATGTGTGGGGC
CAGGGAACAACTGTCACCGTCTCCTCAGCTTCCACCAAGGGCCCATCCGTCTTCCCCCTGGCGCCC
TGCTCCAGGAGCACCTCCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGGGCACGAAG
ACCTACACCTGCAACGTAGATCACAAGCCCAGCAACACCAAGGTGGACAAGAGAGTTGAGTCCAA
ATATGGTCCCCCATGCCCACCCTGCCCAGCACCTGAGTTCCTGGGGGGACCATCAGTCTTCCTGTTC
CCCCCAAAACCCAAGGACACTCTCATGATCTCCCGGACCCCTGAGGTCACGTGCGTGGTGGTGGAC
GTGAGCCAGGAAGACCCCGAGGTCCAGTTCAACTGGTACGTGGATGGCGTGGAGGTGCATAATGC
CAAGACAAAGCCGCGGGAGGAGCAGTTCAACAGCACGTACCGTGTGGTCAGCGTCCTCACCGTCC
TGCACCAGGACTGGCTGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACAGGTGTACACCCTGCC
CCCATCCCAGGAGGAGATGACCAAGAACCAGGTCAGCCTGACCTGCCTGGTCAAAGGCTTCTACC
CCAGCGACATCGCCGTGGAGTGGGAGAGCAATGGGCAGCCGGAGAACAACTACAAGACCACGCC
TCCCGTGCTGGACTCCGACGGCTCCTTCTTCCTCTACAGCAGGCTAACCGTGGACAAGAGCAGGTG
GCAGGAGGGGAATGTCTTCTCATGCTCCGTGATGCATGAGGCTCTGCACAACCACTACACACAGA
AGAGCCTCTCCCTGTCTCTGGGTAAATGA (SEQ ID NO: 148)

H EVQLLESGGGLVQPGGSLRLSCAASGFTFGSYGMTWVRQAPGKGLEWVSVISGSGGGTYYADSVKGR
FTISRDNSKNTLYLQMNSLRAEDTAVYYCAKGPRIVGMDVWGQGTTVTVSSASTKGPSVFPLAPCSRS
TSESTAALGCLVKDYFPEPVTVSWNSGALTSGVHTFPAVLQSSGLYSLSSVVTVPSSSLGTKTYTCNVD
HKPSNTKVDKRVESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK (SEQ ID NO: 149)

VL GACATCCAGATGACCCAGTCTCCATCTTCCGTGTCTGCATCTGTAGGAGACAGAGTCACCATCACT
TGTCGGGCGAGTCAGGGTATTAGCAGCTGGTTAGCCTGGTATCAGCAGAAACCAGGGAAAGCCCC
TAAGCTCCTGATCTATGCTGCATCCAGTTTGCAAAGTGGGGTCCCATCAAGGTTCAGCGGCAGTGG
ATCTGGGACAGATTTCACTCTCACCATCAGCAGCCTGCAGCCTGAAGATTTTGCAACTTATTACTG
TCAGCAGGTATTCAGTTACCCTCTCACTTTTGGCGGAGGGACCAAGGTTGAGATCAAA (SEQ ID
NO: 150)

TABLE 1-continued

| Exemplary ActRII-binding proteins | |
|---|---|
| VL | DIQMTQSPSSVSASVGDRVTITCRASQGISSWLAWYQQKPGKAPKLLIYAASSLQSGVPSRFSGSGSGTD<br>FTLTISSLQPEDFATYYCQQVFSYPLTFGGGTKVEIK (SEQ ID NO: 151)<br>CDR1: RASQGISSWLA (SEQ ID NO: 152; amino acid residues 24-34 of SEQ ID NO: 151)<br>CDR2: AASSLQS (SEQ ID NO: 153; amino acid residues 50-56 of SEQ ID NO: 151)<br>CDR3: QQVFSYPLT (SEQ ID NO: 154; amino acid residues 89-97 of SEQ ID NO: 151) |
| L | GACATCCAGATGACCCAGTCTCCATCTTCCGTGTCTGCATCTGTAGGAGACAGAGTCACCATCACT<br>TGTCGGGCGAGTCAGGGTATTAGCAGCTGGTTAGCCTGGTATCAGCAGAAACCAGGGAAAGCCCC<br>TAAGCTCCTGATCTATGCTGCATCCAGTTTGCAAAGTGGGGTCCCATCAAGGTTCAGCGGCAGTGG<br>ATCTGGGACAGATTTCACTCTCACCATCAGCAGCCTGCAGCCTGAAGATTTTGCAACTTATTACTGT<br>CAGCAGGTATTCAGTTACCCTCTCACTTTTGGCGGAGGGACCAAGGTTGAGATCAAACGAACTGTG<br>GCTGCACCATCTGTCTTCATCTTCCCGCCATCTGATGAGCAGTTGAAATCTGGAACTGCCTCTGTTG<br>TGTGCCTGCTGAATAACTTCTATCCCAGAGAGGCCAAAGTACAGTGGAAGGTGGATAACGCCCTCC<br>AATCGGGTAACTCCCAGGAGAGTGTCACAGAGCAGGACAGCAAGGACAGCACCTACAGCCTCAGC<br>AGCACCCTGACGCTGAGCAAAGCAGACTACGAGAAACACAAAGTCTACGCCTGCGAAGTCACCCA<br>TCAGGGCCTGAGCTCGCCCGTCACAAAGAGCTTCAACAGGGGAGAGTGTTAG (SEQ ID NO: 155) |
| L | DIQMTQSPSSVSASVGDRVTITCRASQGISSWLAWYQQKPGKAPKLLIYAASSLQSGVPSRFSGSGSGTD<br>FTLTISSLQPEDFATYYCQQVFSYPLTFGGGTKVEIKRTVAAPSVFIFPPSDEQLKSGTASVVCLLNNFYP<br>REAKVQWKVDNALQSGNSQESVTEQDSKDSTYSLSSTLTLSKADYEKHKVYACEVTHQGLSSPVTKSF<br>NRGEC (SEQ ID NO: 156) |

| ActRIIB- and ActRIIA--binding Antibodies<br>A02 | |
|---|---|
| VH | CAGGTTCAGCTGGTGCAGTCTGGAGCTGAGGTGAAGAAGCCTGGGGCCTCAGTGAAGGTCTCCTG<br>CAAGGCTTCTGGTTACACCTTTACCAGCTATGGTATCAGCTGGGTGCGACAGGCCCCTGGACAAGG<br>GCTTGAGTGGATGGGATGGATCAGCCCTTACAATGGTAACACAAACTATGCACAGAAGCTCCAGG<br>GCAGAGTCACCATGACCACAGACACATCCACGAGCACAGCCTACATGGAGCTGAGGAGCCTGAGA<br>TCTGACGACACGGCGGTGTACTACTGCGCTAGAGTATCTATGTACGCCCCAGAGCCAATGGACGTA<br>TGGGGCCAGGGAACAACTGTCACCGTCTCCTCA (SEQ ID NO: 83) |
| VH | QVQLVQSGAEVKKPGASVKVSCKASGYTFTSYGISWVRQAPGQGLEWMGWISPYNGNTNYAQKLQG<br>RVTMTTDTSTSTAYMELRSLRSDDTAVYYCARVSMYAPEPMDVWGQGTTVTVSS (SEQ ID NO: 84)<br>CDR1: GYTFTSY (SEQ ID NO: 85; amino acid residues 26-32 of SEQ ID NO: 84)<br>CDR2: SPYNGN (SEQ ID NO: 86; amino acid residues 52-57 of SEQ ID NO: 84)<br>CDR3: VSMYAPEPMDV (SEQ ID NO: 87; amino acid residues 99-109 of SEQ ID NO: 84) |
| H | CAGGTTCAGCTGGTGCAGTCTGGAGCTGAGGTGAAGAAGCCTGGGGCCTCAGTGAAGGTCTCCTG<br>CAAGGCTTCTGGTTACACCTTTACCAGCTATGGTATCAGCTGGGTGCGACAGGCCCCTGGACAAGG<br>GCTTGAGTGGATGGGATGGATCAGCCCTTACAATGGTAACACAAACTATGCACAGAAGCTCCAGG<br>GCAGAGTCACCATGACCACAGACACATCCACGAGCACAGCCTACATGGAGCTGAGGAGCCTGAGA<br>TCTGACGACACGGCGGTGTACTACTGCGCTAGAGTATCTATGTACGCCCCAGAGCCAATGGACGTA<br>TGGGGCCAGGGAACAACTGTCACCGTCTCCTCAGCTAGCACAAAAGGACCAAGCGTGTTTCCACT<br>GGCACCTAGCAGCAAATCCACCAGCGGCGGAACAGCAGCCCTCGGGTGCCTGGTGAAGGATTACT<br>TCCCTGAGCCAGTCACAGTGTCCTGGAACTCCGGAGCCCTGACATCCGGCGTGCACACCTTCCCCG<br>CTGTGCTGCAATCCAGCGGACTGTATAGCCTCAGCTCCGTCGTGACAGTCCCTTCCAGCAGCCTGG<br>GCACACAGACTTACATTTGCAACGTGAACCACAAACCTTCCAACACTAAGGTGGACAAAAAGGTG<br>GAACCCAAATCCTGTGATAAGACCCATACATGCCCACCTTGTCCCGCTCCTGAGCTGCTGGGGGGA<br>CCTTCCGTCTTTCTGTTTCCTCCAAAACCAAAAGACACACTCATGATCAGCCGGACCCCCGAAGTC<br>ACCTGTGTGGTGGTGGACGTCAGCCACGAAGATCCAGAGGTCAAGTTCAATTGGTACGTGGATGG<br>AGTGGAAGTCCACAACGCAAAAACCAAACCTAGAGAAGAACAGTACAATAGCACATACAGGGTG<br>GTGTCCGTCCTGACAGTGCTCCACCAGGACTGGCTCAATGGCAAAGAGTATAAGTGCAAGGTGAG<br>CAACAAGGCCCTGCCTGCACCAATTGAGAAAACAATTAGCAAGGCAAAGGGGCAGCCACGGGAA<br>CCCCAGGTGTATACCCTGCCCCCAAGCCGGGATGAACTGACCAAAAACCAGGTCAGCCTGACATG<br>CCTGGTGAAAGGGTTTTACCCAAGCGATATTGCCGTCGAGTGGGAGAGCAACGGACAGCCAGAAA<br>ACAATTACAAAACCACCCCACCTGTGCTGGACTCCGATGGGAGCTTTTTCCTGTACAGCAAGCTCA<br>CAGTGGACAAGTCCAGATGGCAACAGGGCAACGTGTTTTCCTGCTCCGTGATGCACGAGGCCCTCC<br>ACAACCACTATACACAAAAGTCCCTCTCCCTCAGCCCAGGAAAG (SEQ ID NO: 88) |
| H | QVQLVQSGAEVKKPGASVKVSCKASGYTFTSYGISWVRQAPGQGLEWMGWISPYNGNTNYAQKLQG<br>RVTMTTDTSTSTAYMELRSLRSDDTAVYYCARVSMYAPEPMDVWGQGTTVTVSSASTKGPSVFPLAP<br>SSKSTSGGTAALGCLVKDYFPEPVTVSWNSGALTSGVHTFPAVLQSSGLYSLSSVVTVPSSSLGTQTYIC<br>NVNHKPSNTKVDKKVEPKSCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK (SEQ ID NO: 89) |
| VL | GACATCCAGATGACCCAGTCTCCATCTTCCGTGTCTGCATCTGTAGGAGACAGAGTCACCATCACT<br>TGTCGGGCGAGTCAGGGTATTAGCAGGTGGTTAGCCTGGTATCAGCAGAAACCAGGGAAAGCCCC<br>TAAGCTCCTGATCTATGCTGCATCCAGTTTGCAAAGTGGGGTCCCATCAAGGTTCAGCGGCAGTGG<br>ATCTGGGACAGATTTCACTCTCACCATCAGCAGCCTGCAGCCTGAAGATTTTGCAACTTATTACTGT<br>CAGCAGGCATTCTCCCACCCTTGGACTTTTGGCGGAGGGACCAAGGTTGAGATCAAA (SEQ ID<br>NO: 90) |
| VL | DIQMTQSPSSVSASVGDRVTITCRASQGISRWLAWYQQKPGKAPKLLIYAASSLQSGVPSRFSGSGSGT<br>DFTLTISSLQPEDFATYYCQQAFSHPWTFGGGTKVEIK (SEQ ID NO: 91)<br>CDR1: RASQGISRWLA (SEQ ID NO: 92; amino acid residues 24-34 of SEQ ID NO: 91)<br>CDR2: ASSLQS (SEQ ID NO: 93; amino acid residues 50-56 of SEQ ID NO: 91)<br>CDR3: QQAFSHPWT (SEQ ID NO: 94; amino acid residues 89-97 of SEQ ID NO: 91) |
| L | GACATCCAGATGACCCAGTCTCCATCTTCCGTGTCTGCATCTGTAGGAGACAGAGTCACCATCACT<br>TGTCGGGCGAGTCAGGGTATTAGCAGGTGGTTAGCCTGGTATCAGCAGAAACCAGGGAAAGCCC<br>CTAAGCTCCTGATCTATGCTGCATCCAGTTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTAC<br>TGTCAGCAGGCATTCTCCCACCCTTGGACTTTTGGCGGAGGGACCAAGGTTGAGATCAAACGTAC |

TABLE 1-continued

| | Exemplary ActRII-binding proteins |
|---|---|
| | GGTGGCTGCACCTTCCGTCTTTATCTTTCCACCTTCCGATGAGCAGCTGAAGAGCGGAACAGCAA<br>GCGTGGTGTGTCTGCTGAACAACTTTTATCCCCGGGAGGCAAAGGTGCAGTGGAAAGTCGACAAT<br>GCTCTCCAGTCCGGCAATTCCCAAGAGAGCGTGACAGAGCAAGATTCCAAGGACTCCACTTACAG<br>CCTGTCCAGCACCCTCACACTGAGCAAGGCTGATTACGAGAAACACAAAGTGTACGCTTGTGAAG<br>TCACCCACCAAGGCCTGAGCAGCCCAGTCACTAAGTCCTTTAACCGGGGCGAATGT (SEQ ID NO: 95) |
| L | DIQMTQSPSSVSASVGDRVTITCRASQGISRWLAWYQQKPGKAPKLLIYAASSLQSGVPSRFSGSGSGT<br>DFTLTISSLQPEDFATYYCQQAFSHPWTFGGGTKVEIK (SEQ ID NO: 96) |
| | B02 |
| VH | CAGGTGCAGCTGGTGCAGTCTGGGGCTGAGGTGAAGAAGCCTGGGGCCTCAGTGAAGGTCTCCT<br>GCAAGGCTTCTGGATACACCTTCACCGGCCATAAGATGCACTGGGTGCGACAGGCCCCTGGACAA<br>GGGCTTGAGTGGATGGGATGGATCAACCCTGCTAGTGGTTGGACAAACTATGCACAGAAGTTTCA<br>GGGCAGGGTCACCATGACCAGGGACACGTCCATCAGCACAGCCTACATGGAGCTGAGCAGGCTG<br>AGATCTGACGACACGGCGGTGTACTACTGCGCCAGAGTATCTATGTACGCCCCAGAGCCAATGGA<br>CGTATGGGGCCAGGGAACAACTGTCACCGTCTCCTCA (SEQ ID NO: 97) |
| VH | QVQLVQSGAEVKKPGASVKVSCKASGYTFTGHKMHWVRQAPGQGLEWMGWINPASGWTNYAQKF<br>QGRVTMTRDTSISTAYMELSRLRSDDTAVYYCARVSMYAPEPMDVWGQGTTVTVSS (SEQ ID NO: 98)<br>CDR1: GYTFTGHKMH (SEQ ID NO: 99; amino acid residues 26-35 of SEQ ID NO: 98)<br>CDR2: NPASGW (SEQ ID NO: 100; amino acid residues 52-57 of SEQ ID NO: 98)<br>CDR3: VSMYAPEPMDV (SEQ ID NO: 101; amino acid residues 99-109 of SEQ ID NO: 98) |
| H | CAGGTGCAGCTGGTGCAGTCTGGGGCTGAGGTGAAGAAGCCTGGGGCCTCAGTGAAGGTCTCCT<br>GCAAGGCTTCTGGATACACCTTCACCGGCCATAAGATGCACTGGGTGCGACAGGCCCCTGGACAA<br>GGGCTTGAGTGGATGGGATGGATCAACCCTGCTAGTGGTTGGACAAACTATGCACAGAAGTTTCA<br>GGGCAGGGTCACCATGACCAGGGACACGTCCATCAGCACAGCCTACATGGAGCTGAGCAGGCTG<br>AGATCTGACGACACGGCGGTGTACTACTGCGCCAGAGTATCTATGTACGCCCCAGAGCCAATGGA<br>CGTATGGGGCCAGGGAACAACTGTCACCGTCTCCTCAGCTAGCACAAAAGGACCAAGCGTGTTTC<br>CACTGGCACCTAGCAGCAAATCCACCAGCGGCGGAACAGCAGCCCTCGGGTGCCTGGTGAAGGA<br>TTACTTCCCTGAGCCAGTCACAGTGTCCTGGAACTCCGGAGCCCTGACATCCGGCGTGCACACCT<br>TCCCCGCTGTGCTGCAATCCAGCGGACTGTATAGCCTCAGCTCCGTCGTGACAGTCCCTTCCAGCA<br>GCCTGGGCACACAGACTTACATTTGCAACGTGAACCACAAACCTTCCAACACTAAGGTGGACAA<br>AAAGGTGGAACCCAAATCCTGTGATAAGACCCATACATGCCCACCTTGTCCCGCTCCTGAGCTGC<br>TGGGGGGACCTTCCGTCTTTCTGTTTCCTCCAAAACCAAAAGACACACTCATGATCAGCCGGACC<br>CCCGAAGTCACCTGTGTGGTGGTGGACGTCAGCCACGAAGATCCAGAGGTCAAGTTCAATTGGTA<br>CGTGGATGGAGTGGAAGTCCACAACGCAAAAACCAAACCTAGAGAAGAACAGTACAATAGCAC<br>ATACAGGGTGGTGTCCGTCCTGACAGTGCTCCACCAGGACTGGCTCAATGGCAAAGAGTATAAGT<br>GCAAGGTGAGCAACAAGGCCCTGCCTGCACCAATTGAGAAAACAATTAGCAAGGCAAAGGGGCA<br>GCCACGGGAACCCCAGGTGTATACCCTGCCCCCAAGCCGGGATGAACTGACCAAAAACCAGGTC<br>AGCCTGACATGCCTGGTGAAAGGGTTTTACCCAAGCGATATTGCCGTCGAGTGGGAGAGCAACG<br>GACAGCCAGAAAACAATTACAAAACCACCCCACCTGTGCTGGACTCCGATGGGAGCTTTTTCCTG<br>TACAGCAAGCTCACAGTGGACAAGTCCAGATGGCAACAGGGCAACGTGTTTTCCTGCTCCGTGAT<br>GCACGAGGCCCTCCACAACCACTATACACAAAAGTCCCTCTCCCTCAGCCCAGGAAAG (SEQ ID NO: 102) |
| H | QVQLVQSGAEVKKPGASVKVSCKASGYTFTGHKMHWVRQAPGQGLEWMGWINPASGWTNYAQKF<br>QGRVTMTRDTSISTAYMELSRLRSDDTAVYYCARVSMYAPEPMDVWGQGTTVTVSSASTKGPSVFPL<br>APSSKSTSGGTAALGCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGK (SEQ ID NO: 103) |
| VL | SEQ ID NO: 90 |
| VL | DIQMTQSPSSVSASVGDRVTITCRASQGISRWLAWYQQKPGKAPKLLIYAASSLQSGVPSRFSGSGSGT<br>DFTLTISSLQPEDFATYYCQQAFSHPWTFGGGTKVEIK (SEQ ID NO: 91)<br>CDR1: RASQGISRWLA (SEQ ID NO: 92; amino acid residues 24-34 of SEQ ID NO: 91)<br>CDR2: AASSLQS (SEQ ID NO: 93; amino acid residues 50-56 of SEQ ID NO: 91)<br>CDR3: QQAFSHPWT (SEQ ID NO: 94; amino acid residues 89-97 of SEQ ID NO: 91) |
| L | SEQ ID NO: 95 |
| L | SEQ ID NO: 96 |
| | C02 |
| VH | CAGGTGCAGCTGGTGCAGTCTGGGGCTGAGGTGAAGAAGCCTGGGGCCTCAGTGAAGGTTTCCTG<br>CAAGGCATCTGGATACACCTTCACCAGCTACAATATGGCGTGGGTGCGACAGGCCCCTGGACAAG<br>GGCTTGAGTGGATGGGAATAATCAGGCCTAGTGTTGGTAGCACAAGCTACGCACAGAAGTTCCAG<br>GGCAGAGTCACCATGACCAGGGACACGTCCACGAGCACAGTCTACATGGAGCTGAGCAGCCTGAG<br>ATCTGAGGACACGGCGGTGTACTACTGCGCTAGAGTATCTATGTACGCCCCAGAGCCAATGGACGT<br>ATGGGGCCAGGGAACAACTGTCACCGTCTCCTCA (SEQ ID NO: 104) |
| VH | QVQLVQSGAEVKKPGASVKVSCKASGYTFTSYNMAWVRQAPGQGLEWMGIIRPSVGSTSYAQKFQG<br>RVTMTRDTSTSTVYMELSSLRSEDTAVYYCARVSMYAPEPMDVWGQGTTVTVSS (SEQ ID NO: 105)<br>CDR1: GYTFTSY (SEQ ID NO: 106; amino acid residues 26-32 of SEQ ID NO: 105)<br>CDR2: RPSVGS (SEQ ID NO: 107; amino acid residues 52-57 of SEQ ID NO: 105)<br>CDR3: VSMYAPEPMDV (SEQ ID NO: 108; amino acid residues 99-109 of SEQ ID NO: 105) |
| H | CAGGTGCAGCTGGTGCAGTCTGGGGCTGAGGTGAAGAAGCCTGGGGCCTCAGTGAAGGTTTCCTG<br>CAAGGCATCTGGATACACCTTCACCAGCTACAATATGGCGTGGGTGCGACAGGCCCCTGGACAAG<br>GGCTTGAGTGGATGGGAATAATCAGGCCTAGTGTTGGTAGCACAAGCTACGCACAGAAGTTCCAG<br>GGCAGAGTCACCATGACCAGGGACACGTCCACGAGCACAGTCTACATGGAGCTGAGCAGCCTGAG |

TABLE 1-continued

| Exemplary ActRII-binding proteins | |
|---|---|
| | ATCTGAGGACACGGCGGTGTACTACTGCGCTAGAGTATCTATGTACGCCCCAGAGCCAATGGACGT |
| | ATGGGGCCAGGGAACAACTGTCACCGTCTCCTCAGCTAGCACAAAAGGACCAAGCGTGTTTCCAC |
| | TGGCACCTAGCAGCAAATCCACCAGCGGCGGAACAGCAGCCCTCGGGTGCCTGGTGAAGGATTAC |
| | TTCCCTGAGCCAGTCACAGTGTCCTGGAACTCCGGAGCCCTGACATCCGGCGTGCACACCTTCCCC |
| | GCTGTGCTGCAATCCAGCGGACTGTATAGCCTCAGCTCCGTCGTGACAGTCCCTTCCAGCAGCCTG |
| | GGCACACAGACTTACATTTGCAACGTGAACCACAAACCTTCCAACACTAAGGTGGACAAAAAGGT |
| | GGAACCCAAATCCTGTGATAAGACCCATACATGCCCACCTTGTCCCGCTCCTGAGCTGCTGGGGGG |
| | ACCTTCCGTCTTTCTGTTTCCTCCAAAACCAAAAGACACACTCATGATCAGCCGGACCCCCGAAGT |
| | CACCTGTGTGGTGGTGGACGTCAGCCACGAAGATCCAGAGGTCAAGTTCAATTGGTACGTGGATG |
| | GAGTGGAAGTCCACAACGCAAAAACCAAACCTAGAGAAGAACAGTACAATAGCACATACAGGGT |
| | GGTGTCCGTCCTGACAGTGCTCCACCAGGACTGGCTCAATGGCAAAGAGTATAAGTGCAAGGTGA |
| | GCAACAAGGCCCTGCCTGCACCAATTGAGAAAACAATTAGCAAGGCAAAGGGGCAGCCACGGGA |
| | ACCCCAGGTGTATACCCTGCCCCCAAGCCGGGATGAACTGACCAAAAACCAGGTCAGCCTGACAT |
| | GCCTGGTGAAAGGGTTTTACCCAAGCGATATTGCCGTCGAGTGGGAGAGCAACGGACAGCCAGAA |
| | AACAATTACAAAACCACCCCACCTGTGCTGGACTCCGATGGGAGCTTTTTCCTGTACAGCAAGCTC |
| | ACAGTGGACAAGTCCAGATGGCAACAGGGCAACGTGTTTTCCTGCTCCGTGATGCACGAGGCCCTC |
| | CACAACCACTATACACAAAAGTCCCTCTCCCTCAGCCCAGGAAAG (SEQ ID NO: 109) |
| H | QVQLVQSGAEVKKPGASVKVSCKASGYTFTSYNMAWVRQAPGQGLEWMGIIRPSVGSTSYAQKFQG |
| | RVTMTRDTSTSTVYMELSSLRSEDTAVYYCARVSMYAPEPMDVWGQGTTVTVSSASTKGPSVFPLAPS |
| | SKSTSGGTAALGCLVKDYFPEPVTVSWNSGALTSGVHTFPAVLQSSGLYSLSSVVTVPSSSLGTQTYICN |
| | VNHKPSNTKVDKKVEPKSCDKTHTCPPCPAPELLGGPSVFLFPPKPKDTLMISRTPEVTCVVVDVSHED |
| | PEVKFNWYVDGVEVHNAKTKPREEQYNSTYRVVSVLTVLHQDWLNGKEYKCKVSNKALPAPIEKTIS |
| | KAKGQPREPQVYTLPPSRDELTKNQVSLTCLVKGFYPSDIAVEWESNGQPENNYKTTPPVLDSDGSFFL |
| | YSKLTVDKSRWQQGNVFSCSVMHEALHNHYTQKSLSLSPGK (SEQ ID NO: 110) |
| VL | SEQ ID NO: 90 |
| VL | DIQMTQSPSSVSASVGDRVTITCRASQGISRWLAWYQQKPGKAPKLLIYAASSLQSGVPSRFSGSGSGT |
| | DFTLTISSLQPEDFATYYCQQAFSHPWTFGGGTKVEIK (SEQ ID NO: 91) |
| | CDR1: RASQGISRWLA (SEQ ID NO: 92; amino acid residues 24-34 of SEQ ID NO: 91) |
| | CDR2: AASSLQS (SEQ ID NO: 93; amino acid residues 50-56 of SEQ ID NO: 91) |
| | CDR3: QQAFSHPWT (SEQ ID NO: 94; amino acid residues 89-97 of SEQ ID NO: 91) |
| L | SEQ ID NO: 95 |
| L | SEQ ID NO: 96 |

| D02 | |
|---|---|
| VH | CAGGTGCAGCTGGTGCAGTCTGGGGCTGAGGTGAAGAAGCCTGGGGCCTCAGTGAAGGTTTCCTG |
| | CAAGGCATCTGGATACACCTTCACCTCGTACCGTATGCACTGGGTGCGACAGGCCCCTGGACAAGG |
| | GCTTGAGTGGATGGGATTTATCGTGCCTAGTGGTGGTAGCACAAGCTACGCACAGAAGTTCCAGG |
| | GCAGAGTCACCATGACCAGGGACACGTCCACGAGCACAGTCTACATGGAGCTGAGCAGCCTGAGA |
| | TCTGAGGACACGGCGGTGTACTACTGCGCTAGAGTATCTATGTACGCCCCAGAGCCAATGGACGTA |
| | TGGGGCCAGGGAACAACTGTCACCGTCTCCTCA (SEQ ID NO: 111) |
| VH | QVQLVQSGAEVKKPGASVKVSCKASGYTFTSYRMHWVRQAPGQGLEWMGFIVPSGGSTSYAQKFQG |
| | RVTMTRDTSTSTVYMELSSLRSEDTAVYYCARVSMYAPEPMDVWGQGTTVTVSS (SEQ ID NO: 112) |
| | CDR1: GYTFTSY (SEQ ID NO: 113; amino acid residues 26-32 of SEQ ID NO: 112) |
| | CDR2: VPSGGS (SEQ ID NO: 114; amino acid residues 52-57 of SEQ ID NO: 112) |
| | CDR3: VSMYAPEPMDV (SEQ ID NO: 115; amino acid residues 99-109 of SEQ ID NO: 112) |
| H | CAGGTGCAGCTGGTGCAGTCTGGGGCTGAGGTGAAGAAGCCTGGGGCCTCAGTGAAGGTTTCCTG |
| | CAAGGCATCTGGATACACCTTCACCTCGTACCGTATGCACTGGGTGCGACAGGCCCCTGGACAAGG |
| | GCTTGAGTGGATGGGATTTATCGTGCCTAGTGGTGGTAGCACAAGCTACGCACAGAAGTTCCAGG |
| | GCAGAGTCACCATGACCAGGGACACGTCCACGAGCACAGTCTACATGGAGCTGAGCAGCCTGAGA |
| | TCTGAGGACACGGCGGTGTACTACTGCGCTAGAGTATCTATGTACGCCCCAGAGCCAATGGACGTA |
| | TGGGGCCAGGGAACAACTGTCACCGTCTCCTCAGCTAGCACAAAAGGACCAAGCGTGTTTCCACT |
| | GGCACCTAGCAGCAAATCCACCAGCGGCGGAACAGCAGCCCTCGGGTGCCTGGTGAAGGATTACT |
| | TCCCTGAGCCAGTCACAGTGTCCTGGAACTCCGGAGCCCTGACATCCGGCGTGCACACCTTCCCCG |
| | CTGTGCTGCAATCCAGCGGACTGTATAGCCTCAGCTCCGTCGTGACAGTCCCTTCCAGCAGCCTGG |
| | GCACACAGACTTACATTTGCAACGTGAACCACAAACCTTCCAACACTAAGGTGGACAAAAAGGTG |
| | GAACCCAAATCCTGTGATAAGACCCATACATGCCCACCTTGTCCCGCTCCTGAGCTGCTGGGGGGA |
| | CCTTCCGTCTTTCTGTTTCCTCCAAAACCAAAAGACACACTCATGATCAGCCGGACCCCCGAAGTC |
| | ACCTGTGTGGTGGTGGACGTCAGCCACGAAGATCCAGAGGTCAAGTTCAATTGGTACGTGGATGG |
| | AGTGGAAGTCCACAACGCAAAAACCAAACCTAGAGAAGAACAGTACAATAGCACATACAGGGTG |
| | GTGTCCGTCCTGACAGTGCTCCACCAGGACTGGCTCAATGGCAAAGAGTATAAGTGCAAGGTGAG |
| | CAACAAGGCCCTGCCTGCACCAATTGAGAAAACAATTAGCAAGGCAAAGGGGCAGCCACGGGAA |
| | CCCCAGGTGTATACCCTGCCCCCAAGCCGGGATGAACTGACCAAAAACCAGGTCAGCCTGACATG |
| | CCTGGTGAAAGGGTTTTACCCAAGCGATATTGCCGTCGAGTGGGAGAGCAACGGACAGCCAGAAA |
| | ACAATTACAAAACCACCCCACCTGTGCTGGACTCCGATGGGAGCTTTTTCCTGTACAGCAAGCTCA |
| | CAGTGGACAAGTCCAGATGGCAACAGGGCAACGTGTTTTCCTGCTCCGTGATGCACGAGGCCCTCC |
| | ACAACCACTATACACAAAAGTCCCTCTCCCTCAGCCCAGGAAAG (SEQ ID NO: 116) |
| H | QVQLVQSGAEVKKPGASVKVSCKASGYTFTSYRMHWVRQAPGQGLEWMGFIVPSGGSTSYAQKFQG |
| | RVTMTRDTSTSTVYMELSSLRSEDTAVYYCARVSMYAPEPMDVWGQGTTVTVSSASTKGPSVFPLAPS |
| | SKSTSGGTAALGCLVKDYFPEPVTVSWNSGALTSGVHTFPAVLQSSGLYSLSSVVTVPSSSLGTQTYICN |
| | VNHKPSNTKVDKKVEPKSCDKTHTCPPCPAPELLGGPSVFLFPPKPKDTLMISRTPEVTCVVVDVSHED |
| | PEVKFNWYVDGVEVHNAKTKPREEQYNSTYRVVSVLTVLHQDWLNGKEYKCKVSNKALPAPIEKTIS |
| | KAKGQPREPQVYTLPPSRDELTKNQVSLTCLVKGFYPSDIAVEWESNGQPENNYKTTPPVLDSDGSFFL |
| | YSKLTVDKSRWQQGNVFSCSVMHEALHNHYTQKSLSLSPGK (SEQ ID NO: 117) |
| VL | SEQ ID NO: 90 |
| VL | DIQMTQSPSSVSASVGDRVTITCRASQGISRWLAWYQQKPGKAPKLLIYAASSLQSGVPSRFSGSGSGT |
| | DFTLTISSLQPEDFATYYCQQAFSHPWTFGGGTKVEIK (SEQ ID NO: 91) |
| | CDR1: RASQGISRWLA (SEQ ID NO: 92; amino acid residues 24-34 of SEQ ID NO: 91) |

TABLE 1-continued

Exemplary ActRII-binding proteins

CDR2: AASSLQS (SEQ ID NO: 93; amino acid residues 50-56 of SEQ ID NO: 91)
CDR3: QQAFSHPWT (SEQ ID NO: 94; amino acid residues 89-97 of SEQ ID NO: 91)
L SEQ ID NO: 95
L SEQ ID NO: 96

D03

VH CAGGTGCAGCTGGTGCAGTCTGGGGCTGAGGTGAAGAAGCCTGGGGCCTCAGTGAAGGTTTCCTG
CAAGGCATCTGGATACACCTTCACCTCGTACCGTATGCACTGGGTGCGACAGGCCCCTGGACAAGG
GCTTGAGTGGATGGGATTTATCGTGCCTAGTGGTGGTAGCACAGGCTACGCACAGAAGTTCCAGG
GCAGAGTTACCATGACCAGGGACACGTCCACGAGCACAGTCTACATGGAGCTGAGCAGCCTGAGA
TCTGAGGACACGGCGGTGTACTACTGCGCTAGAGTATCTAGGTACGCCCCAGAGCCAATGGACGT
ATGGGGCCAGGGAACAACTGTCACCGTCTCCTCA (SEQ ID NO: 118)
VH QVQLVQSGAEVKKPGASVKVSCKASGYTFTSYRMHWVRQAPGQGLEWMGFIVPSGGSTGYAQKFQG
RVTMTRDTSTSTVYMELSSLRSEDTAVYYCARVSRYAPEPMDVWGQGTTVTVSS (SEQ ID NO: 119)
CDR1: GYTFTSY (SEQ ID NO: 113; amino acid residues 26-32 of SEQ ID NO: 119)
CDR2: VPSGGS (SEQ ID NO: 120; amino acid residues 52-57 of SEQ ID NO: 119)
CDR3: VSRYAPEPMDV (SEQ ID NO: 121; amino acid residues 99-109 of SEQ ID NO: 119)
H CAGGTGCAGCTGGTGCAGTCTGGGGCTGAGGTGAAGAAGCCTGGGGCCTCAGTGAAGGTTTCCTG
CAAGGCATCTGGATACACCTTCACCTCGTACCGTATGCACTGGGTGCGACAGGCCCCTGGACAAGG
GCTTGAGTGGATGGGATTTATCGTGCCTAGTGGTGGTAGCACAGGCTACGCACAGAAGTTCCAGG
GCAGAGTTACCATGACCAGGGACACGTCCACGAGCACAGTCTACATGGAGCTGAGCAGCCTGAGA
TCTGAGGACACGGCGGTGTACTACTGCGCTAGAGTATCTAGGTACGCCCCAGAGCCAATGGACGT
ATGGGGCCAGGGAACAACTGTCACCGTCTCCTCAGCTAGCACAAAAGGACCAAGCGTGTTTCCAC
TGGCACCTAGCAGCAAATCCACCAGCGGCGGAACAGCAGCCCTCGGGTGCCTGGTGAAGGATTAC
TTCCCTGAGCCAGTCACAGTGTCCTGGAACTCCGGAGCCCTGACATCCGGCGTGCACACCTTCCCC
GCTGTGCTGCAATCCAGCGGACTGTATAGCCTCAGCTCCGTCGTGACAGTCCCTTCCAGCAGCCTG
GGCACACAGACTTACATTTGCAACGTGAACCACAAACCTTCCAACACTAAGGTGGACAAAAAGGT
GGAACCCAAATCCTGTGATAAGACCCATACATGCCCACCTTGTCCCGCTCCTGAGCTGCTGGGGGG
ACCTTCCGTCTTTCTGTTTCCTCCAAAACCAAAAGACACACTCATGATCAGCCGGACCCCCGAAGT
CACCTGTGTGGTGGTGGACGTCAGCCACGAAGATCCAGAGGTCAAGTTCAATTGGTACGTGGATG
GAGTGGAAGTCCACAACGCAAAAACCAAACCTAGAGAAGAACAGTACAATAGCACATACAGGGT
GGTGTCCGTCCTGACAGTGCTCCACCAGGACTGGCTCAATGGCAAAGAGTATAAGTGCAAGGTGA
GCAACAAGGCCCTGCCTGCACCAATTGAGAAAACAATTAGCAAGGCAAAGGGGCAGCCACGGGA
ACCCCAGGTGTATACCCTGCCCCCAAGCCGGGATGAACTGACCAAAAACCAGGTCAGCCTGACAT
GCCTGGTGAAAGGGTTTTACCCAAGCGATATTGCCGTCGAGTGGGAGAGCAACGGACAGCCAGAA
AACAATTACAAAACCACCCCACCTGTGCTGGACTCCGATGGGAGCTTTTTCCTGTACAGCAAGCTC
ACAGTGGACAAGTCCAGATGGCAACAGGGCAACGTGTTTTCCTGCTCCGTGATGCACGAGGCCCTC
CACAACCACTATACACAAAAGTCCCTCTCCCTCAGCCCAGGAAAG (SEQ ID NO: 122)
H QVQLVQSGAEVKKPGASVKVSCKASGYTFTSYRMHWVRQAPGQGLEWMGFIVPSGGSTGYAQKFQG
RVTMTRDTSTSTVYMELSSLRSEDTAVYYCARVSRYAPEPMDVWGQGTTVTVSSASTKGPSVFPLAPS
SKSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK (SEQ ID NO: 123
VL DIQMTQSPSSVSASVGDRVTITCRASQGISRWLAWYQQKPGKAPKLLIYAASSLQSGVPSRFSGSGSGT
DFTLTISSLQPEDFATYYCQQAFSHPWTFGGGTKVEIK (SEQ ID NO: 91)
CDR1: RASQGISRWLA (SEQ ID NO: 92; amino acid residues 24-34 of SEQ ID NO: 91)
CDR2: AASSLQS (SEQ ID NO: 93; amino acid residues 50-56 of SEQ ID NO: 91)
CDR3: QQAFSHPWT (SEQ ID NO: 94; amino acid residues 89-97 of SEQ ID NO: 91)
L SEQ ID NO: 95
L SEQ ID NO: 96

D04

VH CAGGTGCAGCTGGTGCAGTCTGGGGCTGAGGTGAAGAAGCCTGGGGCCTCAGTGAAGGTTTCCTG
CAAGGCATCTGGATACACCTTCACCTCGTACCGTATGCACTGGGTGCGACAGGCCCCTGGACAAGG
GCTTGAGTGGATGGGATTTATCGTGCCTAGTGGTGGTAGCACAGGCTACGCACAGAAGTTCCAGGG
CAGAGTTACCATGACCAGGGACACGTCCACGAGCACAGTCTACATGGAGCTGAGCAGCCTGAGAT
CTGAGGACACGGCGGTGTACTACTGCGCTAGAGTATCTAGGTACGCCCCAGAGCCAATGGACGTA
TGGGGCCAGGGAACAACTGTCACCGTCTCCTCA (SEQ ID NO: 164)
VH QVQLVQSGAEVKKPGASVKVSCKASGYTFTSYRMHWVRQAPGQGLEWMGFIVPSGGSTGYAQKFQG
RVTMTRDTSTSTVYMELSSLRSEDTAVYYCARVSRYAPEPMDVWGQGTTVTVSS (SEQ ID NO: 165)
CDR1: SYRMH (SEQ ID NO: 166; amino acid residues 31-35 of SEQ ID NO: 165)
CDR2: FIVPSGGSTGYAQKFQG (SEQ ID NO: 167; amino acid residues 50-66 of SEQ ID NO: 165)
CDR3: VSRYAPEPMDV (SEQ ID NO: 168; amino acid residues 99-109 of SEQ ID NO: 165)
H CAGGTGCAGCTGGTGCAGTCTGGGGCTGAGGTGAAGAAGCCTGGGGCCTCAGTGAAGGTTTCCTG
CAAGGCATCTGGATACACCTTCACCTCGTACCGTATGCACTGGGTGCGACAGGCCCCTGGACAAGG
GCTTGAGTGGATGGGATTTATCGTGCCTAGTGGTGGTAGCACAGGCTACGCACAGAAGTTCCAGGG
CAGAGTTACCATGACCAGGGACACGTCCACGAGCACAGTCTACATGGAGCTGAGCAGCCTGAGAT
CTGAGGACACGGCGGTGTACTACTGCGCTAGAGTATCTAGGTACGCCCCAGAGCCAATGGACGTA
TGGGGCCAGGGAACAACTGTCACCGTCTCCTCAGCTTCCACCAAGGGCCCATCCGTCTTCCCCCTG
GCGCCCTGCTCCAGGAGCACCTCCGAGAGCACAGCCGCCCTGGGCTGCCTGGTCAAGGACTACTTC
CCCGAACCGGTGACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCCCTCCAGCAGCTTGGGC
ACGAAGACCTACACCTGCAACGTAGATCACAAGCCCAGCAACACCAAGGTGGACAAGAGAGTTGA
GTCCAAATATGGTCCCCCATGCCCACCCTGCCCAGCACCTGAGTTCCTGGGGGGACCATCAGTCTT TABLE 1-continued

| | Exemplary ActRII-binding proteins |
|---|---|
| | CCTGTTCCCCCCAAAACCCAAGGACACTCTCATGATCTCCCGGACCCCTGAGGTCACGTGCGTGGT<br>GGTGGACGTGAGCCAGGAAGACCCCGAGGTCCAGTTCAACTGGTACGTGGATGGCGTGGAGGTGC<br>ATAATGCCAAGACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTCTCCAACAAAGGCCT<br>CCCGTCCTCCATCGAGAAAACCATCTCCAAAGCCAAAGGGCAGCCCCGAGAGCCACAGGTGTACA<br>CCCTGCCCCCATCCCAGGAGGAGATGACCAAGAACCAGGTCAGCCTGACCTGCCTGGTCAAAGGC<br>TTCTACCCCAGCGACATCGCCGTGGAGTGGGAGAGCAATGGGCAGCCGGAGAACAACTACAAGAC<br>CACGCCTCCCGTGCTGGACTCCGACGGCTCCTTCTTCCTCTACAGCAGGCTAACCGTGGACAAGAG<br>CAGGTGGCAGGAGGGGAATGTCTTCTCATGCTCCGTGATGCATGAGGCTCTGCACAACCACTACAC<br>ACAGAAGAGCCTCTCCCTGTCTCTGGGTAAATGA (SEQ ID NO: 169) |
| H | QVQLVQSGAEVKKPGASVKVSCKASGYTFTSYRMHWVRQAPGQGLEWMGFIVPSGGSTGYAQKFQG<br>RVTMTRDTSTSTVYMELSSLRSEDTAVYYCARVSRYAPEPMDVWGQGTTVTVSSASTKGPSVFPLAP<br>CSRSTSESTAALGCLVKDYFPEPVTVSWNSGALTSGVHTFPAVLQSSGLYSLSSVVTVPSSSLGTKTYT<br>CNVDHKPSNTKVDKRVESKYGPPCPPCPAPEFLGGPSVFLFPPKPKDTLMISRTPEVTCVVVDVSQEDP<br>EVQFNWYVDGVEVHNAKTKPREEQFNSTYRVVSVLTVLHQDWLNGKEYKCKVSNKGLPSSIEKTISK<br>AKGQPREPQVYTLPPSQEEMTKNQVSLTCLVKGFYPSDIAVEWESNGQPENNYKTTPPVLDSDGSFFL<br>YSRLTVDKSRWQEGNVFSCSVMHEALHNHYTQKSLSLSLGK (SEQ ID NO: 170) |
| VL | GACATCCAGATGACCCAGTCTCCATCTTCCGTGTCTGCATCTGTAGGAGACAGAGTCACCATCACT<br>TGTCGGGCGAGTCAGGGTATTAGCAGGTGGTTAGCCTGGTATCAGCAGAAACCAGGGAAAGCCCC<br>TAAGCTCCTGATCTATGCTGCATCCAGTTTGCAAAGTGGGGTCCCATCAAGGTTCAGCGGCAGTGG<br>ATCTGGGACAGATTTCACTCTCACCATCAGCAGCCTGCAGCCTGAAGATTTTGCAACTTATTACTG<br>TCAGCAGGCATTCTCCCACCCTTGGACTTTTGGCGGAGGGACCAAGGTTGAGATCAAA (SEQ ID<br>NO: 171) |
| VL | DIQMTQSPSSVSASVGDRVTITCRASQGISRWLAWYQQKPGKAPKLLIYAASSLQSGVPSRFSGSGSGT<br>DFTLTISSLQPEDFATYYCQQAFSHPWTFGGGTKVEIK (SEQ ID NO: 172)<br>CDR1: RASQGISRWLA (SEQ ID NO: 173; amino acid residues 24-34 of SEQ ID NO: 172)<br>CDR2: AASSLQS (SEQ ID NO: 174; amino acid residues 50-56 of SEQ ID NO: 172)<br>CDR3: QQAFSHPWT (SEQ ID NO: 175; amino acid residues 89-97 of SEQ ID NO: 172) |
| L | GACATCCAGATGACCCAGTCTCCATCTTCCGTGTCTGCATCTGTAGGAGACAGAGTCACCATCACT<br>TGTCGGGCGAGTCAGGGTATTAGCAGGTGGTTAGCCTGGTATCAGCAGAAACCAGGGAAAGCCCC<br>TAAGCTCCTGATCTATGCTGCATCCAGTTTGCAAAGTGGGGTCCCATCAAGGTTCAGCGGCAGTGG<br>ATCTGGGACAGATTTCACTCTCACCATCAGCAGCCTGCAGCCTGAAGATTTTGCAACTTATTACTGT<br>CAGCAGGCATTCTCCCACCCTTGGACTTTTGGCGGAGGGACCAAGGTTGAGATCAAACGTAAGGG<br>GCTCACAGTTAATTAATTGAGGTCTGGACATATACATGGGTGACAATGACATCCACTTTGCCTTTCT<br>CTCCACAGGAACTGTGGCTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGCAGGACAGCAAGGACAG<br>CACCTACAGCCTCAGCAGCACCCTGACGCTGAGCAAAGCAGACTACGAGAAACACAAAGTCTACG<br>CCTGCGAAGTCACCCATCAGGGCCTGAGCTCGCCCGTCACAAAGAGCTTCAACAGGGGAGAGTGT<br>TAG (SEQ ID NO: 176) |
| L | DIQMTQSPSSVSASVGDRVTITCRASQGISRWLAWYQQKPGKAPKLLIYAASSLQSGVPSRFSGSGSGT<br>DFTLTISSLQPEDFATYYCQQAFSHPWTFGGGTKVEIKRTVAAPSVFIFPPSDEQLKSGTASVVCLLNNF<br>YPREAKVQWKVDNALQSGNSQESVTEQDSKDSTYSLSSTLTLSKADYEKHKVYACEVTHQGLSSPVT<br>KSFNRGEC (SEQ ID NO: 177) |
| | ActRIIA-binding Antibodies<br>G02 |
| VH | CAGGTGCAGCTGCAGGAGTCGGGCCCAGGACTGGTGAAGCCTTCACAGACCCTGTCCCTCACCTGT<br>ACTGTCTCTGGTGGCTCCATCAGCAGTGGTAGCTACTACTGGAGCTGGATCCGCCAGCACCCAGGG<br>AAGGGCCTGGAGTGGATTGGGTACATCTATTACAGTGGGAGCACCTACTACAACCCGTCCCTCAAG<br>AGTCGAGTTACCATATCAGTAGACACGTCTAAGAACCAGTTCTCCCTGAAGCTGAGTTCTGTGACC<br>GCCGCAGACACGGCGGTGTACTACTGCGCCAGAGGACTAGGAATGTACTACCACGTGCCATTCGA<br>CATATGGGGTCAGGGTACAATGGTCACCGTCTCCTCA (SEQ ID NO: 124) |
| VH | QVQLQESGPGLVKPSQTLSLTCTVSGGSISSGSYYWSWIRQHPGKGLEWIGYIYYSGSTYYNPSLKSRVT<br>ISVDTSKNQFSLKLSSVTAADTAVYYCARGLGMYYHVPFDIWGQGTMVTVSS (SEQ ID NO: 125)<br>CDR1: GGSISSGSY (SEQ ID NO: 126; amino acid residues 26-34 of SEQ ID NO: 125)<br>CDR2: YYSGS (SEQ ID NO: 127; amino acid residues 54-58 of SEQ ID NO: 125)<br>CDR3: GLGMYYHVPFDI (SEQ ID NO: 128; amino acid residues 100-111 of SEQ ID NO: 12) |
| H | CAGGTGCAGCTGCAGGAGTCGGGCCCAGGACTGGTGAAGCCTTCACAGACCCTGTCCCTCACCTGT<br>ACTGTCTCTGGTGGCTCCATCAGCAGTGGTAGCTACTACTGGAGCTGGATCCGCCAGCACCCAGGG<br>AAGGGCCTGGAGTGGATTGGGTACATCTATTACAGTGGGAGCACCTACTACAACCCGTCCCTCAAG<br>AGTCGAGTTACCATATCAGTAGACACGTCTAAGAACCAGTTCTCCCTGAAGCTGAGTTCTGTGACC<br>GCCGCAGACACGGCGGTGTACTACTGCGCCAGAGGACTAGGAATGTACTACCACGTGCCATTCGA<br>CATATGGGGTCAGGGTACAATGGTCACCGTCTCCTCAGCTAGCACAAAAGGACCAAGCGTGTTTCC<br>ACTGGCACCTAGCAGCAAATCCACCAGCGGCGGAACAGCAGCCCTCGGGTGCCTGGTGAAGGATT<br>ACTTCCCTGAGCCAGTCACAGTGTCCTGGAACTCCGGAGCCCTGACATCCGGCGTGCACACCTTCC<br>CCGCTGTGCTGCAATCCAGCGGACTGTATAGCCTCAGCTCCGTCGTGACAGTCCCTTCCAGCAGCC<br>TGGGCACACAGACTTACATTTGCAACGTGAACCACAAACCTTCCAACACTAAGGTGGACAAAAAG<br>GTGGAACCCAAATCCTGTGATAAGACCCATACATGCCCACCTTGTCCCGCTCCTGAGCTGCTGGGG<br>GGACCTTCCGTCTTTCTGTTTCCTCCAAAACCAAAAGACACACTCATGATCAGCCGGACCCCCGAA<br>GTCACCTGTGTGGTGGTGGACGTCAGCCACGAAGATCCAGAGGTCAAGTTCAATTGGTACGTGGAT<br>GGAGTGGAAGTCCACAACGCAAAAACCAAACCTAGAGAAGAACAGTACAATAGCACATACAGGG<br>TGGTGTCCGTCCTGACAGTGCTCCACCAGGACTGGCTCAATGGCAAAGAGTATAAGTGCAAGGTGA<br>GCAACAAGGCCCTGCCTGCACCAATTGAGAAAACAATTAGCAAGGCAAAGGGGCAGCCACGGGA<br>ACCCCAGGTGTATACCCTGCCCCCAAGCCGGGATGAACTGACCAAAAACCAGGTCAGCCTGACAT |

TABLE 1-continued

| Exemplary ActRII-binding proteins | |
|---|---|
| | GCCTGGTGAAAGGGTTTTACCCAAGCGATATTGCCGTCGAGTGGGAGAGCAACGGACAGCCAGAA AACAATTACAAAACCACCCCACCTGTGCTGGACTCCGATGGAGCTTTTTCCTGTACAGCAAGCTC ACAGTGGACAAGTCCAGATGGCAACAGGGCAACGTGTTTTCCTGCTCCGTGATGCACGAGGCCCTC CACAACCACTATACACAAAAGTCCCTCTCCCTCAGCCCAGGAAAG (SEQ ID NO: 129) |
| H | QVQLQESGPGLVKPSQTLSLTCTVSGGSISSGSYYWSWIRQHPGKGLEWIGYIYYSGSTYYNPSLKSRVT ISVDTSKNQFSLKLSSVTAADTAVYYCARGLGMYYHVPFDIWGQGTMVTVSSASTKGPSVFPLAPSSKS TSGGTAALGCLVKDYFPEPVTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK (SEQ ID NO: 130) |
| VL | GAAATTGTGTTGACACAGTCTCCAGCCACCCTGTCTTTGTCTCCAGGGGAAAGAGCCACCCTCTCCT GCAGGGCCAGTCAGAGTGTTAGCAGCTACTTAGCCTGGTACCAACAGAAACCTGGCCAGGCTCCC AGGCTCCTCATCTATGATGCATCCAACAGGGCCACTGGCATCCCAGCCAGGTTCAGTGGCAGTGGG TCTGGGACAGACTTCACTCTCACCATCAGCAGCCTAGAGCCTGAAGATTTTGCAGTTTATTACTGTC AGCAGTACTTCCACTGGCCTCCTACTTTTGGCGGAGGGACCAAGGTTGAGATCAAA (SEQ ID NO: 131) |
| VL | EIVLTQSPATLSLSPGERATLSCRASQSVSSYLAWYQQKPGQAPRLLIYDASNRATGIPARFSGSGSGTDF TLTISSLEPEDFAVYYCQQYFHWPPTFGGGTKVEIK (SEQ ID NO: 132)<br>CDR1: RASQSVSSYLA (SEQ ID NO: 133; amino acid residues 24-34 of SEQ ID NO: 132)<br>CDR2: DASNRAT (SEQ ID NO: 134; amino acid residues 50-56 of SEQ ID NO: 132)<br>CDR3: QQYFHWPPT (SEQ ID NO: 135; amino acid residues 89-97 of SEQ ID NO: 132) |
| L | GAAATTGTGTTGACACAGTCTCCAGCCACCCTGTCTTTGTCTCCAGGGGAAAGAGCCACCCTCTCC TGCAGGGCCAGTCAGAGTGTTAGCAGCTACTTAGCCTGGTACCAACAGAAACCTGGCCAGGCTCC CAGGCTCCTCATCTATGATGCATCCAACAGGGCCACTGGCATCCCAGCCAGGTTCAGTGGCAGTG GGTCTGGGACAGACTTCACTCTCACCATCAGCAGCCTAGAGCCTGAAGATTTTGCAGTTTATTACT GTCAGCAGTACTTCCACTGGCCTCCTACTTTTGGCGGAGGGACCAAGGTTGAGATCAAACGTACG GTGGCTGCACCTTCCGTCTTTATCTTTCCACCTTCCGATGAGCAGCTGAAGAGCGGAACAGCAAG CGTGGTGTGTCTGCTGAACAACTTTTATCCCCGGGAGGCAAAGGTGCAGTGGAAAGTCGACAATG CTCTCCAGTCCGGCAATTCCCAAGAGAGCGTGACAGAGCAAGATTCCAAGGACTCCACTTACAGC CTGTCCAGCACCCTCACACTGAGCAAGGCTGATTACGAGAAACACAAAGTGTACGCTTGTGAAGT CACCCACCAAGGCCTGAGCAGCCCAGTCACTAAGTCCTTTAACCGGGGCGAATGT (SEQ ID NO: 136) |
| L | EIVLTQSPATLSLSPGERATLSCRASQSVSSYLAWYQQKPGQAPRLLIYDASNRATGIPARFSGSGSGTD FTLTISSLEPEDFAVYYCQQYFHWPPTFGGGTKVEIKRTVAAPSVFIFPPSDEQLKSGTASVVCLLNNFY PREAKVQWKVDNALQSGNSQESVTEQDSKDSTYSLSSTLTLSKADYEKHKVYACEVTHQGLSSPVTK SFNRGEC (SEQ ID NO: 137) |

SPR (BIACORE™-based analysis) and cell-based reporter assay was used to more fully characterize the binding of the ActRII-binding proteins described in Table 1.

A01 Lineage Antibodies

Kinetic characterization of A01 antibody lineage (A01 (naïve parent), B01, C01, D01, E01 and F01) binding to monomeric and dimeric hActRIIB and hActRIIA was performed using standard BIACORE®-based analysis at 37° C. In brief, antibodies were captured on anti-hFcIgG Biacore chips and different concentrations of dimeric and monomeric ActRIIB or ActRIIA were injected in duplicates over the captured antibody and control surface. To obtain kinetic rate constants the data were double referenced and fit to a 1:1 interaction model using BiaEvaluation software (GE Healthcare). The equilibrium binding constant $K_D$ was determined by the ratio of binding rate constants $k_d/k_a$ The results of the binding parameter analysis of the A01 lineage antibodies A01-F01 are presented in Table 2 and FIGS. 1A-1N.

TABLE 2

A01 lineage improved binding to ActRIIB

| | ActRIIB MONOMER | | | ActRIIB DIMER | | | ActRIIA MONOMER | | | ActRIIA DIMER | | |
|---|---|---|---|---|---|---|---|---|---|---|---|---|
| mAb | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| A01 Parent | $1.72 \times 10^5$ | $1.98 \times 10^{--1}$ | 1150000 | $1.06 \times 10^5$ | $1.28 \times 10^{--4}$ | 1207 | No binding | | | No binding | | |
| B01 | $1.09 \times 10^6$ | $3.40 \times 10^{--3}$ | 3637 | $6.26 \times 10^5$ | $2.46 \times 10^{--4}$ | 393 | No binding | | | No binding | | |
| C01 | $1.37 \times 10^6$ | $7.12 \times 10^{--3}$ | 5218 | $7.97 \times 10^5$ | $1.88 \times 10^{--4}$ | 236 | No binding | | | No binding | | |
| D01 | $1.61 \times 10^6$ | $3.54 \times 10^{--3}$ | 2191 | $8.28 \times 10^5$ | $2.50 \times 10^{--4}$ | 302 | No binding | | | No binding | | |
| E01 | $1.70 \times 10^6$ | $4.15 \times 10^{--3}$ | 2446 | $7.77 \times 10^5$ | $2.92 \times 10^{--4}$ | 376 | No binding | | | No binding | | |
| F01 | $1.34 \times 10^6$ | $4.44 \times 10^{--3}$ | 3323 | $6.01 \times 10^5$ | $2.16 \times 10^{--4}$ | 360 | No binding | | | No binding | | |

The optimized A01 lineage antibodies B01, C01, D01, E01, and F01 each displayed improved equilibrium dissociation constant (KD) kinetic parameters for ActRIIB monomer and dimer binding over the A01 parent antibody.

The ActRIIB neutralizing ability of A01 lineage antibodies A01, B01, C01, D01, E01 and F01 was assessed in a cell-based activin A signaling assay in F2.35 (IIA knockout) cells obtained by CRISPE-Cas9 modification of 293FT cells. Cells were co-transfected with experimental luciferase reporter plasmid containing Smad2/3 response element pGL3(CAGA)12 and control luciferase reporter plasmid pRL-CMV. The next day, serial dilutions of the mAb was made and added to the transfected cells and incubated for 30 minutes, after which activating factors such as Activin A was added (final concentration 5 ng/ml) for an additional 6 hour incubation. Cells were washed 1× in PBS, lysed and assayed using the Dual-Luciferase Reporter Assay System (Promega) according to the manufacturer's instructions. Chemiluminescence was measured using the Infinite M200 plate reader. The luciferase activity of the experimental reporter was normalized by the luciferase activity obtained from control reporter. [. To evaluate anti-ActRIIA neutralizing activity, A204 cells were transfected with the same reporter genes. A204 express ActRIIA and a low level of endogenous ActRIIB. The transfected cells were assayed as above.

Each of the optimized A01 lineage antibodies, B01, C01, D01, E01, and F01, displayed increased ActRIIB-mediated signal inhibition compared to the A01 parent antibody. See, FIG. 2.

G01 Lineage Antibodies

Kinetic characterization of the G01 (naïve parent) and optimized H01 antibodies to monomeric and dimeric hActRIIB and hActRIIA was performed using standard BIACORE®-based analysis at 37° C.

The results of the binding parameter analysis of the G01 and H01 antibodies are presented in Table 3 and FIGS. 3A-3F.

TABLE 3

G02 lineage improved binding to ActRIIB

| mAb | ActRIIB MONOMER $k_a$ (1/Ms) | ActRIIB MONOMER $k_d$ (1/s) | ActRIIB MONOMER $K_D$ (pM) | ActRIIB DIMER $k_a$ (1/Ms) | ActRIIB DIMER $k_d$ (1/s) | ActRIIB DIMER $K_D$ (pM) | ActRIIA MONOMER $k_a$ (1/Ms) | ActRIIA MONOMER $k_d$ (1/s) | ActRIIA MONOMER $K_D$ (pM) | ActRIIA DIMER $k_a$ (1/Ms) | ActRIIA DIMER $k_d$ (1/s) | ActRIIA DIMER $K_D$ (pM) |
|---|---|---|---|---|---|---|---|---|---|---|---|---|
| G01 Parent | $9.05 \times 10^5$ | $1.52 \times 10^{-2}$ | 16790 | $1.76 \times 10^5$ | $2.20 \times 10^{-4}$ | 1139 | No binding | | | No binding | | |
| H01 | $1.95 \times 10^6$ | $2.30 \times 10^{-2}$ | 11790 | $3.58 \times 10^5$ | $1.27 \times 10^{-4}$ | 353 | No binding | | | No binding | | |

The H02 optimized antibody displated improved equilibrium dissociation constant (KD) kinetic parameters for ActRIIB monomer and dimer binding over the G01 parent antibody.

The ActRIIB neutralizing ability of the parent G01 and optimized H01 antibodies was assessed in a cell-based activin A signaling assay in F2.35 (IIA knockout) cells. The H01 optimized antibody displayed an increased ActRIIB-mediated signal inhibition compared to the G01 parent antibody. See, FIG. 4.

A02 Lineage Antibodies

Kinetic characterization of A02 antibody lineage (A01 (naïve parent), B02, C02, D02, and D03) binding to monomeric and dimeric hActRIIB and hActRIIA was performed using standard BIACORE®-based analysis at 37° C.

The results of the binding parameter analysis of the A02 lineage antibodies A02-D02 are presented in Table 4 and FIGS. 5A-5T.

TABLE 4

A02 lineage improved binding to ActRIIB and ActRIIA

| mAb | ActRIIB MONOMER $k_a$ (1/Ms) | ActRIIB MONOMER $k_d$ (1/s) | ActRIIB MONOMER $K_D$ (pM) | ActRIIB DIMER $k_a$ (1/Ms) | ActRIIB DIMER $k_d$ (1/s) | ActRIIB DIMER $K_D$ (pM) | ActRIIA MONOMER $k_a$ (1/Ms) | ActRIIA MONOMER $k_d$ (1/s) | ActRIIA MONOMER $K_D$ (pM) | ActRIIA DIMER $k_a$ (1/Ms) | ActRIIA DIMER $k_d$ (1/s) | ActRIIA DIMER $K_D$ (pM) |
|---|---|---|---|---|---|---|---|---|---|---|---|---|
| A02 Parent | $3.02 \times 10^6$ | $6.62 \times 10^{-2}$ | 21960 | $2.19 \times 10^5$ | $1.12 \times 10^{-4}$ | 511 | No binding | | | $3.53 \times 10^5$ | $6.27 \times 10^{-4}$ | 1777 |
| B02 | $9.05 \times 10^5$ | $1.00 \times 10^{-3}$ | 1105 | $3.23 \times 10^5$ | $2.10 \times 10^{-4}$ | 649 | $7.29 \times 10^6$ | $5.93 \times 10^{-3}$ | 8134 | $4.95 \times 10^5$ | $1.67 \times 10^{-4}$ | 338 |
| C02 | $9.75 \times 10^5$ | $5.15 \times 10^{-4}$ | 528 | $2.89 \times 10^5$ | $9.64 \times 10^{-5}$ | 333 | $6.30 \times 10^6$ | $1.66 \times 10^{-3}$ | 26370 | $5.24 \times 10^5$ | $8.02 \times 10^{-5}$ | 153 |
| D02 | $4.47 \times 10^5$ | $2.91 \times 10^{-4}$ | 650 | $1.70 \times 10^5$ | $1.23 \times 10^{-4}$ | 727 | $3.69 \times 10^6$ | $6.84 \times 10^{-3}$ | 18560 | $3.36 \times 10^5$ | $1.06 \times 10^{-4}$ | 316 |
| D03 | $1.05 \times 10^6$ | $2.03 \times 10^{-4}$ | 194 | $4.59 \times 10^5$ | $1.04 \times 10^{-5}$ | 22.6 | $8.09 \times 10^5$ | $2.93 \times 10^{-3}$ | 3635 | $4.71 \times 10^5$ | $9.39 \times 10^{-5}$ | 199 |

The optimized A02 lineage antibodies B02, C02, D02, and D03 each displayed improved equilibrium dissociation constants (KD) for binding ActRIIB and ActRIIA monomers, and ActRIIA dimers over the A02 parent antibody.

The ActRIIB neutralizing ability of antibodies A02, B02, C02, D02, and D03 was assessed in a cell-based activin A signaling assay in F2.35 (IIA knockout) cells. Each of the optimized antibodies, B02, C02, D02, and D03 displayed increased ActRIIB-mediated signal inhibition compared to the A02 antibody. See, FIGS. 6A-6B.

E02 Lineage Antibodies

Kinetic characterization of the E02 (naïve parent) and optimized F02 antibodies to monomeric and dimeric hActRIIB and hActRIIA was performed using standard BIACORE®-based analysis at 37° C.

The results of the binding parameter analysis of the E02 and F02 antibodies are presented in Table 5 and FIGS. 7A-7F.

TABLE 5

E02 lineage improved binding to ActRIIB

| | ActRIIB MONOMER | | | ActRIIB DIMER | | | ActRIIA MONOMER | | | ActRIIA DIMER | | |
|---|---|---|---|---|---|---|---|---|---|---|---|---|
| mAb | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| E02 | $1.02 \times 10^5$ | $6.92 \times 10^{-4}$ | 6798 | $3.81 \times 10^4$ | $7.60 \times 10^{-5}$ | 1995 | No binding | | | No binding | | |
| F02 | $1.19 \times 10^5$ | $3.13 \times 10^{-4}$ | 2632 | $4.69 \times 10^4$ | $3.46 \times 10^{-5}$ | 738 | No binding | | | No binding | | |

The F02 optimized antibody displayed improved kinetic parameters equilibrium dissociation constant (KD) over for ActRIIB monomer and dimer binding over the E02 parent antibody.

The ActRIIB neutralizing ability of the E02 and F02 antibodies was assessed in a cell-based activin A signaling assay in F2.35 (IIA knockout) cells. FIG. 9 depicts the neutralizing activity of E02 parent and F02 variant antibodies in the assay. As demonstrated, the F02 antibody displayed increased signal inhibition compared to the E02.

G02 Antibody

Kinetic characterization of G02 antibody binding to monomeric and dimeric hActRIIB and hActRIIA was performed using standard BIACORE®-based analysis at 37° C. FIGS. 8A-8D show kinetic characterization of G02 antibody binding to monomeric and dimeric hActRIIB and hActRIIA (FIG. 8A-8D, respectively) as determined by BIACORE®-based analysis at 37° C. The results of the binding parameter analysis of the G02 antibody is presented in Table 6.

TABLE 6

G02 antibody binding to ActRIIA

| | ActRIIB MONOMER | | | ActRIIB DIMER | | | ActRIIA MONOMER | | | ActRIIA DIMER | | |
|---|---|---|---|---|---|---|---|---|---|---|---|---|
| mAb | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| G02 | No binding | | | No binding | | | $1.14 \times 10^6$ | $6.61 \times 10^{-2}$ | 58020 | $1.86 \times 10^5$ | $2.75 \times 10^{-4}$ | 1480 |

Example 3.

Reporter Gene Assay in A204 Cells

A reporter gene assay in A204 cells can be used to determine the ability of ActRII-binding proteins such as anti-ActRII Fabs and recombinant antibodies to neutralize ActRII (e.g., ActRIIB). This assay can be based on a human rhabdomyosarcoma cell line transfected with a pGL3 (CAGA)12 reporter plasmid (Dennler et al., *EMBO* 17:3091-3100 (1998)) as well as a ReniUa reporter plasmid (pRLCMV) to control for transfection efficiency. The CAGA12 motif is present in TGF-beta responsive genes (PAI-1 gene), so this vector is of general use for factors signaling through Smad2 and Smad3. Since the A204 cell line expresses primarily ActRIIA rather than ActRIIB, it is not possible to directly test antibodies for potential ActRIIB neutralizing ability. Instead, this assay can be designed to detect the ability of test articles to neutralize the inhibitory effect of the soluble fusion protein ActRIIB-Fc on activation of endogenous ActRIIA by ligands (such as activin A, GDF11, or myostatin) that can bind with high affinity to both ActRIIB and ActRIIA.

Thus, in this assay, ligand-mediated activation of ActRIIA will occur despite the presence of ActRIIB-Fc if the anti-ActRIIB Fab or antibody is neutralizing. On the first day of the assay, A204 cells (ATCC HTB-82) are distributed in 48-well plates at $10^5$ cells per well. On the second day, a solution containing 10 μg pGL3(CAGA)12, 1 μg pRLCMV, 30 μl Fugene 6 (Roche Diagnostics), and 970 μl OptiMEM (Invitrogen) is preincubated for 30 min, then added to McCoy's growth medium, which is applied to the plated cells (500 μl/well) for incubation overnight at room temperature. On the third day, medium is removed, and cells are incubated for 6 h at 37° C. with a mixture of ligands and inhibitors prepared as described below.

To evaluate the neutralizing potency of test ActRII-binding proteins, a serial dilution of the test article is made in a 48-well plate in a 200 μl volume of assay buffer (McCoy's medium+0.1% BSA). An equal volume of ActRIIB-Fc (200 μg/ml) in assay buffer is then added. The test solutions are incubated at 37° C. for 30 minutes, then 400 μl of GDF11 (10 ng/ml) or activin A (10 ng/ml) is added to all wells, and 350 μl of this mixture is added to each well of the 48-well plate of A204 cells. Each concentration of test ActRII-binding protein is tested in duplicate. The final concentration of ActRIIB-Fc is 50 ng/ml (which is the $IC_{50}$ for this inhibitor of activin A signaling when the final concentration of activin A is 5 ng/ml). After incubation with test solutions for 6 h, cells are rinsed with phosphate-buffered saline containing 0.1% BSA, then lysed with passive lysis buffer (Promega El 941) and stored overnight at −70° C. On the fourth and final day, plates are warmed to room temperature with gentle shaking. Cell lysates are transferred in duplicate to a chemoluminescence plate (96-well) and analyzed in a luminometer with reagents from a Dual-Luciferase Reporter Assay system (Promega El 980) to determine normalized luciferase activity. Differences in luciferase activity between the test article and a control in which the test article is absent reflect differences in cellular signaling resulting from the presence of the test article.

Example 4.

Precision Epitope Mapping

Mapping of the ActRIIB and ActRIIA ECD epitopes recognized by the antibodies was performed by Pepscan Presto BV using custom made peptide libraries. Sequences of ECDs of human ActRIIB and ActRIIA were converted into libraries of overlapping linear 15-mers and circularized 15-mer CLIPS using combinatorial matrix design. CLIPS (Chemical Linkage of Peptides onto Scaffolds) technology structurally fixes peptides into defined three-dimensional structures (single, double, triple, etc. loops) creating functional mimics of complex binding sites. Peptides were synthesized on solid support. Binding of antibodies to each of the synthesized peptides was tested by ELISA and binding affinities were quantified. Peptide constructs representing both parts of the discontinuous epitope in the correct conformation bind specific antibody with the highest affinity. Peptide constructs presenting an incomplete epitope bind specific antibody with lower affinity, whereas constructs not containing correct epitope did not bind at all. Each peptide was given a score based on affinity.

Antibody D04 was determined to bind across three sequence stretches on AcRIIA, with binding epitopes mapped to amino acid residues 9 through to 20 (ECLFF-NANWEKD (SEQ ID NO:162)), amino acid residues 58 through to 69 (CWLDDINCYDRT (SEQ ID NO:163)) and amino acid residues 84 through to 93 (CCEGNMCNEK (SEQ ID NO:161)) of SEQ ID NO: 138.

Antibody D04 was also determined to bind across three sequence stretches on AcRIIB, with binding epitopes mapped to amino acids 9 through to 17 (NANWELERT (SEQ ID NO:157)), amino acids 52 through to 63 (GCWL-DDFNCYDR (SEQ ID NO:160)) and a binding site of amino acids 79 through to 88 (CCEGNFCNER (SEQ ID NO:59)) of SEQ ID NO: 138.

Antibody I01 was determined to bind across two stretches of sites on AcRIIB, with binding epitopes mapped to amino acids 9 through to 17 (NANWELERT (SEQ ID NO:157)) and amino acids 49 through to 63 (VKKGCWLDD (SEQ ID NO:158)) of SEQ ID NO: 139.

The invention claimed is:

1. An ActRII-binding antibody comprising a set of CDRs in which:

(a) (i) VH-CDR1 has the amino acid sequence of SEQ ID NO:166;
(ii) VH-CDR2 has the amino acid sequence of SEQ ID NO:167;
(iii) VH-CDR3 has the amino acid sequence of SEQ ID NO:168;
(iv) VL-CDR1 has the amino acid sequence of SEQ ID NO:173;
(v) VL-CDR2 has the amino acid sequence of SEQ ID NO:174; and
(vi) VL-CDR3 has the amino acid sequence of SEQ ID NO:175;

and wherein the antibody binds ActRIIB;

(b) (i) VH-CDR1 has the amino acid sequence of SEQ ID NO: 3 or 17;
(ii) VH-CDR2 has the amino acid sequence of SEQ ID NO: 4 or 18;
(iii) VH-CDR3 has the amino acid sequence of SEQ ID NO: 5;
(iv) VL-CDR1 has the amino acid sequence of SEQ ID NO: 10;
(v) VL-CDR2 has the amino acid sequence of SEQ ID NO: 11; and
(vi) VL-CDR3 has the amino acid sequence of SEQ ID NO: 12;

and wherein the antibody binds ActRIIB;

(c) (i) VH-CDR1 has the amino acid sequence of SEQ ID NO: 64 or 78;
(ii) VH-CDR2 has the amino acid sequence of SEQ ID NO: 65 or 79;
(iii) VH-CDR3 has the amino acid sequence of SEQ ID NO: 66 or 80;
(iv) VL-CDR1 has the amino acid sequence of SEQ ID NO: 71;
(v) VL-CDR2 has the amino acid sequence of SEQ ID NO: 72; and
(vi) VL-CDR3 has the amino acid sequence of SEQ ID NO:73;

and wherein the antibody binds ActRIIB;

(d) (i) VH-CDR1 has the amino acid sequence of SEQ ID NO: 3 or 58;
(ii) VH-CDR2 has the amino acid sequence of SEQ ID NO: 4 or 59;
(iii) VH-CDR3 has the amino acid sequence of SEQ ID NO: 46;
(iv) VL-CDR1 has the amino acid sequence of SEQ ID NO: 51;
(v) VL-CDR2 has the amino acid sequence of SEQ ID NO: 52; and
(vi) VL-CDR3 has the amino acid sequence of SEQ ID NO: 53;

and wherein the antibody binds ActRIIB;

(e) (i) VH-CDR1 has the amino acid sequence of SEQ ID NO: 145;
(ii) VH-CDR2 has the amino acid sequence of SEQ ID NO: 146;
(iii) VH-CDR3 has the amino acid sequence of SEQ ID NO: 147;
(iv) VL-CDR1 has the amino acid sequence of SEQ ID NO: 152;
(v) VL-CDR2 has the amino acid sequence of SEQ ID NO: 153; and
(vi) VL-CDR3 has the amino acid sequence of SEQ ID NO: 154;

and wherein the antibody binds ActRIIB;

(f) (i) VH-CDR1 has the amino acid sequence of SEQ ID NO: 85 or 99;
(ii) VH-CDR2 has the amino acid sequence of SEQ ID NO: 86 or 100;
(iii) VH-CDR3 has the amino acid sequence of SEQ ID NO: 87 or 101;
(iv) VL-CDR1 has the amino acid sequence of SEQ ID NO: 92;
(v) VL-CDR2 has the amino acid sequence of SEQ ID NO: 93; and
(vi) VL-CDR3 has the amino acid sequence of SEQ ID NO: 94;

and wherein the antibody binds ActRIIB and ActRIIA;

(g) (i) VH-CDR1 has the amino acid sequence of SEQ ID NO: 126;
(ii) VH-CDR2 has the amino acid sequence of SEQ ID NO: 127;
(iii) VH-CDR3 has the amino acid sequence of SEQ ID NO: 128;
(iv) VL-CDR1 has the amino acid sequence of SEQ ID NO: 133;
(v) VL-CDR2 has the amino acid sequence of SEQ ID NO: 134; and
(vi) VL-CDR3 has the amino acid sequence of SEQ ID NO: 135;

and wherein the antibody binds ActRIIA;

h) (i) VH-CDR1 has the amino acid sequence of SEQ ID NO: 3 or 17;

(ii) VH-CDR2 has the amino acid sequence of SEQ ID NO: 24 or 30;

(iii) VH-CDR3 has the amino acid sequence of SEQ ID NO: 5:

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB;

(i) (i) VH-CDR1 has the amino acid sequence of SEQ ID NO: 3 or 17;

(ii) VH-CDR2 has the amino acid sequence of SEQ ID NO: 36;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB;

(j) (i) VH-CDR1 has the amino acid sequence of SEQ ID NO: 23 or 29;

(ii) VH-CDR2 has the amino acid sequence of SEQ ID NO: 4 or 18;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB;

(k) (i) VH-CDR1 has the amino acid sequence of SEQ ID NO: 23 or 29;

(ii) VH-CDR2 has the amino acid sequence of SEQ ID NO: 24 or 30;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB;

(l) (i) VH-CDR1 has the amino acid sequence of SEQ ID NO: 23 or 29;

(ii) VH-CDR2 has the amino acid sequence of SEQ ID NO: 36;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB:

(m) (i) VH-CDR1 has the amino acid sequence of SEQ ID NO: 35 or 41;

(ii) VH-CDR2 has the amino acid sequence of SEQ ID NO: 4 or 18;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB:

(n) (i) VH-CDR1 has the amino acid sequence of SEQ ID NO: 35 or 41;

(ii) VH-CDR2 has the amino acid sequence of SEQ ID NO: 24 or 30;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB;

(o) (i) VH-CDR1 has the amino acid sequence of SEQ ID NO: 35 or 41;

(ii) VH-CDR2 has the amino acid sequence of SEQ ID NO: 36;

(iii) VH-CDR3 has the amino acid sequence of SEQ ID NO: 5;

(iv) VL-CDR1 has the amino acid sequence of SEQ ID NO: 10;

(v) VL-CDR2 has the amino acid sequence of SEQ ID NO: 11; and (vi) VL-CDR3 has the amino acid sequence of SEQ ID NO: 12;

and wherein the antibody binds ActRIIB;

(p) (i) VH-CDR1 has the amino acid sequence of SEQ ID NO: 85 or 99;

(ii) VH-CDR2 has the amino acid sequence of SEQ ID NO: 86 or 100;

(iii) VH-CDR3 has the amino acid sequence of SEQ ID NO: 108 or 115

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(g) (i) VH-CDR1 has the amino acid sequence of SEQ ID NO: 85 or 99;

(ii) VH-CDR2 has the amino acid sequence of SEQ ID NO: 86 or 100;

(iii) VH-CDR3 has the amino acid sequence of SEQ ID NO: 121;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(r) (i) VH-CDR1 has the amino acid sequence of SEQ ID NO: 85 or 99;

(ii) VH-CDR2 has the amino acid sequence of SEQ ID NO: 107 or 114;

(iii) VH-CDR3 has the amino acid sequence of SEQ ID NO: 87 or 101;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(s) (i) VH-CDR1 has the amino acid sequence of SEQ ID NO: 85 or 99;

(ii) VH-CDR2 has the amino acid sequence of SEQ ID NO: 107 or 114;

(iii) VH-CDR3 has the amino acid sequence of SEQ ID NO: 108 or 115;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(t) (i) VH-CDR1 has the amino acid sequence of SEQ ID NO: 85 or 99;

(ii) VH-CDR2 has the amino acid sequence of SEQ ID NO: 107 or 114;

(iii) VH-CDR3 has the amino acid sequence of SEQ ID NO: 121;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(u) (i) VH-CDR1 has the amino acid sequence of SEQ ID NO: 85 or 99;

(ii) VH-CDR2 has the amino acid sequence of SEQ ID NO: 120;

(iii) VH-CDR3 has the amino acid sequence of SEQ ID NO: 87 or 101;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(v) (i) VH-CDR1 has the amino acid sequence of SEQ ID NO: 85 or 99;

(ii) VH-CDR2 has the amino acid sequence of SEQ ID NO: 120;

(iii) VH-CDR3 has the amino acid sequence of SEQ ID NO: 108 or 115;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(w) (i) VH-CDR1 has the amino acid sequence of SEQ ID NO: 85 or 99;

(ii) VH-CDR2 has the amino acid sequence of SEQ ID NO: 120;

(iii) VH-CDR3 has the amino acid sequence of SEQ ID NO: 121;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(x) (i) VH-CDR1 has the amino acid sequence of SEQ ID NO: 106 or 113;

(ii) VH-CDR2 has the amino acid sequence of SEQ ID NO: 86 or 100;

(iii) VH-CDR3 has the amino acid sequence of SEQ ID NO: 87 or 101;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(y) (i) VH-CDR1 has the amino acid sequence of SEQ ID NO: 106 or 113;

(ii) VH-CDR2 has the amino acid sequence of SEQ ID NO: 86 or 100;

(iii) VH-CDR3 has the amino acid sequence of SEQ ID NO: 108 or 115;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(z) (i) VH-CDR1 has the amino acid sequence of SEQ ID NO: 106 or 113;

(ii) VH-CDR2 has the amino acid sequence of SEQ ID NO: 86 or 100;

(iii) VH-CDR3 has the amino acid sequence of SEQ ID NO: 121;

(iv) VL-CDR has the amino acid sequence of SEQ ID NO: 92;

(v) VL-CDR2 has the amino acid sequence of SEQ ID NO:93; and (vi) VL-CDR3 has the amino acid sequence of SEQ ID NO: 94;

and wherein the antibody binds ActRIIB and ActRIIA;

(aa) (i) VH-CDR1 has the amino acid sequence of SEQ ID NO: 106 or 113;

(ii) VH-CDR2 has the amino acid sequence of SEQ ID NO: 107 or 114;

(iii) VH-CDR3 has the amino acid sequence of SEQ ID NO: 87 or 101;

(iv) VL-CDR1 has the amino acid sequence of SEQ ID NO: 92;

(v) VL-CDR2 has the amino acid sequence of SEQ ID NO: 93; and (vi) VL-CDR3 has the amino acid sequence of SEQ ID NO: 94;

and wherein the antibody binds ActRIIB and ActRIIA;

(bb) (i) VH-CDR1 has the amino acid sequence of SEQ ID NO: 106 or 113;
(ii) VH-CDR2 has the amino acid sequence of SEQ ID NO: 107 or 114;
(iii) VH-CDR3 has the amino acid sequence of SEQ ID NO: 108 or 115;
(iv) VL-CDR1 has the amino acid sequence of SEQ ID NO: 92;
(v) VL-CDR2 has the amino acid sequence of SEQ ID NO: 93; and
(vi) VL-CDR3 has the amino acid sequence of SEQ ID NO: 94;

and wherein the antibody binds ActRIIB and ActRIIA;

(cc) (i) VH-CDR1 has the amino acid sequence of SEQ ID NO: 106 or 113;
(ii) VH-CDR2 has the amino acid sequence of SEQ ID NO: 107 or 114;
(iii) VH-CDR3 has the amino acid sequence of SEQ ID NO: 121;
(iv) VL-CDR1 has the amino acid sequence of SEQ ID NO: 92;
(v) VL-CDR2 has the amino acid sequence of SEQ ID NO: 93; and
(vi) VL-CDR3 has the amino acid sequence of SEQ ID NO: 94;

and wherein the antibody binds ActRIIB and ActRIIA;

(dd) (i) VH-CDRI has the amino acid sequence of SEQ ID NO: 106 or 113;
(ii) VH-CDR2 has the amino acid sequence of SEQ ID NO: 120;
(iii) VH-CDR3 has the amino acid sequence of SEQ ID NO: 87 or 101;
(iv) VL-CDRI has the amino acid sequence of SEQ ID NO: 92;
(v) VL-CDR2 has the amino acid sequence of SEQ ID NO: 93; and
(vi) VL-CDR3 has the amino acid sequence of SEQ ID NO: 94;

and wherein the antibody binds ActRIIB and ActRIIA;

(ee) (i) VH-CDR1 has the amino acid sequence of SEQ ID NO: 106 or 113;
(ii) VH-CDR2 has the amino acid sequence of SEQ ID NO: 120;
(iii) VH-CDR3 has the amino acid sequence of SEQ ID NO: 108 or 115;
(iv) VL-CDR1 has the amino acid sequence of SEQ ID NO: 92;
(v) VL-CDR2 has the amino acid sequence of SEQ ID NO: 93; and
(vi) VL-CDR3 has the amino acid sequence of SEQ ID NO: 94;

and wherein the antibody binds ActRIIB and ActRIIA;

(ff) (i) VH-CDR1 has the amino acid sequence of SEQ ID NO: 106 or 113;
(ii) VH-CDR2 has the amino acid sequence of SEQ ID NO: 120;
(iii) VH-CDR3 has the amino acid sequence of SEQ ID NO: 121;
(iv) VL-CDR1 has the amino acid sequence of SEQ ID NO: 92;
(v) VL-CDR2 has the amino acid sequence of SEQ ID NO: 93; and
(vi) VL-CDR3 has the amino acid sequence of SEQ ID NO: 94;

and wherein the antibody binds ActRIIB and ActRIIA.

2. The ActRII-binding antibody of claim 1, which comprises a VH and a VL pair selected from:
(a) a VH sequence of SEQ ID NO:165 and a VL sequence of SEQ ID NO:172;
(b) a VH sequence of SEQ ID NO:2 and a VL sequence of SEQ ID NO:9;
(c) a VH sequence of SEQ ID NO:16 and a VL sequence of SEQ ID NO:9;
(d) a VH sequence of SEQ ID NO:22 and a VL sequence of SEQ ID NO:9;
(e) a VH sequence of SEQ ID NO:28 and a VL sequence of SEQ ID NO:9;
(f) a VH sequence of SEQ ID NO:34 and a VL sequence of SEQ ID NO:9;
(g) a VH sequence of SEQ ID NO:40 and a VL sequence of SEQ ID NO:9;
(h) a VH sequence of SEQ ID NO:45 and a VL sequence of SEQ ID NO:50;
(i) a VH sequence of SEQ ID NO:57 and a VL sequence of SEQ ID NO:50;
(j) a VH sequence of SEQ ID NO:63 and a VL sequence of SEQ ID NO:70;
(k) a VH sequence of SEQ ID NO:77 and a VL sequence of SEQ ID NO:70;
(l) a VH sequence of SEQ ID NO:144 and a VL sequence of SEQ ID NO:151;
(m) a VH sequence of SEQ ID NO:84 and a VL sequence of SEQ ID NO:91;
(n) a VH sequence of SEQ ID NO:98 and a VL sequence of SEQ ID NO:91;
(o) a VH sequence of SEQ ID NO:105 and a VL sequence of SEQ ID NO:91;
(p) a VH sequence of SEQ ID NO:112 and a VL sequence of SEQ ID NO:91;
(q) a VH sequence of SEQ ID NO:119 and a sequence of SEQ ID NO:91; and
(r) a VH sequence of SEQ ID NO:125 and a sequence of SEQ ID NO:132.

3. The ActRII-binding antibody of claim 1, wherein the antibody has at least one characteristic selected from:
(a) competing with activin A, activin B, BMP7, BMP9, BMP10, GDF8 (myostatin), GDF11, or Nodal, for binding to ActRIIB or ActRIIA;
(b) decreasing the phosphorylation of one or more Smads in cells expressing ActRIIB and/or ActRIIA in the presence of an ActRIIB or ActRIIA ligand;
(c) decreasing the phosphorylation of ALK4 or ALK7 in cells expressing ActRIIB or ActRIIA and ALK4 or ALK7 in the presence of an ActRIIB or ActRIIA ligand; and
(d) binding to ActRIIB or ActRIIA with a KD of ≤1 nM and ≥1 pM, as determined by BIACORE® analysis.

4. The ActRII-binding antibody of claim 1, wherein the antibody is a monoclonal antibody, a recombinant antibody, a human antibody, a humanized antibody, a chimeric antibody, a bi-specific antibody, a multi-specific antibody, or an ActRII-binding antibody fragment.

5. The ActRII-binding antibody of claim 4, wherein the ActRII-binding antibody fragment is selected from a Fab fragment, a Fab' fragment, a F(ab')2 fragment, a Fv fragment, a diabody, or a single chain antibody molecule.

6. The ActRII-binding antibody of claim 4, wherein the antibody further comprises a heavy chain immunoglobulin constant domain selected from:
(a) a human IgA constant domain;
(b) a human IgD constant domain;
(c) a human IgE constant domain;

(d) a human IgG1 constant domain;

(e) a human IgG2 constant domain;

(f) a human IgG3 constant domain;

(g) a human IgG4 constant domain; and (h) a human IgM constant domain.

7. The ActRII-binding antibody of claim 4, wherein the antibody further comprises a light chain immunoglobulin constant domain selected from:

(a) a human Ig kappa constant domain; and (b) a human Ig lambda constant domain.

8. The ActRII-binding antibody of claim 4, wherein the antibody further comprises a human IgG1 heavy chain constant domain and a human lambda light chain constant domain.

9. An isolated nucleic acid molecule or a set of nucleic acid molecules that encodes the ActRII-binding antibody of claim 1.

10. A vector comprising the nucleic acid molecule or the set of nucleic acid molecules according to claim 9.

11. A host cell comprising the nucleic acid molecule or the set of nucleic acid molecules according to claim 9.

12. A method of making an ActRII-binding antibody, said method comprising culturing the host cell according to claim 11 under suitable conditions for producing the ActRII-binding antibody.

13. An ActRII-binding antibody produced using the method of claim 12.

14. A pharmaceutical composition comprising the ActRII-binding antibody according to claim 1 and a pharmaceutically acceptable carrier.

* * * * *

UNITED STATES PATENT AND TRADEMARK OFFICE

CERTIFICATE OF CORRECTION

PATENT NO. : 10,307,455 B2
APPLICATION NO. : 15/456392
DATED : June 4, 2019
INVENTOR(S) : Ravindra Kumar et al.

It is certified that error appears in the above-identified patent and that said Letters Patent is hereby corrected as shown below:

In the Claims

In Column 288, Lines 57-58, cancel the text:
"(g) (i) VH-CDR1 has the amino acid sequence of SEQ ID NO: 85 or 99;"
And insert:
--(q) (i) VH-CDR1 has the amino acid sequence of SEQ ID NO: 85 or 99;--.

In Column 290, Lines 49-50, cancel the text:
"(iv) VL-CDR has the amino acid sequence of SEQ ID NO: 92"
And insert:
--(iv) VL-CDR1 has the amino acid sequence of SEQ ID NO: 92;--.

In Column 291, Lines 29-30, cancel the text:
"(dd) (i) VH-CDRI has the amino acid sequence of SEQ ID NO: 106 or 113;"
And insert:
--(dd) (i) VH-CDR1 has the amino acid sequence of SEQ ID NO: 106 or 113;--.

In Column 291, Lines 35-36, cancel the text:
"(iv) VL-CDRI has the amino acid sequence of SEQ ID NO: 92;"
And insert:
--(iv) VL-CDR1 has the amino acid sequence of SEQ ID NO: 92;--.

In Column 292, Lines 35-36, cancel the text:
"(q) a VH sequence of SEQ ID NO:119 and a sequence of SEQ ID NO:91; and"
And insert:
--(q) a VH sequence of SEQ ID NO:119 and a VL sequence of SEQ ID NO:91; and--.

Signed and Sealed this
Thirtieth Day of July, 2019

Andrei Iancu
*Director of the United States Patent and Trademark Office*

In Column 292, Lines 37-38, cancel the text:
"(r) a VH sequence of SEQ ID NO:125 and a sequence of SEQ ID NO:132."
And insert:
--(r) a VH sequence of SEQ ID NO:125 and a VL sequence of SEQ ID NO:132.--.

SEQUENCE LISTING

```
<160> NUMBER OF SEQ ID NOS: 177

<210> SEQ ID NO 1
<211> LENGTH: 390
<212> TYPE: DNA
<213> ORGANISM: Homo sapian

<400> SEQUENCE: 1

cagctgcagc tgcaggagtc gggcccagga ctggtgaagc cttcggagac cctgtccctc      60

acctgcactg tctctggtgg ctccatcagc agtagtagtt acgcatgggg ctggatccgc     120

cagcccccag ggaaggggct ggagtggatt gggagtatct attatagtgg gagcacctac     180

tacaacccgt ccctcaagag tcgagtcacc atatccgtag acacgtccaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca                                      390


<210> SEQ ID NO 2
<211> LENGTH: 130
<212> TYPE: PRT
<213> ORGANISM: Homo sapian

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ala Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60
```

```
Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser
    130


<210> SEQ ID NO 3
<211> LENGTH: 9
<212> TYPE: PRT
<213> ORGANISM: Homo sapian

<400> SEQUENCE: 3

Gly Gly Ser Ile Ser Ser Ser Ser Tyr
1               5


<210> SEQ ID NO 4
<211> LENGTH: 5
<212> TYPE: PRT
<213> ORGANISM: Homo sapian

<400> SEQUENCE: 4

Tyr Tyr Ser Gly Ser
1               5


<210> SEQ ID NO 5
<211> LENGTH: 20
<212> TYPE: PRT
<213> ORGANISM: Homo sapian

<400> SEQUENCE: 5

Asp Ser Gly Ile Gly Tyr Ser Tyr Ala Ser Ser His Gly Tyr Tyr Tyr
1               5                   10                  15

Tyr Met Asp Val
            20


<210> SEQ ID NO 6
<211> LENGTH: 1380
<212> TYPE: DNA
<213> ORGANISM: Homo sapian

<400> SEQUENCE: 6

cagctgcagc tgcaggagtc gggcccagga ctggtgaagc cttcggagac cctgtccctc      60

acctgcactg tctctggtgg ctccatcagc agtagtagtt acgcatgggg ctggatccgc     120

cagcccccag ggaaggggct ggagtggatt gggagtatct attatagtgg gagcacctac     180

tacaacccgt ccctcaagag tcgagtcacc atatccgtag acacgtccaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca gctagcacaa aggaccaag cgtgtttcca      420

ctggcaccta gcagcaaatc caccagcggc ggaacagcag ccctcgggtg cctggtgaag     480

gattacttcc ctgagccagt cacagtgtcc tggaactccg gagccctgac atccggcgtg     540

cacaccttcc ccgctgtgct gcaatccagc ggactgtata gcctcagctc cgtcgtgaca     600
```

```
gtcccttcca gcagcctggg cacacagact tacatttgca acgtgaacca caaaccttcc    660

aacactaagg tggacaaaaa ggtggaaccc aaatcctgtg ataagaccca tacatgccca    720

ccttgtcccg ctcctgagct gctgggggga ccttccgtct ttctgtttcc tccaaaacca    780

aaagacacac tcatgatcag ccggaccccc gaagtcacct gtgtggtggt ggacgtcagc    840

cacgaagatc cagaggtcaa gttcaattgg tacgtggatg gagtggaagt ccacaacgca    900

aaaaccaaac ctagagaaga acagtacaat agcacataca gggtggtgtc cgtcctgaca    960

gtgctccacc aggactggct caatggcaaa gagtataagt gcaaggtgag caacaaggcc   1020

ctgcctgcac caattgagaa aacaattagc aaggcaaagg ggcagccacg ggaaccccag   1080

gtgtataccc tgcccccaag ccgggatgaa ctgaccaaaa accaggtcag cctgacatgc   1140

ctggtgaaag ggttttaccc aagcgatatt gccgtcgagt gggagagcaa cggacagcca   1200

gaaaacaatt acaaaaccac cccacctgtg ctggactccg atgggagctt tttcctgtac   1260

agcaagctca cagtggacaa gtccagatgg caacagggca acgtgttttc ctgctccgtg   1320

atgcacgagg ccctccacaa ccactataca caaaagtccc tctccctcag cccaggaaag   1380
```

<210> SEQ ID NO 7
<211> LENGTH: 460
<212> TYPE: PRT
<213> ORGANISM: Homo sapian

<400> SEQUENCE: 7

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ala Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240
```

```
Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 8
<211> LENGTH: 321
<212> TYPE: DNA
<213> ORGANISM: Homo sapian

<400> SEQUENCE: 8

gaaatagtgt tgacgcagtc tccagccacc ctgtctgtgt ctccagggga aagagccacc      60

ctctcctgca gggccagtca gagtgttggc agcaacttag cctggtacca gcagaaacct     120

ggccaggctc ccaggctcct catctatggt gcatccacca gggccactgg tatcccagcc     180

aggttcagtg gcagtgggtc tgggacagag ttcactctca ccatcagcag cctgcagtct     240

gaagattttg cagtttatta ctgtcagcag tacttccact tccctctcac ttttggcgga     300

gggaccaagg ttgagatcaa a                                               321


<210> SEQ ID NO 9
<211> LENGTH: 107
<212> TYPE: PRT
<213> ORGANISM: Homo sapian

<400> SEQUENCE: 9

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45
```

```
Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Phe His Phe Pro Leu
                85                  90                  95

Thr Phe Gly Gly Gly Thr Lys Val Glu Ile Lys
            100                 105


<210> SEQ ID NO 10
<211> LENGTH: 11
<212> TYPE: PRT
<213> ORGANISM: Homo sapian

<400> SEQUENCE: 10

Arg Ala Ser Gln Ser Val Gly Ser Asn Leu Ala
1               5                   10


<210> SEQ ID NO 11
<211> LENGTH: 7
<212> TYPE: PRT
<213> ORGANISM: Homo sapian

<400> SEQUENCE: 11

Gly Ala Ser Thr Arg Ala Thr
1               5


<210> SEQ ID NO 12
<211> LENGTH: 9
<212> TYPE: PRT
<213> ORGANISM: Homo sapian

<400> SEQUENCE: 12

Gln Gln Tyr Phe His Phe Pro Leu Thr
1               5


<210> SEQ ID NO 13
<211> LENGTH: 642
<212> TYPE: DNA
<213> ORGANISM: Homo sapian

<400> SEQUENCE: 13

gaaatagtgt tgacgcagtc tccagccacc ctgtctgtgt ctccagggga aagagccacc     60

ctctcctgca gggccagtca gagtgttggc agcaacttag cctggtacca gcagaaacct    120

ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tacttccact tccctctcac ttttggcgga    300

gggaccaagg ttgagatcaa acgtacggtg gctgcacctt ccgtctttat ctttccacct    360

tccgatgagc agctgaagag cggaacagca agcgtggtgt gtctgctgaa caacttttat    420

ccccgggagg caaaggtgca gtggaaagtc gacaatgctc tccagtccgg caattcccaa    480

gagagcgtga cagagcaaga ttccaaggac tccacttaca gcctgtccag caccctcaca    540

ctgagcaagg ctgattacga gaaacacaaa gtgtacgctt gtgaagtcac ccaccaaggc    600

ctgagcagcc cagtcactaa gtcctttaac cggggcgaat gt                       642


<210> SEQ ID NO 14
<211> LENGTH: 214
```

<212> TYPE: PRT
<213> ORGANISM: Homo sapian

<400> SEQUENCE: 14

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Phe His Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 390
<212> TYPE: DNA
<213> ORGANISM: Homo sapian

<400> SEQUENCE: 15

```
caggtgcagc tgcaggagtc gggcccagga ctggtgaagc cttcacagac cctgtccctc     60

acctgtactg tctctggtgg ctccatcggg agtggtggtt actactggag ctggatccgc    120

cagcacccag ggaagggcct ggagtggatt gggggggatct atggtagtgg gagcacctac    180

tacaacccgt ccctcaagag tcgagttacc atatcagtag acacgtctaa gaaccagttc    240

tccctgaagc tgagttctgt gaccgccgca gacacggcgg tgtactactg cgccagagac    300

tcaggaatag gatacagcta cgcctcatca catggctact actactacat ggacgtatgg    360

ggcaagggta caactgtcac cgtctcctca                                     390
```

<210> SEQ ID NO 16
<211> LENGTH: 130
<212> TYPE: PRT
<213> ORGANISM: Homo sapian

<400> SEQUENCE: 16

```
Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Gly Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Gly Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser
    130


<210> SEQ ID NO 17
<211> LENGTH: 9
<212> TYPE: PRT
<213> ORGANISM: Homo sapian

<400> SEQUENCE: 17

Gly Gly Ser Ile Gly Ser Gly Gly Tyr
1               5


<210> SEQ ID NO 18
<211> LENGTH: 4
<212> TYPE: PRT
<213> ORGANISM: Homo sapian

<400> SEQUENCE: 18

Tyr Gly Ser Gly
1


<210> SEQ ID NO 19
<211> LENGTH: 1380
<212> TYPE: DNA
<213> ORGANISM: Homo sapian

<400> SEQUENCE: 19

caggtgcagc tgcaggagtc gggcccagga ctggtgaagc cttcacagac cctgtccctc      60

acctgtactg tctctggtgg ctccatcggg agtggtggtt actactggag ctggatccgc     120

cagcacccag ggaagggcct ggagtggatt gggggggatct atggtagtgg gagcacctac     180

tacaacccgt ccctcaagag tcgagttacc atatcagtag acacgtctaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca gctagcacaa aaggaccaag cgtgtttcca     420

ctggcaccta gcagcaaatc caccagcggc ggaacagcag ccctcgggtg cctggtgaag     480

gattacttcc ctgagccagt cacagtgtcc tggaactccg gagccctgac atccggcgtg     540

cacaccttcc ccgctgtgct gcaatccagc ggactgtata gcctcagctc cgtcgtgaca     600

gtcccttcca gcagcctggg cacacagact tacatttgca acgtgaacca caaaccttcc     660

aacactaagg tggacaaaaa ggtggaaccc aaatcctgtg ataagaccca tacatgccca     720
```

```
ccttgtcccg ctcctgagct gctgggggga ccttccgtct ttctgtttcc tccaaaacca    780

aaagacacac tcatgatcag ccggaccccc gaagtcacct gtgtggtggt ggacgtcagc    840

cacgaagatc cagaggtcaa gttcaattgg tacgtggatg gagtggaagt ccacaacgca    900

aaaaccaaac ctagagaaga acagtacaat agcacataca gggtggtgtc cgtcctgaca    960

gtgctccacc aggactggct caatggcaaa gagtataagt gcaaggtgag caacaaggcc   1020

ctgcctgcac caattgagaa aacaattagc aaggcaaagg ggcagccacg ggaaccccag   1080

gtgtataccc tgcccccaag ccgggatgaa ctgaccaaaa accaggtcag cctgacatgc   1140

ctggtgaaag ggttttaccc aagcgatatt gccgtcgagt gggagagcaa cggacagcca   1200

gaaaacaatt acaaaaccac cccacctgtg ctggactccg atgggagctt tttcctgtac   1260

agcaagctca cagtggacaa gtccagatgg caacagggca acgtgttttc ctgctccgtg   1320

atgcacgagg ccctccacaa ccactataca caaaagtccc tctccctcag cccaggaaag   1380
```

```
<210> SEQ ID NO 20
<211> LENGTH: 460
<212> TYPE: PRT
<213> ORGANISM: Homo sapian

<400> SEQUENCE: 20

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Gly Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Gly Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
```

```
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 21
<211> LENGTH: 390
<212> TYPE: DNA
<213> ORGANISM: Homo sapian

<400> SEQUENCE: 21

caggtgcagc tgcaggagtc gggcccagga ctggtgaagc cttcacagac cctgtccctc      60

acctgtactg tctctggtgg ctccatcaag agtggtgggt actactggag ctggatccgc     120

cagcacccag ggaagggcct ggagtggatt ggggggatct atccgagtgg gagcacctac     180

tacaacccgt ccctcaagag tcgagttacc atatcagtag acacgtctaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca                                      390


<210> SEQ ID NO 22
<211> LENGTH: 130
<212> TYPE: PRT
<213> ORGANISM: Homo sapian

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Lys Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Pro Ser Gly Ser Thr Tyr Tyr Asn Pro Ser
    50                  55                  60
```

```
Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser
    130


<210> SEQ ID NO 23
<211> LENGTH: 9
<212> TYPE: PRT
<213> ORGANISM: Homo sapian

<400> SEQUENCE: 23

Gly Gly Ser Ile Lys Ser Gly Gly Tyr
1               5


<210> SEQ ID NO 24
<211> LENGTH: 13
<212> TYPE: PRT
<213> ORGANISM: Homo sapian

<400> SEQUENCE: 24

Trp Ile Gly Gly Ile Tyr Pro Ser Gly Ser Thr Tyr Tyr
1               5                   10


<210> SEQ ID NO 25
<211> LENGTH: 1380
<212> TYPE: DNA
<213> ORGANISM: Homo sapian

<400> SEQUENCE: 25

caggtgcagc tgcaggagtc gggcccagga ctggtgaagc cttcacagac cctgtccctc     60

acctgtactg tctctggtgg ctccatcaag agtggtgggt actactggag ctggatccgc    120

cagcacccag ggaagggcct ggagtggatt ggggggatct atccgagtgg gagcacctac    180

tacaacccgt ccctcaagag tcgagttacc atatcagtag acacgtctaa gaaccagttc    240

tccctgaagc tgagttctgt gaccgccgca gacacggcgg tgtactactg cgccagagac    300

tcaggaatag gatacagcta cgcctcatca catggctact actactacat ggacgtatgg    360

ggcaagggta caactgtcac cgtctcctca gctagcacaa aggaccaag cgtgtttcca    420

ctggcaccta gcagcaaatc caccagcggc ggaacagcag ccctcgggtg cctggtgaag    480

gattacttcc ctgagccagt cacagtgtcc tggaactccg gagccctgac atccggcgtg    540

cacaccttcc ccgctgtgct gcaatccagc ggactgtata gcctcagctc cgtcgtgaca    600

gtcccttcca gcagcctggg cacacagact tacatttgca acgtgaacca caaaccttcc    660

aacactaagg tggacaaaaa ggtggaaccc aaatcctgtg ataagaccca tacatgccca    720

ccttgtcccg ctcctgagct gctgggggga ccttccgtct ttctgtttcc tccaaaacca    780

aaagacacac tcatgatcag ccggaccccc gaagtcacct gtgtggtggt ggacgtcagc    840

cacgaagatc cagaggtcaa gttcaattgg tacgtggatg gagtggaagt ccacaacgca    900

aaaaccaaac ctagagaaga acagtacaat agcacataca gggtggtgtc cgtcctgaca    960

gtgctccacc aggactggct caatggcaaa gagtataagt gcaaggtgag caacaaggcc   1020
```

```
ctgcctgcac caattgagaa aacaattagc aaggcaaagg ggcagccacg ggaaccccag   1080

gtgtataccc tgcccccaag ccgggatgaa ctgaccaaaa accaggtcag cctgacatgc   1140

ctggtgaaag ggttttaccc aagcgatatt gccgtcgagt gggagagcaa cggacagcca   1200

gaaaacaatt acaaaaccac cccacctgtg ctggactccg atgggagctt tttcctgtac   1260

agcaagctca cagtggacaa gtccagatgg caacagggca acgtgttttc ctgctccgtg   1320

atgcacgagg ccctccacaa ccactataca caaaagtccc tctccctcag cccaggaaag   1380
```

<210> SEQ ID NO 26
<211> LENGTH: 460
<212> TYPE: PRT
<213> ORGANISM: Homo sapian

<400> SEQUENCE: 26

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Lys Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Pro Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
```

```
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 27
<211> LENGTH: 390
<212> TYPE: DNA
<213> ORGANISM: Homo sapian

<400> SEQUENCE: 27

caggtgcagc tgcaggagtc gggcccagga ctggtgaagc cttcacagac cctgtccctc      60

acctgtactg tctctggtgg ctccatcgag agcggtggtt actactggag ctggatccgc     120

cagcacccag ggaagggcct ggagtggatt gggggtatct atgggagtgg gagcacctac     180

tacaacccgt ccctcaagag tcgagttacc atatcagtag acacgtctaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca                                      390


<210> SEQ ID NO 28
<211> LENGTH: 130
<212> TYPE: PRT
<213> ORGANISM: Homo sapian

<400> SEQUENCE: 28

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Leu Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Tyr Ser Gly Lys Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110
```

```
Tyr Tyr Tyr Tyr Met Asp Val Trp Gly Lys Gly Thr Thr Val Thr Val
        115                 120                 125

Ser Ser
    130


<210> SEQ ID NO 29
<211> LENGTH: 9
<212> TYPE: PRT
<213> ORGANISM: Homo sapian

<400> SEQUENCE: 29

Gly Gly Ser Ile Leu Ser Gly Gly Tyr
1               5


<210> SEQ ID NO 30
<211> LENGTH: 5
<212> TYPE: PRT
<213> ORGANISM: Homo sapian

<400> SEQUENCE: 30

Tyr Tyr Ser Gly Lys
1               5


<210> SEQ ID NO 31
<211> LENGTH: 1380
<212> TYPE: DNA
<213> ORGANISM: Homo sapian

<400> SEQUENCE: 31

caggtgcagc tgcaggagtc gggcccagga ctggtgaagc cttcacagac cctgtccctc     60

acctgtactg tctctggtgg ctccatcgag agcggtggtt actactggag ctggatccgc    120

cagcacccag ggaagggcct ggagtggatt gggggtatct atgggagtgg gagcacctac    180

tacaacccgt ccctcaagag tcgagttacc atatcagtag acacgtctaa gaaccagttc    240

tccctgaagc tgagttctgt gaccgccgca gacacggcgg tgtactactg cgccagagac    300

tcaggaatag gatacagcta cgcctcatca catggctact actactacat ggacgtatgg    360

ggcaagggta caactgtcac cgtctcctca gctagcacaa aggaccaag cgtgtttcca     420

ctggcaccta gcagcaaatc caccagcggc ggaacagcag ccctcgggtg cctggtgaag    480

gattacttcc ctgagccagt cacagtgtcc tggaactccg gagccctgac atccggcgtg    540

cacaccttcc ccgctgtgct gcaatccagc ggactgtata gcctcagctc cgtcgtgaca    600

gtcccttcca gcagcctggg cacacagact tacatttgca acgtgaacca caaaccttcc    660

aacactaagg tggacaaaaa ggtggaaccc aaatcctgtg ataagaccca tacatgccca    720

ccttgtcccg ctcctgagct gctgggggga ccttccgtct ttctgtttcc tccaaaacca    780

aaagacacac tcatgatcag ccggaccccc gaagtcacct gtgtggtggt ggacgtcagc    840

cacgaagatc cagaggtcaa gttcaattgg tacgtggatg gagtggaagt ccacaacgca    900

aaaaccaaac ctagagaaga acagtacaat agcacataca gggtggtgtc cgtcctgaca    960

gtgctccacc aggactggct caatggcaaa gagtataagt gcaaggtgag caacaaggcc   1020

ctgcctgcac caattgagaa aacaattagc aaggcaaagg ggcagccacg ggaaccccag   1080

gtgtataccc tgcccccaag ccgggatgaa ctgaccaaaa accaggtcag cctgacatgc   1140

ctggtgaaag ggttttaccc aagcgatatt gccgtcgagt gggagagcaa cggacagcca   1200

gaaaacaatt acaaaaccac cccacctgtg ctggactccg atgggagctt tttcctgtac   1260
```

```
agcaagctca cagtggacaa gtccagatgg caacagggca acgtgttttc ctgctccgtg   1320

atgcacgagg ccctccacaa ccactataca caaaagtccc tctccctcag cccaggaaag   1380


<210> SEQ ID NO 32
<211> LENGTH: 460
<212> TYPE: PRT
<213> ORGANISM: Homo sapian

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Gly Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
```

```
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 33
<211> LENGTH: 390
<212> TYPE: DNA
<213> ORGANISM: Homo sapian

<400> SEQUENCE: 33

caggtgcagc tgcaggagtc gggcccagga ctggtgaagc cttcacagac cctgtccctc      60

acctgtactg tctctggtgg ctccatctct agtggtggtt acttttggag ctggatccgc     120

cagcacccag ggaagggcct ggagtggatt ggggggatct attacagtgg gcggacctac     180

tacaacccgt ccctcaagag tcgagttacc atatcagtag acacgtctaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca                                      390


<210> SEQ ID NO 34
<211> LENGTH: 130
<212> TYPE: PRT
<213> ORGANISM: Homo sapian

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Phe Trp Ser Trp Ile Arg Gln His Pro Gly Lys Gly Leu Glu
        35                  40                  45

Trp Ile Gly Gly Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser
    130


<210> SEQ ID NO 35
```

<211> LENGTH: 9
<212> TYPE: PRT
<213> ORGANISM: Homo sapian

<400> SEQUENCE: 35

Gly Gly Ser Ile Ser Ser Gly Gly Tyr
1 5

<210> SEQ ID NO 36
<211> LENGTH: 6
<212> TYPE: PRT
<213> ORGANISM: Homo sapian

<400> SEQUENCE: 36

Tyr Tyr Ser Gly Arg Thr
1 5

<210> SEQ ID NO 37
<211> LENGTH: 1380
<212> TYPE: DNA
<213> ORGANISM: Homo sapian

<400> SEQUENCE: 37
caggtgcagc tgcaggagtc gggcccagga ctggtgaagc cttcacagac cctgtccctc 60
acctgtactg tctctggtgg ctccatctct agtggtggtt acttttggag ctggatccgc 120
cagcacccag ggaagggcct ggagtggatt gggggggatct attacagtgg gcggacctac 180
tacaacccgt ccctcaagag tcgagttacc atatcagtag acacgtctaa gaaccagttc 240
tccctgaagc tgagttctgt gaccgccgca gacacggcgg tgtactactg cgccagagac 300
tcaggaatag gatacagcta cgcctcatca catggctact actactacat ggacgtatgg 360
ggcaagggta caactgtcac cgtctcctca gctagcacaa aggaccaag cgtgtttcca 420 ctggcaccta gcagcaaatc caccagcggc ggaacagcag ccctcgggtg cctggtgaag 480
gattacttcc ctgagccagt cacagtgtcc tggaactccg gagccctgac atccggcgtg 540
cacaccttcc ccgctgtgct gcaatccagc ggactgtata gcctcagctc cgtcgtgaca 600
gtcccttcca gcagcctggg cacacagact tacatttgca acgtgaacca caaaccttcc 660
aacactaagg tggacaaaaa ggtggaaccc aaatcctgtg ataagaccca tacatgccca 720
ccttgtcccg ctcctgagct gctgggggga ccttccgtct ttctgtttcc tccaaaacca 780
aaagacacac tcatgatcag ccggaccccc gaagtcacct gtgtggtggt ggacgtcagc 840
cacgaagatc cagaggtcaa gttcaattgg tacgtggatg gagtggaagt ccacaacgca 900
aaaaccaaac ctagagaaga acagtacaat agcacataca gggtggtgtc cgtcctgaca 960
gtgctccacc aggactggct caatggcaaa gagtataagt gcaaggtgag caacaaggcc 1020
ctgcctgcac caattgagaa aacaattagc aaggcaaagg ggcagccacg ggaaccccag 1080
gtgtataccc tgcccccaag ccgggatgaa ctgaccaaaa accaggtcag cctgacatgc 1140
ctggtgaaag ggttttaccc aagcgatatt gccgtcgagt gggagagcaa cggacagcca 1200
gaaaacaatt acaaaaccac cccacctgtg ctggactccg atgggagctt tttcctgtac 1260
agcaagctca cagtggacaa gtccagatgg caacagggca acgtgttttc ctgctccgtg 1320
atgcacgagg ccctccacaa ccactataca caaaagtccc tctccctcag cccaggaaag 1380

<210> SEQ ID NO 38
<211> LENGTH: 460
<212> TYPE: PRT
<213> ORGANISM: Homo sapian

<400> SEQUENCE: 38

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Phe Trp Ser Trp Ile Arg Gln His Pro Gly Lys Gly Leu Glu
        35                  40                  45

Trp Ile Gly Gly Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
```

```
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 39
<211> LENGTH: 390
<212> TYPE: DNA
<213> ORGANISM: Homo sapian

<400> SEQUENCE: 39

caggtgcagc tgcaggagtc gggcccagga ctggtgaagc cttcacagac cctgtccctc      60

acctgtactg tctctggtgg ctccatcgag agcggtggtt actactggag ctggatccgc     120

cagcacccag ggaagggcct ggagtggatt gggggtatct atgggagtgg gagcacctac     180

tacaacccgt ccctcaagag tcgagttacc atatcagtag acacgtctaa gaaccagttc     240

tccctgaagc tgagttctgt gaccgccgca gacacggcgg tgtactactg cgccagagac     300

tcaggaatag gatacagcta cgcctcatca catggctact actactacat ggacgtatgg     360

ggcaagggta caactgtcac cgtctcctca                                      390


<210> SEQ ID NO 40
<211> LENGTH: 130
<212> TYPE: PRT
<213> ORGANISM: Homo sapian

<400> SEQUENCE: 40

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Gly Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser
    130


<210> SEQ ID NO 41
<211> LENGTH: 9
<212> TYPE: PRT
<213> ORGANISM: Homo sapian

<400> SEQUENCE: 41

Gly Gly Ser Ile Glu Ser Gly Gly Tyr
1               5
```

<210> SEQ ID NO 42
<211> LENGTH: 1380
<212> TYPE: DNA
<213> ORGANISM: Homo sapian

<400> SEQUENCE: 42

```
caggtgcagc tgcaggagtc gggcccagga ctggtgaagc cttcacagac cctgtccctc     60
acctgtactg tctctggtgg ctccatcgag agcggtggtt actactggag ctggatccgc    120
cagcacccag ggaagggcct ggagtggatt gggggtatct atgggagtgg gagcacctac    180
tacaacccgt ccctcaagag tcgagttacc atatcagtag acacgtctaa gaaccagttc    240
tccctgaagc tgagttctgt gaccgccgca gacacggcgg tgtactactg cgccagagac    300
tcaggaatag gatacagcta cgcctcatca catggctact actactacat ggacgtatgg    360
ggcaagggta caactgtcac cgtctcctca gctagcacaa aggaccaag cgtgtttcca     420
ctggcaccta gcagcaaatc caccagcggc ggaacagcag ccctcgggtg cctggtgaag    480
gattacttcc ctgagccagt cacagtgtcc tggaactccg gagccctgac atccggcgtg    540
cacaccttcc ccgctgtgct gcaatccagc ggactgtata gcctcagctc cgtcgtgaca    600
gtcccttcca gcagcctggg cacacagact tacatttgca acgtgaacca caaaccttcc    660
aacactaagg tggacaaaaa ggtggaaccc aaatcctgtg ataagaccca tacatgccca    720
ccttgtcccg ctcctgagct gctgggggga ccttccgtct ttctgtttcc tccaaaacca    780
aaagacacac tcatgatcag ccggaccccc gaagtcacct gtgtggtggt ggacgtcagc    840
cacgaagatc cagaggtcaa gttcaattgg tacgtggatg gagtggaagt ccacaacgca    900
aaaaccaaac ctagagaaga acagtacaat agcacataca gggtggtgtc cgtcctgaca    960
gtgctccacc aggactggct caatggcaaa gagtataagt gcaaggtgag caacaaggcc   1020
ctgcctgcac caattgagaa aacaattagc aaggcaaagg ggcagccacg ggaaccccag   1080
gtgtataccc tgcccccaag ccgggatgaa ctgaccaaaa accaggtcag cctgacatgc   1140
ctggtgaaag ggttttaccc aagcgatatt gccgtcgagt gggagagcaa cggacagcca   1200
gaaaacaatt acaaaaccac cccacctgtg ctggactccg atgggagctt tttcctgtac   1260
agcaagctca cagtggacaa gtccagatgg caacagggca acgtgttttc ctgctccgtg   1320
atgcacgagg ccctccacaa ccactataca caaaagtccc tctccctcag cccaggaaag   1380
```

<210> SEQ ID NO 43
<211> LENGTH: 460
<212> TYPE: PRT
<213> ORGANISM: Homo sapian

<400> SEQUENCE: 43

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Gly Tyr Tyr Trp Ser Trp Ile Arg Gln His Pro Gly Lys Gly Leu Glu
        35                  40                  45

Trp Ile Gly Gly Ile Tyr Gly Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg Asp Ser Gly Ile Gly Tyr Ser Tyr Ala Ser Ser His Gly
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 44
<211> LENGTH: 363
<212> TYPE: DNA
<213> ORGANISM: Homo sapian

<400> SEQUENCE: 44

```
cagctgcagc tgcaggagtc gggcccagga ctggtgaagc cttcggagac cctgtccctc      60
```

acctgcactg tctctggtgg ctccatcagc agtagtagtt acgcatgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagttctgt gaccgccgca gacacggcgg tgtactactg cgccagagct 300
ggaaaatacc gatggcacgg aatggacgta tggggccagg gaacaactgt caccgtctcc 360
tca 363

<210> SEQ ID NO 45
<211> LENGTH: 121
<212> TYPE: PRT
<213> ORGANISM: Homo sapian

<400> SEQUENCE: 45

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ala Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Gly Lys Tyr Arg Trp His Gly Met Asp Val Trp Gly
            100                 105                 110

Gln Gly Thr Thr Val Thr Val Ser Ser
        115                 120
```

<210> SEQ ID NO 46
<211> LENGTH: 11
<212> TYPE: PRT
<213> ORGANISM: Homo sapian

<400> SEQUENCE: 46

```
Ala Gly Lys Tyr Arg Trp His Gly Met Asp Val
1               5                   10
```

<210> SEQ ID NO 47
<211> LENGTH: 1353
<212> TYPE: DNA
<213> ORGANISM: Homo sapian

<400> SEQUENCE: 47
cagctgcagc tgcaggagtc gggcccagga ctggtgaagc cttcggagac cctgtccctc 60
acctgcactg tctctggtgg ctccatcagc agtagtagtt acgcatgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagttctgt gaccgccgca gacacggcgg tgtactactg cgccagagct 300
ggaaaatacc gatggcacgg aatggacgta tggggccagg gaacaactgt caccgtctcc 360
tcagctagca caaaaggacc aagcgtgttt ccactggcac ctagcagcaa atccaccagc 420
ggcggaacag cagccctcgg gtgcctggtg aaggattact tccctgagcc agtcacagtg 480

```
tcctggaact ccggagccct gacatccggc gtgcacacct tccccgctgt gctgcaatcc    540

agcggactgt atagcctcag ctccgtcgtg acagtccctt ccagcagcct gggcacacag    600

acttacattt gcaacgtgaa ccacaaacct tccaacacta aggtggacaa aaaggtggaa    660

cccaaatcct gtgataagac ccatacatgc ccaccttgtc ccgctcctga gctgctgggg    720

ggaccttccg tctttctgtt tcctccaaaa ccaaaagaca cactcatgat cagccggacc    780

cccgaagtca cctgtgtggt ggtggacgtc agccacgaag atccagaggt caagttcaat    840

tggtacgtgg atggagtgga agtccacaac gcaaaaacca aacctagaga agaacagtac    900

aatagcacat acagggtggt gtccgtcctg acagtgctcc accaggactg gctcaatggc    960

aaagagtata agtgcaaggt gagcaacaag gccctgcctg caccaattga gaaaacaatt   1020

agcaaggcaa aggggcagcc acgggaaccc caggtgtata ccctgccccc aagccgggat   1080

gaactgacca aaaaccaggt cagcctgaca tgcctggtga aagggtttta cccaagcgat   1140

attgccgtcg agtgggagag caacggacag ccagaaaaca attacaaaac caccccacct   1200

gtgctggact ccgatgggag ctttttcctg tacagcaagc tcacagtgga caagtccaga   1260

tggcaacagg gcaacgtgtt ttcctgctcc gtgatgcacg aggccctcca caaccactat   1320

acacaaaagt ccctctccct cagcccagga aag                                1353
```

<210> SEQ ID NO 48
<211> LENGTH: 451
<212> TYPE: PRT
<213> ORGANISM: Homo sapian

<400> SEQUENCE: 48

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ala Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Gly Lys Tyr Arg Trp His Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

```
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 49
<211> LENGTH: 321
<212> TYPE: DNA
<213> ORGANISM: Homo sapian

<400> SEQUENCE: 49

```
gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct gcatccaatt tgcaaagtgg ggtcccatca    180

aggttcagcg gcagtggatc tgggacagat ttcactctca ccatcagcag cctgcagcct    240

gaagattttg caacttatta ctgtcagcag gcacccgacc tccctatcac ttttggcgga    300

gggaccaagg ttgagatcaa a                                              321
```

<210> SEQ ID NO 50
<211> LENGTH: 107
<212> TYPE: PRT
<213> ORGANISM: Homo sapian

<400> SEQUENCE: 50

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
```

```
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Pro Asp Leu Pro Ile
                85                  90                  95

Thr Phe Gly Gly Gly Thr Lys Val Glu Ile Lys
            100                 105


<210> SEQ ID NO 51
<211> LENGTH: 11
<212> TYPE: PRT
<213> ORGANISM: Homo sapian

<400> SEQUENCE: 51

Arg Ala Ser Gln Gly Ile Ser Ser Trp Leu Ala
1               5                   10


<210> SEQ ID NO 52
<211> LENGTH: 7
<212> TYPE: PRT
<213> ORGANISM: Homo sapian

<400> SEQUENCE: 52

Ala Ala Ser Asn Leu Gln Ser
1               5


<210> SEQ ID NO 53
<211> LENGTH: 9
<212> TYPE: PRT
<213> ORGANISM: Homo sapian

<400> SEQUENCE: 53

Gln Gln Ala Pro Asp Leu Pro Ile Thr
1               5


<210> SEQ ID NO 54
<211> LENGTH: 642
<212> TYPE: DNA
<213> ORGANISM: Homo sapian

<400> SEQUENCE: 54

gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct gcatccaatt tgcaaagtgg ggtcccatca    180

aggttcagcg gcagtggatc tgggacagat ttcactctca ccatcagcag cctgcagcct    240

gaagattttg caacttatta ctgtcagcag gcacccgacc tccctatcac ttttggcgga    300

gggaccaagg ttgagatcaa acgtacggtg gctgcacctt ccgtctttat ctttccacct    360

tccgatgagc agctgaagag cggaacagca agcgtggtgt gtctgctgaa caacttttat    420

ccccgggagg caaaggtgca gtggaaagtc gacaatgctc tccagtccgg caattcccaa    480

gagagcgtga cagagcaaga ttccaaggac tccacttaca gcctgtccag caccctcaca    540

ctgagcaagg ctgattacga gaaacacaaa gtgtacgctt gtgaagtcac ccaccaaggc    600

ctgagcagcc cagtcactaa gtcctttaac cggggcgaat gt                       642
```

<210> SEQ ID NO 55
<211> LENGTH: 214
<212> TYPE: PRT
<213> ORGANISM: Homo sapian

<400> SEQUENCE: 55

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Pro Asp Leu Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 56
<211> LENGTH: 360
<212> TYPE: DNA
<213> ORGANISM: Homo sapian

<400> SEQUENCE: 56

```
caggtgcagc tgcaggagtc gggcccagga ctggtgaagc cttcggagac cctgtccctc     60

acctgcgctg tctctggtta ctccatcagc agtggtgttt actggatgtg gatccggcag    120

cccccaggga aggggctgga gtggattggg agtatcgttc atagtgggca tacctactac    180

aacccgtccc tcaagagtcg agtcaccata tcagtagaca cgtccaagaa ccagttctcc    240

ctgaagctga gttctgtgac cgccgcagac acggcggtgt actactgcgc cagagctgga    300

aaataccgat ggcacggaat ggacgtatgg ggccagggaa caactgtcac cgtctcctca    360
```

<210> SEQ ID NO 57
<211> LENGTH: 120
<212> TYPE: PRT
<213> ORGANISM: Homo sapian

<400> SEQUENCE: 57

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Val Tyr Trp Met Trp Ile Arg Gln Pro Pro Gly Lys Gly Leu Glu Trp
        35                  40                  45

Ile Gly Ser Ile Val His Ser Gly His Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Gly Lys Tyr Arg Trp His Gly Met Asp Val Trp Gly Gln
            100                 105                 110

Gly Thr Thr Val Thr Val Ser Ser
        115                 120


<210> SEQ ID NO 58
<211> LENGTH: 8
<212> TYPE: PRT
<213> ORGANISM: Homo sapian

<400> SEQUENCE: 58

Gly Tyr Ser Ile Ser Ser Gly Val
1               5


<210> SEQ ID NO 59
<211> LENGTH: 5
<212> TYPE: PRT
<213> ORGANISM: Homo sapian

<400> SEQUENCE: 59

Val His Ser Gly His
1               5


<210> SEQ ID NO 60
<211> LENGTH: 1350
<212> TYPE: DNA
<213> ORGANISM: Homo sapian

<400> SEQUENCE: 60

caggtgcagc tgcaggagtc gggcccagga ctggtgaagc cttcggagac cctgtccctc      60

acctgcgctg tctctggtta ctccatcagc agtggtgttt actggatgtg gatccggcag     120

cccccaggga aggggctgga gtggattggg agtatcgttc atagtgggca tacctactac     180

aacccgtccc tcaagagtcg agtcaccata tcagtagaca cgtccaagaa ccagttctcc     240

ctgaagctga gttctgtgac cgccgcagac acggcggtgt actactgcgc cagagctgga     300

aaataccgat ggcacggaat ggacgtatgg ggccagggaa caactgtcac cgtctcctca     360

gctagcacaa aaggaccaag cgtgtttcca ctggcaccta gcagcaaatc caccagcggc     420

ggaacagcag ccctcgggtg cctggtgaag gattacttcc ctgagccagt cacagtgtcc     480

tggaactccg gagccctgac atccggcgtg cacaccttcc ccgctgtgct gcaatccagc     540

ggactgtata gcctcagctc cgtcgtgaca gtcccttcca gcagcctggg cacacagact     600

tacatttgca acgtgaacca caaaccttcc aacactaagg tggacaaaaa ggtggaaccc     660

aaatcctgtg ataagaccca tacatgccca ccttgtcccg ctcctgagct gctgggggga     720

ccttccgtct ttctgtttcc tccaaaacca aaagacacac tcatgatcag ccggaccccc     780
```

```
gaagtcacct gtgtggtggt ggacgtcagc cacgaagatc cagaggtcaa gttcaattgg    840

tacgtggatg gagtggaagt ccacaacgca aaaaccaaac ctagagaaga acagtacaat    900

agcacataca gggtggtgtc cgtcctgaca gtgctccacc aggactggct caatggcaaa    960

gagtataagt gcaaggtgag caacaaggcc ctgcctgcac caattgagaa aacaattagc   1020

aaggcaaagg ggcagccacg ggaaccccag gtgtataccc tgcccccaag ccgggatgaa   1080

ctgaccaaaa accaggtcag cctgacatgc ctggtgaaag ggttttaccc aagcgatatt   1140

gccgtcgagt gggagagcaa cggacagcca gaaaacaatt acaaaaccac cccacctgtg   1200

ctggactccg atgggagctt tttcctgtac agcaagctca cagtggacaa gtccagatgg   1260

caacagggca acgtgttttc ctgctccgtg atgcacgagg ccctccacaa ccactataca   1320

caaaagtccc tctccctcag cccaggaaag                                     1350
```

<210> SEQ ID NO 61
<211> LENGTH: 450
<212> TYPE: PRT
<213> ORGANISM: Homo sapian

<400> SEQUENCE: 61

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Val Tyr Trp Met Trp Ile Arg Gln Pro Pro Gly Lys Gly Leu Glu Trp
        35                  40                  45

Ile Gly Ser Ile Val His Ser Gly His Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Gly Lys Tyr Arg Trp His Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 62
<211> LENGTH: 363
<212> TYPE: DNA
<213> ORGANISM: Homo sapian

<400> SEQUENCE: 62

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagga attagtggta gtggtggtag cacatactac     180

gcagactccg tgaagggccg gttcaccatc tccagagaca attccaagaa cacgctgtat     240

ctgcaaatga acagcctgag agccgaggac acggcggtgt actactgcgc caaggaccct     300

ttgtctctac ttctaggcta ctttgactac tggggacagg gtgcattggt caccgtctcc     360

tca                                                                   363


<210> SEQ ID NO 63
<211> LENGTH: 121
<212> TYPE: PRT
<213> ORGANISM: Homo sapian

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Leu Ser Leu Leu Leu Gly Tyr Phe Asp Tyr Trp Gly
            100                 105                 110

Gln Gly Ala Leu Val Thr Val Ser Ser
        115                 120


<210> SEQ ID NO 64
<211> LENGTH: 7
<212> TYPE: PRT
<213> ORGANISM: Homo sapian

<400> SEQUENCE: 64

Gly Phe Thr Phe Ser Ser Tyr
1               5


<210> SEQ ID NO 65
<211> LENGTH: 6
<212> TYPE: PRT
<213> ORGANISM: Homo sapian

<400> SEQUENCE: 65

Ser Gly Ser Gly Gly Ser
1               5


<210> SEQ ID NO 66
<211> LENGTH: 12
<212> TYPE: PRT
<213> ORGANISM: Homo sapian

<400> SEQUENCE: 66

Asp Pro Leu Ser Leu Leu Leu Gly Tyr Phe Asp Tyr
1               5                   10


<210> SEQ ID NO 67
<211> LENGTH: 1353
<212> TYPE: DNA
<213> ORGANISM: Homo sapian

<400> SEQUENCE: 67

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagga attagtggta gtggtggtag cacatactac     180

gcagactccg tgaagggccg gttcaccatc tccagagaca attccaagaa cacgctgtat     240

ctgcaaatga acagcctgag agccgaggac acggcggtgt actactgcgc caaggaccct     300

ttgtctctac ttctaggcta ctttgactac tggggacagg gtgcattggt caccgtctcc     360

tcagctagca caaaaggacc aagcgtgttt ccactggcac ctagcagcaa atccaccagc     420

ggcggaacag cagccctcgg gtgcctggtg aaggattact tccctgagcc agtcacagtg     480

tcctggaact ccggagccct gacatccggc gtgcacacct tccccgctgt gctgcaatcc     540

agcggactgt atagcctcag ctccgtcgtg acagtccctt ccagcagcct gggcacacag     600

acttacattt gcaacgtgaa ccacaaacct tccaacacta aggtggacaa aaaggtggaa     660

cccaaatcct gtgataagac ccatacatgc ccaccttgtc ccgctcctga gctgctgggg     720

ggaccttccg tctttctgtt tcctccaaaa ccaaaagaca cactcatgat cagccggacc     780
```

```
cccgaagtca cctgtgtggt ggtggacgtc agccacgaag atccagaggt caagttcaat     840

tggtacgtgg atggagtgga agtccacaac gcaaaaacca aacctagaga agaacagtac     900

aatagcacat acagggtggt gtccgtcctg acagtgctcc accaggactg gctcaatggc     960

aaagagtata agtgcaaggt gagcaacaag gccctgcctg caccaattga gaaaacaatt    1020

agcaaggcaa aggggcagcc acgggaaccc caggtgtata ccctgccccc aagccgggat    1080

gaactgacca aaaaccaggt cagcctgaca tgcctggtga aagggtttta cccaagcgat    1140

attgccgtcg agtgggagag caacggacag ccagaaaaca attacaaaac caccccacct    1200

gtgctggact ccgatgggag ctttttcctg tacagcaagc tcacagtgga caagtccaga    1260

tggcaacagg gcaacgtgtt ttcctgctcc gtgatgcacg aggccctcca caaccactat    1320

acacaaaagt ccctctccct cagcccagga aag                                 1353
```

```
<210> SEQ ID NO 68
<211> LENGTH: 451
<212> TYPE: PRT
<213> ORGANISM: Homo sapian

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Leu Ser Leu Leu Leu Gly Tyr Phe Asp Tyr Trp Gly
            100                 105                 110

Gln Gly Ala Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 69
<211> LENGTH: 321
<212> TYPE: DNA
<213> ORGANISM: Homo sapian

<400> SEQUENCE: 69

gacatccaga tgacccagtc tccttccacc ctgtctgcat ctgtaggaga cagagtcacc     60

atcacttgcc gggccagtca gagtattagt agctggttgg cctggtatca gcagaaacca    120

gggaaagccc ctaagctcct gatctatgat gcctccagtt tggaaagtgg ggtcccatca    180

aggttcagcg gcagtggatc tgggacagaa ttcactctca ccatcagcag cctgcagcct    240

gatgattttg caacttatta ctgccagcag tacaatcgcc actctcctac ttttggcgga    300

gggaccaagg ttgagatcaa a                                              321


<210> SEQ ID NO 70
<211> LENGTH: 107
<212> TYPE: PRT
<213> ORGANISM: Homo sapian

<400> SEQUENCE: 70

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys Gln Gln Tyr Asn Arg His Ser Pro
                85                  90                  95

Thr Phe Gly Gly Gly Thr Lys Val Glu Ile Lys
            100                 105


<210> SEQ ID NO 71
<211> LENGTH: 11
<212> TYPE: PRT
<213> ORGANISM: Homo sapian

<400> SEQUENCE: 71

Arg Ala Ser Gln Ser Ile Ser Ser Trp Leu Ala
1               5                   10


<210> SEQ ID NO 72
<211> LENGTH: 7
<212> TYPE: PRT
<213> ORGANISM: Homo sapian

<400> SEQUENCE: 72

Asp Ala Ser Ser Leu Glu Ser
1               5


<210> SEQ ID NO 73
<211> LENGTH: 9
<212> TYPE: PRT
<213> ORGANISM: Homo sapian

<400> SEQUENCE: 73

Gln Gln Tyr Asn Arg His Ser Pro Thr
1               5


<210> SEQ ID NO 74
<211> LENGTH: 642
<212> TYPE: DNA
<213> ORGANISM: Homo sapian

<400> SEQUENCE: 74

gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctatgat gcctccagtt tggaaagtgg ggtcccatca     180

aggttcagcg gcagtggatc tgggacagaa ttcactctca ccatcagcag cctgcagcct     240

gatgattttg caacttatta ctgccagcag tacaatcgcc actctcctac ttttggcgga     300

gggaccaagg ttgagatcaa acgtacggtg gctgcacctt ccgtctttat ctttccacct     360

tccgatgagc agctgaagag cggaacagca agcgtggtgt gtctgctgaa caacttttat     420

ccccgggagg caaaggtgca gtggaaagtc gacaatgctc tccagtccgg caattcccaa     480

gagagcgtga cagagcaaga ttccaaggac tccacttaca gcctgtccag caccctcaca     540

ctgagcaagg ctgattacga gaaacacaaa gtgtacgctt gtgaagtcac ccaccaaggc     600

ctgagcagcc cagtcactaa gtcctttaac cggggcgaat gt                        642


<210> SEQ ID NO 75
<211> LENGTH: 214
<212> TYPE: PRT
<213> ORGANISM: Homo sapian

<400> SEQUENCE: 75

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Arg His Ser Pro
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 76
<211> LENGTH: 363
<212> TYPE: DNA
<213> ORGANISM: Homo sapian

<400> SEQUENCE: 76
gaggtgcagc tgttggagtc tgggggaggc ttggtacagc ctggggggtc cctgagactc 60
tcctgtgcag cctctggatt cacctttagc cgttatgcca tgtcgtgggt ccgccaggct 120
ccagggaagg ggctggagtg ggtctcaggt attagtggaa gtggtggtgc gacatactac 180
gcagactccg tgaagggccg gttcaccatc tccagagaca attccaagaa cacgctgtat 240
ctgcaaatga acagcctgag agccgaggac acggcggtgt actactgcgc caaggaccct 300
ttgtctctac ttctaggcta ctttgactac tggggacagg gtgcattggt caccgtctcc 360
tca 363

<210> SEQ ID NO 77
<211> LENGTH: 121
<212> TYPE: PRT
<213> ORGANISM: Homo sapian

<400> SEQUENCE: 77

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Ala Met Ser Trp Val Arg Gln Ala Pro Gly Lys Gly Leu Glu Trp Val
35 40 45

```
Ser Gly Ile Ser Gly Ser Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Leu Ser Leu Leu Leu Gly Tyr Phe Asp Tyr Trp Gly
            100                 105                 110

Gln Gly Ala Leu Val Thr Val Ser Ser
        115                 120


<210> SEQ ID NO 78
<211> LENGTH: 7
<212> TYPE: PRT
<213> ORGANISM: Homo sapian

<400> SEQUENCE: 78

Gly Phe Thr Phe Ser Arg Tyr
1               5


<210> SEQ ID NO 79
<211> LENGTH: 6
<212> TYPE: PRT
<213> ORGANISM: Homo sapian

<400> SEQUENCE: 79

Ser Gly Ser Gly Gly Ala
1               5


<210> SEQ ID NO 80
<211> LENGTH: 12
<212> TYPE: PRT
<213> ORGANISM: Homo sapian

<400> SEQUENCE: 80

Asp Pro Leu Ser Leu Leu Leu Gly Tyr Phe Asp Tyr
1               5                   10


<210> SEQ ID NO 81
<211> LENGTH: 1353
<212> TYPE: DNA
<213> ORGANISM: Homo sapian

<400> SEQUENCE: 81

gaggtgcagc tgttggagtc tgggggaggc ttggtacagc ctggggggtc cctgagactc     60

tcctgtgcag cctctggatt cacctttagc cgttatgcca tgtcgtgggt ccgccaggct    120

ccagggaagg ggctggagtg ggtctcaggt attagtggaa gtggtggtgc gacatactac    180

gcagactccg tgaagggccg gttcaccatc tccagagaca attccaagaa cacgctgtat    240

ctgcaaatga acagcctgag agccgaggac acggcggtgt actactgcgc caaggaccct    300

ttgtctctac ttctaggcta ctttgactac tggggacagg gtgcattggt caccgtctcc    360

tcagctagca caaaaggacc aagcgtgttt ccactggcac ctagcagcaa atccaccagc    420

ggcggaacag cagccctcgg gtgcctggtg aaggattact tccctgagcc agtcacagtg    480

tcctggaact ccggagccct gacatccggc gtgcacacct tccccgctgt gctgcaatcc    540

agcggactgt atagcctcag ctccgtcgtg acagtccctt ccagcagcct gggcacacag    600

acttacattt gcaacgtgaa ccacaaacct tccaacacta aggtggacaa aaaggtggaa    660

cccaaatcct gtgataagac ccatacatgc ccaccttgtc ccgctcctga gctgctgggg    720
```

```
ggaccttccg tctttctgtt tcctccaaaa ccaaaagaca cactcatgat cagccggacc    780

cccgaagtca cctgtgtggt ggtggacgtc agccacgaag atccagaggt caagttcaat    840

tggtacgtgg atggagtgga agtccacaac gcaaaaacca aacctagaga agaacagtac    900

aatagcacat acagggtggt gtccgtcctg acagtgctcc accaggactg gctcaatggc    960

aaagagtata agtgcaaggt gagcaacaag gccctgcctg caccaattga gaaaacaatt   1020

agcaaggcaa aggggcagcc acgggaaccc caggtgtata ccctgccccc aagccgggat   1080

gaactgacca aaaaccaggt cagcctgaca tgcctggtga aagggtttta cccaagcgat   1140

attgccgtcg agtgggagag caacggacag ccagaaaaca attacaaaac caccccacct   1200

gtgctggact ccgatgggag ctttttcctg tacagcaagc tcacagtgga caagtccaga   1260

tggcaacagg gcaacgtgtt ttcctgctcc gtgatgcacg aggccctcca caaccactat   1320

acacaaaagt ccctctccct cagcccagga aag                                1353


<210> SEQ ID NO 82
<211> LENGTH: 451
<212> TYPE: PRT
<213> ORGANISM: Homo sapian

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Leu Ser Leu Leu Leu Gly Tyr Phe Asp Tyr Trp Gly
            100                 105                 110

Gln Gly Ala Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 83
<211> LENGTH: 360
<212> TYPE: DNA
<213> ORGANISM: Homo sapian

<400> SEQUENCE: 83

caggttcagc tggtgcagtc tggagctgag gtgaagaagc ctggggcctc agtgaaggtc      60

tcctgcaagg cttctggtta cacctttacc agctatggta tcagctgggt gcgacaggcc     120

cctggacaag ggcttgagtg gatgggatgg atcagccctt acaatggtaa cacaaactat     180

gcacagaagc tccagggcag agtcaccatg accacagaca catccacgag cacagcctac     240

atggagctga ggagcctgag atctgacgac acggcggtgt actactgcgc tagagtatct     300

atgtacgccc cagagccaat ggacgtatgg ggccagggaa caactgtcac cgtctcctca     360


<210> SEQ ID NO 84
<211> LENGTH: 120
<212> TYPE: PRT
<213> ORGANISM: Homo sapian

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Leu
    50                  55                  60
```

```
Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser
        115                 120


<210> SEQ ID NO 85
<211> LENGTH: 7
<212> TYPE: PRT
<213> ORGANISM: Homo sapian

<400> SEQUENCE: 85

Gly Tyr Thr Phe Thr Ser Tyr
1               5


<210> SEQ ID NO 86
<211> LENGTH: 6
<212> TYPE: PRT
<213> ORGANISM: Homo sapian

<400> SEQUENCE: 86

Ser Pro Tyr Asn Gly Asn
1               5


<210> SEQ ID NO 87
<211> LENGTH: 11
<212> TYPE: PRT
<213> ORGANISM: Homo sapian

<400> SEQUENCE: 87

Val Ser Met Tyr Ala Pro Glu Pro Met Asp Val
1               5                   10


<210> SEQ ID NO 88
<211> LENGTH: 1350
<212> TYPE: DNA
<213> ORGANISM: Homo sapian

<400> SEQUENCE: 88

caggttcagc tggtgcagtc tggagctgag gtgaagaagc ctggggcctc agtgaaggtc      60

tcctgcaagg cttctggtta cacctttacc agctatggta tcagctgggt gcgacaggcc     120

cctggacaag ggcttgagtg gatgggatgg atcagccctt acaatggtaa cacaaactat     180

gcacagaagc tccagggcag agtcaccatg accacagaca catccacgag cacagcctac     240

atggagctga ggagcctgag atctgacgac acggcggtgt actactgcgc tagagtatct     300

atgtacgccc cagagccaat ggacgtatgg ggccagggaa caactgtcac cgtctcctca     360

gctagcacaa aggaccaag cgtgtttcca ctggcaccta gcagcaaatc caccagcggc      420

ggaacagcag ccctcgggtg cctggtgaag gattacttcc ctgagccagt cacagtgtcc     480

tggaactccg gagccctgac atccggcgtg cacaccttcc ccgctgtgct gcaatccagc     540

ggactgtata gcctcagctc cgtcgtgaca gtcccttcca gcagcctggg cacacagact     600

tacatttgca acgtgaacca caaaccttcc aacactaagg tggacaaaaa ggtggaaccc     660

aaatcctgtg ataagaccca tacatgccca ccttgtcccg ctcctgagct gctgggggga     720

ccttccgtct ttctgtttcc tccaaaacca aaagacacac tcatgatcag ccggaccccc     780
```

```
gaagtcacct gtgtggtggt ggacgtcagc cacgaagatc cagaggtcaa gttcaattgg     840

tacgtggatg gagtggaagt ccacaacgca aaaaccaaac ctagagaaga acagtacaat     900

agcacataca gggtggtgtc cgtcctgaca gtgctccacc aggactggct caatggcaaa     960

gagtataagt gcaaggtgag caacaaggcc ctgcctgcac caattgagaa aacaattagc    1020

aaggcaaagg ggcagccacg ggaaccccag gtgtataccc tgcccccaag ccgggatgaa    1080

ctgaccaaaa accaggtcag cctgacatgc ctggtgaaag ggttttaccc aagcgatatt    1140

gccgtcgagt gggagagcaa cggacagcca gaaaacaatt acaaaaccac cccacctgtg    1200

ctggactccg atgggagctt tttcctgtac agcaagctca cagtggacaa gtccagatgg    1260

caacagggca acgtgttttc ctgctccgtg atgcacgagg ccctccacaa ccactataca    1320

caaaagtccc tctccctcag cccaggaaag                                     1350


<210> SEQ ID NO 89
<211> LENGTH: 450
<212> TYPE: PRT
<213> ORGANISM: Homo sapian

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 90
<211> LENGTH: 321
<212> TYPE: DNA
<213> ORGANISM: Homo sapian

<400> SEQUENCE: 90

gacatccaga tgacccagtc tccatcttcc gtgtctgcat ctgtaggaga cagagtcacc     60

atcacttgtc gggcgagtca gggtattagc aggtggttag cctggtatca gcagaaacca    120

gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag gcattctccc acccttggac ttttggcgga    300

gggaccaagg ttgagatcaa a                                              321


<210> SEQ ID NO 91
<211> LENGTH: 107
<212> TYPE: PRT
<213> ORGANISM: Homo sapian

<400> SEQUENCE: 91

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ala Phe Ser His Pro Trp
                85                  90                  95

Thr Phe Gly Gly Gly Thr Lys Val Glu Ile Lys
            100                 105


<210> SEQ ID NO 92
<211> LENGTH: 11
<212> TYPE: PRT
<213> ORGANISM: Homo sapian

<400> SEQUENCE: 92

Arg Ala Ser Gln Gly Ile Ser Arg Trp Leu Ala
1               5                   10


<210> SEQ ID NO 93
<211> LENGTH: 6
<212> TYPE: PRT
<213> ORGANISM: Homo sapian

<400> SEQUENCE: 93

Ala Ser Ser Leu Gln Ser
1               5


<210> SEQ ID NO 94
<211> LENGTH: 9
<212> TYPE: PRT
<213> ORGANISM: Homo sapian

<400> SEQUENCE: 94

Gln Gln Ala Phe Ser His Pro Trp Thr
1               5


<210> SEQ ID NO 95
<211> LENGTH: 642
<212> TYPE: DNA
<213> ORGANISM: Homo sapian

<400> SEQUENCE: 95

gacatccaga tgacccagtc tccatcttcc gtgtctgcat ctgtaggaga cagagtcacc     60

atcacttgtc gggcgagtca gggtattagc aggtggttag cctggtatca gcagaaacca    120

gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag gcattctccc acccttggac ttttggcgga    300

gggaccaagg ttgagatcaa acgtacggtg gctgcacctt ccgtctttat ctttccacct    360

tccgatgagc agctgaagag cggaacagca agcgtggtgt gtctgctgaa caacttttat    420

ccccgggagg caaaggtgca gtggaaagtc gacaatgctc tccagtccgg caattcccaa    480

gagagcgtga cagagcaaga ttccaaggac tccacttaca gcctgtccag caccctcaca    540

ctgagcaagg ctgattacga gaaacacaaa gtgtacgctt gtgaagtcac ccaccaaggc    600

ctgagcagcc cagtcactaa gtcctttaac cggggcgaat gt                       642


<210> SEQ ID NO 96
<211> LENGTH: 107
<212> TYPE: PRT
<213> ORGANISM: Homo sapian

<400> SEQUENCE: 96

Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Ser His Pro Trp
                85                  90                  95

Thr Phe Gly Gly Gly Thr Lys Val Glu Ile Lys
            100                 105
```

<210> SEQ ID NO 97
<211> LENGTH: 360
<212> TYPE: DNA
<213> ORGANISM: Homo sapian

<400> SEQUENCE: 97

```
caggtgcagc tggtgcagtc tggggctgag gtgaagaagc ctggggcctc agtgaaggtc      60

tcctgcaagg cttctggata caccttcacc ggccataaga tgcactgggt gcgacaggcc     120

cctggacaag ggcttgagtg gatgggatgg atcaaccctg ctagtggttg gacaaactat     180

gcacagaagt ttcagggcag ggtcaccatg accagggaca cgtccatcag cacagcctac     240

atggagctga gcaggctgag atctgacgac acggcggtgt actactgcgc cagagtatct     300

atgtacgccc cagagccaat ggacgtatgg ggccagggaa caactgtcac cgtctcctca     360
```

<210> SEQ ID NO 98
<211> LENGTH: 120
<212> TYPE: PRT
<213> ORGANISM: Homo sapian

<400> SEQUENCE: 98

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Lys Met His Trp Val Arg Gln Ala Pro Gly Gln Gly Leu Glu Trp Met
        35                  40                  45

Gly Trp Ile Asn Pro Ala Ser Gly Trp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser
        115                 120
```

<210> SEQ ID NO 99
<211> LENGTH: 10
<212> TYPE: PRT
<213> ORGANISM: Homo sapian

<400> SEQUENCE: 99

```
Gly Tyr Thr Phe Thr Gly His Lys Met His
1               5                   10


<210> SEQ ID NO 100
<211> LENGTH: 6
<212> TYPE: PRT
<213> ORGANISM: Homo sapian

<400> SEQUENCE: 100

Asn Pro Ala Ser Gly Trp
1               5


<210> SEQ ID NO 101
<211> LENGTH: 11
<212> TYPE: PRT
<213> ORGANISM: Homo sapian

<400> SEQUENCE: 101

Val Ser Met Tyr Ala Pro Glu Pro Met Asp Val
1               5                   10


<210> SEQ ID NO 102
<211> LENGTH: 1350
<212> TYPE: DNA
<213> ORGANISM: Homo sapian

<400> SEQUENCE: 102

caggtgcagc tggtgcagtc tggggctgag gtgaagaagc ctggggcctc agtgaaggtc     60

tcctgcaagg cttctggata caccttcacc ggccataaga tgcactgggt gcgacaggcc    120

cctggacaag ggcttgagtg gatgggatgg atcaaccctg ctagtggttg gacaaactat    180

gcacagaagt ttcagggcag ggtcaccatg accagggaca cgtccatcag cacagcctac    240

atggagctga gcaggctgag atctgacgac acggcggtgt actactgcgc cagagtatct    300

atgtacgccc cagagccaat ggacgtatgg ggccagggaa caactgtcac cgtctcctca    360

gctagcacaa aggaccaag cgtgtttcca ctggcaccta gcagcaaatc caccagcggc    420

ggaacagcag ccctcgggtg cctggtgaag gattacttcc ctgagccagt cacagtgtcc    480

tggaactccg gagccctgac atccggcgtg cacaccttcc ccgctgtgct gcaatccagc    540

ggactgtata gcctcagctc cgtcgtgaca gtcccttcca gcagcctggg cacacagact    600

tacatttgca acgtgaacca caaaccttcc aacactaagg tggacaaaaa ggtggaaccc    660

aaatcctgtg ataagaccca tacatgccca ccttgtcccg ctcctgagct gctgggggga    720

ccttccgtct ttctgtttcc tccaaaacca aaagacacac tcatgatcag ccggaccccc    780

gaagtcacct gtgtggtggt ggacgtcagc cacgaagatc cagaggtcaa gttcaattgg    840

tacgtggatg gagtggaagt ccacaacgca aaaaccaaac ctagagaaga acagtacaat    900

agcacataca gggtggtgtc cgtcctgaca gtgctccacc aggactggct caatggcaaa    960

gagtataagt gcaaggtgag caacaaggcc ctgcctgcac caattgagaa aacaattagc   1020

aaggcaaagg ggcagccacg ggaaccccag gtgtataccc tgcccccaag ccgggatgaa   1080

ctgaccaaaa accaggtcag cctgacatgc ctggtgaaag ggttttaccc aagcgatatt   1140

gccgtcgagt gggagagcaa cggacagcca gaaaacaatt acaaaaccac cccacctgtg   1200

ctggactccg atgggagctt tttcctgtac agcaagctca cagtggacaa gtccagatgg   1260

caacagggca acgtgtttc ctgctccgtg atgcacgagg ccctccacaa ccactataca   1320

caaaagtccc tctccctcag cccaggaaag                                   1350
```

<210> SEQ ID NO 103
<211> LENGTH: 450
<212> TYPE: PRT
<213> ORGANISM: Homo sapian

<400> SEQUENCE: 103

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Lys Met His Trp Val Arg Gln Ala Pro Gly Gln Gly Leu Glu Trp Met
        35                  40                  45

Gly Trp Ile Asn Pro Ala Ser Gly Trp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 104
<211> LENGTH: 360
<212> TYPE: DNA
<213> ORGANISM: Homo sapian

<400> SEQUENCE: 104

caggtgcagc tggtgcagtc tggggctgag gtgaagaagc ctggggcctc agtgaaggtt      60

tcctgcaagg catctggata caccttcacc agctacaata tggcgtgggt gcgacaggcc     120

cctggacaag ggcttgagtg gatgggaata atcaggccta gtgttggtag cacaagctac     180

gcacagaagt tccagggcag agtcaccatg accagggaca cgtccacgag cacagtctac     240

atggagctga gcagcctgag atctgaggac acggcggtgt actactgcgc tagagtatct     300

atgtacgccc cagagccaat ggacgtatgg ggccagggaa caactgtcac cgtctcctca     360


<210> SEQ ID NO 105
<211> LENGTH: 120
<212> TYPE: PRT
<213> ORGANISM: Homo sapian

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met Ala Trp Val Arg Gln Ala Pro Gly Gln Gly Leu Glu Trp Met
        35                  40                  45

Gly Ile Ile Arg Pro Ser Val Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser
        115                 120


<210> SEQ ID NO 106
<211> LENGTH: 7
<212> TYPE: PRT
<213> ORGANISM: Homo sapian

<400> SEQUENCE: 106

Gly Tyr Thr Phe Thr Ser Tyr
1               5
```

<210> SEQ ID NO 107
<211> LENGTH: 6
<212> TYPE: PRT
<213> ORGANISM: Homo sapian

<400> SEQUENCE: 107

Arg Pro Ser Val Gly Ser
1               5

<210> SEQ ID NO 108
<211> LENGTH: 11
<212> TYPE: PRT
<213> ORGANISM: Homo sapian

<400> SEQUENCE: 108

Val Ser Met Tyr Ala Pro Glu Pro Met Asp Val
1               5                   10

<210> SEQ ID NO 109
<211> LENGTH: 1350
<212> TYPE: DNA
<213> ORGANISM: Homo sapian

<400> SEQUENCE: 109
caggtgcagc tggtgcagtc tggggctgag gtgaagaagc ctggggcctc agtgaaggtt 60
tcctgcaagg catctggata caccttcacc agctacaata tggcgtgggt gcgacaggcc 120
cctggacaag ggcttgagtg gatgggaata atcaggccta gtgttggtag cacaagctac 180
gcacagaagt tccagggcag agtcaccatg accagggaca cgtccacgag cacagtctac 240
atggagctga gcagcctgag atctgaggac acggcggtgt actactgcgc tagagtatct 300
atgtacgccc cagagccaat ggacgtatgg ggccagggaa caactgtcac cgtctcctca 360
gctagcacaa aggaccaag cgtgtttcca ctggcaccta gcagcaaatc caccagcggc 420
ggaacagcag ccctcgggtg cctggtgaag gattacttcc ctgagccagt cacagtgtcc 480
tggaactccg gagccctgac atccggcgtg cacaccttcc ccgctgtgct gcaatccagc 540
ggactgtata gcctcagctc cgtcgtgaca gtcccttcca gcagcctggg cacacagact 600
tacatttgca acgtgaacca caaaccttcc aacactaagg tggacaaaaa ggtggaaccc 660
aaatcctgtg ataagaccca tacatgccca ccttgtcccg ctcctgagct gctgggggga 720
ccttccgtct ttctgtttcc tccaaaacca aaagacacac tcatgatcag ccggaccccc 780
gaagtcacct gtgtggtggt ggacgtcagc cacgaagatc cagaggtcaa gttcaattgg 840
tacgtggatg gagtggaagt ccacaacgca aaaaccaaac ctagagaaga acagtacaat 900
agcacataca gggtggtgtc cgtcctgaca gtgctccacc aggactggct caatggcaaa 960
gagtataagt gcaaggtgag caacaaggcc ctgcctgcac caattgagaa aacaattagc 1020
aaggcaaagg ggcagccacg ggaaccccag gtgtataccc tgcccccaag ccgggatgaa 1080
ctgaccaaaa accaggtcag cctgacatgc ctggtgaaag ggttttaccc aagcgatatt 1140
gccgtcgagt gggagagcaa cggacagcca gaaaacaatt acaaaaccac cccacctgtg 1200
ctggactccg atgggagctt tttcctgtac agcaagctca cagtggacaa gtccagatgg 1260
caacagggca acgtgttttc ctgctccgtg atgcacgagg ccctccacaa ccactataca 1320
caaaagtccc tctccctcag cccaggaaag 1350

<210> SEQ ID NO 110
<211> LENGTH: 450

<212> TYPE: PRT
<213> ORGANISM: Homo sapian

<400> SEQUENCE: 110

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met Ala Trp Val Arg Gln Ala Pro Gly Gln Gly Leu Glu Trp Met
        35                  40                  45

Gly Ile Ile Arg Pro Ser Val Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 111
<211> LENGTH: 360
<212> TYPE: DNA
<213> ORGANISM: Homo sapian

<400> SEQUENCE: 111

caggtgcagc tggtgcagtc tggggctgag gtgaagaagc ctggggcctc agtgaaggtt      60

tcctgcaagg catctggata caccttcacc tcgtaccgta tgcactgggt gcgacaggcc     120

cctggacaag ggcttgagtg gatgggattt atcgtgccta gtggtggtag cacaagctac     180

gcacagaagt tccagggcag agtcaccatg accagggaca cgtccacgag cacagtctac     240

atggagctga gcagcctgag atctgaggac acggcggtgt actactgcgc tagagtatct     300

atgtacgccc cagagccaat ggacgtatgg ggccagggaa caactgtcac cgtctcctca     360


<210> SEQ ID NO 112
<211> LENGTH: 120
<212> TYPE: PRT
<213> ORGANISM: Homo sapian

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Phe Ile Val Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser
        115                 120


<210> SEQ ID NO 113
<211> LENGTH: 7
<212> TYPE: PRT
<213> ORGANISM: Homo sapian

<400> SEQUENCE: 113

Gly Tyr Thr Phe Thr Ser Tyr
1               5


<210> SEQ ID NO 114
<211> LENGTH: 6
```

<212> TYPE: PRT
<213> ORGANISM: Homo sapian

<400> SEQUENCE: 114

Val Pro Ser Gly Gly Ser
1 5

<210> SEQ ID NO 115
<211> LENGTH: 11
<212> TYPE: PRT
<213> ORGANISM: Homo sapian

<400> SEQUENCE: 115

Val Ser Met Tyr Ala Pro Glu Pro Met Asp Val
1 5 10

<210> SEQ ID NO 116
<211> LENGTH: 1350
<212> TYPE: DNA
<213> ORGANISM: Homo sapian

<400> SEQUENCE: 116
caggtgcagc tggtgcagtc tggggctgag gtgaagaagc ctggggcctc agtgaaggtt 60
tcctgcaagg catctggata caccttcacc tcgtaccgta tgcactgggt gcgacaggcc 120
cctggacaag ggcttgagtg gatgggattt atcgtgccta gtggtggtag cacaagctac 180
gcacagaagt tccagggcag agtcaccatg accagggaca cgtccacgag cacagtctac 240
atggagctga gcagcctgag atctgaggac acggcggtgt actactgcgc tagagtatct 300
atgtacgccc cagagccaat ggacgtatgg ggccagggaa caactgtcac cgtctcctca 360
gctagcacaa aggaccaag cgtgtttcca ctggcaccta gcagcaaatc caccagcggc 420
ggaacagcag ccctcgggtg cctggtgaag gattacttcc ctgagccagt cacagtgtcc 480
tggaactccg gagccctgac atccggcgtg cacaccttcc ccgctgtgct gcaatccagc 540
ggactgtata gcctcagctc cgtcgtgaca gtcccttcca gcagcctggg cacacagact 600
tacatttgca acgtgaacca caaaccttcc aacactaagg tggacaaaaa ggtggaaccc 660
aaatcctgtg ataagaccca tacatgccca ccttgtcccg ctcctgagct gctgggggga 720
ccttccgtct ttctgtttcc tccaaaacca aaagacacac tcatgatcag ccggaccccc 780
gaagtcacct gtgtggtggt ggacgtcagc cacgaagatc cagaggtcaa gttcaattgg 840
tacgtggatg gagtggaagt ccacaacgca aaaaccaaac ctagagaaga acagtacaat 900
agcacataca gggtggtgtc cgtcctgaca gtgctccacc aggactggct caatggcaaa 960
gagtataagt gcaaggtgag caacaaggcc ctgcctgcac caattgagaa aacaattagc 1020
aaggcaaagg ggcagccacg ggaaccccag gtgtataccc tgcccccaag ccgggatgaa 1080
ctgaccaaaa accaggtcag cctgacatgc ctggtgaaag ggttttaccc aagcgatatt 1140
gccgtcgagt gggagagcaa cggacagcca gaaaacaatt acaaaaccac cccacctgtg 1200
ctggactccg atgggagctt tttcctgtac agcaagctca cagtggacaa gtccagatgg 1260
caacagggca acgtgttttc ctgctccgtg atgcacgagg ccctccacaa ccactataca 1320
caaaagtccc tctccctcag cccaggaaag 1350

<210> SEQ ID NO 117
<211> LENGTH: 450
<212> TYPE: PRT
<213> ORGANISM: Homo sapian

<400> SEQUENCE: 117

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Phe Ile Val Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Met Tyr Ala Pro Glu Pro Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 118
<211> LENGTH: 360
<212> TYPE: DNA
<213> ORGANISM: Homo sapian

<400> SEQUENCE: 118

caggtgcagc tggtgcagtc tggggctgag gtgaagaagc ctggggcctc agtgaaggtt      60

tcctgcaagg catctggata caccttcacc tcgtaccgta tgcactgggt gcgacaggcc     120

cctggacaag ggcttgagtg gatgggattt atcgtgccta gtggtggtag cacaggctac     180

gcacagaagt tccagggcag agttaccatg accagggaca cgtccacgag cacagtctac     240

atggagctga gcagcctgag atctgaggac acggcggtgt actactgcgc tagagtatct     300

aggtacgccc cagagccaat ggacgtatgg ggccagggaa caactgtcac cgtctcctca     360


<210> SEQ ID NO 119
<211> LENGTH: 120
<212> TYPE: PRT
<213> ORGANISM: Homo sapian

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Phe Ile Val Pro Ser Gly Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Arg Tyr Ala Pro Glu Pro Met Asp Val Trp Gly Gln
            100                 105                 110

Gly Thr Thr Val Thr Val Ser Ser
        115                 120


<210> SEQ ID NO 120
<211> LENGTH: 6
<212> TYPE: PRT
<213> ORGANISM: Homo sapian

<400> SEQUENCE: 120

Val Pro Ser Gly Gly Ser
1               5


<210> SEQ ID NO 121
<211> LENGTH: 11
<212> TYPE: PRT
<213> ORGANISM: Homo sapian
```

<400> SEQUENCE: 121

Val Ser Arg Tyr Ala Pro Glu Pro Met Asp Val
1 5 10

<210> SEQ ID NO 122
<211> LENGTH: 1350
<212> TYPE: DNA
<213> ORGANISM: Homo sapian

<400> SEQUENCE: 122
caggtgcagc tggtgcagtc tggggctgag gtgaagaagc ctggggcctc agtgaaggtt 60
tcctgcaagg catctggata caccttcacc tcgtaccgta tgcactgggt gcgacaggcc 120
cctggacaag ggcttgagtg gatgggattt atcgtgccta gtggtggtag cacaggctac 180
gcacagaagt tccagggcag agttaccatg accagggaca cgtccacgag cacagtctac 240
atggagctga gcagcctgag atctgaggac acggcggtgt actactgcgc tagagtatct 300
aggtacgccc cagagccaat ggacgtatgg ggccagggaa caactgtcac cgtctcctca 360
gctagcacaa aggaccaag cgtgtttcca ctggcaccta gcagcaaatc caccagcggc 420
ggaacagcag ccctcgggtg cctggtgaag gattacttcc ctgagccagt cacagtgtcc 480
tggaactccg gagccctgac atccggcgtg cacaccttcc ccgctgtgct gcaatccagc 540
ggactgtata gcctcagctc cgtcgtgaca gtcccttcca gcagcctggg cacacagact 600
tacatttgca acgtgaacca caaaccttcc aacactaagg tggacaaaaa ggtggaaccc 660
aaatcctgtg ataagaccca tacatgccca ccttgtcccg ctcctgagct gctgggggga 720
ccttccgtct ttctgtttcc tccaaaacca aaagacacac tcatgatcag ccggaccccc 780
gaagtcacct gtgtggtggt ggacgtcagc cacgaagatc cagaggtcaa gttcaattgg 840
tacgtggatg gagtggaagt ccacaacgca aaaaccaaac ctagagaaga acagtacaat 900
agcacataca gggtggtgtc cgtcctgaca gtgctccacc aggactggct caatggcaaa 960
gagtataagt gcaaggtgag caacaaggcc ctgcctgcac caattgagaa aacaattagc 1020
aaggcaaagg ggcagccacg ggaaccccag gtgtataccc tgcccccaag ccgggatgaa 1080
ctgaccaaaa accaggtcag cctgacatgc ctggtgaaag ggttttaccc aagcgatatt 1140
gccgtcgagt gggagagcaa cggacagcca gaaaacaatt acaaaaccac cccacctgtg 1200
ctggactccg atgggagctt tttcctgtac agcaagctca cagtggacaa gtccagatgg 1260
caacagggca acgtgttttc ctgctccgtg atgcacgagg ccctccacaa ccactataca 1320
caaaagtccc tctccctcag cccaggaaag 1350

<210> SEQ ID NO 123
<211> LENGTH: 450
<212> TYPE: PRT
<213> ORGANISM: Homo sapiens

<400> SEQUENCE: 123

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Arg Met His Trp Val Arg Gln Ala Pro Gly Gln Gly Leu Glu Trp Met
35 40 45

Gly Phe Ile Val Pro Ser Gly Gly Ser Thr Gly Tyr Ala Gln Lys Phe
50 55 60

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Arg Tyr Ala Pro Glu Pro Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 124
<211> LENGTH: 366
<212> TYPE: DNA

<213> ORGANISM: Homo sapian

<400> SEQUENCE: 124

```
caggtgcagc tgcaggagtc gggcccagga ctggtgaagc cttcacagac cctgtccctc     60

acctgtactg tctctggtgg ctccatcagc agtggtagct actactggag ctggatccgc    120

cagcacccag ggaagggcct ggagtggatt gggtacatct attacagtgg gagcacctac    180

tacaacccgt ccctcaagag tcgagttacc atatcagtag acacgtctaa gaaccagttc    240

tccctgaagc tgagttctgt gaccgccgca gacacggcgg tgtactactg cgccagagga    300

ctaggaatgt actaccacgt gccattcgac atatggggtc agggtacaat ggtcaccgtc    360

tcctca                                                               366
```

<210> SEQ ID NO 125
<211> LENGTH: 122
<212> TYPE: PRT
<213> ORGANISM: Homo sapian

<400> SEQUENCE: 125

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Leu Gly Met Tyr Tyr His Val Pro Phe Asp Ile Trp
            100                 105                 110

Gly Gln Gly Thr Met Val Thr Val Ser Ser
        115                 120
```

<210> SEQ ID NO 126
<211> LENGTH: 9
<212> TYPE: PRT
<213> ORGANISM: Homo sapian

<400> SEQUENCE: 126

```
Gly Gly Ser Ile Ser Ser Gly Ser Tyr
1               5
```

<210> SEQ ID NO 127
<211> LENGTH: 5
<212> TYPE: PRT
<213> ORGANISM: Homo sapian

<400> SEQUENCE: 127

```
Tyr Tyr Ser Gly Ser
1               5
```

<210> SEQ ID NO 128
<211> LENGTH: 12
<212> TYPE: PRT
<213> ORGANISM: Homo sapian

<400> SEQUENCE: 128

```
Gly Leu Gly Met Tyr Tyr His Val Pro Phe Asp Ile
1               5                   10
```

<210> SEQ ID NO 129
<211> LENGTH: 1356
<212> TYPE: DNA
<213> ORGANISM: Homo sapian

<400> SEQUENCE: 129

```
caggtgcagc tgcaggagtc gggcccagga ctggtgaagc cttcacagac cctgtccctc     60

acctgtactg tctctggtgg ctccatcagc agtggtagct actactggag ctggatccgc    120

cagcacccag ggaagggcct ggagtggatt gggtacatct attacagtgg gagcacctac    180

tacaacccgt ccctcaagag tcgagttacc atatcagtag acacgtctaa gaaccagttc    240

tccctgaagc tgagttctgt gaccgccgca gacacggcgg tgtactactg cgccagagga    300

ctaggaatgt actaccacgt gccattcgac atatggggtc agggtacaat ggtcaccgtc    360

tcctcagcta gcacaaaagg accaagcgtg tttccactgg cacctagcag caaatccacc    420

agcggcggaa cagcagccct cgggtgcctg gtgaaggatt acttccctga gccagtcaca    480

gtgtcctgga actccggagc cctgacatcc ggcgtgcaca ccttccccgc tgtgctgcaa    540

tccagcggac tgtatagcct cagctccgtc gtgacagtcc cttccagcag cctgggcaca    600

cagacttaca tttgcaacgt gaaccacaaa ccttccaaca ctaaggtgga caaaaaggtg    660

gaacccaaat cctgtgataa gacccataca tgcccacctt gtcccgctcc tgagctgctg    720

gggggacctt ccgtctttct gtttcctcca aaaccaaaag acacactcat gatcagccgg    780

acccccgaag tcacctgtgt ggtggtggac gtcagccacg aagatccaga ggtcaagttc    840

aattggtacg tggatggagt ggaagtccac aacgcaaaaa ccaaacctag agaagaacag    900

tacaatagca catacagggt ggtgtccgtc ctgacagtgc tccaccagga ctggctcaat    960

ggcaaagagt ataagtgcaa ggtgagcaac aaggccctgc ctgcaccaat tgagaaaaca   1020

attagcaagg caaaggggca gccacgggaa ccccaggtgt ataccctgcc cccaagccgg   1080

gatgaactga ccaaaaacca ggtcagcctg acatgcctgg tgaaagggtt ttacccaagc   1140

gatattgccg tcgagtggga gagcaacgga cagccagaaa acaattacaa aaccacccca   1200

cctgtgctgg actccgatgg gagcttttc ctgtacagca agctcacagt ggacaagtcc   1260

agatggcaac agggcaacgt gttttcctgc tccgtgatgc acgaggccct ccacaaccac   1320

tatacacaaa agtccctctc cctcagccca ggaaag                             1356
```

<210> SEQ ID NO 130
<211> LENGTH: 452
<212> TYPE: PRT
<213> ORGANISM: Homo sapian

<400> SEQUENCE: 130

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
```

```
65                  70                  75                  80

Ser Leu Lys Leu Ser Ser Val Thr Ala Ala Asp Thr Ala Val Tyr Tyr
                85                  90                  95

Cys Ala Arg Gly Leu Gly Met Tyr Tyr His Val Pro Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 131
<211> LENGTH: 321
<212> TYPE: DNA
<213> ORGANISM: Homo sapian

<400> SEQUENCE: 131

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tacttccact ggcctcctac ttttggcgga    300

gggaccaagg ttgagatcaa a                                              321
```

<210> SEQ ID NO 132
<211> LENGTH: 107
<212> TYPE: PRT
<213> ORGANISM: Homo sapian

<400> SEQUENCE: 132

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Phe His Trp Pro Pro
                85                  90                  95

Thr Phe Gly Gly Gly Thr Lys Val Glu Ile Lys
            100                 105
```

<210> SEQ ID NO 133
<211> LENGTH: 11
<212> TYPE: PRT
<213> ORGANISM: Homo sapian

<400> SEQUENCE: 133

```
Arg Ala Ser Gln Ser Val Ser Ser Tyr Leu Ala
1               5                   10
```

<210> SEQ ID NO 134
<211> LENGTH: 7
<212> TYPE: PRT
<213> ORGANISM: Homo sapian

<400> SEQUENCE: 134

```
Asp Ala Ser Asn Arg Ala Thr
1               5
```

<210> SEQ ID NO 135
<211> LENGTH: 9
<212> TYPE: PRT
<213> ORGANISM: Homo sapian

<400> SEQUENCE: 135

```
Gln Gln Tyr Phe His Trp Pro Pro Thr
1               5
```

<210> SEQ ID NO 136

<211> LENGTH: 642
<212> TYPE: DNA
<213> ORGANISM: Homo sapian

<400> SEQUENCE: 136

```
gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcag tacttccact ggcctcctac ttttggcgga     300

gggaccaagg ttgagatcaa acgtacggtg gctgcacctt ccgtctttat ctttccacct     360

tccgatgagc agctgaagag cggaacagca agcgtggtgt gtctgctgaa caacttttat     420

ccccgggagg caaaggtgca gtggaaagtc gacaatgctc tccagtccgg caattcccaa     480

gagagcgtga cagagcaaga ttccaaggac tccacttaca gcctgtccag caccctcaca     540

ctgagcaagg ctgattacga gaaacacaaa gtgtacgctt gtgaagtcac ccaccaaggc     600

ctgagcagcc cagtcactaa gtcctttaac cggggcgaat gt                        642
```

<210> SEQ ID NO 137
<211> LENGTH: 214
<212> TYPE: PRT
<213> ORGANISM: Homo sapian

<400> SEQUENCE: 137

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Phe His Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 138
<211> LENGTH: 118
<212> TYPE: PRT
<213> ORGANISM: Homo sapian

<400> SEQUENCE: 138

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Tyr Tyr Asn
        115
```

<210> SEQ ID NO 139
<211> LENGTH: 106
<212> TYPE: PRT
<213> ORGANISM: Homo sapian

<400> SEQUENCE: 139

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro
            100                 105
```

<210> SEQ ID NO 140
<211> LENGTH: 9
<212> TYPE: PRT
<213> ORGANISM: Artificial Sequence
<220> FEATURE:
<223> OTHER INFORMATION: human antigen binding domain of D03 antibody

<400> SEQUENCE: 140

```
Tyr Thr Phe Thr Ser Tyr Arg Met His
1               5
```

<210> SEQ ID NO 141
<211> LENGTH: 17
<212> TYPE: PRT
<213> ORGANISM: Artificial Sequence
<220> FEATURE:

<223> OTHER INFORMATION: human antigen binding domain of DO3 antibody

<400> SEQUENCE: 141

```
Phe Ile Val Pro Ser Gly Gly Ser Thr Gly Tyr Ala Gln Lys Phe Gln
1               5                   10                  15

Gly
```

<210> SEQ ID NO 142
<211> LENGTH: 13
<212> TYPE: PRT
<213> ORGANISM: Artificial Sequence
<220> FEATURE:
<223> OTHER INFORMATION: human antigen binding domain of DO3 antibody

<400> SEQUENCE: 142

```
Ala Arg Val Ser Arg Tyr Ala Pro Glu Pro Met Asp Val
1               5                   10
```

<210> SEQ ID NO 143
<211> LENGTH: 354
<212> TYPE: DNA
<213> ORGANISM: Artificial Sequence
<220> FEATURE:
<223> OTHER INFORMATION: VH sequence

<400> SEQUENCE: 143

```
gaggtgcagc tgttggagtc tgggggaggc ttggtacagc ctggggggtc cctgagactc     60

tcctgtgcag cctctggatt cacctttggg agctatggca tgacttgggt ccgccaggct    120

ccagggaagg ggctggagtg ggtctcagtt attagtggaa gtggtggtgg gacatactac    180

gcagactccg tgaagggccg gttcaccatc tccagagaca attccaagaa cacgctgtat    240

ctgcaaatga acagcctgag agccgaggac acggcggtgt actactgcgc caagggtcct    300

agaatagtgg gcatggatgt gtggggccag ggaacaactg tcaccgtctc ctca          354
```

<210> SEQ ID NO 144
<211> LENGTH: 117
<212> TYPE: PRT
<213> ORGANISM: Artificial Sequence
<220> FEATURE:
<223> OTHER INFORMATION: VH sequence

<400> SEQUENCE: 144

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met Thr Trp Val Arg Gln Ala Pro Gly Lys Gly Leu Glu Trp Val
        35                  40                  45

Ser Val Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Arg Ile Val Gly Met Asp Val Trp Gly Gln Gly Thr
            100                 105                 110

Thr Val Thr Val Ser
        115
```

<210> SEQ ID NO 145
<211> LENGTH: 5
<212> TYPE: PRT
<213> ORGANISM: Artificial Sequence
<220> FEATURE:
<223> OTHER INFORMATION: CDR1 amino acid residues 31-35 of SEQ ID NO 144

<400> SEQUENCE: 145

Ser Tyr Gly Met Thr
1 5

<210> SEQ ID NO 146
<211> LENGTH: 17
<212> TYPE: PRT
<213> ORGANISM: Artificial Sequence
<220> FEATURE:
<223> OTHER INFORMATION: CDR2 amino acid residues 50-65 of SEQ ID NO 144

<400> SEQUENCE: 146

Val Ile Ser Gly Ser Gly Gly Gly Thr Tyr Tyr Ala Asp Ser Val Lys
1 5 10 15

Gly

<210> SEQ ID NO 147
<211> LENGTH: 9
<212> TYPE: PRT
<213> ORGANISM: Artificial Sequence
<220> FEATURE:
<223> OTHER INFORMATION: CDR3 amino acid residues 95-102 of SEQ ID NO 144

<400> SEQUENCE: 147

Gly Pro Arg Ile Val Gly Met Asp Val
1 5

<210> SEQ ID NO 148
<211> LENGTH: 1338
<212> TYPE: DNA
<213> ORGANISM: Artificial Sequence
<220> FEATURE:
<223> OTHER INFORMATION: H sequence

<400> SEQUENCE: 148
gaggtgcagc tgttggagtc tgggggaggc ttggtacagc ctggggggtc cctgagactc 60
tcctgtgcag cctctggatt cacctttggg agctatggca tgacttgggt ccgccaggct 120
ccagggaagg ggctggagtg ggtctcagtt attagtggaa gtggtggtgg gacatactac 180
gcagactccg tgaagggccg gttcaccatc tccagagaca attccaagaa cacgctgtat 240
ctgcaaatga acagcctgag agccgaggac acggcggtgt actactgcgc caagggtcct 300
agaatagtgg gcatggatgt gtggggccag ggaacaactg tcaccgtctc ctcagcttcc 360
accaagggcc catccgtctt ccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccaccctg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840

```
gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

<210> SEQ ID NO 149
<211> LENGTH: 445
<212> TYPE: PRT
<213> ORGANISM: Artificial Sequence
<220> FEATURE:
<223> OTHER INFORMATION: H sequence

<400> SEQUENCE: 149

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met Thr Trp Val Arg Gln Ala Pro Gly Lys Gly Leu Glu Trp Val
        35                  40                  45

Ser Val Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Arg Ile Val Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 150
<211> LENGTH: 321
<212> TYPE: DNA
<213> ORGANISM: Artificial Sequence
<220> FEATURE:
<223> OTHER INFORMATION: VL sequence

<400> SEQUENCE: 150

```
gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag gtattcagtt accctctcac ttttggcgga    300

gggaccaagg ttgagatcaa a                                              321
```

<210> SEQ ID NO 151
<211> LENGTH: 107
<212> TYPE: PRT
<213> ORGANISM: Artificial Sequence
<220> FEATURE:
<223> OTHER INFORMATION: VL sequence

<400> SEQUENCE: 151

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Val Phe Ser Tyr Pro Leu
                85                  90                  95

Thr Phe Gly Gly Gly Thr Lys Val Glu Ile Lys
            100                 105


<210> SEQ ID NO 152
<211> LENGTH: 11
<212> TYPE: PRT
<213> ORGANISM: Artificial Sequence
<220> FEATURE:
<223> OTHER INFORMATION: CDR1 amino acid residues 24-34 of SEQ ID NO 151

<400> SEQUENCE: 152

Arg Ala Ser Gln Gly Ile Ser Ser Trp Leu Ala
1               5                   10


<210> SEQ ID NO 153
<211> LENGTH: 7
<212> TYPE: PRT
<213> ORGANISM: Artificial Sequence
<220> FEATURE:
<223> OTHER INFORMATION: CDR2 amino acid residues 50-56 of SEQ ID NO 151

<400> SEQUENCE: 153

Ala Ala Ser Ser Leu Gln Ser
1               5


<210> SEQ ID NO 154
<211> LENGTH: 9
<212> TYPE: PRT
<213> ORGANISM: Artificial Sequence
<220> FEATURE:
<223> OTHER INFORMATION: CDR3 amino acid residues 89-97 of SEQ ID NO 151

<400> SEQUENCE: 154

Gln Gln Val Phe Ser Tyr Pro Leu Thr
1               5


<210> SEQ ID NO 155
<211> LENGTH: 645
<212> TYPE: DNA
<213> ORGANISM: Artificial Sequence
<220> FEATURE:
<223> OTHER INFORMATION: L sequence

<400> SEQUENCE: 155

gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag gtattcagtt accctctcac ttttggcgga    300

gggaccaagg ttgagatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 156
<211> LENGTH: 214
<212> TYPE: PRT
<213> ORGANISM: Artificial Sequence
<220> FEATURE:
<223> OTHER INFORMATION: L sequence

<400> SEQUENCE: 156

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Phe Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 157
<211> LENGTH: 9
<212> TYPE: PRT
<213> ORGANISM: Artificial Sequence
<220> FEATURE:
<223> OTHER INFORMATION: Peptide sequence of human ActRIIB

<400> SEQUENCE: 157

```
Asn Ala Asn Trp Glu Leu Glu Arg Thr
1               5
```

<210> SEQ ID NO 158
<211> LENGTH: 9
<212> TYPE: PRT
<213> ORGANISM: Artificial Sequence
<220> FEATURE:
<223> OTHER INFORMATION: Peptide sequence of human ActRIIB

<400> SEQUENCE: 158

```
Val Lys Lys Gly Cys Trp Leu Asp Asp
1               5
```

<210> SEQ ID NO 159

<211> LENGTH: 10
<212> TYPE: PRT
<213> ORGANISM: Artificial Sequence
<220> FEATURE:
<223> OTHER INFORMATION: Peptide sequence of human ActRIIB

<400> SEQUENCE: 159

Cys Cys Glu Gly Asn Phe Cys Asn Glu Arg
1 5 10

<210> SEQ ID NO 160
<211> LENGTH: 12
<212> TYPE: PRT
<213> ORGANISM: Artificial Sequence
<220> FEATURE:
<223> OTHER INFORMATION: Peptide sequence of human ActRIIB

<400> SEQUENCE: 160

Gly Cys Trp Leu Asp Asp Phe Asn Cys Tyr Asp Arg
1 5 10

<210> SEQ ID NO 161
<211> LENGTH: 10
<212> TYPE: PRT
<213> ORGANISM: Artificial Sequence
<220> FEATURE:
<223> OTHER INFORMATION: Peptide sequence of human ActRIIA

<400> SEQUENCE: 161

Cys Cys Glu Gly Asn Met Cys Asn Glu Lys
1 5 10

<210> SEQ ID NO 162
<211> LENGTH: 12
<212> TYPE: PRT
<213> ORGANISM: Artificial Sequence
<220> FEATURE:
<223> OTHER INFORMATION: Peptide sequence of human ActRIIA

<400> SEQUENCE: 162

Glu Cys Leu Phe Phe Asn Ala Asn Trp Glu Lys Asp
1 5 10

<210> SEQ ID NO 163
<211> LENGTH: 12
<212> TYPE: PRT
<213> ORGANISM: Artificial Sequence
<220> FEATURE:
<223> OTHER INFORMATION: Peptide sequence of human ActRIIA

<400> SEQUENCE: 163

Cys Trp Leu Asp Asp Ile Asn Cys Tyr Asp Arg Thr
1 5 10

<210> SEQ ID NO 164
<211> LENGTH: 360
<212> TYPE: DNA
<213> ORGANISM: Artificial Sequence
<220> FEATURE:
<223> OTHER INFORMATION: VH sequence

<400> SEQUENCE: 164
caggtgcagc tggtgcagtc tggggctgag gtgaagaagc ctggggcctc agtgaaggtt 60
tcctgcaagg catctggata caccttcacc tcgtaccgta tgcactgggt gcgacaggcc 120
cctggacaag ggcttgagtg gatgggattt atcgtgccta gtggtggtag cacaggctac 180

```
gcacagaagt tccagggcag agttaccatg accagggaca cgtccacgag cacagtctac    240

atggagctga gcagcctgag atctgaggac acggcggtgt actactgcgc tagagtatct    300

aggtacgccc cagagccaat ggacgtatgg ggccagggaa caactgtcac cgtctcctca    360


<210> SEQ ID NO 165
<211> LENGTH: 120
<212> TYPE: PRT
<213> ORGANISM: Artificial Sequence
<220> FEATURE:
<223> OTHER INFORMATION: VH sequence

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Phe Ile Val Pro Ser Gly Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Arg Tyr Ala Pro Glu Pro Met Asp Val Trp Gly Gln
            100                 105                 110

Gly Thr Thr Val Thr Val Ser Ser
        115                 120


<210> SEQ ID NO 166
<211> LENGTH: 5
<212> TYPE: PRT
<213> ORGANISM: Artificial Sequence
<220> FEATURE:
<223> OTHER INFORMATION: CDR1 amino acid residues 31-35 of SEQ ID NO 165

<400> SEQUENCE: 166

Ser Tyr Arg Met His
1               5


<210> SEQ ID NO 167
<211> LENGTH: 17
<212> TYPE: PRT
<213> ORGANISM: Artificial Sequence
<220> FEATURE:
<223> OTHER INFORMATION: CDR2 amino acid residues 50-66 of SEQ ID NO 165

<400> SEQUENCE: 167

Phe Ile Val Pro Ser Gly Gly Ser Thr Gly Tyr Ala Gln Lys Phe Gln
1               5                   10                  15

Gly


<210> SEQ ID NO 168
<211> LENGTH: 11
<212> TYPE: PRT
<213> ORGANISM: Artificial Sequence
<220> FEATURE:
<223> OTHER INFORMATION: CDR3 amino acid residues 99-109 of SEQ ID NO
      165

<400> SEQUENCE: 168
```

Val Ser Arg Tyr Ala Pro Glu Pro Met Asp Val
1 5 10

<210> SEQ ID NO 169
<211> LENGTH: 1344
<212> TYPE: DNA
<213> ORGANISM: Artificial Sequence
<220> FEATURE:
<223> OTHER INFORMATION: H sequence

<400> SEQUENCE: 169

```
caggtgcagc tggtgcagtc tggggctgag gtgaagaagc ctggggcctc agtgaaggtt     60
tcctgcaagg catctggata caccttcacc tcgtaccgta tgcactgggt gcgacaggcc    120
cctggacaag ggcttgagtg gatgggattt atcgtgccta gtggtggtag cacaggctac    180
gcacagaagt tccagggcag agttaccatg accagggaca cgtccacgag cacagtctac    240
atggagctga gcagcctgag atctgaggac acggcggtgt actactgcgc tagagtatct    300
aggtacgccc cagagccaat ggacgtatgg ggccagggaa caactgtcac cgtctcctca    360
gcttccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accctgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga gatgaccaag   1080
aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcaggtg gcaggagggg   1260
aatgtcttct catgctccgt gatgcatgag gctctgcaca accactacac acagaagagc   1320
ctctccctgt ctctgggtaa atga                                          1344
```

<210> SEQ ID NO 170
<211> LENGTH: 447
<212> TYPE: PRT
<213> ORGANISM: Artificial Sequence
<220> FEATURE:
<223> OTHER INFORMATION: H sequence

<400> SEQUENCE: 170

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Arg Met His Trp Val Arg Gln Ala Pro Gly Gln Gly Leu Glu Trp Met
35 40 45

Gly Phe Ile Val Pro Ser Gly Gly Ser Thr Gly Tyr Ala Gln Lys Phe

```
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Arg Tyr Ala Pro Glu Pro Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 171
<211> LENGTH: 321
<212> TYPE: DNA
<213> ORGANISM: Artificial Sequence

```
<220> FEATURE:
<223> OTHER INFORMATION: VL sequence

<400> SEQUENCE: 171

gacatccaga tgacccagtc tccatcttcc gtgtctgcat ctgtaggaga cagagtcacc      60

atcacttgtc gggcgagtca gggtattagc aggtggttag cctggtatca gcagaaacca     120

gggaaagccc ctaagctcct gatctatgct gcatccagtt tgcaaagtgg ggtcccatca     180

aggttcagcg gcagtggatc tgggacagat ttcactctca ccatcagcag cctgcagcct     240

gaagattttg caacttatta ctgtcagcag gcattctccc acccttggac ttttggcgga     300

gggaccaagg ttgagatcaa a                                               321


<210> SEQ ID NO 172
<211> LENGTH: 107
<212> TYPE: PRT
<213> ORGANISM: Artificial Sequence
<220> FEATURE:
<223> OTHER INFORMATION: VL sequence

<400> SEQUENCE: 172

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Ser His Pro Trp
                85                  90                  95

Thr Phe Gly Gly Gly Thr Lys Val Glu Ile Lys
            100                 105


<210> SEQ ID NO 173
<211> LENGTH: 11
<212> TYPE: PRT
<213> ORGANISM: Artificial Sequence
<220> FEATURE:
<223> OTHER INFORMATION: CDR1 amino acid residues 24-34 of SEQ ID NO 172

<400> SEQUENCE: 173

Arg Ala Ser Gln Gly Ile Ser Arg Trp Leu Ala
1               5                   10


<210> SEQ ID NO 174
<211> LENGTH: 7
<212> TYPE: PRT
<213> ORGANISM: Artificial Sequence
<220> FEATURE:
<223> OTHER INFORMATION: CDR2 amino acid residues 50-56 of SEQ ID NO 172

<400> SEQUENCE: 174

Ala Ala Ser Ser Leu Gln Ser
1               5


<210> SEQ ID NO 175
<211> LENGTH: 9
<212> TYPE: PRT
<213> ORGANISM: Artificial Sequence
```

<220> FEATURE:
<223> OTHER INFORMATION: CDR3 amino acid residues 89-97 of SEQ ID NO 172

<400> SEQUENCE: 175

```
Gln Gln Ala Phe Ser His Pro Trp Thr
1               5
```

<210> SEQ ID NO 176
<211> LENGTH: 727
<212> TYPE: DNA
<213> ORGANISM: Artificial Sequence
<220> FEATURE:
<223> OTHER INFORMATION: L sequence

<400> SEQUENCE: 176

```
gacatccaga tgacccagtc tccatcttcc gtgtctgcat ctgtaggaga cagagtcacc      60

atcacttgtc gggcgagtca gggtattagc aggtggttag cctggtatca gcagaaacca     120

gggaaagccc ctaagctcct gatctatgct gcatccagtt tgcaaagtgg ggtcccatca     180

aggttcagcg gcagtggatc tgggacagat ttcactctca ccatcagcag cctgcagcct     240

gaagattttg caacttatta ctgtcagcag gcattctccc acccttggac ttttggcgga     300

gggaccaagg ttgagatcaa acgtaagggg ctcacagtta attaattgag gtctggacat     360

atacatgggt gacaatgaca tccactttgc ctttctctcc acaggaactg tggctgcacc     420

atctgtcttc atcttcccgc catctgatga gcagttgaaa tctggaactg cctctgttgt     480

gtgcctgctg aataacttct atcccagaga ggccaaagta cagtggaagg tggataacgc     540

cctccaatcg ggtaactccc aggagagtgt cacagagcag gacagcaagg acagcaccta     600

cagcctcagc agcaccctga cgctgagcaa agcagactac gagaaacaca aagtctacgc     660

ctgcgaagtc acccatcagg gcctgagctc gcccgtcaca aagagcttca acaggggaga     720

gtgttag                                                                727
```

<210> SEQ ID NO 177
<211> LENGTH: 214
<212> TYPE: PRT
<213> ORGANISM: Artificial Sequence
<220> FEATURE:
<223> OTHER INFORMATION: L sequence

<400> SEQUENCE: 177

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Ser His Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

-continued

```
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```